(12) United States Patent
Mortimore et al.

(10) Patent No.: US 7,410,956 B2
(45) Date of Patent: Aug. 12, 2008

(54) CASPASE INHIBITOR PRODRUGS

(75) Inventors: Michael Mortimore, Burford (GB);
Julian M. C. Golec, Swindon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 730 days.

(21) Appl. No.: 10/366,192

(22) Filed: Feb. 11, 2003

(65) Prior Publication Data
US 2004/0019017 A1    Jan. 29, 2004

Related U.S. Application Data

(60) Provisional application No. 60/355,889, filed on Feb. 11, 2002.

(51) Int. Cl.
  *A61K 31/664* (2006.01)
  *A61K 31/67* (2006.01)
  *A61K 31/675* (2006.01)
  *C07F 9/09* (2006.01)
  *C07F 9/41* (2006.01)

(52) U.S. Cl. .................... 514/79; 514/80; 514/85; 514/89; 514/91; 514/92; 514/114; 544/57; 544/232; 546/22; 548/112; 548/113; 558/70

(58) Field of Classification Search .................. 548/112, 548/113; 546/22; 544/57, 232; 558/70; 540/522; 514/79, 80, 85, 89, 91, 92, 114
See application file for complete search history.

(56) References Cited

U.S. PATENT DOCUMENTS

| 6,184,210 | B1 | 2/2001 | Keana et al. |
| 6,184,244 | B1 | 2/2001 | Karanewsky et al. |
| 6,187,771 | B1 | 2/2001 | Karanewsky et al. |
| 6,197,750 | B1 | 3/2001 | Karanewsky et al. |
| 6,242,422 | B1 | 6/2001 | Karanewsky et al. |
| 6,355,618 | B1 | 3/2002 | Cai et al. |
| 2002/0169177 | A1 | 11/2002 | Kay et al. |

FOREIGN PATENT DOCUMENTS

| WO | WO 94/22483 | 10/1994 |
| WO | WO 96/03982 | 2/1996 |
| WO | WO 99/02485 | 1/1999 |
| WO | WO-00/31083 | * 6/2000 |
| WO | WO 00/31083 | * 6/2000 |
| WO | WO 00/55114 | 9/2000 |
| WO | WO 00/55127 | 9/2000 |
| WO | WO 00/61542 | 10/2000 |
| WO | WO 01/05772 | 1/2001 |
| WO | WO 01/10383 | 2/2001 |
| WO | WO 01/16093 | 3/2001 |
| WO | WO 01/19320 | * 3/2001 |
| WO | WO 01/44216 | 6/2001 |
| WO | WO 01/72707 | 10/2001 |
| WO | WO 01/90070 | 11/2001 |
| WO | WO 01/94351 | 12/2001 |
| WO | WO 02/11666 | 2/2002 |
| WO | WO 02/22611 | 3/2002 |
| WO | WO 03/000173 | 1/2003 |

OTHER PUBLICATIONS

Smyth, Emily, "The Trouble with Inhibitors," Signalling Scissors, Horizon Symposia 2003, pp. 1-4.*
Y. Cheng et al., "Caspase Inhibitor Affords Neuroprotection with Delayed Administration in a Rat Model of Neonatal Hypoxic-Ischemic Brain Injury." *J. Clin. Invest.*, 101(9), 1992-1999 (1998).
R.E. Ellis et al., "Mechanisms and Functions of Cell Death." *Annu. Rev. Cell Biol.*, 7, 663-698 (1991).
M. Endres et al., "Attenuation of Delayed Neuronal Death After Mild Focal Ischemia in Mice by Inhibition of the Caspase Family." *Journal of Cerebral Blood Flow and Metabolism*, 18, 238-247 (1998).
P. Goldstein, "Cell Death in Us and Others." *Science*, 281 (1998).
S.R. Grobmyer et al., "Peptidomimetic Fluoromethylketone Rescues Mice from Lethal Endotoxic Shock." *Molecular Medicine*, 5, 585-594 (1999).
Y.A. Lazebnik et al., "Cleavage of Poly(ADP-Ribose) Polymerase by a Proteinase with Properties Like Ice." *Nature*, 371, 346-347 (1994).
J.J. Plattner and D.W. Norbeck, "Obstacles to Drug Development from Peptide Leads." in *Drug Discover Technologies*, C.R. Clark and W.H. Moos, Eds., Ellis Horwood, Chichester, England, 92-126 (1990).
J.C.R. Randle et al., "ICE/Caspase-1 Inhibitors as Novel Anti-Inflammatory Drugs." *Expert Opin. Investig. Drugs*, 10(7), 1-3 (2001).
S. Roggo et al., "P2/3 Oxo Azepino Indoles: A New Class of Potent Broad Spectrum Caspase Inhibitors with In Vivo Activity in the pMCAO Model." *ACS Meeting*, San Diego, Apr. 2001.
I. Rodriguez et al., "Systemic Injection of a Tripeptide Inhibits the Intracellular Activation of CPP32-like Proteases In Vivo and Fully Protects Mice Against Fas-Mediated Fulminant Liver Destruction and Death." *J. Exp. Med.*, 184, 2067-2072 (1996).
T.V. Talanian et al., "Caspases as Targets for Anti-Inflammatory and Anti-Apoptotic Drug Discovery." *Journal of Medicinal Chemistry*, 43, 3351-3371 (2000).
N.A. Thornberry, "Caspases: Key Mediators of Apoptosis." *Chemistry & Biology*, 5, R97-R103 (1998).
K.P. Wilson et al., "Structure and Mechanism of Interleukin-1b Converting Enzyme." *Nature*, 370, 270-275 (1994).
A.G. Yakovlev et al., "Activation of CPP32-like Caspases Contributes to Neuronal Apoptosis and Neurological Dysfunction after Traumatic Brain Injury." *The Journal of Neuroscience*, 17(19), 7415-7424 (1997).
H. Yaoita et al., "Attenuation of Ischemia/Reperfusion Injury in Rats by a Caspase Inhibitor." *Circulation*, 97(3), 276-281 (1998).

* cited by examiner

*Primary Examiner*—Kamal A. Saeed
*Assistant Examiner*—Janet L. Coppins
(74) *Attorney, Agent, or Firm*—Ropes & Gray LLP; James F. Haley, Jr.; Nina R. Horan

(57) ABSTRACT

The present invention relates to compounds of formula I which are prodrugs of caspase inhibitors and pharmaceutically acceptable salts thereof. This invention further relates to the release of caspase inhibitors from these compounds through selective bond cleavage. This invention further relates to pharmaceutical compositions comprising these compounds, which are particularly well-suited for treatment of caspase-mediated diseases, including inflammatory and degenerative diseases. This invention further relates to methods for preparing compounds of this invention.

15 Claims, 206 Drawing Sheets

1. A compound having the Formulae I or II or III:

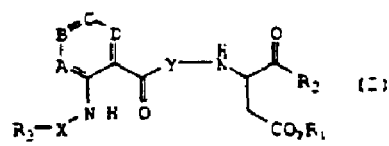 (I)

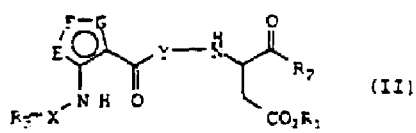 (II)

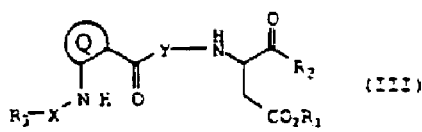 (III)

or a pharmaceutically acceptable salt or prodrug thereof, wherein:

$R_1$ is an optionally substituted alkyl or hydrogen;

$R_3$ is an N-protecting group;

$R_7$ is hydrogen or optionally substituted alkyl;

Q is an optionally substituted saturated or partially saturated carbocycle or heterocycle;

X is a peptide of 1-4 amino acids or a bond;

Y is a peptide of 1-4 amino acids or a bond;

A is $CR_6$ or nitrogen;

B is $CR_7$ or nitrogen;

C is $CR_8$ or nitrogen;

D is $CR_9$ or nitrogen;

provided that not more than two of A, B, C or D is nitrogen; and $R_6$-$R_9$ independently are hydrogen, halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl,

Fig. 1(a)

nitro, amino, cyano, $C_1$-$C_6$ acylamino, hydroxy, $C_1$-$C_6$ acyloxy, $C_1$-$C_6$ alkoxy, alkylthio, or carboxy; or one of $R_6$ and $R_7$, or $R_7$ and $R_8$, or $R_8$ and $R_9$ are taken together with the carbon atoms to which they are attached to form a carbocycle or heterocycle;

E is $C_{14}$, nitrogen, oxygen or sulfur;

F is $C_{15}$, nitrogen, oxygen or sulfur;

G is $C_{16}$, nitrogen, oxygen or sulfur;

provided that only one of E, F, G is nitrogen, oxygen or sulfur and $R_{14}$-$R_{16}$ are independently hydrogen, halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, cyano, $C_1$-$C_6$ acylamino, hydroxy, $C_1$-$C_6$ acyloxy, $C_1$-$C_6$ alkoxy, alkylthio, or carboxy; or one of $R_{14}$ and $R_{15}$, or $R_{15}$ and $R_{16}$, are taken together with the carbon atoms to which they are attached to form a carbocycle or heterocycle.

2. A compound according to claim 1, wherein $R_1$ is t-butyloxycarbonyl, acetyl or benzyloxycarbonyl.

3. A compound according to claim 1, wherein $R_1$ is H, Me, Et or acetoxymethyl.

4. A compound according to claim 1, wherein $R_2$ is hydrogen, fluoromethyl, acyloxymethyl, arylacyloxymethyl or aminomethyl.

5. A compound according to claim 1, wherein X is a bond.

6. A compound according to claim 1, wherein A, B, C and D are CH.

Fig. 1(b)

7. A compound according to claim 1, wherein A is nitrogen, and B, C and D are CH.

8. A compound according to claim 1, wherein G is sulfur, and E and F are CH.

9. A compound according to claim 1, wherein Q is cyclohexyl or cyclopentyl.

10. A compound according to claim 1, wherein said compound has the Formula IV:

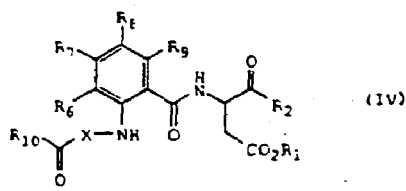

or a pharmaceutically acceptable salt or prodrug thereof, wherein $R_2$ is hydrogen or optionally substituted alkyl, wherein the substituent is halo, hydroxy, alkoxy, aryloxy, alkylthio, arylthio, amino, acyloxy, or arylacyloxy;

$R_4$-$R_9$ independently are hydrogen, halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, cyano, $C_1$-$C_6$ acylamino, hydroxy, $C_1$-$C_6$ acyloxy, $C_1$-$C_6$ alkoxy, alkylthio, or carboxy; or one of $R_4$ and $R_7$, or $R_7$ and $R_8$, or $R_8$ and $R_9$ are taken together with the carbon atoms to which they are attached to form a carbocycle or heterocycle, selected from the group consisting of —OCH$_2$O—, —OCF$_2$O—, —(CH$_2$)$_3$—, —(CH$_2$)$_4$—, —OCH$_2$CH$_2$O—, —CH$_2$N(R$_{13}$)CH$_2$—, —CH$_2$CH$_2$N(R$_{13}$)CH$_2$—, —CH$_2$N(R$_{13}$)CH$_2$CH$_2$— and —CH=CH—CH=CH—; wherein $R_{13}$ is hydrogen, alkyl or cycloalkyl;

Fig. 1(c)

$R_{10}$ is hydrogen, $C_1$-$C_6$ alkoxy, $C_1$-$C_6$ alkyl, $C_1$-$C_6$ haloalkyl, $C_6$-$C_{10}$ aryl, $C_4$-$C_7$ cycloalkyl, $C_6$-$C_{10}$ aryl($C_1$-$C_6$)alkyl, benzyloxy, substituted benzyloxy, or $NR_{11}R_{12}$; wherein $R_{11}$ and $R_{12}$ independently are hydrogen, $C_1$-$C_6$ alkyl, $C_1$-$C_6$ haloalkyl, $C_6$-$C_{10}$ aryl, $C_4$-$C_7$ cycloalkyl, $C_6$-$C_{10}$ aryl($C_1$-$C_6$)alkyl, or $R_{11}$ and $R_{12}$ are combined to form a heterocyclic ring system selected from the group consisting of pyrrolidine, piperidine, piperazine, and morpholine.

11. A compound according to claim 10, wherein $R_2$ is hydrogen, fluoromethyl, acyloxymethyl, arylacyloxymethyl or aminomethyl.

12. A compound according to claim 10, wherein $R_{10}$ is benzyloxy.

13. A compound according to claim 10, wherein $R_1$ is H, Me or acetoxymethyl.

14. A compound according to claim 10, wherein X is a peptide of 1-2 amino acids or a bond.

Fig. 1(d)

| |
|---|
| 2-(Z-Amino)benzoyl-Asp-fmk |
| 2-(Z-Amino)-6-methylbenzoyl-Asp-fmk |
| 2-(Z-Amino)-5-methylbenzoyl-Asp-fmk |
| 2-(Z-Amino)-3-methylbenzoyl-Asp-fmk |
| 2-(Z-Amino)-3-methylbenzoyl-Asp-fmk |
| 2-(Z-Amino)-5-fluorobenzoyl-Asp-fmk |
| cis-2-(Z-Amino)cyclohexanecarboxyl-Asp-fmk |
| 2-(Z-Amino)-3,5-dimethylbenzoyl-Asp-fmk |
| 2-(Z-Amino)-5-chlorobenzoyl-Asp-fmk |
| 2-(Z-Amino)-6-chlorobenzoyl-Asp-fmk |
| 2-(Z-Amino)-4-methylbenzoyl-Asp-fmk |
| 3-(Z-Amino)thiophene-3-carboxyl-Asp-fmk |
| 3-(Methoxycarbonylamino)thiophene-2-carboxyl-Asp-fmk |
| Cis-2-(Z-Amino)cyclopentanecarboxyl-Asp-fmk |
| Trans-2-(Z-Amino)cyclohexanecarboxyl-Asp-fmk |
| Z-Glu-(2-aminobenzoyl)-Asp-fmk |
| Z-Val-(2-Aminobenzoyl)-Asp-fmk |
| 2-(Z-Amino)benzoyl-Asp-DCB-methylketone |
| Methoxycarbonyl-Val-(2-aminobenzoyl)-Asp-fmk |

Fig. 1(e)

| 1  | 2-(Z-Amino)benzoyl-Asp-fmk |
|----|----------------------------|
| 2  | 2-(Z-Amino)-6-methylbenzoyl-Asp-fmk |
| 3  | 2-(Z-Amino)-5-methylbenzoyl-Asp-fmk |
| 4  | 2-(Z-Amino)-3-methylbenzoyl-Asp-fmk |
| 5  | 2-(Z-Amino)-3-methylbenzoyl-Asp-fmk |
| 6  | 2-(Z-Amino)-5-fluorobenzoyl-Asp-fmk |
| 7  | cis-2-(Z-Amino)cyclohexanecarboxyl-Asp-fmk |
| 8  | 2-(Z-Amino)-3,5-dimethylbenzoyl-Asp-fmk |
| 9  | 2-(Z-Amino)-5-chlorobenzoyl-Asp-fmk |
| 10 | 2-(Z-Amino)-6-chlorobenzoyl-Asp-fmk |
| 11 | 2-(Z-Amino)-4-methylbenzoyl-Asp-fmk |
| 12 | 3-(Z-Amino)thiophene-3-carboxyl-Asp-fmk |
| 13 | 3-(Methoxycarbonylamino)thiophene-2-carboxyl-Asp-fmk |
| 14 | Cis-2-(Z-Amino)cyclopentanecarboxyl-Asp-fmk |
| 15 | Trans-2-(Z-Amino)cyclohexanecarboxyl-Asp-fmk |
| 16 | Z-Glu-(2-aminobenzoyl)-Asp-fmk |
| 17 | Z-Val-(2-Aminobenzoyl)-Asp-fmk |
| 18 | 2-(Z-Amino)benzoyl-Asp-DCB-methylketone |
| 19 | Methoxycarbonyl-Val-(2-aminobenzoyl)-Asp-fmk |

Z: benzyloxycarbonyl
fmk: fluoromethylketone
DCB: 2,6-dichlorobenzoyloxy

Fig. 1(f)

1. A compound represented by formula I:

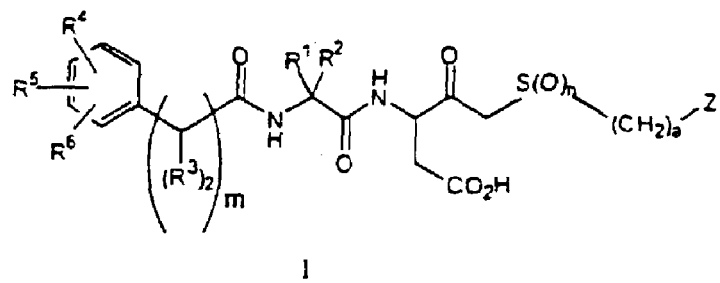

I or a pharmaceutically acceptable salt, ester or hydrate, wherein:

a is 0 or 1 and m and n are 0, 1 or 2;

Z is selected from the group consisting of:
   1) $C_{1-6}$alkyl,
   2) $C_{3-11}$cycloalkyl, said alkyl and cycloalkyl groups being optionally substituted with 1-4 halo groups,
   3) phenyl or naphthyl, optionally substituted by one or two groups selected from the group consisting of: halo, nitro, $C_{1-4}$alkyl and $C_{1-4}$alkoxy, said alkyl and alkoxy groups being optionally substituted with 1-3 halo groups; and
   4) $HET^1$ wherein $HET^1$ represents a 5 or 6 membered aromatic or non-aromatic ring, and the benzofused analogs thereof, containing from 1-3 heteroatoms selected from O, S and N, and optionally substituted with 1-2 groups selected from halo, $C_{1-4}$alkyl and $C_{1-4}$acyl;

$R^1$ represents a member selected from the group consisting of: H, aryl, $C_{1-4}$alkyl optionally substituted by $OR^7$, and $C_{5-7}$cycloalkyl optionally containing one heteroatom selected from O, S and $NR^8$,
and
$R^2$ represents H,

Fig. 2-1(a)

or in the alternative, $R^1$ and $R^2$ are taken in combination and represent a ring of 4-7 members, said ring optionally containing one heteroatom selected from O, S and $NR^x$;

$R^3$ is selected from the group consisting of: H, $C_{1-4}$alkyl and benzyl optionally substituted with 1-2 groups selected from halo, $C_{1-4}$alkyl and $C_{1-4}$alkoxy; and $R^x$ is H or $C_{1-4}$alkyl;

each $R^5$ is independently selected from the group consisting of: H, $C_{1-4}$alkyl optionally containing 1-2 oxo groups, $C_{1-4}$alkoxy and halo;

$R^a$, $R^b$ and $R^c$ are independently selected from the group consisting of:

1) H,
2) halo,
3) $C_{1-4}$alkoxy optionally substituted with 1-3 halo atoms,
4) $NO_2$,
5) OH,
6) benzyloxy, the benzyl portion of which is optionally substituted with 1-2 members selected from the group consisting of: halo, CN, $C_{1-4}$alkyl and $C_{1-4}$alkoxy, said alkyl and alkoxy being optionally substituted with 1-3 halo groups,
7) $NH-C_{1-4}$acyl,
8) $C_{1-4}$acyl,
9) $O-C_{1-4}$alkyl-$CO_2H$, optionally esterified with a $C_{1-6}$ alkyl or $C_{5-7}$ cycloalkyl group,
10) $CH=CH-CO_2H$,
11) $C_{0-4}$alkyl$CO_2H$,
12) $C_{0-4}$alkyl$C(O)NH_2$, optionally substituted on the nitrogen atom by 1-2 $C_{1-4}$alkyl groups;
13) $C_{0-2}$alkyl$S(O)_{0-2}C_{1-4}$alkyl;
14) $S(O)_{0-2}-C_{1-6}$ alkyl or $S(O)_{0-2}$-phenyl, said alkyl and phenyl portions thereof being optionally substituted with 1-3 members selected from the group consisting of: halo, CN, $C_{1-4}$alkyl and $C_{1-4}$alkoxy, said alkyl and alkoxy being optionally substituted by 1-3 halo groups,
15) benzoyl optionally substituted by 1-2 members selected from the group consisting of: halo, CN, $C_{1-4}$alkyl and $C_{1-4}$alkoxy, said alkyl and alkoxy groups being optionally substituted by 1-3 halo groups,

Fig. 2-1(b)

16) phenyl or naphthyl, optionally substituted with 1-2 members selected from the group consisting of: halo, CN, C₁₋₄alkyl and C₁₋₄alkoxy, said alkyl and alkoxy being optionally substituted with 1-3 halo groups,

17) CN,

18) -C₁₋₄alkyl-HET², wherein HET² represents a 5-7 membered aromatic or non-aromatic ring containing 1-4 heteroatoms selected from O, S and NRˣ and optionally containing 1-2 oxo groups, and optionally substituted with 1-3 C₁₋₄ alkyl, OH, halo or C₁₋₄acyl groups;

19) -OC₁₋₄alkyl-HET³, wherein HET³ is a 5 or 6 membered aromatic or non-aromatic ring containing from 1 to 3 heteroatoms selected from O, S and N, and optionally substituted with one or two groups selected from halo and C₁₋₄alkyl, and optionally containing 1-2 oxo groups, and 20) HET⁴, wherein HET⁴ is a 5 or 6 membered aromatic or non-aromatic ring, and the benzofused analogs thereof, containing from 1 to 4 heteroatoms selected from O, S and N, and is optionally substituted by one or two groups selected from halo, C₁₋₄alkyl and C₁₋₄acyl, or R⁴ and R⁵ are taken in combination and represent a fused heteroaryl ring as shown below:

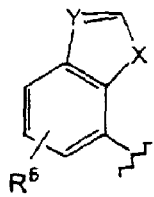

wherein Y is selected from the group consisting of CH and N, and X is selected from O, S and NH, and R⁶ is as defined above.

2. A compound in accordance with claim 1 wherein a is 1.

3. A compound in accordance with claim 1 wherein m is 1.

Fig. 2-1(c)

4. A compound in accordance with claim 1 wherein n is 0.

5. A compound in accordance with claim 1 wherein Z is phenyl optionally substituted by one or two groups selected from halo, nitro, $C_{1-4}$alkoxy optionally substituted by up to 3 halogen atoms, or $C_{1-4}$alkyl optionally substituted by up to 3 halogen atoms.

6. A compound in accordance with claim 1 wherein $R^1$ is $C_{1-5}$ alkyl optionally substituted by $OR^7$.

7. A compound in accordance with claim wherein $R^2$ is hydrogen.

8. A compound in accordance with claim 1 wherein $R^3$ is hydrogen.

9. A compound in accordance with claim 1 wherein $R^2$ is H and n is 0.

10. A compound in accordance with claim 9 wherein $R^1$ represents a member selected from the group consisting of: H, $C_{1-4}$alkyl optionally substituted by $OR^7$ and $C_{5-7}$cycloalkyl optionally containing one heteroatom selected from O, S and $NR^8$.

11. A compound in accordance with claim 1 wherein Z represents $HET^1$ and $HET^1$ represents a 5 or 6 membered aromatic ring, or the benzofused analog thereof, containing from 1-3 heteroatoms selected from O, S and N, and optionally substituted with 1-2 groups selected from halo, $C_{1-4}$alkyl and $C_{1-4}$acyl.

12. A compound in accordance with claim 11 wherein $HET^1$ represents a member selected from the group consisting of: pyridine, pyrimidine, pyridazine, furan, thiophene, thiazole and oxazole.

Fig. 2-1(d)

13. A compound in accordance with claim 1 wherein HET² is selected from the group consisting of: butyrolactone, tetrahydrofuran, tetrahydropyran and 2-pyrrolidinone.

14. A compound in accordance with claim 1 wherein HET³ is selected from pyridine and pyrimidine.

15. A compound in accordance with claim 1 wherein HET⁴ is selected from the group consisting of: 1,2,3-oxadiazole, 1,2,4-oxadiazole, 1,3,4-oxadiazole, 1,2,3-thiadiazole, 1,2,4-thiadiazole, 1,3,4-thiadiazole, thiophene, pyrrole, pyridine, tetrazole, oxazole, thiazole, 1,2,3-triazole, 1,2,4-triazole and 1,3,4-triazole.

16. A compound in accordance with claim 1 wherein:

a and m are 1;

n is 0;

Z is phenyl optionally substituted by one or two groups selected from halo, nitro, $C_{1-4}$alkoxy optionally substituted by up to 3 halogen atoms, or $C_{1-4}$alkyl optionally substituted by up to 3 halogen atoms;

$R^1$ represents a member selected from the group consisting of: H, $C_{1-4}$alkyl optionally substituted by $OR^7$ and $C_{3-7}$cycloalkyl optionally containing one heteroatom selected from O, S and $NR^8$.

$R^2$ is hydrogen;

$R^3$ is hydrogen

Z represents HET¹ and HET¹ represents pyridine, pyrimidine, pyridazine, furan, thiophene, thiazole or oxazole, optionally substituted with 1-2 groups selected from halo, $C_{1-4}$alkyl and $C_{1-4}$acyl;

HET² is selected from the group consisting of: butyrolactone, tetrahydrofuran, tetrahydropyran and 2-pyrrolidinone;

HET³ is selected from the group consisting of: butyrolactone, tetrahydrofuran, tetrahydropyran, 2-pyrrolidinone, pyridine and pyrimidine;

and HET⁴ is selected from the group consisting of: 1,2,3-oxadiazole, 1,2,4-oxadiazole, 1,3,4-oxadiazole, 1,2,3-thiadiazole, 1,2,4-thiadiazole, 1,3,4-thiadiazole, thiophene, pyrrole, pyridine, tetrazole, oxazole, thiazole, 1,2,3-triazole, 1,2,4-triazole and 1,3,4-triazole, and all other variables are as defined therein.

Fig. 2-1(e)

| TABLE 1 | |
|---|---|
| 1 | 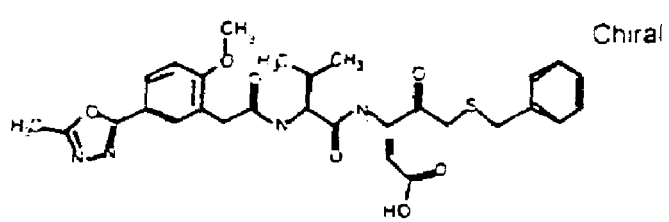 Chiral |
| 2 | 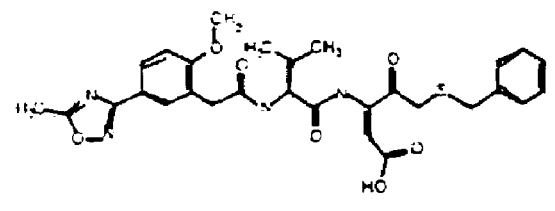 |
| 3 | 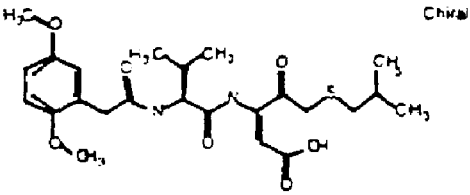 Chiral |
| 4 | 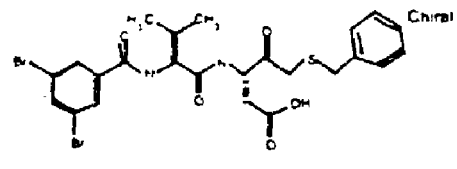 Chiral |
Fig. 2-1(f)

| 145 | 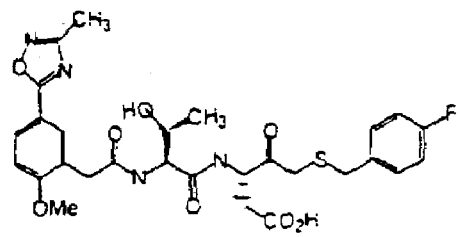 |
| 146 | 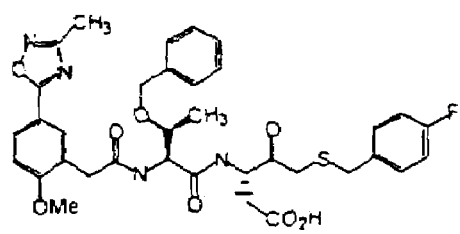 |
| 147 | 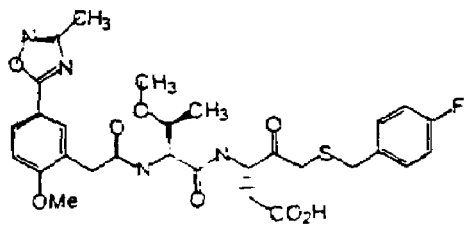 |
| 148 | 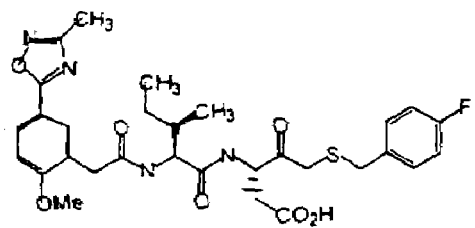 |
Fig. 2-2(r)

1. A compound having the Formula I:

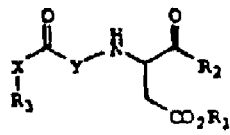

or pharmaceutically acceptable salts or prodrugs thereof, wherein:

$R_1$ is an optionally substituted alkyl or hydrogen;

$R_2$ is hydrogen or optionally substituted alkyl;

$R_3$ is an alkyl, saturated carbocyclic, partially saturated carbocyclic, aryl, saturated heterocyclic, partially saturated heterocyclic or heteroaryl group, wherein said group is optionally substituted;

X is O, S, $NR_4$ or $(CR_4R_5)_n$, where $R_4$ and $R_5$ are, at each occurrence, independently selected from the group consisting of hydrogen, alkyl and cycloalkyl, and n is 0, 1, 2 or 3; or X is $NR_4$, and $R_3$ and $R_4$ are taken together with the nitrogen atom to which they are attached to form a saturated heterocyclic, partially saturated heterocyclic or heteroaryl group, wherein said group is optionally substituted; or X is $CR_4R_5$, and $R_3$ and $R_4$ are taken together with the carbon atom to which they are attached to form a saturated carbocyclic, partially saturated carbocyclic, aryl, saturated heterocyclic, partially saturated heterocyclic or oxygen-containing heteroaryl group, wherein said group is optionally substituted; and Y is a residue of a natural or non-natural amino acid;

provided that when X is O, then $R_3$ is not unsubstituted benzyl or t-butyl; and when X is $CH_2$, then $R_3$ is not hydrogen.

Fig. 3(a)

2. The compound of claim 1, wherein $R_1$ is hydrogen, methyl, ethyl or acetoxymethyl.

3. The compound of claim 1, wherein $R_2$ is hydrogen, fluoromethyl, acyloxymethyl, arylacyloxymethyl, aryloxymethyl, phosphinyloxymethyl, or aminomethyl.

4. The compound of claim 1, wherein Y is valine, isoleucine, leucine, alanine, phenylalanine, cyclohexylalanine, 2-aminobutyric acid, phenylglycine or cyclohexylglycine.

5. The compound of claim 1, wherein:
$R_3$ is optionally substituted alkyl, $C_4$-$C_7$ cycloalkyl, saturated heterocyclic, partially saturated heterocyclic, aryl or heteroaryl; and
X is O, S, $NR_4$ or $(CR_4R_5)_n$, wherein $R_4$ and $R_5$ are independently hydrogen, alkyl or cycloalkyl, and n is 0, 1, 2 or 3.

6. The compound of claim 1, wherein X is O, NH or $CH_2$.

7. The compound of claim 1, wherein $R_3$ is straight-chained or branched $C_{1-6}$ alkyl.

8. The compound of claim 1, wherein $R_3$ is straight-chained or branched $C_{1-6}$ alkyl optionally substituted by hydroxy, carboxy, halogen, $C_4$-$C_7$ cycloalkyl, saturated or unsaturated heterocyclic group, aryl or heteroaryl.

9. The compound of claim 1, wherein $R_3$ is optionally substituted benzyl.

Fig. 3(b)

10. The compound of claim 1, wherein $R_3$ is optionally substituted pyridylmethyl.
11. The compound of claim 1, wherein $R_3-X-C(O)-$ is an antioxidant group.
12. The compound of claim 11, wherein said antioxidant group is
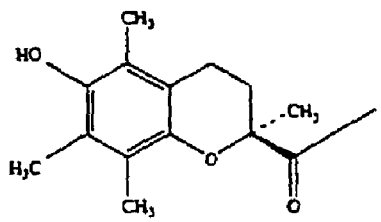
13. The compound of claim 12, wherein said compound is
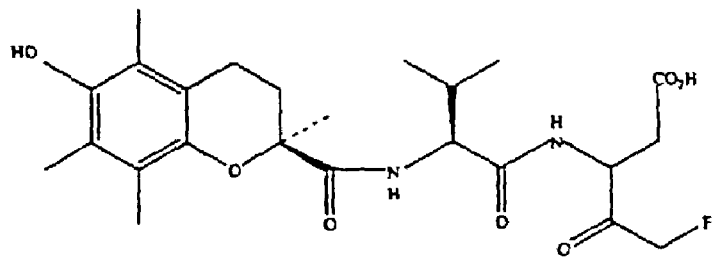
14. The compound of claim 1, wherein $R_3-X-C(O)-$ is a fluorescent group.
Fig. 3(c)

15. The compound of claim 14, wherein said fluorescent group is
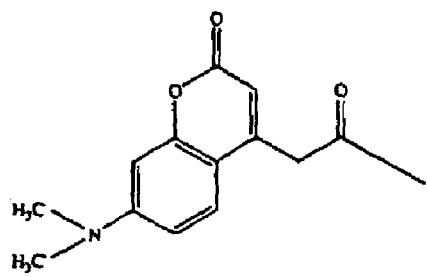
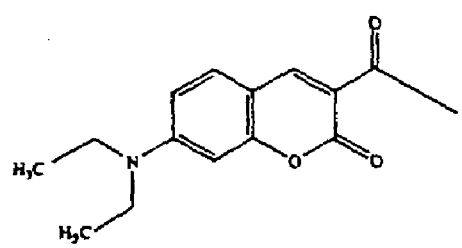
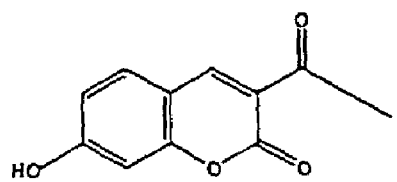
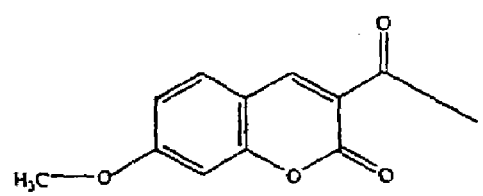 or
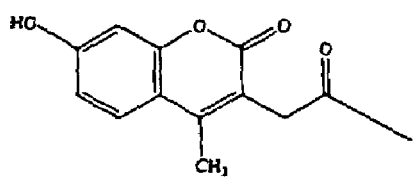
Fig. 3(d)

16. The compound of claim 14, wherein said compound is selected from the group consisting of
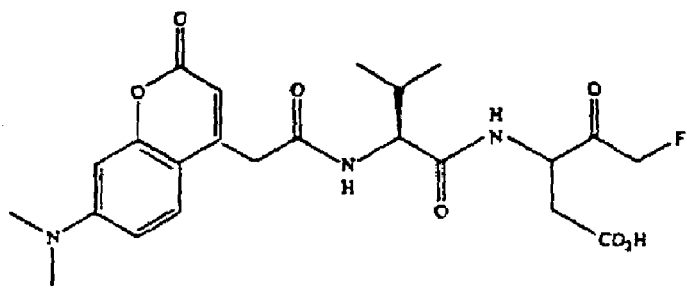
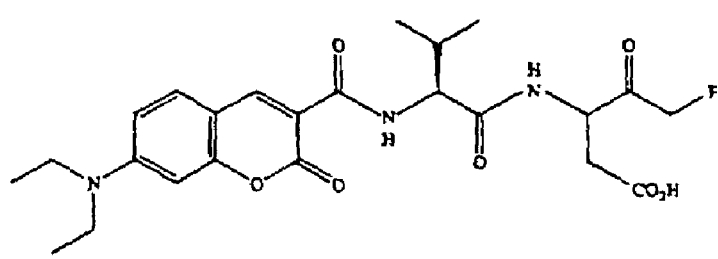
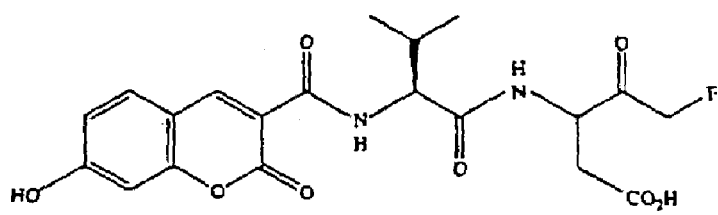
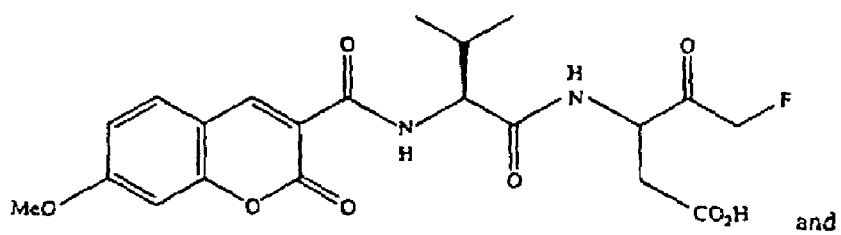 and
Fig. 3(e)

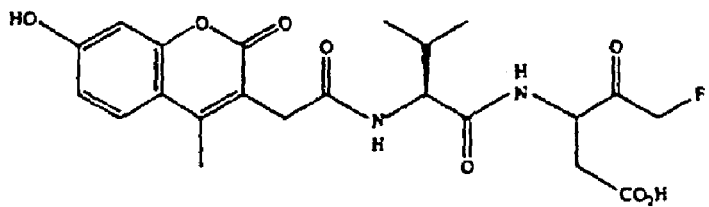

17. A compound having the Formula II:

or pharmaceutically acceptable salts or prodrugs thereof wherein:

$R_1$ is an optionally substituted alkyl or hydrogen;

$R_2$ is hydrogen or optionally substituted alkyl;

X is O, S, $NR_4$ or $(CR_4R_5)_n$, wherein $R_4$ and $R_5$ are, at each occurrence, independently selected from the group consisting of hydrogen, alkyl, and cycloalkyl, and n is 0, 1, 2 or 3;

Y is a residue of a natural or non-natural amino acid;

A is $CR_6$ or nitrogen;

B is $CR_7$ or nitrogen;

C is $CR_8$ or nitrogen;

D is $CR_9$ or nitrogen;

E is $CR_{10}$ or nitrogen; provided that not more than three of A, B, C, D and E are nitrogen; and $R_6$-$R_{10}$ independently are hydrogen, halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, cyano, $C_1$-$C_6$ acylamino, hydroxy, $C_1$-$C_6$ acyloxy, $C_1$-$C_6$ alkoxy, alkylthio, or carboxy; or

Fig. 3(f)

one of $R_6$ and $R_7$, or $R_7$ and $R_8$, or $R_8$ and $R_9$, or $R_9$ and $R_{10}$ are taken together with the carbon atoms to which they are attached to form a carbocycle or heterocycle, selected from the group consisting of —OCH$_2$O—, —OCF$_2$O—, —(CH$_2$)$_3$—, —(CH$_2$)$_4$—, —OCH$_2$CH$_2$O—, —CH$_2$N(R$_{13}$)CH$_2$—, —CH$_2$CH$_2$N(R$_{13}$)CH$_2$—, —CH$_2$N(R$_{13}$)CH$_2$CH$_2$—, -N(R$_{13}$)-CH=CH-, -CH=CH-N(R$_{13}$)-, -O-CH=CH-, -CH=CH-O-, -S-CH=CH-, -CH=CH-S-, -N=CH-CH=CH-, -CH=N-CH=CH-, -CH=CH-N=CH-, -CH=CH-CH=N-, -N=CH-CH=N-, and —CH=CH—CH=CH—; wherein $R_{13}$ is hydrogen, alkyl or cycloalkyl;

provided that when X is O, A is CR$_6$, B is CR$_7$, C is CR$_8$, D is CR$_9$ and E is CR$_{10}$, then at least one of the $R_6$-$R_{10}$ is not hydrogen.

18. The compound of claim 17, wherein $R_2$ is hydrogen, fluoromethyl, acyloxymethyl, arylacyloxymethyl, aryloxymethyl, phosphinyloxymethyl, or aminomethyl.

19. The compound of claim 17, wherein $R_1$ is hydrogen, methyl, ethyl or acetoxymethyl.

20. The compound of claim 17, wherein Y is valine, isoleucine, leucine, alanine, phenylalanine, cyclohexylalanine, 2-aminobutyric acid, phenylglycine or cyclohexylglycine.

21. The compound of claim 17, wherein X is O, A is CR$_6$, B is CR$_7$, C is CR$_8$, D is CR$_9$, and E is CR$_{10}$.

22. The compound of claim 17, wherein X is O, and one of A, B, C, D or E is nitrogen.

Fig. 3(g)

23. The compound of claim 17, wherein X is $CH_2$, A is $CR_6$, B is $CR_7$, C is $CR_8$, D is $CR_9$ and E is $CR_{10}$.

24. A compound having the Formula III:

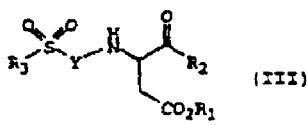

or pharmaceutically acceptable salts or prodrugs thereof, wherein:

$R_1$ is an optionally substituted alkyl or hydrogen;

$R_2$ is hydrogen or optionally substituted alkyl;

$R_3$ is an alkyl, saturated carbocyclic, partially saturated carbocyclic, aryl, saturated heterocyclic, partially saturated heterocyclic or heteroaryl group, wherein said group is optionally substituted; and Y is a residue of a natural or non-natural amino acid.

25. The compound of claim 24, wherein $R_1$ is hydrogen, methyl, ethyl or acetoxymethyl.

26. The compound of claim 24, wherein $R_2$ is hydrogen, fluoromethyl, acyloxymethyl, arylacyloxymethyl, aryloxymethyl, phosphinyloxymethyl, or aminomethyl.

27. The compound of claim 24, wherein Y is valine, isoleucine, leucine, alanine, phenylalanine, cyclohexylalanine, 2-aminobutyric acid, phenylglycine or cyclohexylglycine.

Fig. 3(h)

28. The compound of claim 24, wherein $R_3$ is straight-chained or branched $C_{1-6}$ alkyl.

29. The compound of claim 24, wherein $R_3$ is straight-chained or branched $C_{1-6}$ alkyl optionally substituted by hydroxy, carboxy, halogen $C_4$-$C_7$ cycloalkyl, saturated or unsaturated heterocyclic group, aryl or heteroaryl.

30. The compound of claim 24, wherein $R_3$ is methylphenyl or dimethylaminonaphthyl.

31. The compound of claim 1, wherein said compound is selected from the group consisting of:

2-Chlorobenzyloxycarbonyl-Val-Asp-fmk,
3-Chlorobenzyloxycarbonyl-Val-Asp-fmk,
4-Chlorobenzyloxycarbonyl-Val-Asp-fmk,
Phenethoxycarbonyl-Val-Asp-fmk,
Cyclohexylmethoxycarbonyl-Val-Asp-fmk,
Methoxycarbonyl-Val-Asp-fmk,
Ethoxycarbonyl-Val-Asp-fmk,
Isopropyloxycarbonyl-Val-Asp-fmk,
2-Chlorobenzyloxycarbonyl-Ile-Asp-fmk,
3-Chlorobenzyloxycarbonyl-Ile-Asp-fmk,
4-Chlorobenzyloxycarbonyl-Ile-Asp-fmk,
Phenylacetyl-Val-Asp-fmk,
4-Nitrobenzyloxycarbonyl-Val-Asp-fmk,
2,5-Dimethylbenzyloxycarbonyl-Val-Asp-fmk,
3,4-Dichlorobenzyloxycarbonyl-Val-Asp-fmk,
3,5-Dichlorobenzyloxycarbonyl-Val-Asp-fmk,
2,5-Dichlorobenzyloxycarbonyl-Val-Asp-fmk,
2,6-Dichlorobenzyloxycarbonyl-Val-Asp-fmk,

Fig. 3(i)

2,4-Dichlorobenzyloxycarbonyl-Val-Asp-fmk, 2,4-Dimethylbenzyloxycarbonyl-Val-Asp-fmk, 4-Ethylbenzyloxycarbonyl-Val-Asp-fmk, 4-Bromobenzyloxycarbonyl-Val-Asp-fmk, 4-Fluorobenzyloxycarbonyl-Val-Asp-fmk, Cyclopentylmethoxycarbonyl-Val-Asp-fmk, 4-Trifluoromethylbenzyloxycarbonyl-Val-Asp-fmk, 3-Phenylpropionyl-Val-Asp-fmk, Benzylaminocarbonyl-Val-Asp-fmk, 3-Phenylpropyloxycarbonyl-Val-Asp-fmk, 2,4-Difluorobenzyloxycarbonyl-Val-Asp-fmk, 3,4-Difluorobenzyloxycarbonyl-Val-Asp-fmk, 4-Morpholinecarbonyl-Val-Asp-fmk, 4-Pyridylmethoxycarbonyl-Val-Asp-fmk, 2-Pyridylmethoxycarbonyl-Val-Asp-fmk, 2,6-Dichlorobenzyloxycarbonyl-Val-Asp-DCB-methylketone, Isobutoxycarbonyl-Val-Asp-fmk, Propionyl-Val-Asp-fmk, Benzyl-glutaryl-Val-Asp-fmk, Glutaryl-Val-Asp-fmk, 3-(2-Phenyloxyphenyl)propionyl-Val-Asp-fmk, 3-(5-Bromo-2-hydroxyphenyl)propionyl-Val-Asp-fmk, 3-Fluorobenzyloxycarbonyl-Val-Asp-fmk, 2-Fluorobenzyloxycarbonyl-Val-Asp-fmk, 3-Methylbenzyloxycarbonyl-Val-Asp-fmk, 2-Chloro-4-fluorobenzyloxycarbonyl-Val-Asp-fmk, and 2-Naphthylmethoxycarbonyl-Val-Asp-fmk.

32. The compound of claim 24, wherein said compound is selected from the group consisting of:

*p*-Toluenesulfonyl-Val-Asp-fmk, and

*p*-Toluenesulfonyl-Phe-Asp-fmk.

Fig. 3(j)

Table 1
| Compound Number | |
|---|---|
| 1 | 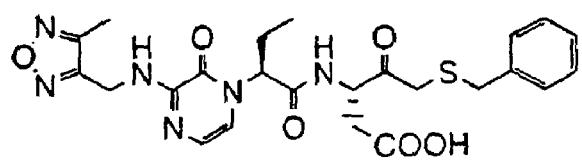 |
| 2 | 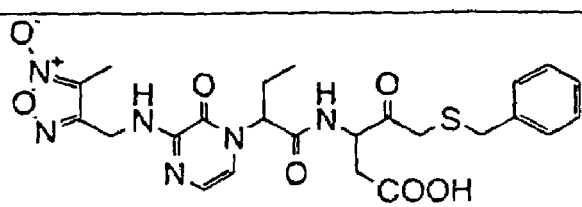 |
| 3 | 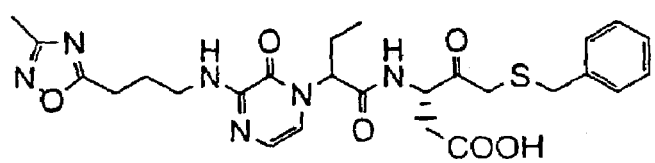 |
| 4 | 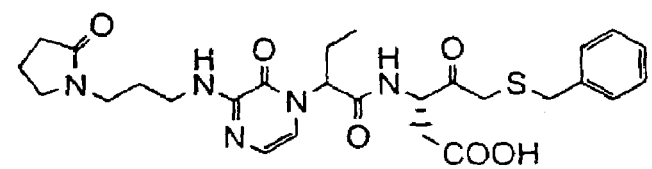 |
| 5 | 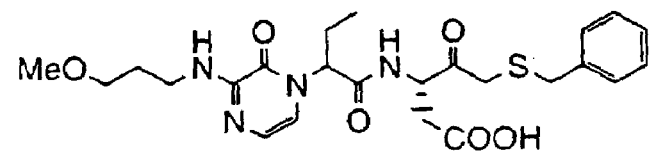 |
| 6 | 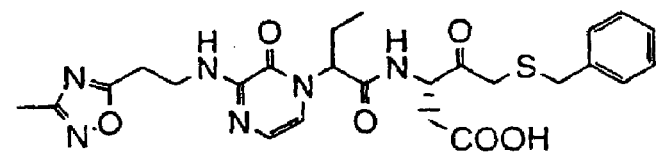 |
Fig. 4(a)

| 21 | 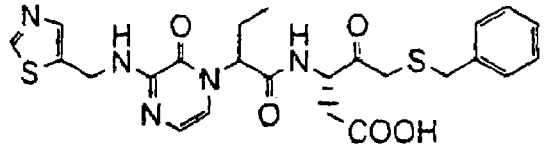 |
| 22 | 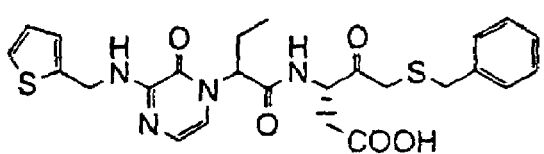 |
| 23 | 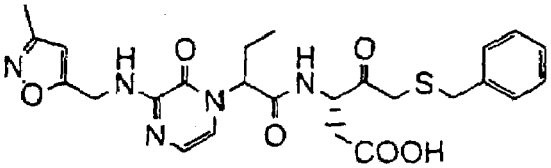 |
| 24 | 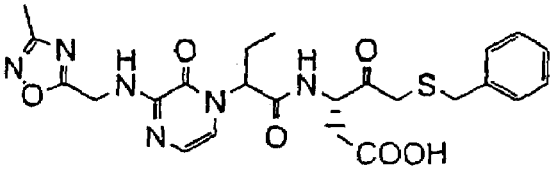 |
| 25 | 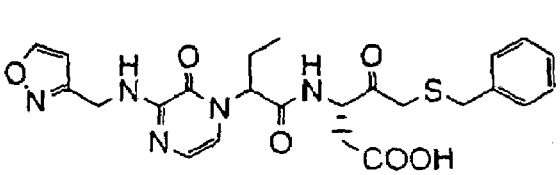 |
| 26 | 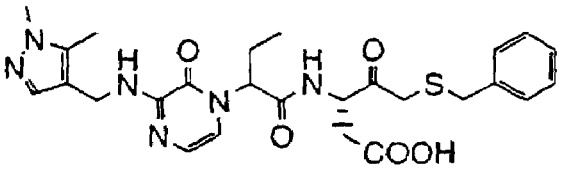 |
| 27 | 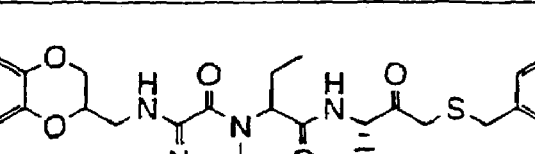 |
Fig. 4(d)

| 35 | 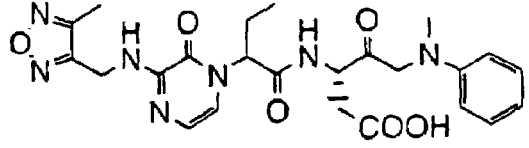 |
| 36 | 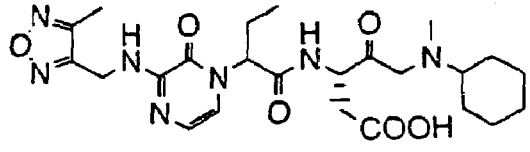 |
| 37 | 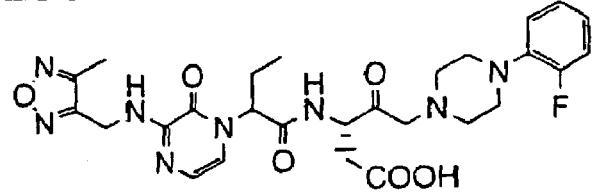 |
| 38 | 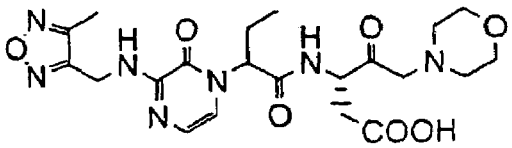 |
| 39 | 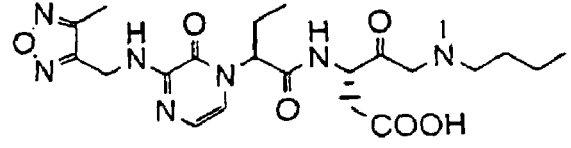 |
| 40 | 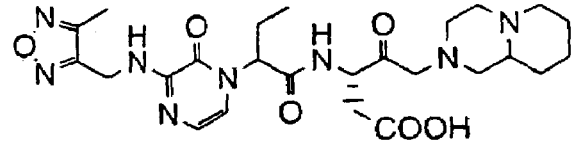 |
| 41 | 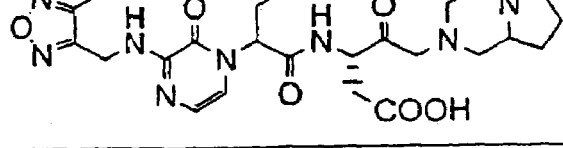 |
Fig. 4(f)

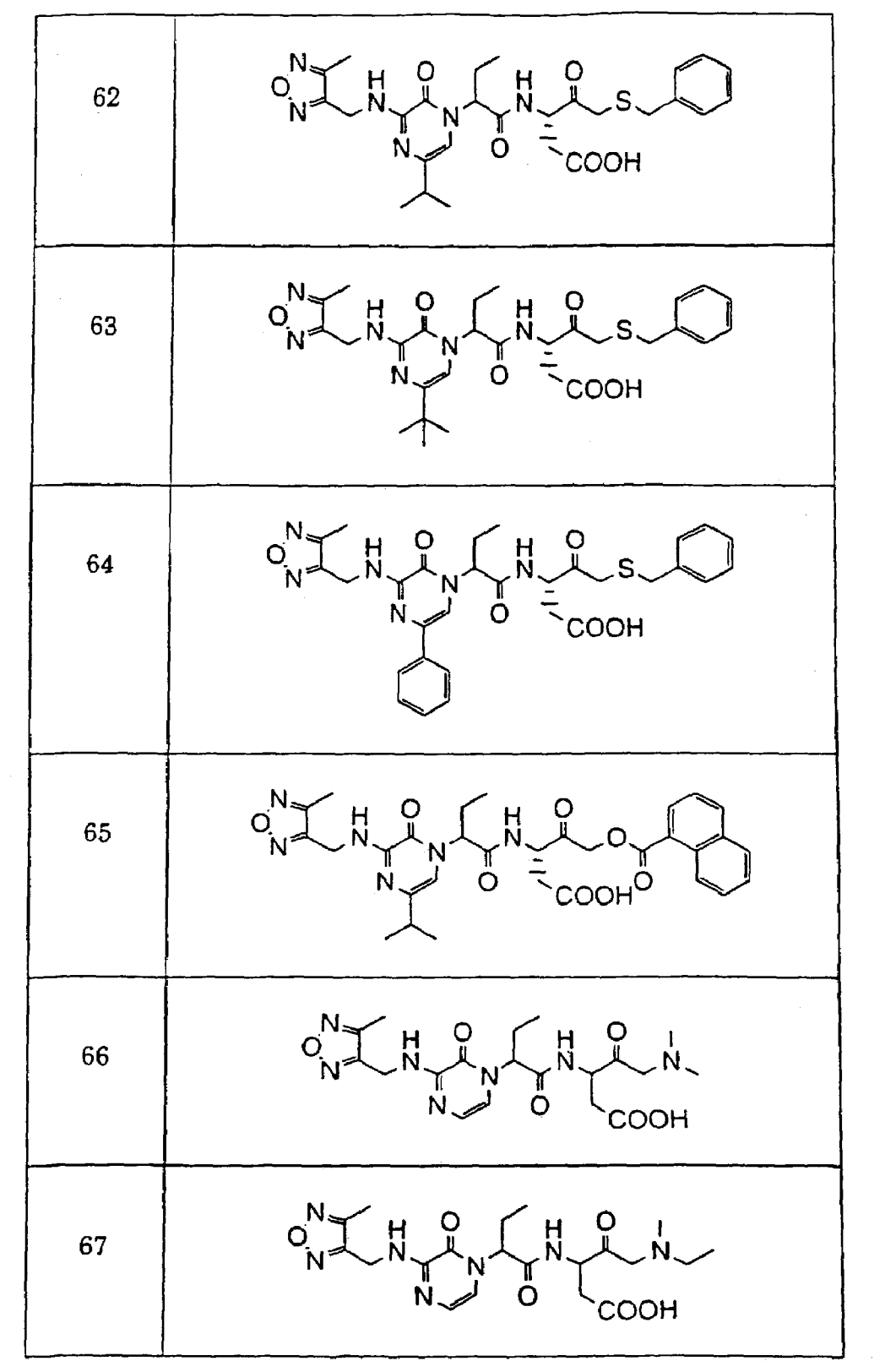

| 62 | |
|----|---|
| 63 | |
| 64 | |
| 65 | |
| 66 | |
| 67 | |

Fig. 4(j)

| 68 | 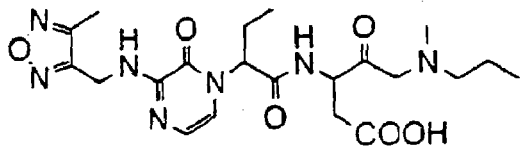 |
| 69 | 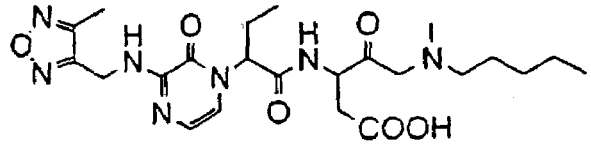 |
| 70 | 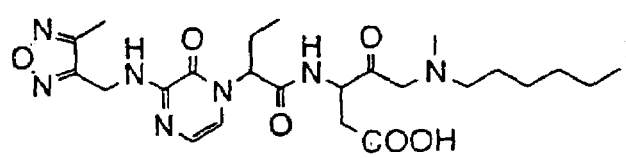 |
| 71 | 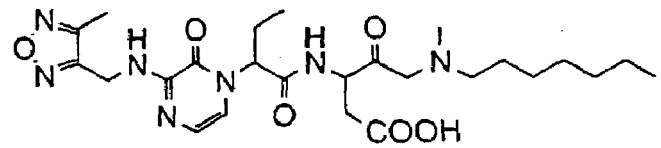 |
| 72 | 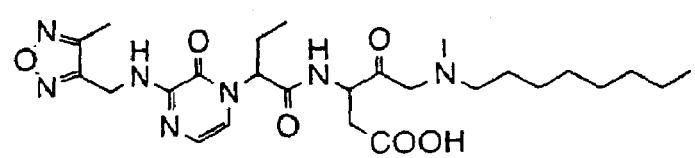 |
| 73 | 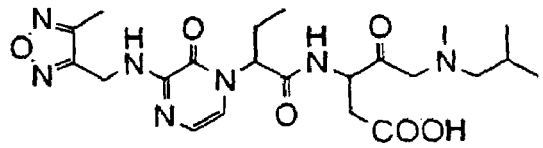 |
| 75 | 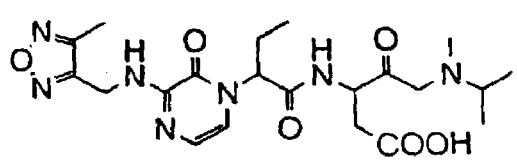 |
Fig. 4(k)

| 76 | 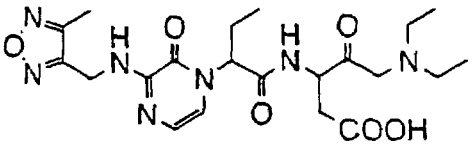 |
| --- | --- |
| 77 | 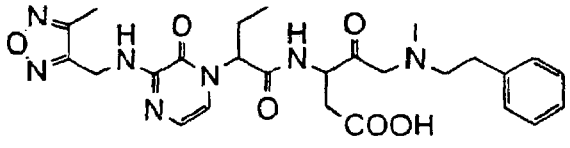 |
| 78 | 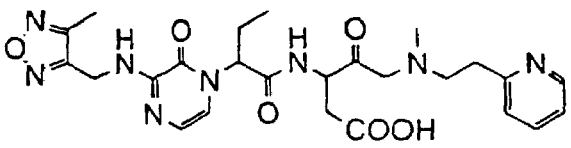 |
| 79 | 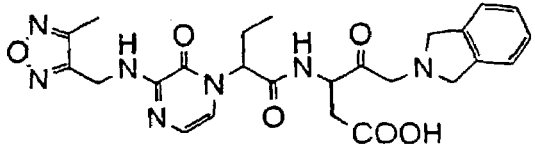 |
| 80 | 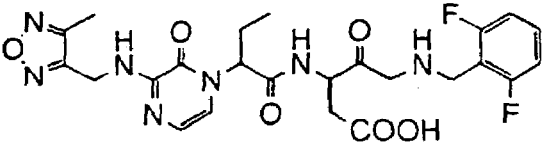 |
| 81 | 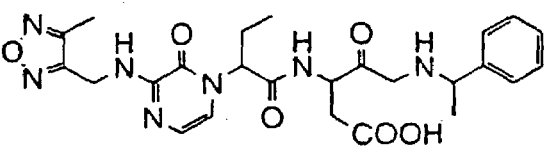 |
| 82 | 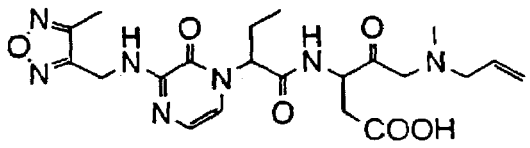 |
Fig. 4(l)

| 83 | 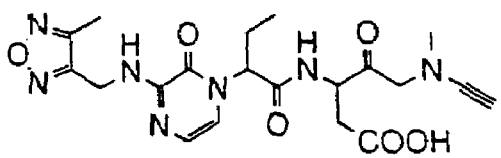 |
|---|---|
| 84 | 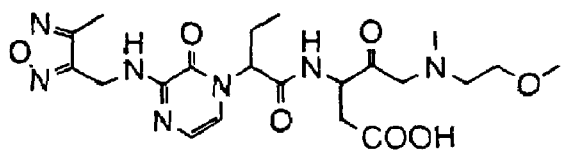 |
| 85 | 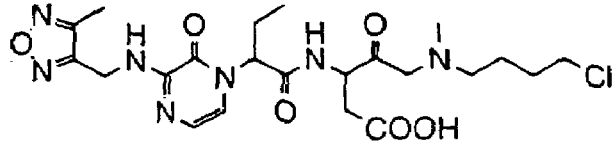 |
| 86 | 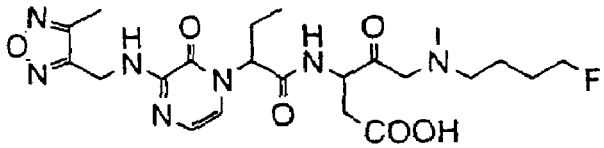 |
| 87 | 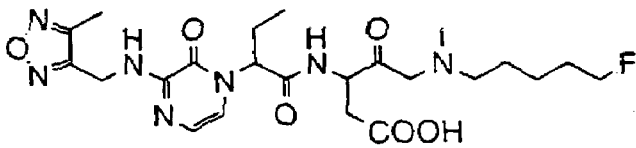 |
| 88 | 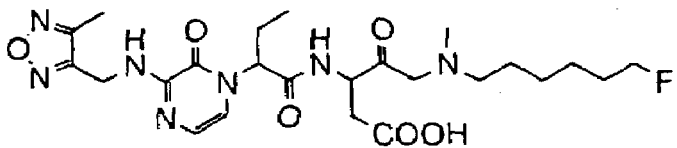 |
Fig. 4(m)

1. A compound represented by formula I:

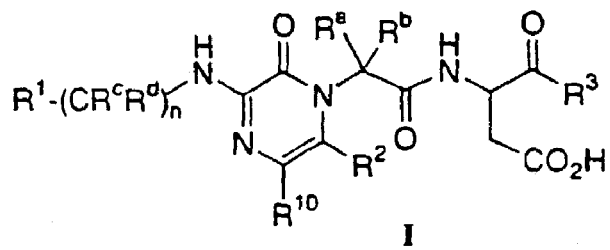

I or a pharmaceutically acceptable salt, ester, N-oxide or hydrate thereof wherein:

$R^1$ is selected from the group consisting of:
OH, $C_{1-6}$alkyl, HET, Aryl, $C_{1-6}$alkoxy, $NH_2$, $NHC_{1-6}$alkyl, $N(C_{1-6}$ alkyl$)_2$, $C_{1-6}$ alkylC(O), $C_{1-6}$ alkylS(O)$_y$, Aryl-S(O)$_y$, HET- S(O)$_y$ wherein y is 0, 1 or 2, , Aryl-C(O) and HET-C(O), the alkyl and alkyl portions of which being optionally substituted with 1-2 members selected from the group consisting of: OH, Aryl$^1$, HET, halo, $NH_2$, $NHCH_3$, $N(CH_3)_2$, $CO_2H$, $CF_3$ and $C_{1-4}$-acyl;

Aryl represents a $C_{6-14}$ aromatic 1-3 ring system optionally substituted with 1-3 members selected from OH, $C_{1-6}$ alkyl, $OC_{1-6}$ alkyl, Aryl$^1$, HET, halo, $NH_2$, $NHCH_3$, $N(CH_3)_2$, $CF_3$, $CO_2H$ and $C_{1-4}$acyl;

Aryl$^1$ represents a $C_{6-14}$ membered aromatic ring system having 1-3 rings and optionally substituted with 1-3 members selected from the group consisting of: OH, HET, halo, $NH_2$, $NHCH_3$, $N(CH_3)_2$, $CO_2H$ and $C_{1-4}$-acyl;

HET represents a 5 to 15 membered aromatic, partially aromatic or non-aromatic ring system, containing 1-4 heteroatoms selected from O, S and N, and optionally substituted with 1-2 oxo groups and 1-3 groups selected from halo, $C_{1-4}$alkyl, $C_{1-4}$alkoxy, $CF_3$ and $C_{1-4}$acyl;

FIG.4(o)

$R^a$ and $R^b$ independently represent a member selected from the group consisting of: H, Aryl, $C_{1-6}$alkyl optionally substituted by 1-3 of halo, $OR^4$, $SR^4$ and $C_{5-7}$cycloalkyl optionally containing one heteroatom selected from O, S and $NR^5$, or in the alternative, $R^a$ and $R^b$ are taken in combination and represent a non-aromatic carbocyclic 4-7 membered ring, optionally containing one heteroatom selected from O, S and $NR^5$;

$R^4$ is selected from the group consisting of: H, $C_{1-5}$alkyl, Aryl and Aryl-$C_{1-4}$alkyl optionally substituted with 1-2 groups selected from halo and $C_{1-4}$alkyl;

$R^5$ is H, $C_{1-4}$alkyl or $C_{1-4}$acyl;

$R^c$ and $R^d$ each independently represents a member selected from the group consisting of: H, $C_{1-6}$alkyl and Aryl, or in the alternative, $R^c$ and $R^d$ are taken in combination and represent a non-aromatic carbocyclic ring of 3-7 members, optionally containing one heteroatom selected from O, S and $NR^5$;

n is an integer from 0-6 inclusive;

$R^2$ represents H, halo or $C_{1-6}$alkyl;

$R^3$ represents H, $C_{1-6}$alkyl, Aryl, HET, $C_{1-6}$alkyl$SR^6$, $C_{1-6}$alkyl$OR^6$, $C_{1-6}$alkylOC(O)$R^7$ or $C_{1-6}$alkyl$NR^8R^9$;

$R^6$ represents $C_{1-6}$alkyl, Aryl, HET or Aryl-$C_{1-6}$alkyl, said alkyl and the alkyl portions being optionally substituted with 1-3 members selected from the group consisting of: OH, halo, $NH_2$, $NHCH_3$, $N(CH_3)_2$, $CO_2H$, $CF_3$ and $C_{1-4}$ acyl;

$R^7$ represents $C_{1-8}$alkyl, Aryl or HET;

$R^8$ and $R^9$ independently represent H, $C_{1-10}$alkyl, Aryl, HET, $C_{1-6}$alkylN($C_{1-6}$alkyl)$_{0-2}$, Aryl-$C_{1-6}$alkyl, $C_{1-6}$alkylOH, or $C_{1-6}$alkylO$C_{1-6}$alkyl, or $R^8$ and $R^9$ are taken in combination with the nitrogen atom to which they are attached and represent a 3-10 membered ring system containing 1-4 heteroatoms selected from O, S, N and optionally substituted with 1-2 oxo groups, and 1-3 groups selected from $C_{1-6}$alkyl, HET, $CO_2R^c$ and $C(O)N(R^c)_2$,

FIG.4(p)

said alkyl and alkyl portions being optionally substituted with 1-3 groups selected from halo, $C_{1-3}$alkyl, hydroxy$C_{1-3}$ alkyl, $C_{1-3}$alkoxy, $C_{1-3}$alkoxy$C_{1-3}$alkyl and Aryl$^1$, and $R^{10}$ represents H, $C_{1-20}$ alkyl, aryl or HET, with aryl and HET as previously described.

2. A compound represented by formula I':

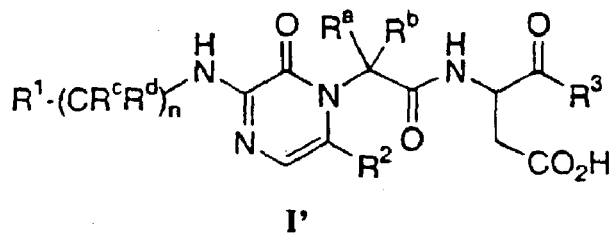

I' or a pharmaceutically acceptable salt, ester, N-oxide or hydrate thereof wherein:

$R^1$ is selected from the group consisting of:
OH, $C_{1-6}$alkyl, HET, Aryl, $C_{1-6}$alkoxy, $NH_2$, $NHC_{1-6}$alkyl, $N(C_{1-6}$ alkyl$)_2$, $C_{1-6}$ alkylC(O), $C_{1-6}$ alkylS(O)$_y$, Aryl-S(O)$_y$, HET- S(O)$_y$ wherein y is 0, 1 or 2, , Aryl-C(O) and HET-C(O), the alkyl and alkyl portions of which being optionally substituted with 1-2 members selected from the group consisting of: OH, Aryl$^1$, HET, halo, $NH_2$, $NHCH_3$, $N(CH_3)_2$, $CO_2H$, $CF_3$ and $C_{1-4}$-acyl;

Aryl represents a $C_{6-14}$ aromatic 1-3 ring system optionally substituted with 1-3 members selected from OH, $C_{1-6}$ alkyl, $OC_{1-6}$ alkyl, Aryl$^1$, HET, halo, $NH_2$, $NHCH_3$, $N(CH_3)_2$, $CF_3$, $CO_2H$ and $C_{1-4}$acyl;

Aryl$^1$ represents a $C_{6-14}$ membered aromatic ring system having 1-3 rings and optionally substituted with 1-3 members selected from the group consisting of: OH, HET, halo, $NH_2$, $NHCH_3$, $N(CH_3)_2$, $CO_2H$ and $C_{1-4}$-acyl;

HET represents a 5 to 15 membered aromatic, partially aromatic or non-aromatic ring system, containing 1-4 heteroatoms selected from O, S and N, and

FIG.4(q)

optionally substituted with 1-2 oxo groups and 1-3 groups selected from halo, $C_{1-4}$alkyl, $C_{1-4}$alkoxy, $CF_3$ and $C_{1-4}$acyl;

$R^a$ and $R^b$ independently represent a member selected from the group consisting of: H, Aryl, $C_{1-6}$alkyl optionally substituted by 1-3 of halo, $OR^4$, $SR^4$ and $C_{5-7}$cycloalkyl optionally containing one heteroatom selected from O, S and $NR^5$, or in the alternative, $R^a$ and $R^b$ are taken in combination and represent a non-aromatic carbocyclic 4-7 membered ring, optionally containing one heteroatom selected from O, S and $NR^5$;

$R^4$ is selected from the group consisting of: H, $C_{1-5}$alkyl, Aryl and Aryl-$C_{1-4}$alkyl optionally substituted with 1-2 groups selected from halo and $C_{1-4}$alkyl;

$R^5$ is H or $C_{1-4}$alkyl;

$R^c$ and $R^d$ each independently represents a member selected from the group consisting of: H, $C_{1-6}$alkyl and Aryl, or in the alternative, $R^c$ and $R^d$ are taken in combination and represent a non-aromatic carbocyclic ring of 3-7 members, optionally containing one heteroatom selected from O, S and $NR^5$;

n is an integer from 0-6 inclusive;

$R^2$ represents H, halo or $C_{1-6}$alkyl;

$R^3$ represents H, $C_{1-6}$alkyl, Aryl, HET, $C_{1-6}$alkyl$SR^6$, $C_{1-6}$alkyl$OR^6$, $C_{1-6}$alkylOC(O)$R^7$ or $C_{1-6}$alkyl$NR^8R^9$;

$R^6$ represents $C_{1-6}$alkyl, Aryl, HET or Aryl-$C_{1-6}$alkyl, said alkyl and the alkyl portions being optionally substituted with 1-3 members selected from the group consisting of: OH, halo, $NH_2$, $NHCH_3$, $N(CH_3)_2$, $CO_2H$, $CF_3$ and $C_{1-4}$ acyl;

$R^7$ represents $C_{1-8}$alkyl, Aryl or HET;

$R^8$ and $R^9$ independently represent H, $C_{1-10}$alkyl, Aryl, HET, $C_{1-6}$alkylN($C_{1-6}$alkyl)$_{0-2}$, Aryl-$C_{1-6}$alkyl, $C_{1-6}$alkylOH, or $C_{1-6}$alkylO$C_{1-6}$alkyl, or $R^8$ and $R^9$ are taken in combination with the nitrogen atom to which they are attached and

FIG.4(r)

represent a 3-10 membered ring system containing 1-4 heteroatoms selected from O, S, N and optionally substituted with 1-2 oxo groups, and 1-3 groups selected from $C_{1-6}$alkyl, HET, $CO_2R^c$ and $C(O)N(R^c)_2$, said alkyl and alkyl portions being optionally substituted with 1-3 groups selected from halo, $C_{1-3}$alkyl, hydroxy$C_{1-3}$ alkyl, $C_{1-3}$alkoxy, $C_{1-3}$alkoxy$C_{1-3}$alkyl and Aryl¹.

3. A compound in accordance with claim 1 wherein $R^1$ represents HET or Aryl, said HET representing a 5 to 15 membered aromatic, partially aromatic or non-aromatic ring or ring system, containing from 1-4 heteroatoms selected from O, S and N, and optionally substituted with 1-2 groups selected from oxo, halo, $C_{1-4}$alkyl $C_{1-4}$alkoxy and $C_{1-4}$acyl, and said Aryl being selected from phenyl and naphthyl, and being optionally substituted with 1-3 members selected from the group consisting of: OH, Aryl', HET, halo, $NH_2$, $NHCH_3$, $N(CH_3)_2$, $CO_2H$ and $C_{1-4}$-acyl.

4. A compound in accordance with claim 3 wherein $R^1$ represents HET optionally substituted with 1-2 groups selected from oxo, halo, $C_{1-4}$alkyl, $C_{1-4}$alkoxy and $C_{1-4}$acyl.

5. A compound in accordance with claim 4 wherein $R^1$ represents HET substituted with 1-2 groups selected from oxo, halo, $C_{1-4}$alkyl, $C_{1-4}$alkoxy and $C_{1-4}$acyl.

6. A compound in accordance with claim 5 wherein $R^1$ represents HET selected from the group consisting of: pyridinyl, pyrazinyl, pyrrolyl, furanyl, pyrazolyl, imidazolyl, benzimidazolyl, oxathiazolyl, thiazolyl, benzothiazolyl, oxazolyl, pyrrazolyl, 1,2-diazolyl, 1,2,3- and 1,2,4-triazolyl, 1,2,4- and 1,2,5-oxadiazolyl, 1,2,4-and 1,2,5-thiadiazolyl, tetrazolyl, isoxazolyl, thienyl, azepinyl, pyrrolidinyl, piperidinyl, piperazinyl, optionally substituted with 1-2 groups selected from halo, $C_{1-4}$alkyl and $C_{1-4}$alkoxy.

FIG.4(s)

7. A compound in accordance with claim 3 wherein $R^1$ represents Aryl, said Aryl being phenyl optionally substituted with 1-3 members selected from the group consisting of: OH, $Aryl^1$, HET, halo, $NH_2$, $NHCH_3$, $N(CH_3)_2$, $CO_2H$ and $C_{1-4}$-acyl.

8. A compound in accordance with claim 1 wherein $R^c$ and $R^d$ represent H, and n is an integer of from 0-3 inclusive.

9. A compound in accordance with claim 1 wherein $R^a$ and $R^b$ independently represent H or $C_{1-6}$alkyl, optionally substituted with halo, $OR^4$, $SR^4$ or $C_{5-7}$cycloalkyl optionally containing one heteroatom selected from O, S and $NR^5$.

10. A compound in accordance with claim 9 wherein one of $R^a$ and $R^b$ represents H and the other represents $C_{1-6}$alkyl.

11. A compound in accordance with claim 10 wherein one of $R^a$ and $R^b$ represents H and the other represents ethyl.

12. A compound in accordance with claim 1 wherein $R^2$ represents H or halo.

13. A compound in accordance with claim 1 wherein:
$R^3$ is selected from the group consisting of H, $C_{1-6}$alkyl, $C_{1-6}$alkyl$SR^6$ and $C_{1-6}$alkyl$NR^8R^9$;

$R^6$ represents $C_{1-6}$alkyl, Aryl, HET or Aryl-$C_{1-6}$alkyl, said alkyl, aryl, and the alkyl group and alkyl portions being optionally substituted with 1-3 members selected from the group consisting of: OH, halo, $NH_2$, $NHCH_3$, $N(CH_3)_2$, $CO_2H$, $CF_3$ and $C_{1-4}$ acyl, and said HET being optionally substituted with 1-2 oxo groups and 1-3 groups selected from halo, $C_{1-4}$alkyl, $C_{1-4}$alkoxy, $CF_3$ and $C_{1-4}$ acyl; and $R^8$ and $R^9$ independently represent H, $C_{1-10}$alkyl, Aryl, HET, $C_{1-6}$alkyl$N(C_{1-6}$alkyl$)_{0-2}$, Aryl-$C_{1-6}$alkyl, $C_{1-6}$alkylOH, or $C_{1-6}$alkyl$OC_{1-6}$alkyl, or $R^8$ and $R^9$ are taken in combination with the nitrogen atom to which they are attached and represent a 3-10 membered ring system containing 1-4 heteroatoms selected from O,

FIG.4(t)

S, N and optionally substituted with 1-2 oxo groups, and 1-3 groups selected from $C_{1-6}$alkyl, HET, $CO_2R^c$ and $C(O)N(R^c)_2$, said alkyl and alkyl portions being optionally substituted with 1-3 groups selected from halo, $C_{1-3}$alkyl, hydroxy$C_{1-3}$ alkyl, $C_{1-3}$alkoxy, $C_{1-3}$alkoxy$C_{1-3}$alkyl and Aryl$^1$.

14. A compound in accordance with claim 13 wherein:

$R^3$ is selected from the group consisting of: H, $C_{1-6}$alkyl, $C_{1-6}$alkylSR$^6$, and $C_{1-6}$alkylNR$^8$R$^9$;

$R^6$ represents Aryl, HET or Aryl-$C_{1-6}$alkyl, said alkyl, aryl, and the alkyl group and alkyl portions being optionally substituted with 1-3 members selected from the group consisting of: OH, halo, $NH_2$, $NHCH_3$, $N(CH_3)_2$, $CO_2H$, $CF_3$ and $C_{1-4}$ acyl, and said HET being optionally substituted with 1-2 oxo groups and 1-3 groups selected from halo and $C_{1-4}$alkyl; and $R^8$ and $R^9$ independently represent H, $C_{1-10}$alkyl, Aryl, HET, $C_{1-6}$alkylN($C_{1-6}$alkyl)$_{0-2}$, Aryl-$C_{1-6}$alkyl or $C_{1-6}$alkylOC$_{1-6}$alkyl, or $R^8$ and $R^9$ are taken in combination with the nitrogen atom to which they are attached and represent a 3-10 membered ring system containing 1-4 heteroatoms selected from O, S, N and optionally substituted with 1-2 oxo groups, and 1-3 groups selected from $C_{1-6}$alkyl, HET, $CO_2R^c$ and $C(O)N(R^c)_2$, said alkyl and alkyl portions being optionally substituted with 1-3 groups selected from halo, $C_{1-3}$alkyl, $C_{1-3}$alkoxy$C_{1-3}$alkyl and Aryl$^1$.

15. A compound in accordance with claim 1 wherein:

$R^1$ represents HET or Aryl, said HET representing a 5 to 15 membered aromatic, partially aromatic or non-aromatic ring or ring system, containing from 1-4 heteroatoms selected from O, S and N, and optionally substituted with 1-2 groups selected from oxo, halo, $C_{1-4}$alkyl $C_{1-4}$alkoxy and $C_{1-4}$acyl, and said Aryl being selected from phenyl and naphthyl, and being optionally substituted with 1-3 members selected from the group consisting of: OH, Aryl$^1$, HET, halo, $NH_2$, $NHCH_3$, $N(CH_3)_2$, $CO_2H$ and $C_{1-4}$-acyl;

$R^c$ and $R^d$ represent H, and n is an integer of from 0-3 inclusive;

FIG.4(u)

$R^a$ and $R^b$ independently represent H or $C_{1-6}$alkyl optionally substituted with halo, $OR^4$, $SR^4$ or $C_{5-7}$cycloalkyl optionally containing one heteroatom selected from O, S and $NR^5$;

$R^3$ is selected from the group consisting of H, $C_{1-6}$alkyl, $C_{1-6}$alkyl$SR^6$, and $C_{1-6}$alkyl$NR^8R^9$;

$R^6$ represents $C_{1-6}$alkyl, Aryl, HET or Aryl-$C_{1-6}$alkyl, said alkyl, aryl, and the alkyl group and alkyl portions being optionally substituted with 1-3 members selected from the group consisting of: OH, halo, $NH_2$, $NHCH_3$, $N(CH_3)_2$, $CO_2H$, $CF_3$ and $C_{1-4}$ acyl, and said HET being optionally substituted with 1-2 oxo groups and 1-3 groups selected from halo, $C_{1-4}$alkyl, $C_{1-4}$alkoxy, $CF_3$ and $C_{1-4}$ acyl; and $R^8$ and $R^9$ independently represent H, $C_{1-10}$alkyl, Aryl, HET, $C_{1-6}$alkyl$N(C_{1-6}$alkyl$)_{0-2}$, Aryl-$C_{1-6}$alkyl, $C_{1-6}$alkylOH, or $C_{1-6}$alkyl$OC_{1-6}$alkyl, or $R^8$ and $R^9$ are taken in combination with the nitrogen atom to which they are attached and represent a 3-10 membered ring system containing 1-4 heteroatoms selected from O, S, N and optionally substituted with 1-2 oxo groups, and 1-3 groups selected from $C_{1-6}$alkyl, HET, $CO_2R^c$ and $C(O)N(R^c)_2$, said alkyl and alkyl portions being optionally substituted with 1-3 groups selected from halo, $C_{1-3}$alkyl, hydroxy$C_{1-3}$ alkyl, $C_{1-3}$alkoxy, $C_{1-3}$alkoxy$C_{1-3}$alkyl and Aryl[1]. Within this subset, all other variables are as originally defined.

16. A compound in accordance with claim 1 wherein n represents 1-6.

FIG.4(v)

1. A compound of formula

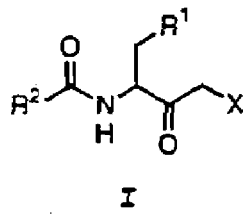

I wherein X is F or Cl;
$R^1$ is COOH, COO(alkyl), or an isostere thereof; and
$R^2$ is an aryl group.

2. The compound of claim 1 having one or more of the following features: (a) X is F; (b) $R^1$ is COOH; and/or (c) $R^2$ is an optionally substituted group selected from phenyl, naphthyl, or a five, six, nine or ten membered heteroaryl having one or two heteroatoms.

3. The compound of claim 2 having the following features: (a) X is F; (b) $R^1$ is COOH; and (c) $R^2$ is an optionally substituted group selected from phenyl, naphthyl, or five, six, nine or ten membered heteroaryl having one or two heteroatoms.

Fig. 5(a)

| 1 | 3-Benzoylamino-5-fluoro-4-oxo-pentanoic acid |
|---|---|
| 2 | 5-Fluoro-3-(3-methyl-benzoylamino)-4-oxo-pentanoic acid |
| 3 | 5-Fluoro-3-(4-methyl-benzoylamino)-4-oxo-pentanoic acid |
| 4 | 3-(2-Chlorobenzoylamino)-5-fluoro-4-oxo-pentanoic acid |
| 5 | 3-(3-Chlorobenzoylamino)-5-fluoro-4-oxo-pentanoic acid |
| 6 | 3-(4-Chlorobenzoylamino)-5-fluoro-4-oxo-pentanoic acid |
| 7 | 3-(3,4-Dichlorobenzoylamino)-5-fluoro-4-oxo-pentanoic acid |
| 8 | 3-(3,5-Dichlorobenzoylamino)-5-fluoro-4-oxo-pentanoic acid |
| 9 | 5-Fluoro-3-(2-fluorobenzoylamino)-4-oxo-pentanoic acid |
| 10 | 5-Fluoro-3-(3-fluorobenzoylamino)-4-oxo-pentanoic acid |
| 11 | 5-Fluoro-3-(4-fluorobenzoylamino)-4-oxo-pentanoic acid |
| 12 | 5-Fluoro-4-oxo-3-(3-trifluoromethylbenzoylamino)-pentanoic acid |
| 13 | 5-Fluoro-3-(4-trifluoromethylbenzoylamino)-4-oxo-pentanoic acid |
| 14 | 3-(Biphenyl-3-carboxamido)-5-fluoro-4-oxo-pentanoic acid |
| 15 | 3-(Biphenyl-4-carboxamido)-5-fluoro-4-oxo-pentanoic acid |
| 16 | 5-Fluoro-3-(3-methoxybenzoylamino)-4-oxo-pentanoic acid |
| 17 | 5-Fluoro-3-(4-methoxy-benzoylamino)-4-oxo-pentanoic acid |
| 18 | 2-(3-Acetylaminobenzoylamino)-4-fluoro-3-oxo-butyric acid |
| 19 | 3-(3-Cyanobenzoylamino)-5-fluoro-4-oxo-pentanoic acid |
| 20 | 3-(4-Cyano benzoylamino)-5-fluoro-4-oxo-pentanoic acid |
| 21 | 5-Fluoro-3-(3-iodo-benzoylamino)-4-oxo-pentanoic acid |
| 22 | 5-Fluoro-3-(naphthyl-1-carboxamido)-4-oxo-pentanoic acid |
| 23 | 5-Fluoro-3-(naphthyl-2-carboxamido]-4-oxo-pentanoic acid |
| 24 | 5-Fluoro-4-oxo-3-(pyridyl-4-carboxamido)-pentanoic acid trifluoroacetate salt |
| 25 | 5-Fluoro-4-oxo-3-(pyridyl-3-carboxamido)-pentanoic acid trifluoroacetate salt |
| 26 | 5-Fluoro-3-(furyl-3-carboxamido-4-oxo-pentanoic acid |
| 27 | 5-Fluoro-3-(1-methyl-1*H*-pyrrolyl-2-carboxamido)-4-oxo-pentanoic acid |

Fig. 5(b)

| 28 | 5-Fluoro-4-oxo-3-(thienyl-2-carboxamido)-pentanoic acid |
| --- | --- |
| 29 | 5-Fluoro-4-oxo-3-(thienyl-3-carboxamido)-pentanoic acid |
| 30 | 5-Fluoro-4-oxo-3-(thiazolyl-2-carboxamido)-pentanoic acid |
| 31 | 5-Fluoro-3-(1$H$-indolyl-2-carboxamido)-4-oxo-pentanoic acid |
| 32 | 3-(3-Carboxybenzoylamino)-5-fluoro-4-oxo-pentanoic acid |
| 33 | 3-(4-Methylamidobenzoylamino)-5-fluoro-4-oxo-pentanoic acid |
| 34 | 5-Fluoro-3-(5-phenyl-furyl-2-carboxamido)-4-oxo-pentanoic acid |
| 35 | 3-(3-Benzyloxybenzoylamino)-5-fluoro-4-oxo-pentanoic acid |
| 36 | 3-(3-(2-Phenylethoxy)benzoylamino)-5-fluoro-4-oxo-pentanoic acid |
| 37 | 5-Fluoro-4-oxo-3-(3-phenoxybenzoylamino)-pentanoic acid |
| 38 | 5-Fluoro-3-(1-naphthylacetamido)-4-oxo-pentanoic acid |
| 39 | 3-Benzoylamino-5-chloro-4-oxo-pentanoic acid |

Fig. 5(c)

1. A compound having the Formula I:

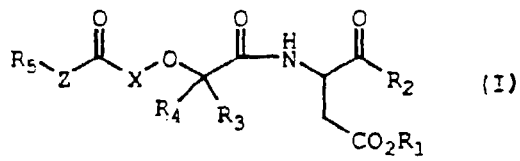

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1-2 amino acids or a bond.

2. The compound of claim 1, wherein $R_3$ and $R_4$ independently are hydrogen, aryl, heterocyclic, heteroaryl, $C_{1-10}$ alkyl, alkenyl, alkynyl, or $C_{1-10}$ alkyl substituted by one or more hydroxy, halogen, carboxy, amino, amide, ester, guanadino, thiol, alkylthiol, aryl, heterocyclic, or heteroaryl groups; and $R_5$ is an optionally substituted alkyl, $C_4$-$C_7$ cycloalkyl, saturated or unsaturated heterocyclic, aryl or heteroaryl group.

3. A compound according to claim 1, wherein $R_1$ is H, Me, Et or acetoxymethyl.

Fig. 6(a)

4. A compound according to claim 1, wherein $R_2$ is hydrogen, fluoromethyl, acyloxymethyl, arylacyloxymethyl, aryloxymethyl, heteroaryloxymethyl, or aminomethyl.

5. A compound according to claim 1, wherein X is a bond.

6. A compound according to claim 1, wherein Z is O, S, NH or $CH_2$.

7. A compound according to claim 1, wherein $R_3$ is hydrogen and $R_4$ is straight-chained or branched $C_{1-6}$ alkyl, cycloalkyl, aryl or heteoaryl.

8. A compound according to claim 1, wherein $R_3$ is hydrogen and $R_4$ is straight-chained or branched $C_{1-6}$ alkyl optionally substituted by hydroxy, halogen, carboxy, amino, amide, ester, guanadino, thiol, alkylthiol, aryl, heterocyclic or heteroaryl.

9. A compound according to claim 1, wherein $R_5$ is optionally substituted benzyl.

10. A compound according to claim 1, wherein $R_5$ is optionally substituted phenyl, naphthyl or heteroaryl.

11. A compound according to claim 1, wherein said compound has the Formula II:

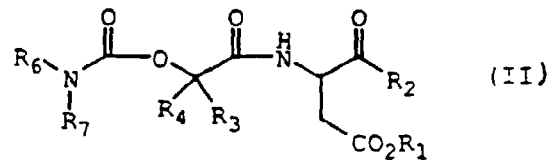

(II)

or a pharmaceutically acceptable salt or prodrug thereof wherein

Fig. 6(b)

$R_6$ and $R_7$ independently are hydrogen, alkyl, optionally substituted alkyl, $C_4$-$C_7$ cycloalkyl, heterocyclic, aryl, heteroaryl, or $R_6$ and $R_7$ are combined together with the nitrogen to form a heterocycle.

12. A compound according to claim 11, wherein $R_2$ is hydrogen, fluoromethyl, acyloxymethyl, arylacyloxymethyl, aryloxymethyl, heteroaryloxymethyl, or aminomethyl.

13. A compound according to claim 11, wherein $R_1$ is H, Me, Et or acetoxymethyl.

14. A compound according to claim 11, wherein $R_3$ is hydrogen and $R_4$ is straight-chained or branched $C_{1-6}$ alkyl, cycloalkyl, aryl or heteoaryl.

15. A compound according to claim 11, wherein $R_3$ is hydrogen and $R_4$ is straight-chained or branched $C_{1-6}$ alkyl optionally substituted by hydroxy, halogen, carboxy, amino, amide, ester, guanadino, thiol, alkylthiol, aryl, heterocyclic or heteroaryl.

16. A compound according to claim 11, wherein $R_6$ is hydrogen and $R_7$ is optionally substituted phenyl, naphthyl, heteroaryl or benzyl.

17. A compound according to claim 11, wherein $R_6$ is hydrogen and $R_7$ is an optionally substituted alkyl.

18. A compound according to claim 1, wherein said compound is selected from the group consisting of:
1-(Carbonyl-Asp-CH$_2$F)ethyl N-phenylcarbamate,
1-(Carbonyl-Asp-CH$_2$F)ethyl N-benzylcarbamate,
2-Methyl-1-(carbonyl-Asp-CH$_2$F)propyl N-phenylcarbamate,
2-Methyl-1-(carbonyl-Asp-CH$_2$F)propyl N-benzylcarbamate,

Fig. 6(c)

2-Methyl-1-(carbonyl-Asp-CH$_2$F)propyl N-(2,6-dichlorophenyl)carbamate,

2-Methyl-1-(carbonyl-Asp-CH$_2$F)propyl N-(2,5-dichlorophenyl)-carbamate,

2-Methyl-1-(carbonyl-Asp-CH$_2$F)propyl N-(2,4-dichlorophenyl)-carbamate,

2-Methyl-1-(carbonyl-Asp-CH$_2$DCB)propyl N-phenylcarbamate,

2-Methyl-1-(carbonyl-Asp-CH$_2$DCB)propyl N-(2,6-dichlorophenyl)-carbamate,

2-Methyl-1-(carbonyl-Asp-CH$_2$PTP)propyl N-phenylcarbamate,

2-Methyl-1-(carbonyl-Asp-CH$_2$PTP)propyl N-(2,6-dichlorophenyl)-carbamate,

2-Methyl-1-(carbonyl-Asp-CH$_2$DPP)propyl N-phenylcarbamate,

2-Methyl-1-(carbonyl-Asp-CH$_2$DPP)propyl N-(2,6-dichlorophenyl)-carbamate,

2-Methyl-1-(carbonyl-Asp-CH$_2$F)propyl N-(2-methyl-1-methoxycarbonyl-propyl)carbamate, and Z-Valine 2-methyl-1-(carbonyl-Asp-CH$_2$F)propyl ester.

19. A compound according to claim 1, wherein said compound is selected from the group consisting of:

2-Methyl-1-(carbonyl-Asp-CH$_2$F)propyl N-(3-fluorophenyl)carbamate,

2-Methyl-1-(carbonyl-Asp-CH$_2$F)propyl N-(4-fluorophenyl)carbamate,

2-Methyl-1-(carbonyl-Asp-CH$_2$F)propyl N-(3,4-difluorophenyl)carbamate,

2-Methyl-1-(carbonyl-Asp-CH$_2$F)propyl N-(4-phenoxyphenyl)carbamate, 1-(Carbonyl-Asp-CH$_2$F)propyl N-phenylcarbamate, 1-(Carbonyl-Asp-CH$_2$F)butyl N-phenylcarbamate, 1-(Carbonyl-Asp-CH$_2$F)-2-propenyl N-phenylcarbamate, 2-(4-Imidazolyl)-1-(carbonyl-Asp-CH$_2$F)ethyl N-phenylcarbamate, 2-Phenyl-1-(carbonyl-Asp-CH$_2$F)ethyl N-phenylcarbamate, 2-Methyl-1-(carbonyl-Asp-CH$_2$F)butyl N-phenylcarbamate, 3-Methyl-1-(carbonyl-Asp-CH$_2$F)butyl N-phenylcarbamate, 1-Phenyl-1-(carbonyl-Asp-CH$_2$F)methyl N-phenylcarbamate, 1-(2-Chlorophenyl)-1-(carbonyl-Asp-CH$_2$F)methyl N-phenylcarbamate, 1-(4-Chlorophenyl)-1-(carbonyl-Asp-CH$_2$F)methyl N-phenylcarbamate,

Fig. 6(d)

1-Cyclohexyl-1-(carbonyl-Asp-CH₂F)methyl N-phenylcarbamate,

2-Chloro-1-(carbonyl-Asp-CH₂F)ethyl N-phenylcarbamate, and 2,2,2-trifluoro-1-(carbonyl-Asp-CH₂F)ethyl N-phenylcarbamate.

Fig. 6(e)

| 1 | S-1-(Cabornyl-Asp-CH$_2$F)ethyl N-Phenylcarbamate |
|---|---|
| 2 | 2-Methyl-1-(carbonyl-Asp-CH$_2$F)propyl N-Phenylcarbamate |
| 3 | S-2-Methyl-1-(carbonyl-Asp-CH$_2$F)propyl N-Phenylcarbamate |
| 4 | S-1-(Carbonyl-Asp-CH$_2$F)ethyl N-Benzylcarbamate |
| 5 | 2-Methyl-1-(carbonyl-Asp-CH$_2$F)propyl N-Benzylcarbamate |
| 6 | S-2-Methyl-1-(carbornyl-Asp-CH$_2$F)propyl N-Benzylcarbamate |
| 7 | S,S-2-Methyl-1-(carbonyl-Asp-CH$_2$F)propyl N-(2-Methyl-1-methoxycarbonylpropyl)-carbamate |
| 8 | S-2-Methyl-1-(carbonyl-Asp-CH$_2$DCB)propyl N-Phenylcarbamate |
| 9 | S-2-Methyl-1-(carbonyl-Asp-CH$_2$F)propyl N-(3 Flurophenyl)carbamate |
| 10 | S-2-Methyl-1-(carbonyl-Asp-CH$_2$F)propyl N-(4 Flurophenyl)carbamate |
| 11 | S-2-Methyl-1-(carbonyl-Asp-CH$_2$F)propyl N-(3,4-Difluorophenyl)carbamate |
| 12 | S-2-Methyl-1-(carbonyl-Asp-CH$_2$F)propyl N-(4-Phenoxyphenyl)carbamate |
| 13 | S-1-Cyclohexyl-1-(carbonyl-Asp-CH$_2$F)methyl N-Phenylcarbamate |
| 14 | S-2-Methyl-1-(carbonyl-Asp-CH$_2$F)propyl N-(2,5-Dichloroyphenyl)carbamate |
| 15 | S-2-Methyl-1-(carbonyl-Asp-CH$_2$F)propyl N-(2,4-Dichloroyphenyl)carbamate |
| 16 | S-2-Methyl-1-(carbonyl-Asp-CH$_2$F)propyl N-(2,5-Dichloroyphenyl)carbamate |
| 17 | S-2-Methyl-1-(carbonyl-Asp-CH$_2$PTP)propyl N-Phenylcarbamate |

Asp: Aspartic acid

Fig. 6(f)

1. A compound of the formula (I):

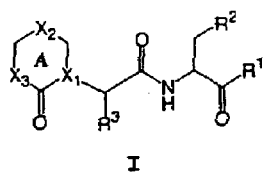

I where $R^1$ is hydrogen, CN, $CHN_2$, R, or $-CH_2Y$;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or $-OPO(R^8)(R^9)$;

$R^8$ and $R^9$ are independently selected from R or OR;

$R^2$ is $CO_2H$, $CH_2CO_2H$, or esters, amides or isosteres thereof;

$R^3$ is hydrogen or a $C_{1-6}$ straight chained or branched alkyl;

Ring A contains zero to two double bonds, and is optionally fused to a saturated or unsaturated five to seven membered ring containing zero to three heteroatoms;

$X_1$ and $X_3$ in Ring A are independently selected from nitrogen or carbon, and $X_2$ is selected from a valence bond, oxygen, sulfur, nitrogen or carbon, wherein any X with suitable valence may bear a substituent;

each carbon with suitable valence in Ring A, including the fused ring if present, is independently substituted by hydrogen, halo, R, OR, SR, OH, $NO_2$, CN, $NH_2$, NHR,

Fig. 7(a)

N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, NHS(O)$_2$R, =O, =S, =NNHR, =NNR$_2$, =N-OR, =NNHCOR, =NNHCO$_2$R, =NNHSO$_2$R, or =NR;

each substitutable nitrogen in Ring A is substituted by hydrogen, R, COR, S(O)$_2$R, or CO$_2$R;

provided that when X$_3$ is a carbon, a substituent on X$_3$ is attached by an atom other than nitrogen;

and further provided that at least one X in Ring A is a nitrogen.

2. The compound of claim 1 where R$^2$ is CO$_2$H or an ester, amide or carboxylic acid isoster.

3. The compound of claim 2 where R$^1$ is CH$_2$Y and Y is F, OR, SR, or -OC=O(R).

4. The compound of claim 3 where R$^3$ is hydrogen or C$_{1-3}$ alkyl.

5. A compound of formula IA:

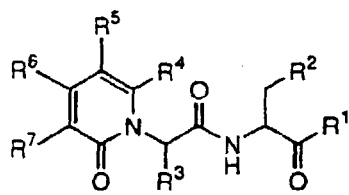

IA where R$^1$ is hydrogen, CN, CHN$_2$, R, -CH$_2$Y;

R is an aliphatic group, a substituted aliphatic group, an aryl group, a substituted aryl group, an aralkyl group, a substituted aralkyl group, a non-aromatic

Fig. 7(b)

heterocyclic group or a substituted non-aromatic heterocyclic group;

Y is an electronegative leaving group, -OR, -SR, -OC=O(R), or -OPO($R^8$)($R^9$);

$R^8$ and $R^9$ are each independently selected from R or OR;

$R^2$ is $CO_2H$, $CH_2CO_2H$, or esters, amides or isosteres thereof;

$R^3$ is hydrogen or a $C_{1-6}$ straight chained or branched alkyl;

each of $R^4$-$R^6$ is independently selected from hydrogen, halo, R, OR, SR, aryl, substituted aryl, OH, $NO_2$, CN, $NH_2$, NHR, N(R)$_2$, NHCOR, NHCONHR, NHCON(R)$_2$, NRCOR, $NHCO_2R$, $CO_2R$, $CO_2H$, COR, CONHR, CON(R)$_2$, S(O)$_2$R, $SONH_2$, S(O)R, $SO_2$NHR, or NHS(O)$_2$R; and $R^7$ is selected from hydrogen, halo, R, OR, SR, aryl, substituted aryl, OH, CN, $CO_2R$, $CO_2H$, COR, CONHR, CON(R)$_2$, S(O)$_2$R, $SONH_2$, S(O)R, or $SO_2$NHR.

6. The compound of claim 5 where $R^1$ is $CH_2Y$ and Y is F, -OR, -SR, or -OC=O(R); $R^2$ is $CO_2H$ or esters, amides or isosteres thereof; $R^3$ is hydrogen or $C_{1-3}$ alkyl, each of $R^4$-$R^6$ is independently selected from hydrogen, R, phenyl or substituted phenyl; and $R^7$ is hydrogen, R, phenyl or substituted phenyl.

7. A compound of formula IB:

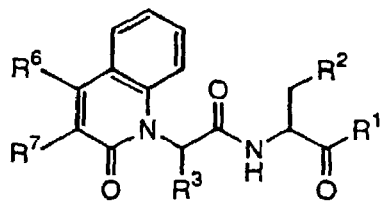

Fig. 7(c)

where $R^1$ is hydrogen CN, $CHN_2$, R, or $-CH_2Y$;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or $-OPO(R^8)(R^9)$;

$R^8$ and $R^9$ are each independently selected from R or OR;

$R^2$ is $CO_2H$, $CH_2CO_2H$, or esters, amides or isosteres thereof;

$R^3$ is hydrogen or a $C_{1-6}$ straight chained or branched alkyl;

$R^6$ is selected from hydrogen, halo, R, OR, SR, aryl, substituted aryl, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, $S(O)_2R$, $SONH_2$, $S(O)R$, $SO_2NHR$, or $NHS(O)_2R$; and $R^7$ is selected from hydrogen, halo, R, OR, SR, aryl, substituted aryl, OH, CN, $CO_2R$, $CO_2H$, COR, CONHR, $CON(R)_2$, $S(O)_2R$, $SONH_2$, $S(O)R$, or $SO_2NHR$.

8. The compound of claim 7 where $R^1$ is $CH_2Y$ and Y is F, -OR, -SR, or -OC=O(R); $R^2$ is $CO_2H$ or esters, amides or isosters thereof; and $R^3$ is hydrogen or $C_{1-3}$ alkyl, $R^6$ and $R^7$ are each hydrogen.

9. A compound of formula IC:

Fig. 7(d)

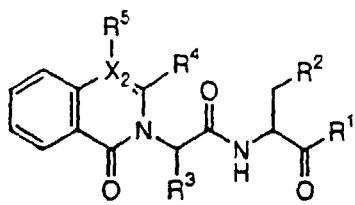

IC where $R^1$ is hydrogen, CN, $CHN_2$, R, or $-CH_2Y$;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or $-OPO(R^8)(R^9)$;

$R^8$ and $R^9$ are independently selected from R or OR;

$R^2$ is $CO_2H$, $CH_2CO_2H$, or esters, amides or isosteres thereof;

$R^3$ is hydrogen or a $C_{1-6}$ straight chained or branched alkyl;

$R^4$ and $R^5$ are each independently selected from hydrogen, halo, R, OR, SR, aryl, substituted aryl, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, $S(O)_2R$, $SONH_2$, S(O)R, $SO_2NHR$, $NHS(O)_2R$, =O, =S, =NNHR, $=NNR_2$, =N-OR, =NNHCOR, $=NNHCO_2R$, $=NNHSO_2R$, or =NR.

10. The compound of claim 9 where $R^1$ is $CH_2Y$ and Y is F, -OR, -SR, or -OC=O(R); $R^2$ is $CO_2H$ or esters, amides or isosters thereof; $R^3$ is hydrogen or $C_{1-3}$ alkyl; $R^4$ is hydrogen; and $R^5$ is hydrogen when $X_2$ is nitrogen or carbon.

11. A compound of formula ID:

Fig. 7(e)

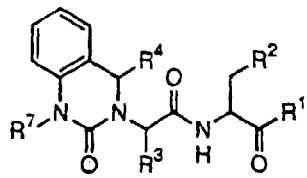

ID where $R^1$ is hydrogen, CN, CHN$_2$, R, -CH$_2$Y;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or -OPO($R^8$)($R^9$);

$R^8$ and $R^9$ are independently selected from R or OR;

$R^2$ is CO$_2$H, CH$_2$CO$_2$H, or esters, amides or isosteres thereof;

$R^3$ is hydrogen or a C$_{1-6}$ straight chained or branched alkyl;

$R^4$ is independently selected from hydrogen, halo, R, OR, SR, aryl, substituted aryl, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, or NHS(O)$_2$R;

$R^7$ is selected from hydrogen, halo, R, OR, SR, aryl, substituted aryl, OH, CN, CO$_2$R, CO$_2$H, COR, CONHR, CON(R)$_2$, S(O)$_2$R, SONH$_2$, S(O)R, or SO$_2$NHR.

12. The compound of claim 11 where $R^1$ is CH$_2$Y and Y is F, -OR, -SR, or -OC=O(R); $R^2$ is CO$_2$H or esters, amides or isosters thereof; $R^3$ is hydrogen or C$_{1-3}$ alkyl; $R^4$ is hydrogen and $R^7$ is aralkyl.

Fig. 7(f)

13. A compound of formula IE:

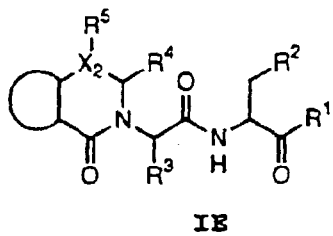

IE where $R^1$ is hydrogen, CN, CHN$_2$, R, -CH$_2$Y;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or -OPO($R^8$)($R^9$);

$R^8$ and $R^9$ are independently selected from R or OR;

$R^2$ is CO$_2$H, CH$_2$CO$_2$H, or esters or isosteres thereof;

$R^3$ is hydrogen or a C$_{1-6}$ straight chained or branched alkyl;

$R^4$ and $R^5$ are each independently selected from hydrogen, halo, R, OR, SR, aryl, substituted aryl, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, or NHS(O)$_2$R; and the fused ring is an aromatic or non-aromatic heterocyclic ring.

14. The compound of claim 13 where $R^1$ is CH$_2$Y and Y is F, -OR, -SR, -OC=O(R), $R^2$ is CO$_2$H and esters, amides or isosters thereof, $R^3$ is H or C$_{1-3}$ alkyl, and the

Fig. 7(g)

fused ring is a five or six membered heterocycle having one ring heteroatom.

15. A compound of formula IF:

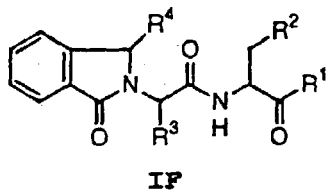

IF where $R^1$ is hydrogen, CN, CHN$_2$, R, or -CH$_2$Y;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or -OPO(R$^8$)(R$^9$);

$R^8$ and $R^9$ are independently selected from R or OR;

$R^2$ is CO$_2$H, CH$_2$CO$_2$H, or esters, amides or isosteres thereof;

$R^3$ is hydrogen or a C$_{1-6}$ straight chained or branched alkyl; and $R^4$ is independently selected from hydrogen, halo, R, OR, SR, aryl, substituted aryl, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR or NHS(O)$_2$R.

16. The compound of claim 15 where $R^1$ is CH$_2$Y and Y is F, -OR, -SR, or -OC=O(R); $R^2$ is CO$_2$H or esters, amides or isosters thereof; $R^3$ is hydrogen or C$_{1-3}$ alkyl; and $R^4$ is H$_2$ or =O.

Fig. 7(h)

17. A compound of formula IG:

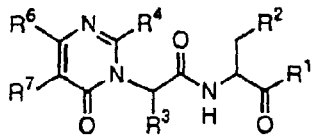

IG where $R^1$ is hydrogen, CN, $CHN_2$, R, or $-CH_2Y$;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or $-OPO(R^8)(R^9)$;

$R^8$ and $R^9$ are independently selected from R or OR;

$R^2$ is $CO_2H$, $CH_2CO_2H$, or esters, amides or isosteres thereof;

$R^3$ is hydrogen or a $C_{1-6}$ straight chained or branched alkyl;

each of $R^4$ and $R^6$ is independently selected from hydrogen, halo, R, OR, SR, aryl, substituted aryl, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, $S(O)_2R$, $SONH_2$, S(O)R, $SO_2NHR$, or $NHS(O)_2R$; and $R^7$ is selected from hydrogen, halo, R, OR, SR, aryl, substituted aryl, OH, CN, $CO_2R$, $CO_2H$, COR, CONHR, $CON(R)_2$, $S(O)_2R$, $SONH_2$, S(O)R, or $SO_2NHR$.

18. The compound of claim 17 where $R^1$ is $CH_2Y$ and Y is F, -OR, -SR, or -OC=O(R); $R^2$ is $CO_2H$ or esters, amides or isosters thereof; $R^3$ is hydrogen or $C_{1-3}$ alkyl; and $R^4$, $R^6$ and $R^7$ are each hydrogen.

Fig. 7(i)

| 1 | 5-Fluoro-4-oxo-3-[(S)-2-(2-oxo-2*H*-pyridin-1-yl)-propionylamino]-pentanoic acid |
|---|---|
| 2 | 5-Fluoro-3-[2-(2-oxo-2*H*-pyridin-1-yl)-acetylamino]-4-oxo-pentanoic acid |
| 3 | 5-Fluoro-3-[2-(6-methyl-2-oxo-2*H*-pyridin-1-yl)-acetylamino]-4-oxo-pentanoic acid |
| 4 | 5-Fluoro-3-[2-(4-phenyl-2-oxo-2*H*-pyridin-1-yl)-acetylamino]-4-oxo-pentanoic acid |
| 5 | 5-Fluoro-3-[2-(3-phenyl-2-oxo-2*H*-pyridin-1-yl)-acetylamino]-4-oxo-pentanoic acid |
| 6 | 5-Fluoro-4-oxo-3-[(S)-2-(2-oxo-2*H*-quinolin-1-yl)-propionylamino]-pentanoic acid |
| 7 | 5-Fluoro-4-oxo-3-[(S)-(R)-2-(2-oxo-2*H*-quinolin-1-yl)-acetylamino]-pentanoic acid |
| 8 | 5-Fluoro-4-oxo-3-[2-(1-oxo-1*H*-isoquinolin-2-yl)-acetylamino]-pentanoic acid |
| 9 | 5-Fluoro-4-oxo-3-[(S)-2-(1-oxo-1*H*-isoquinolin-2-yl)-propionylamino]-pentanoic acid |
| 10 | 5-Fluoro-4-oxo-3-[2-(1-oxo-1*H*-isoquinolin-2-yl)-acetylamino]-pentanoic acid |
| 11 | 5-Fluoro-4-oxo-3-[2-(1-oxo-3,4-dihydro-1*H*-isoquinolin-2-yl)-acetylamino]-pentanoic acid (1C-4) |
| 12 | 5-Fluoro-4-oxo-3-[2-(4-oxo-4*H*-thieno[2,3-*d*]pyrimidin-3-yl)-acetylamino]-pentanoic acid |
| 13 | 5-Fluoro-4-oxo-3-[2-(1-oxo-1,3-dihydro-isoindol-2-yl)-acetylamino]-pentanoic acid |
| 14 | 5-Fluoro-4-oxo-3-[(2S)-2-(1-oxo-1,3-dihydro-isoindol-2-yl)-propionylamino]-pentanoic acid |
| 15 | 5-Fluoro-4-oxo-3-[(2S)-2-(1,3-dioxo-1,3-dihydro-isoindol-2-yl)-propionylamino]-pentanoic acid |
| 16 | 2,6-Dichloro-benzoic acid 4-carboxy-2-oxo-3-[2-(1-oxo-1*H*-isoquinolin-2-yl)-propionylamino]-butyl ester (1C-5) Step 1: 2,6-dichloro-benzoic acid 4-*tert*-butoxycarbonyl-2-hydroxy-3-[2-(1-oxo-1*H*-isoquinolin-2-yl)-propionylamino]-butyl ester |
| 17 | 5-Fluoro-3-[2-(6-ethyl-2-oxo-2*H*-pyridin-1-yl)-acetylamino]-4-oxo-pentanoic acid |

Fig. 7(j)

| 18 | 5-Fluoro-4-oxo-3-[(2S)-2-(4-oxo-4H-quinazolin-3-yl)-propionylamino]-pentanoic acid |
|---|---|
| 19 | 2,6-Dichloro-benzoic acid 4-carboxy-2-oxo-3-[2-(4-oxo-4H-quinazolin-3-yl)-propionylamino]-butyl ester |
| 20 | 5-Fluoro-4-oxo-3-[2-(1-oxo-1H-[2,6]naphthyridin-2-yl)-acetylamino-pentanoic acid |
| 21 | 5-Fluoro-4-oxo-3-[(2S)-2-(4-oxo-4H-quinazolin-3-yl)-butyrylamino]-pentanoic acid |
| 22 | 5-Fluoro-4-oxo-3-[(2S)-2-(6-methoxy-oxo-4H-quinazolin-3-yl)-butyrylamino]-pentanoic acid |
| 23 | 5-Fluoro-4-oxo-3-[(2S)-3-methyl-2-(-4-oxo-4H-quinazolin-3-yl)-butyrylamino]-pentanoic acid |
| 24 | 5-Fluoro-4-oxo-3-[(2S)-2-(4-oxo-4H-quinazolin-3-yl)-pentanoylamino]-pentanoic acid |
| 25 | 5-Fluoro-4-oxo-3-[(2S)-2-(6-oxo-6H-pyrimidin-1-yl)-butyrylamino]-pentanoic acid |
| 26 | (3S)-4-Oxo-3[(2S)-2-(4-oxo-4H-quinazolin-3-yl)-butyrylamino]-butanoic acid |
| 27 | 5-Fluoro-4-oxo-3-[(2S)-2-[1-(3-chlorobenzyl)-2-oxo-1,4-dihydro-2H-quinazolin-3-yl]-3-methyl-butyrylamino]-pentanoic acid |

Fig. 7(k)

22. A compound of formula I:

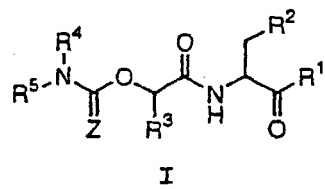

I or a pharmaceutically-acceptable derivative thereof, wherein:

Z is oxygen or sulfur;

$R^1$ is hydrogen, $-CHN_2$, $-R$, $-CH_2OR$, $-CH_2SR$, or $-CH_2Y$;

R is a $C_{1-12}$ aliphatic, aryl, aralkyl, heterocyclyl, or heterocyclylalkyl;

Y is an electronegative leaving group;

$R^2$ is $CO_2H$, $CH_2CO_2H$, or esters, amides or isosteres thereof;

$R^3$ is a group capable of fitting into the S2 sub-site of a caspase; and $R^4$ and $R^5$ taken together with the intervening nitrogen form a mono-, bi- or tricyclic hetero ring system having 1-6 heteroatoms selected from nitrogen, oxygen or sulfur.

23. The compound of claim 22 wherein the compound has one or more of the following features:

Fig. 8(a)

(i) Z is oxygen;

(ii) $R^1$ is hydrogen, -R, $-CH_2OR$, $-CH_2SR$, or $-CH_2Y$;

(iii) $R^2$ is $CO_2H$ or an ester, amide or isostere thereof;

(iv) $R^3$ is a group having a molecular weight up to 140 Daltons; or (v) $R^4$ and $R^5$ taken together with the intervening nitrogen form a monocyclic, bicyclic or tricyclic ring system wherein each ring of the system has 5-7 ring atoms.

24. The compound of claim 23 wherein the compound has the following features:

(i) Z is oxygen;

(ii) $R^1$ is hydrogen, -R, $-CH_2OR$, $-CH_2SR$, or $-CH_2Y$;

(iii) $R^2$ is $CO_2H$ or an ester, amide or isosteres thereof;

(iv) $R^3$ is a group having a molecular weight up to 140 Daltons; and (v) $R^4$ and $R^5$ taken together with the intervening nitrogen form a monocyclic, bicyclic or tricyclic heterocyclic or heteroaryl ring system wherein each ring of the system has 5-7 ring atoms.

25. The compound of claim 24 wherein $R^1$ is $-CH_2Y$.

26. The compound of claim 25 wherein $R^1$ is $-CH_2F$ and $R^3$ is a $C_{1-4}$ alkyl group.

27. The compound of claim 26 wherein $R^4$ and $R^5$ taken together with the intervening nitrogen form a bicyclic or

Fig. 8(b)

tricyclic heterocyclic or heteroaryl ring system wherein each ring of the system has 5-7 ring atoms.

28. The compound of claim 27 wherein $R^4$ and $R^5$ taken together with the intervening nitrogen form a tricyclic heterocyclic or heteroaryl ring system wherein each ring of the system has 5-7 ring atoms.

29. The compound of claim 28 wherein the middle ring of the tricyclic ring system is a five- or six-membered ring.

30. The compound of claim 22 wherein the compound has one or more of the following features:
   (i) Z is oxygen;
   (ii) $R^1$ is $-CH_2OR$, $-CH_2SR$, or $-CH_2Y$;
   (iii) $R^2$ is $CO_2H$ or an ester, amide or isostere thereof;
   (iv) $R^3$ is $C_{1-4}$ alkyl; or
   (v) $R^4$ and $R^5$ taken together with the intervening nitrogen form a ring selected from indole, isoindole, indoline, indazole, purine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, carbazole, phenothiazine, phenoxazine, dihydrophenazine, dihydrocinnoline, dihydroquinoxaline, tetrahydroquinoline, tetrahydroisoquinoline, dihydronaphthyridine, tetrahydronaphthyridine, dihydroacridine, β-carboline, pyrido[4,3-b]indole, 2,3,9-

Fig. 8(c)

triazafluorene, 9-thia-2,10-diazaanthracene, 3,6,9-triazafluorene, thieno[3,2-b]pyrrole, or dihydrophenanthridine.

31. The compound of claim 30 wherein the compound has one or more of the following features:
   (i) Z is oxygen;
   (ii) $R^1$ is -CH$_2$OR, -CH$_2$SR, or -CH$_2$Y;
   (iii) $R^2$ is CO$_2$H or an ester, amide or isostere thereof;
   (iv) $R^3$ is C$_{1-4}$ alkyl; or
   (v) $R^4$ and $R^5$ taken together with the intervening nitrogen form a ring selected from indole, isoindole, indoline, indazole, benzimidazole, imidazole, pyrrolidine, pyrazole, triazole, piperidine, morpholine, thiomorpholine, piperazine, carbazole, phenothiazine, phenoxazine, dibenzoazepine, dihydro-dibenzoazepine, dihydrophenazine, dihydrocinnoline, dihydroquinoxaline, tetrahydroquinoline, tetrahydroisoquinoline, dihydronaphthyridine, tetrahydronaphthyridine, dihydroacridine, β-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine.

32. The compound of claim 31 wherein the compound has one or more of the following features:
   (i) Z is oxygen;
   (ii) $R^1$ is -CH$_2$OR, -CH$_2$SR, or -CH$_2$Y;

Fig. 8(d)

(iii) $R^2$ is $CO_2H$ or an ester, amide or isostere thereof;

(iv) $R^3$ is $C_{1-4}$ alkyl; or (v) $R^4$ and $R^5$ taken together with the intervening nitrogen form a substituted or unsubstituted ring system selected from carbazole, phenothiazine, indole, indoline, 5H-dibenzo[b,f]azepine, 10,11-dihydro-5H-dibenzo[b,f]azepine, β-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine.

33. The compound of claim 32 wherein Z is oxygen; $R^1$ is $-CH_2OR$, $-CH_2SR$, or $-CH_2Y$; $R^2$ is $CO_2H$ or an ester, amide or isostere thereof; $R^3$ is $C_{1-4}$ alkyl; and $R^4$ and $R^5$ taken together with the intervening nitrogen form a substituted or unsubstituted ring system selected from carbazole, phenothiazine, indole, indoline, 5H-dibenzo[b,f]azepine, 10,11-dihydro-5H-dibenzo[b,f]azepine, β-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine.

34. The compound of claim 33 wherein $R^1$ is $-CH_2Y$.

35. The compound of claim 34 wherein $R^1$ is $-CH_2F$.

36. The compound of claim 22 wherein the compound is selected from those compounds listed in Table 1.

37. The compound of claim 22 wherein the compound is selected from the following:

Fig. 8(e)

38. A pharmaceutical composition comprising a compound according to any of claims 22-37 and a pharmaceutically acceptable carrier.

| 1 | [3S/R]-5-Fluoro-4-oxo-3-[(S)-3-methyl-2-(carbazole-carbamoyloxy-butyrylamino]-pentanoic acid |
|---|---|
| 2 | [3S/R]-5-Fluoro-4-oxo-3-[(S)-3-methyl-2-(3-chlorocarbazole)-carbamoyloxy-butyrylamino]-pentanoic acid |
| 3 | [3S/R]-5-Fluoro-4-oxo-3-[(S)-3-methyl-2-(3,6-dichlorocarbazole)-carbamoyloxy-butyrylamino]-pentanoic acid |
| 4 | [3S/R]-5-Fluoro-4-oxo-3-[(S)-3-methyl-2-(carbazole-carbamoyloxy-butyrylamino]-pentanoic acid |
| 5 | [3S/R]-5-Fluoro-4-oxo-3-[(S)-3-methyl-2-(2,3-dichlorocarbazole)-carbamoyloxy-butyrylamino]-pentanoic acid |
| 6 | [3S/R]-5-Fluoro-4-oxo-3-[(S)-3-methyl-2-(2-trifluoromethyl)-carbazole-carbamoyloxy-butyrylamino]-pentanoic acid |
| 7 | [3S/R]-5-Fluoro-4-oxo-3-[(S)-3-methyl-2-(2-methylcarbazole)-carbamoyloxy-butyrylamino]-pentanoic acid |
| 8 | [3S/R]-5-Fluoro-4-oxo-3-[(S)-2-(carbazole-carbamoyloxy)-butyrylamino]-pentanoic acid |
| 9 | [3S/R]-5-Fluoro-4-oxo-3-[(S)-3,3-dimethyl-2-(carbazole-carbamoyloxy)-butyrylamino]-pentanoic acid |
| 10 | [3S/R]-5-Fluoro-4-oxo-3-[(S)-2-(2-chlorocarbazole)-carbamoyloxy-butyrylamino]-pentanoic acid |
| 11 | [3S/R]-5-Fluoro-4-oxo-3-[(S)-3-methyl-2-(indole)-carbamoyloxy-butyrylamino]-pentanoic acid |
| 12 | [3S/R]-5-Fluoro-4-oxo-3-[(S)-3-methyl-2-()-carbamoyloxy-butyrylamino]-pentanoic acid |
| 13 | [3S/R]-5-Fluoro-4-oxo-3-[(S)-3-methyl-2-(2-chlorophonothiazine)-carbamoyloxy-butyrylamino]-pentanoic acid |
| 14 | [3S/R]-5-Fluoro-4-oxo-3-[(S)-3-methyl-2-(3-chlorophonothiazine)-carbamoyloxy-butyrylamino]-pentanoic acid |
| 15 | [3S/R]-5-Fluoro-4-oxo-3-[(S)-3-methyl-2-(3,7-dichlorophonothiazine)-carbamoyloxy-butyrylamino]-pentanoic acid |
| 16 | [3S/R]-5-Fluoro-4-oxo-3-[(S)-3-methyl-2-(3,4-dichlorophonothiazine)-carbamoyloxy-butyrylamino]-pentanoic acid |
| 17 | [3S/R]-5-Fluoro-4-oxo-3-[(S)-3-methyl-2-(9,10-Dihydrophenanthridine)-carbamoyloxy-butyrylamino]-pentanoic acid |

Fig. 8(g)

| 18 | Dibenzo[b,f]azepine-5-carboxylic acid 1-(1-carboxymethyl-3-fluoro-2-oxo-propylcarbamoyl)-2-methyl-propyl-ester |
|---|---|
| 19 | 10,11-Dihydro-dibenzo[b,f]azepine-5-carboxylic acid 1-(1-carboxymethyl-3-fluoro-2-oxo-propylcarbamoyl)-2-methyl-propyl ester |
| 20 | [3S/R]-5-Fluoro-4-oxo-3-((S)-2,3-dihydroindole-1-carbamoyloxy-3-methyl-butyrylamino)-pentanoic acid |
| 21 | 21) [3S/R]-5-Fluoro-4-oxo-3-[(S)-3-methyl-2-(carbazole)-carbamoyloxy-butyrylamino]-pentanoic acid, diethylamide |
| 22 | [3S/R]-5-Fluoro-4-oxo-3-[(S)-3-methyl-2-(carbazole)-carbamoyloxy-butyrylamino]-pentanoic acid, ethyl amide |
| 23 | [3S/R]-5-Fluoro-4-oxo-3-[(S)-3-methyl-2-(carbazole)-carbamoyloxy-butyrylamino]-pentanoic acid, piperazine amide |
| 24 | [3S/R]-5-Fluoro-4-oxo-3-[(S)-3-methyl-2-(carbazole)-carbamoyloxy-butyrylamino]-pentanoic acid, N, N-dimethylaminoethyl amide |
| 25 | [3S/R]-5-Fluoro-4-oxo-3-[(S)-3-methyl-2-(carbazole)-carbamoyloxy-butyrylamino]-pentanoamide |
| 26 | [3S/R]-5-Fluoro-4-oxo-3-[(S)-3-methyl-2-(carbazole)-carbamoyloxy-butyrylamino]-pentanoic acid, cyclohexy ester |
| 27 | [3S/R]-5-Fluoro-4-oxo-3-[(S)-3-methyl-2-(carbazole)-carbamoyloxy-butyrylamino]-pentanoic acid, *n*-propyl ester |
| 28 | [3S/R]-5-Fluoro-4-oxo-3-[(S)-3-methyl-2-(carbazole)-carbamoyloxy-butyrylamino]-pentanoic acid, isopropyl ester |
| 29 | [3S/R]-5-Fluoro-4-oxo-3-[(S)-3-methyl-2-(carbazole)-carbamoyloxy-butyrylamino]-pentanoic acid, methyl ester |
| 30 | [3S/R]-5-Fluoro-4-oxo-3-[(S)-3-methyl-2-(carbazole)-carbamoyloxy-butyrylamino]-pentanoic acid, cholesterol ester |

Fig. 8(h)

1. A compound of formula

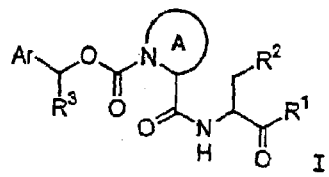

wherein:

Ring A is an optionally substituted piperidine, tetrahydroquinoline or tetrahydroisoquinoline ring;

$R^1$ is hydrogen, $CHN_2$, R, or $-CH_2Y$;

R is an optionally substituted group selected from an aliphatic group, an aryl group, an aralkyl group, a heterocyclic group, or an heterocyclylalkyl group;

Y is an electronegative leaving group;

$R^2$ is $CO_2H$, $CH_2CO_2H$, or esters, amides or isosteres thereof;

Ar is an optionally substituted aryl group; and $R^3$ is hydrogen, an optionally substituted $C_{1-6}$ alkyl, $F_2$, CN, aryl or $R^3$ is attached to Ar to form an unsaturated or partially saturated five or six membered fused ring having 0-2 heteroatoms.

2. The compound of claim 1 having one or more of the following features:

(a) $R^1$ is $CH_2F$;

(b) $R^2$ is $CO_2H$ or esters, amides or isosteres thereof;

(c) $R^3$ is hydrogen or an optionally substituted $C_{1-6}$ alkyl; and (d) Ar is an optionally substituted aryl.

Fig. 9(a)

3. The compound of claim 2 having the following features: (a) $R^1$ is $CH_2F$; (b) $R^2$ is $CO_2H$ or esters, amides or isosteres thereof; (c) $R^3$ is hydrogen or an optionally substituted $C_{1-6}$ alkyl; and (d) Ar is an optionally substituted aryl.

4. The compound of claim 3 where Ring A is a piperidine ring.

5. The compound of claim 3 where Ring A is a tetrahydroquinoline ring.

6. The compound of claim 3 where Ring A is a tetrahydroisoquinoline ring.

7. The compound of claim 1, wherein the compound is selected from the compounds listed in Table 1.

Fig. 9(b)

| 1 | [3S/R, (2S) ]-3-(1-Benzyloxycarbonyl-2-piperidinecarboxamido)-5-fluoro-4-oxo-pentanoic acid |
|---|---|
| 2 | [3S/R, (2S) ]-3-(1-(2-Chlorobenzyloxycarbonyl)-2-piperidinecarbonoxamido)-5-fluoro-4-oxo-pentanoic acid |
| 3 | [3S/R, (2S) ]-3-(1-Benzyloxycarbonyl-1,2,3,4-tetarahydro-quijnolinyl-2-carbonoxamido)-5-fluoro-4-oxo-pentanoic acid |
| 4 | [3S/R, (2S)]-5-Fluoro-4-oxo-3-(1-(2-trifluoromethyl benzyloxycarbonyl)-2-piperidinecarbonoxamido)-pentanoic acid |
| 5 | [3S/R, (2S) ]-3-1-(3-Chlorobenzyloxycarbonyl)-2-piperidinecarboxamido)-5-fluoro-4-oxo-pentanoic acid |
| 6 | [3S/R, (2S) ]-5-Fluoro-4-oxo-3-(1-(3-trifluoromethyl benzyloxycarbonyl)-2-piperidinecarboxamido)-pentanoic acid |
| 7 | [3S/R, (2S) ]-3-(1-(3,4-Dichlorobenzyloxycarbonyl)-2-piperidinecarboxamido)-5-fluoro-4-oxo-pentanoic acid |
| 8 | [3S/R, (2S) ]-5-Fluoro-3-(1-(3-methoxybenzyloxycarbonyl)-2-piperidinecarboxamido)-4-oxo-pentanoic acid |
| 9 | [3S/R, (2S, α-R) ]-5-Fluoro-3-(1-(α-trifluoromethyl benzyloxycarbonyl)-2-piperidinecarboxamido)-4-oxo-pentanoic acid |
| 10 | [3S/R, (2S) ]-5-Fluoro-4-oxo-3-(1-(2-pyridinylmethoxycarbonyl)-2-piperidinecarboxamido)-pentanoic acid |
| 11 | [3S/R, (2S) ]-5-Fluoro-4-oxo-3-(1-(3-thienylmethoxycarbonyl)-2-piperidinecarboxamido-pentanoic acid |
| 12 | [3S/R, (2S) ]-3-(1-(3-Bromobenzyloxycarbonyl)-2-piperidinecarboxamido)-5-fluoro-4-oxo-pentanoic acid |
| 13 | [3S/R, (2S) ]-3-(1-(2,4-Dichlorobenzyloxycarbonyl)-2-piperidinecarboxamido)-5-fluoro-4-oxo-pentanoic acid |
| 14 | [3S/R, (2S) ]-3-(1-(3,5-Dichlorobenzyloxycarbonyl)-2-piperidinecarboxamido)-5-fluoro-4-oxo-pentanoic acid |
| 15 | [3S/R, (2S)-3-(1-(2,4-Bis(trifluoromethyl)benzyloxycarbonyl)-2-piperidinecarboxamidok)-5-Fluoro-4-oxo-pentanoic acid |
| 16 | [3S/R, (2S)]-3-(1-(4-Chlorobenzyloxycarbonyl)-1,2,3,4-tetrahydro-quinolinyl-2-carboxamido)-5-fluoro-4-oxo-pentanoic acid |
| 17 | [3S/R, (2S) ]-3-(1-(3,4-Dichlorobenzyloxycarbonyl)-1,2,3,4-tetrahydro-quinolinyl-2-carboxamido)-5-fluoro-4-oxo-pentanoic acid |

Fig. 9(c)

| 18 | [3S/R, (2S) ]-3-(1-(3-Trifluoromethylbenzyloxycarbonyl)-1,2,3,4-tetrahydro-quinolinyl-2-carboxamido)-5-fluoro-4-oxo-pentanoic acid |
|---|---|
| 19 | [3S/R, (2S) ]-5-Fluoro-3-(1-(3-methylsulphonylbenzyloxycarbonyl)-2-piperidinecarboxamido)-4-oxo-pentanoixc acid |
| 20 | [3S/R, (2S) ]-5-Fluoro-4-oxo-3-(1-(3-phenylbenzyloxycarbonyl)-2-piperidinecarboxamido)-pentanoic acid |
| 21 | [3S/R, (2S) ]-5-Fluoro-3-(1-(23-nitrobenzyloxycarbonyl)-2-piperidinecarboxamido)-4-oxo-pentanoic acid |
| 22 | [3S/R, (2S) ]-5-Fluoro-3-(1-(2,3-dichlorobenzyloxycarbonyl)-2-piperidinecarboxamido)-4-oxo-pentanoic acid |
| 23 | [3S/R, (2S) ]-5-Fluoro-3-(1-(2,5-dichlorobenzyloxycarbonyl)-2-piperidinecarboxamido)-4-oxo-pentanoic acid |
| 24 | [3S/R, (2S) ]-5-Fluoro-4-oxo-3-(1-(2-phenoxybenzyloxycarbonyl)-2-piperidinecarboxamido)-pentanoic acid |
| 25 | [3S/R, (2S) ]-3-(1-(2-Chlorobenzyloxycarbonyl)-1,2,3,4-tetrahydro-quinolinyl-2-carboxamido)-5-fluoro-4-oxo-pentanoic acid |
| 26 | [3S/R, (2S) ]-3-(1-(3-Chlorobenzyloxycarbonyl)-1,2,3,4-tetrahydro-quinolinyl-2-carboxamido)-5-fluoro-4-oxo-pentanoic acid |
| 27 | [3S/R, (2S) ]-3-(1-(2-trifluoro methylbenzyloxycarbonyl)-1,2,3,4-tetrahydro-quinolinyl-2-carboxamido)-5-fluoro-4-oxo-pentanoic acid |
| 28 | [3S/R, (2S) ]-3(1-(2-Chlorobenzyloxycarbonyl)-1,2,3,4-tetrahydro-isoquinolinyl-2-carboxamidl)-5-fluoro-4-oxo-pentanoic acid |
| 29 | [3S/R, (2S) ]-3-(1-(Benzyloxycarbonyl)-1,2,3,4-tetrahydro-isoquinolinyl-2-carboxamido)-5-fluoro-4-oxo-pentranoic acid |
| 30 | [3S/R, (2S) ]-5-Fluoro-3-(1-(3-acetamidobenzyloxycarbonyl))-2-piperidinecarboxamido)-4-oxo-pentanoic acid |
| 31 | [3S/R, (2S) ]-5-Fluoro-3-(1-(3-methanesulfonamido) benzyloxycarbonyl)-2-piperidinecarboxamido)-4-oxo-pentanoic acid |
| 32 | [3S/R, (2S) ]-5-Fluoro-4-oxo-3-(1-(3k-chloro-2-thienylmethoxycarbonyl)-2-piperidinecarboxamido)-pentanoic acid |
| 33 | 2-(1-Carboxymethyl-3-fluoro-2-oxo-propylcarbamoyl)-piperidine-1-carboxylic acid 2,2,2-trifluoro-1-naphthalen-1-yl-ethyl ester |
| 34 | [3S/R, (2S,α-R) ]-5-Fluoro-3-(1-(α-trifluoromethyl (3-chloro benzyloxycarbonyl)-2-piperidinecarboxamido)-4-oxo-pentanoic acid |

Fig. 9(d)

| 35 | [3S/R, (2S, α-R)]-5-Fluoro-3-(1-(α-pentafluoromethyl (benzyloxycarbonyl)-2-piperidinecarboxamido)-4-oxo-pentanoic acid |
|---|---|
| 36 | [3S/R, (2S, α-R)]-5 Fluoro-3-(1-(α-trifluoromethyl benzyloxycarbonyl-1,2,3,4-tetrahydro-quinolinyl-2-carboxamido)-4-oxo-pentanoic acid |
| 37 | [3S/R, (2S, α-R)]-5-Fluoro-3-(1-(α-trifluoromethyl-(3-chloro benzyloxycarbonyl-1,2,3,4-tetrahydroquinolinyl-2-carboxamido)-4-oxo-pentanoic acid |
| 38 | 2-(1-Carbamoylmethy-3-fluoro-2-oxo-propylcarbamoyl)-piperidine-1-carboxylic acid 3,4-dichloro-benzyl ester |
| 39 | 2-(1-Ethylcarbamoylmethyl-3-fluoro-2-oxo-propylcarbamoyl)-piperidine-1-carboxylic acid 3,4-dichloro-benzyl ester |
| 40 | 2-(1-Diethylcarbamoylmethyl-3-fluoro-2-oxo-propylcarbamoyl)-piperidine-1-carboxylic acid 3,4-dichloro-benzyl ester |
| 41 | 2-{1-[(2-Dimethylamino-ethylcarbamoyl)-methyl]-3-fluoro-2-oxo-propylcarbamoyl}-piperidine-1-carboxylic acid 3,4-dichloro-benzyl ester |
| 42 | 2-{3-Fluoro-1-[2-(4-methylk-piperazin-1-yl)-2-oxo-ethyl]-2-oxo-propylcarbamoyl}-piperidine-1-carboxylic acid 3,4-dichloro-benzyl ester |
| 43 | [3S/R, (2S)]-3-(1-(3,4-Dichlorobenzyloxy carbonyl)-2-piperidinecarboxamido)-5-fluoro-4-oxo-pentanoate, N-(4-hydroxy-2-isopropyl disulfanyl-1-methyl-butene)-N-methylformamide ester |
| 44 | [3S/R, (2S)]-3-(1-(5-Chloro-2-fluorobenzyloxycarbonyl)-2-piperidinecarboxamido)-5-fluoro-4-oxo-pentanoic acid |

Fig. 9(e)

1. A compound of formula

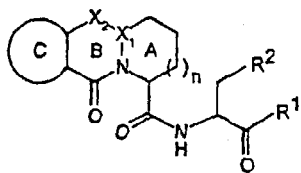

I or a pharmaceutically acceptable derivative thereof, wherein:

$R^1$ is hydrogen, $CHN_2$, R, or $-CH_2Y$;

R is an aliphatic group, an aryl group, an aralkyl group, a heterocyclic group, or a heterocyclylalkyl group;

Y is an electronegative leaving group;

$R^2$ is $CO_2H$, $CH_2CO_2H$, or esters, amides or isosteres thereof;

$X_2-X_1$ is $N(R^3)-C(R^3)$, $C(R^3)_2-C(R^3)$, $C(R^3)_2-N$, $N=C$, $C(R^3)=N$, $C(R^3)=C$, $C(=O)-N$, or $C(=O)-C(R^3)$;

each $R^3$ is independently selected from hydrogen or $C_{1-6}$ aliphatic,

Ring C is a fused aryl ring;

n is 0, 1 or 2; and each methylene carbon in Ring A is optionally and independently substituted by $=O$, or by one or more halogen, $C_{1-4}$ alkyl, or $C_{1-4}$ alkoxy.

2. The compound of claim 1 having one or more of the following features:

(a) $R^1$ is $-CH_2Y$ wherein Y is a halogen, OR, SR, or $-OC=O(R)$, wherein R is an aryl group or heterocyclic group;

Fig. 10(a)

(b)   $R^2$ is $CO_2H$ or esters, amides or isosteres thereof;

(c)   $X_2-X_1$ is N=C, $C(R^3)$=C, or C(=O)-N;

(d)   Ring C is a fused five or six-membered aromatic ring having zero to two heteroatoms; and (e)   n is 0 or 1.

3.   The compound of claim 2 wherein:

(a)   $R^1$ is $-CH_2Y$ wherein Y is a halogen, OR, SR, or -OC=O(R), wherein R is an aryl group or heterocyclic group;

(b)   $R^2$ is $CO_2H$ or esters, amides or isosteres thereof;

(c)   $X_2-X_1$ is N=C, $C(R^3)$=C, or C(=O)-N;

(d)   Ring C is a fused five or six-membered aromatic ring having zero to two heteroatoms; and (e)   n is 0 or 1.

4.   The compound of claim 3 wherein $R^1$ is $-CH_2Y$ wherein Y is F; $R^2$ is $CO_2H$ or an ester or amide thereof; $X_2-X_1$ is N=C, CH=C, or C(=O)-N; Ring C is benzene ring; and n is 0 or 1.

5.   The compound of claim 1, said compound selected from the compounds listed in Table 2.

Fig. 10(b)

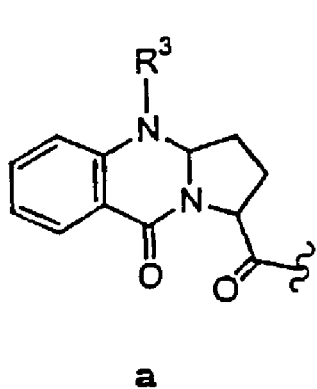
a
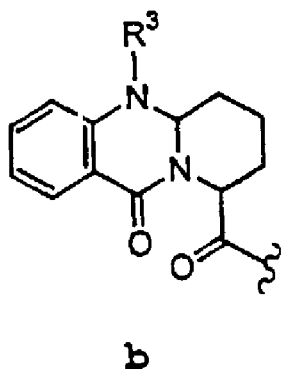
b
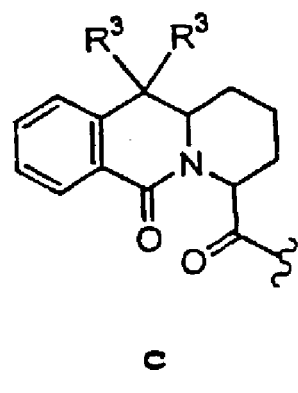
c
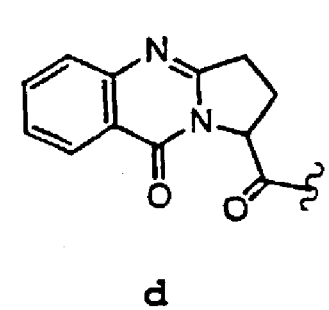
d
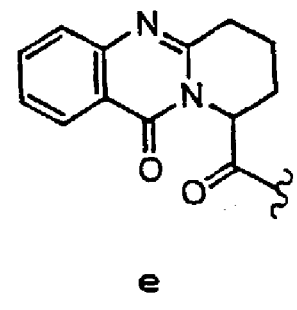
e
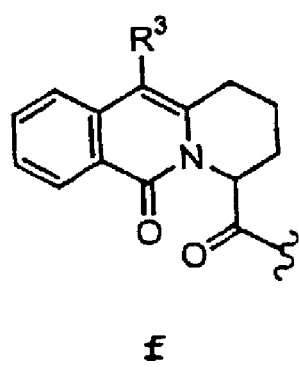
f
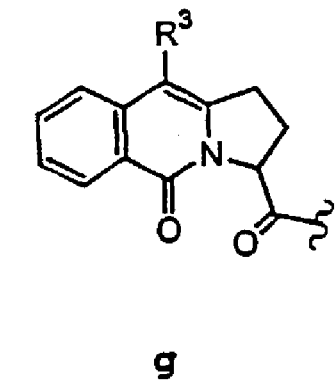
g
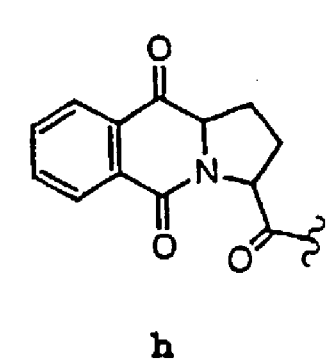
h
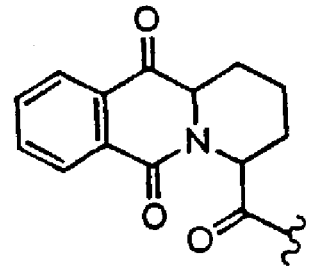
i
Fig. 10(c)

| Example | R¹ | R² | Ring C | n | $X_1$ | $X_2$ |
|---|---|---|---|---|---|---|
| 1 | $CH_2F$ | $CO_2H$ | benzo | 0 | C | N |
| 2 | $CH_2F$ | $CO_2H$ | benzo | 1 | C | N |
| 3 | $CH_2F$ | $CO_2H$ | benzo | 0 | C | C-H |
| 4 | $CH_2F$ | $CO_2H$ | benzo | 1 | C | C-H |
| 5 | $CH_2F$ | $CO_2H$ | benzo | 1 | N | C=O |
| 6 | $CH_2F$ | $CO_2H$ | pyrazino | 1 | N | C=O |

Table 2 compounds of Fig. 10(b)

a compound of formula I:

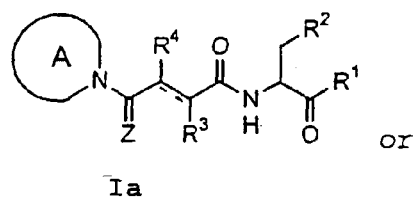 or 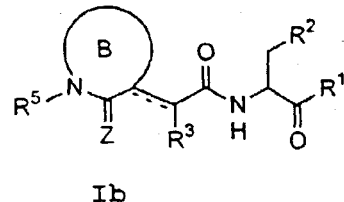

Ia          Ib or a pharmaceutically-acceptable derivative thereof, wherein:

--- next to $R^3$ represents a single or double bond;

Z is oxygen or sulfur;

$R^1$ is hydrogen, $-CHN_2$, $-R$, $-CH_2OR$, $-CH_2SR$, or $-CH_2Y$;

R is a $C_{1-12}$ aliphatic, aryl, aralkyl, heterocyclyl, or heterocyclylalkyl;

Y is an electronegative leaving group;

$R^2$ is $CO_2H$, $CH_2CO_2H$, or esters, amides or isosteres thereof;

$R^3$ is a group capable of fitting into the S2 sub-site of a caspase;

$R^4$ is hydrogen or a $C_{1-6}$ aliphatic group that is optionally interrupted by -O-, -S-, $-SO_2-$, -CO-, -NH-, or $-N(C_{1-4}$ alkyl)-, or $R^3$ and $R^4$ taken together with their intervening atoms optionally form a 3-7 membered ring

Fig. 11(a)

having 0-2 heteroatoms selected from nitrogen, oxygen or sulfur;

Ring A is a nitrogen-containing mono-, bi- or tricyclic ring system having 0-5 additional ring heteroatoms selected from nitrogen, oxygen or sulfur;

Ring B is a nitrogen-containing 5-7 membered ring having 0-2 additional ring heteroatoms selected from nitrogen, oxygen or sulfur;

$R^5$ is $R^6$, $(CH_2)_nR^6$, $COR^6$, $CO_2R^6$, $SO_2R^6$, $CON(R^6)_2$, or $SO_2N(R^6)_2$;

n is one to three; and each $R^6$ is independently selected from hydrogen, an optionally substituted $C_{1-4}$ aliphatic group, an optionally substituted $C_{6-10}$ aryl group, or a mono- or bicyclic heteroaryl group having 5-10 ring atoms.

2. The compound of claim 1 where $≡$ next to $R^3$ represents a single bond and Z is oxygen.

3. The compound of claim 2 wherein the compound is a compound of formula Ia.

4. The compound of claim 3 wherein the compound has one or more of the following features:

(i) $R^1$ is hydrogen, -R, -CH$_2$OR, -CH$_2$SR, or -CH$_2$Y;

(ii) $R^2$ is CO$_2$H or an ester, amide or isostere thereof;

(iii) $R^3$ is a group having a molecular weight up to 140 Daltons;

(iv) $R^4$ is hydrogen or $C_{1-6}$ alkyl; and (v) Ring A is a monocyclic, bicyclic or tricyclic ring system wherein each ring of the system has 5-7 ring atoms.

Fig. 11(b)

5. The compound of claim 4 wherein the compound has the following features:

(i) $R^1$ is hydrogen, -R, -CH$_2$OR, -CH$_2$SR, or -CH$_2$Y;

(ii) $R^2$ is CO$_2$H or an ester, amide or isosteres thereof;

(iii) $R^3$ is a group having a molecular weight up to 140 Daltons;

(iv) $R^4$ is hydrogen or C$_{1-6}$ alkyl; and (v) Ring A is a monocyclic, bicyclic or tricyclic heterocyclic or heteroaryl ring system wherein each ring of the system has 5-7 ring atoms.

6. The compound of claim 5 wherein $R^1$ is -CH$_2$Y.

7. The compound of claim 6 wherein $R^1$ is -CH$_2$F.

8. The compound of claim 7 wherein $R^3$ is a C$_{1-4}$ alkyl group.

9. The compound of claim 8 wherein Ring A is a tricyclic heterocyclic or heteroaryl ring system wherein each ring of the system has 5-7 ring atoms.

10. The compound of claim 9 wherein the middle ring of the tricyclic ring system is a five- or six-membered ring.

11. The compound of claim 4 wherein Ring A is selected from indole, isoindole, indoline, indazole, purine, dihydropyridine, benzimidazole, imidazole, imidazoline,

Fig. 11(c)

pyrrole, pyrrolidine, pyrroline, pyrazole, pyrazoline, pyrazolidine, triazole, piperidine, morpholine, thiomorpholine, piperazine, carbazole, iminostilbene, phenothiazine, phenoxazine, dihydrophenazine, dihydrocinnoline, dihydroquinoxaline, tetrahydroquinoline, tetrahydroisoquinoline, dihydronaphthyridine, tetrahydronaphthyridine, dihydroacridine, β-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine.

12. The compound of claim 5 wherein Ring A is selected from indole, isoindole, indoline, indazole, purine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, carbazole, iminostilbene, phenothiazine, phenoxazine, dihydrophenazine, dihydrocinnoline, dihydroquinoxaline, tetrahydroquinoline, tetrahydroisoquinoline, dihydronaphthyridine, tetrahydronaphthyridine, dihydroacridine, β-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine.

13. The compound of claim 12 wherein Ring A is selected from carbazole, phenothiazine, β-carboline, pyrido[4,3-b]indole, 2,3,9-triazafluorene, 9-thia-2,10-diazaanthracene, 3,6,9-triazafluorene, phenoxazine,

Fig. 11(d)

dibenzoazepine, dihydro-dibenzoazepine, dihydrophenazine, dihydroacridine, or dihydrophenanthridine.

14. The compound of claim 1 wherein the compound is selected from the compounds listed in Table 1.

15. The compound of claim 2 wherein the compound is a compound of formula Ib.

16. The compound of claim 15 wherein the compound has one or more of the following features:
 (i) $R^1$ is -CH$_2$OR, -CH$_2$SR, or -CH$_2$Y;
 (ii) $R^2$ is CO$_2$H or an ester, amide or isostere thereof;
 (iii) $R^3$ is a group having a molecular weight up to about 140 Daltons;
 (iv) Ring B is a nitrogen-containing five to seven membered ring having 0-1 additional ring heteroatoms selected from nitrogen, oxygen or sulfur; and
 (v) $R^5$ is an optionally substituted C$_{1-6}$ aliphatic group, an optionally substituted phenyl or an optionally substituted benzyl group.

17. The compound of claim 16 wherein the compound has the following features:
 (i) $R^1$ is -CH$_2$OR, -CH$_2$SR, or -CH$_2$Y;
 (ii) $R^2$ is CO$_2$H or an ester, amide or isostere thereof;
 (iii) $R^3$ is a group having a molecular weight up to about 140 Daltons;

Fig. 11(e)

(iv) Ring B is a nitrogen-containing five to seven membered ring having 0-1 additional ring heteroatoms selected from nitrogen, oxygen or sulfur; and (v) $R^5$ is an optionally substituted $C_{1-6}$ aliphatic group, an optionally substituted phenyl or an optionally substituted benzyl group.

18. The compound of claim 17 wherein $R^1$ is $-CH_2Y$.

19. The compound of claim 18 wherein $R^1$ is $-CH_2F$.

20. The compound of claim 19 wherein $R^3$ is a $C_{1-4}$ alkyl group.

21. The compound of claim 2 wherein the compound is selected from the compounds listed

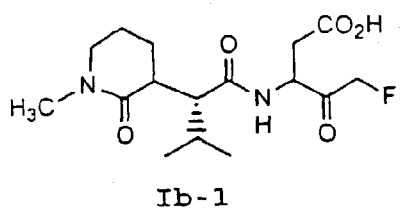

Ib-1

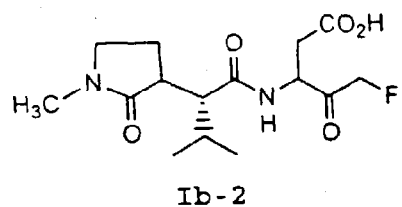

Ib-2

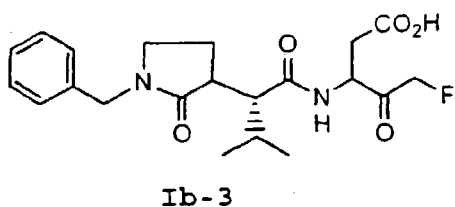

Ib-3

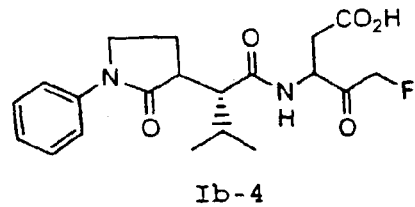

26. A compound of formula Ia:

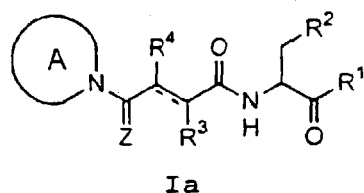

Ia or a pharmaceutically-acceptable derivative thereof, wherein:

⹀ next to $R^3$ represents a single or double bond;

Z is oxygen or sulfur;

$R^1$ is $CH_2Y$;

Y is an electronegative leaving group;

$R^2$ is $CO_2H$, $CH_2CO_2H$, or esters, amides or isosteres thereof;

$R^3$ is a group capable of fitting into the S2 sub-site of a caspase;

$R^4$ is hydrogen or a $C_{1-6}$ aliphatic group that is optionally interrupted by -O-, -S-, -SO$_2$-, -CO-, -NH-, or -N($C_{1-4}$ alkyl)-, or $R^3$ and $R^4$ taken together with their intervening atoms optionally form a 3-7 membered ring

Fig. 11(g)

having 0-2 heteroatoms selected from nitrogen, oxygen or sulfur;

Ring A is a nitrogen-containing mono-, bi- or tricyclic ring system having 0-5 additional ring heteroatoms selected from nitrogen, oxygen or sulfur;

27. The compound of claim 26 wherein Z is oxygen and ═ between $R^3$ and $R^4$ represents a single bond.

28. The compound of claim 27 wherein $R^3$ is a $C_{1-4}$ alkyl group.

29. The compound of claim 28 wherein Ring A is selected from indole, isoindole, indoline, indazole, purine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, carbazole, iminostilbene, phenothiazine, phenoxazine, dihydrophenazine, dihydrocinnoline, dihydroquinoxaline, tetrahydroquinoline, tetrahydroisoquinoline, dihydronaphthyridine, tetrahydronaphthyridine, dihydroacridine, β-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine.

30. The compound of claim 29 wherein Ring A is selected from carbazole, phenothiazine, β-carboline, pyrido[4,3-b]indole, 2,3,9-triazafluorene, 9-thia-2,10-diazaanthracene, 3,6,9-triazafluorene, phenoxazine,

Fig. 11(h)

dibenzoazepine, dihydro-dibenzoazepine, dihydrophenazine, dihydroacridine, or dihydrophenanthridine.

31. The compound of claim 30 wherein Ring A is selected from carbazole, phenothiazine or dihydrophenanthridine.

Fig. 11(i)

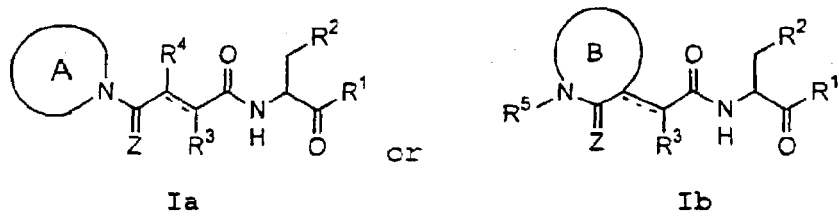

wherein Z is oxygen or sulfur; $R^1$ is hydrogen, $-CHN_2$, R, $CH_2OR$, $CH_2SR$, or $-CH_2Y$; ⁚⁚⁚ between $R^3$ and $R^4$ represents a single or double bond; Y is an electronegative leaving group; $R^2$ is $CO_2H$, $CH_2CO_2H$, or esters, amides or isosteres thereof; $R^3$ is a group capable of fitting into the S2 subsite of a caspase enzyme; $R^4$ is a hydrogen or $C_{1-6}$ alkyl or $R^3$ and $R^4$ taken together form a ring; Ring A and Ring B are each heterocyclic rings, and R and $R^5$ are as described

Fig. 11(j)

Examples of monocyclic rings for Ring A include triazole, piperidine, morpholine, thiomorpholine, imidazole, pyrrolidine, pyrazole, and piperazine. Examples of preferred bicyclic rings for Ring A include indole, isoindole, indoline, indazole, benzimidazole, thieno[3,2-b]pyrrole, dihydroquinoxaline, dihydrocinnoline, dihydronaphthyridine, tetrahydronaphthyridine, tetrahydroquinoline, and tetrahydroisoquinoline, most preferably indole or indoline. Examples of tricyclic rings for Ring A include carbazole, phenothiazine, β-carboline, pyrido[4,3-b]indole, 2,3,9-triazafluorene, 9-thia-2,10-diazaanthracene, 3,6,9-triazafluorene, phenoxazine, dibenzoazepine, dihydrodibenzoazepine, dihydrophenazine, dihydroacridine, or dihydrophenanthridine, carbazole,

| No. | Structure |
|---|---|
| Ia-7 | 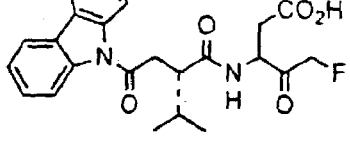 |
| Ia-8 | 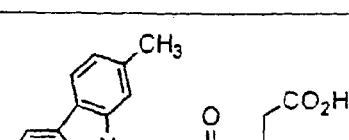 |
| Ia-9 | 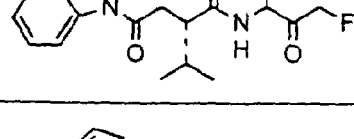 |
| Ia-10 | 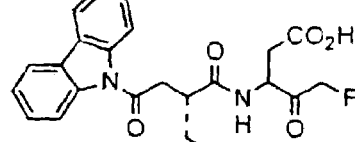 |
| Ia-11 | 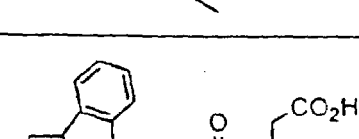 |
| Ia-12 | 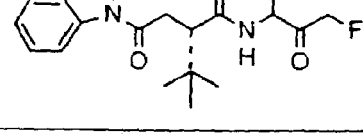 |
Fig. 11(m)

| No. | Structure |
|---|---|
| Ia-13 | 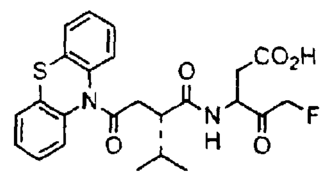 |
| Ia-14 | 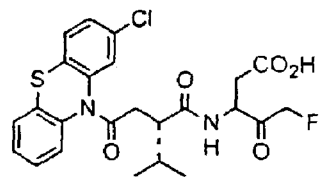 |
| Ia-15 | 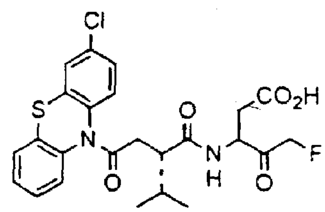 |
| Ia-16 | 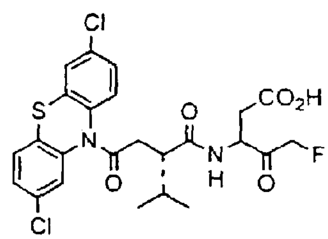 |
| Ia-17 | 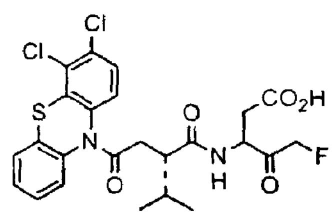 |
| Ia-18 | 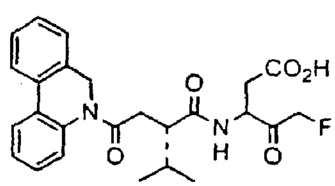 |

Fig. 11(n)

| No. | Structure |
|---|---|
| Ia-19 | 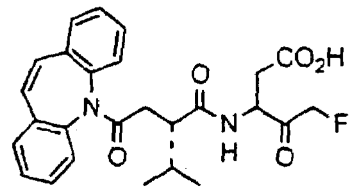 |
| Ia-20 | 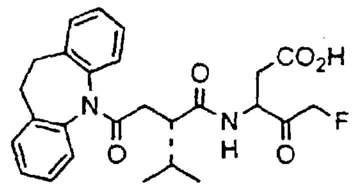 |
| Ia-21 | 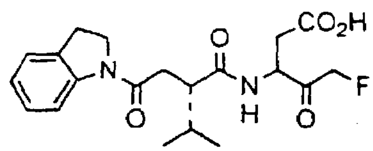 |
| Ia-22 | 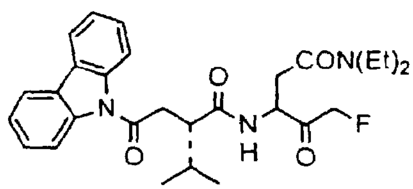 |
| Ia-23 | 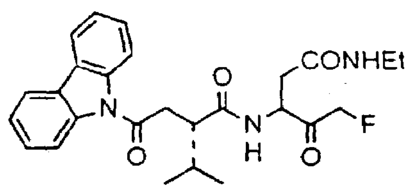 |
| Ia-24 | 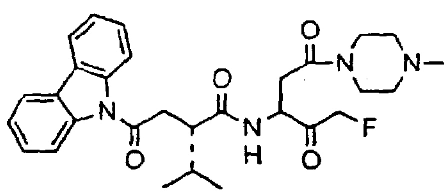 |
| Ia-25 | 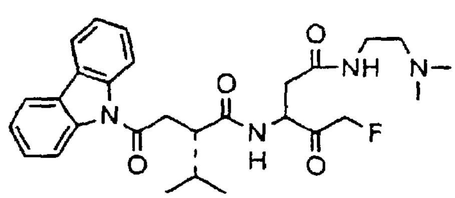 |

Fig. 11(o)

| No. | Structure |
|---|---|
| Ia-26 | 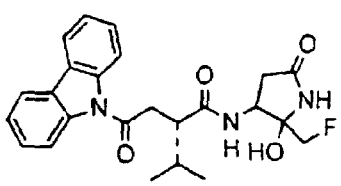 |
| Ia-27 | 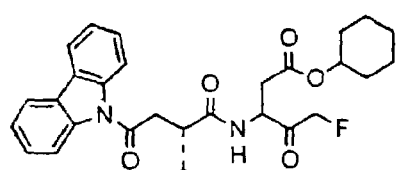 |
| Ia-28 | 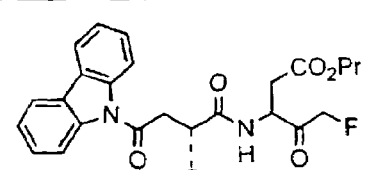 |
| Ia-29 | 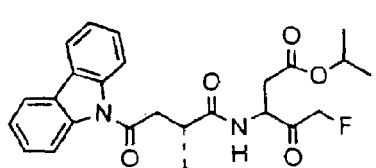 |
| Ia-30 | 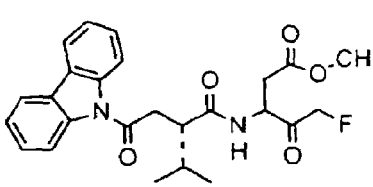 |
| Ia-31 | 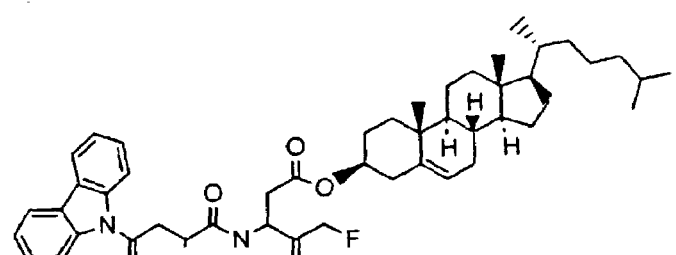 |
Fig. 11(p)

| No. | Structure |
|---|---|
| Ia-32 | 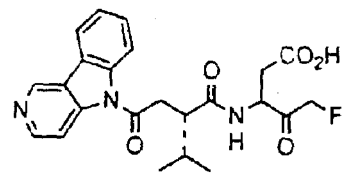 |
| Ia-33 | 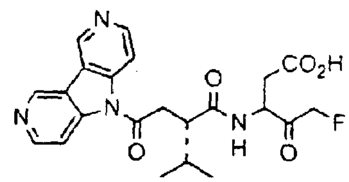 |
| Ia-34 | 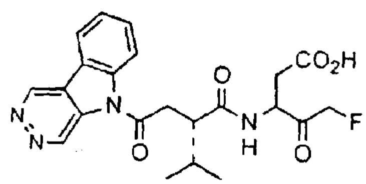 |
| Ia-35 | 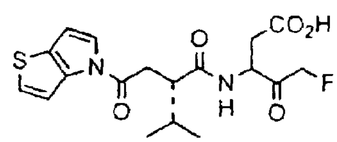 |
| Ia-36 | 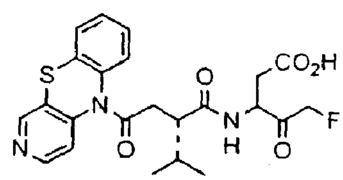 |
| Ia-37 | 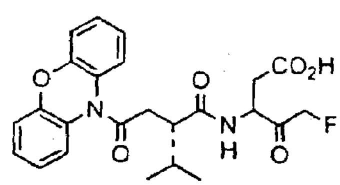 |
| Ia-38 | 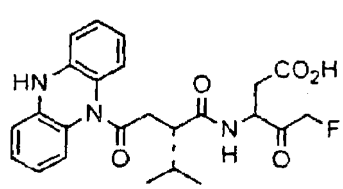 |

Fig. 11(q)

| No. | Structure |
|---|---|
| Ia-39 | 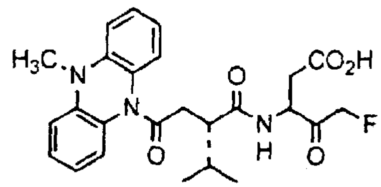 |
| Ia-40 | 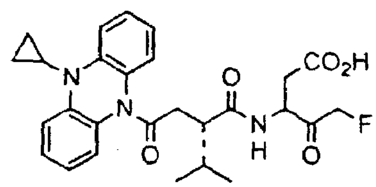 |
| Ia-41 | 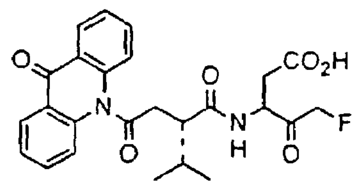 |
| Ia-42 | 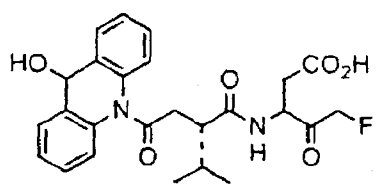 |
| Ia-43 | 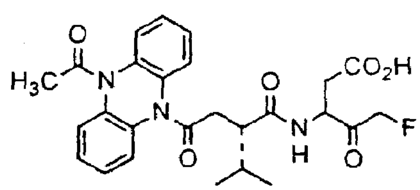 |
| Ia-44 | 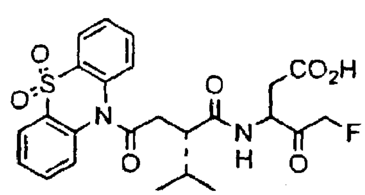 |

Fig. 11(r)

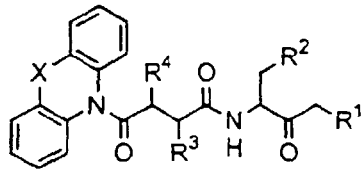

II where X is a bond, -S-, -O-, -CH$_2$-, or -NH-, and R$^1$, R$^2$, R$^3$ and R$^4$ are as described above. Where X is -CH$_2$-, each of the methylene hydrogens may be optionally and independently replaced by -OR, -OH, -SR, protected OH (such as acyloxy), -CN, -NH$_2$, -NHR, -N(R)$_2$, -NHCOR, -NHCONHR, -NHCON(R)$_2$, -NRCOR, -NHCO$_2$R, -CO$_2$R, -CO$_2$H, -COR, -CONHR, -CON(R)$_2$, -S(O)$_2$R, -SONH$_2$, -S(O)R, -SO$_2$NHR, -NHS(O)$_2$R, =O, =S, =NNHR, =NNR$_2$, =N-OR, =NNHCOR, =NNHCO$_2$R, =NNHSO$_2$R, or =NR where R is a C$_{1-4}$ aliphatic group. Where X is -NH-, the NH hydrogen may be replaced by alkyl, CO(alkyl), CO$_2$(alkyl), or SO$_2$(alkyl).

Another embodiment of this invention relates to compounds of formula Ib that have one or more, and preferably all, of the following features:

(i) R$^1$ is hydrogen, -R, -CH$_2$OR, -CH$_2$SR, or -CH$_2$Y. More preferably, R$^1$ is -CH$_2$OR, -CH$_2$SR, or -CH$_2$Y. An even more preferred R$^1$ is -CH$_2$Y. Most preferably, R$^1$ is -CH$_2$F.

(ii) R$^2$ is CO$_2$H or an ester, amide or isostere thereof.

Fig. 11(s)

1. A compound of formula I:

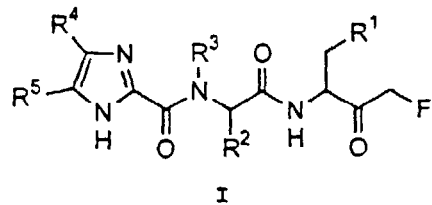

wherein:

$R^1$ is $CO_2H$, $CH_2CO_2H$, or esters, amides or isosteres thereof;

$R^2$ is hydrogen or an optionally substituted $C_1$-$C_6$ aliphatic group;

$R^3$ is hydrogen or an optionally substituted $C_1$-$C_6$ aliphatic group; and $R^4$ and $R^5$ are each independently selected from hydrogen, an optionally substituted $C_1$-$C_6$ aliphatic group, or $R^4$ and $R^5$ taken together with the ring to which they are attached form an optionally substituted bicyclic ring, said bicyclic ring selected from the following:

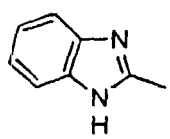  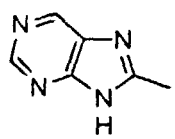  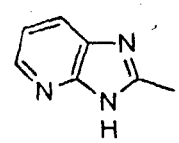  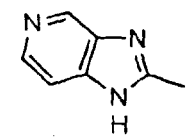

(a)        (b)         (c) ; or    (d).

2. The compound of claim 1 where $R^2$ is an optionally substituted $C_{1-6}$ straight or branched alkyl group.

3. The compound of claim 1 having one or more features selected from the group consisting of:

Fig. 12(a)

a) $R^1$ is $CO_2H$ or esters, amides or isosteres thereof;

b) $R^2$ is a $C_1$-$C_6$ straight chain or branched alkyl group;

c) $R^3$ is hydrogen; and d) $R^4$ and $R^5$ are each hydrogen, or $R^4$ and $R^5$ together with the ring to which they are attached form a benzimidazole ring.

4. The compound of claim 3 having the following features:

a) $R^1$ is $CO_2H$ or esters, amides or isosteres thereof;

b) $R^2$ is a $C_1$-$C_6$ straight chain or branched alky group;

c) $R^3$ is hydrogen; and d) $R^4$ and $R^5$ are each hydrogen, or $R^4$ and $R^5$ together with the ring to which they are attached form a benzimidazole ring.

5. A compound selected from the group consisting of:

[3S/R, (2S)]-5-Fluoro-3-{2-[(1H-imidazole-2-carbonyl)-amino]-propionylamino}-4-oxo-pentanoic acid;

[3S/R, (2S)]-5-Fluoro-3-{2-[(1H-imidazole-2-carbonyl)-amino]-propionylamino}-4-oxo-pentanoic acid tert-butyl ester;

[3S/R, (2S)]-3-{2-[(1H-Benzoimidazole-2-carbonyl)-amino]-propionylamino}-5-fluoro-4-oxo-pentanoic acid;

[3S/R, (2S)]-5-Fluoro-3-{2-[(1H-imidazole-2-carbonyl)-amino]-butyrylamino}-4-oxo-pentanoic acid;

[3S/R, (2S)]-5-Fluoro-3-{2-[(1H-imidazole-2-carbonyl)-amino]-3-methylbutyrylamino}-4-oxo-pentanoic acid;

[3S/R, (2S)]-3-{2-[(1H-Benzoimidazole-2-carbonyl)-amino]-3-methylbutyrylamino}-5-fluoro-4-oxo-pentanoic acid;

Fig. 12(b)

| 1 | [3S/R, (2S)]-5-Fluoro-3-{2-[1H-imidazole-2-carbonyl)-amino]-propionylamino}-4-oxo-pentanoic acid, trifluoroacetate salt |
|---|---|
| 2 | [3S/R, (2S)]-3-Fluoro-2-{2-[1H-Benzoimidazole-2-carbonyl)-amino]-propionylamino}-5-fluoro-4-oxo-pentanoic acid, trifluoroacetate salt |
| 3 | [3S/R, (2S)]-5-Fluoro-3-{2-[1H-imidazole-2-carbonyl)-amino]-butyrylamino}-4-oxo-pentanoic acid, trifluoroacetate salt |
| 4 | [3S/R, (2S)]-5-Fluoro-3-{2-[1H-imidazole-2-carbonyl)-amino]-3-methylbutyrylamino}-4-oxo-pentanoic acid |
| 5 | [3S/R, (2S)]-3-Fluoro-3-{2-[1H-Benzoimidazole-2-carbonyl)-amino]-3-methylbutyrylamino}-5-fluoro-4-oxo-pentanoic acid |

Fig. 12(c)

1. A compound of formula II:

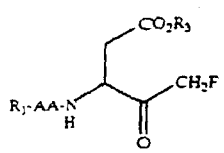

or a pharmaceutically acceptable salt thereof, wherein,
R$_1$ is an N-terminal protecting group selected from the group consisting of t-butoxycarbonyl (Boc), acetyl (Ac) and benzyloxycarbonyl (Cbz);

R$_3$ is alkyl or hydrogen; and
AA is a residue of an amino acid selected from the group consisting of valine (Val), isoleucine (Ile) and leucine (Leu).

2. The compound of claim 1, wherein R$_3$ is methyl or hydrogen.

3. The compound of claim 2, which is Cbz-Val-Asp-CH$_2$F or a pharmaceutically acceptable salt thereof.

4. The compound of claim 2, which is Cbz-Leu-Asp-CH$_2$F or a pharmaceutically acceptable salt thereof.

5. The compound of claim 2, which is Cbz-Ile-Asp-CH$_2$F or a pharmaceutically acceptable salt thereof.

6. The compound of claim 2, which is Ac-Val-Asp-CH$_2$F or a pharmaceutically acceptable salt thereof.

7. The compound of claim 2, which is Ac-Leu-Asp-CH$_2$F or a pharmaceutically acceptable salt thereof.

8. The compound of claim 2, which is Ac-Ile-Asp-CH$_2$F or a pharmaceutically acceptable salt thereof.

9. The compound of claim 2, which is Boc-Val-Asp-CH$_2$F or a pharmaceutically acceptable salt thereof.

10. The compound of claim 2, which is Boc-Leu-Asp-CH$_2$F or a pharmaceutically acceptable salt thereof.

11. The compound of claim 2, which is Boc-Ile-Asp-CH$_2$F or a pharmaceutically acceptable salt thereof.

12. The compound of claim 2, which is Cbz-Val-Asp(OMe)-CH$_2$F.

13. The compound of claim 2, which is Cbz-Leu-Asp(OMe)-CH$_2$F.

14. The compound of claim 2, which is Cbz-Ile-Asp(OMe)-CH$_2$F.

15. A pharmaceutical composition comprising the compound of any one of claims 1-14, and a pharmaceutically acceptable carrier.

Fig. 13(a)

| 1 | t-Butyl 5-fluoro-4-hydroxy-3-nitropentanoate |
|---|---|
| 2 | t-Butyl 3-amino-5-fluoro-4-hydroxy-pentanoate |
| 3 | t-Butyl 3-(Cbz-Val-amido)-5-fluoro-4-hydroxy-pentanoate |
| 4 | Z-Val-Asp-fmk t-butyl ester |
| 5 | Z-Val-Asp-fmk |
| 6 | Z-Leu-Asp-fmk |
| 7 | Z-Ile-Asp-fmk |
| 8 | Z-Ala-Asp-fmk |
| 9 | Ac-Val-Asp-fmk |
| 10 | Z-N-Me-Val-Asp-fmk |
| 11 | Z-ß-Ala-Asp-fmk |
| 12 | Z-Gly-Asp-fmk |
| 13 | Z-Phe-Asp-fmk |
| 14 | Z-Glu-Asp-fmk |
| 15 | Z-Pro-Asp-fmk |
| 16 | Z-His-Asp-fmk |
| 17 | Z-Tyr-Asp-fmk |
| 18 | Z-Val-Asp-fmk Methyl Ester |
| 19 | Z-Leu-Asp-fmk Methyl Ester |
| 20 | Z-Ile-Asp-fmk Methyl Ester | fmk: fluoromethylketone
Z: benzyloxycarbonyl
Val: Valine
Asp: Aspartic acid
Leu: Leucine
Ile: Isoleucine
Ala: Alanine
Gly: Glycine
Phe: Phenylalanine Glu: Glutamic acid
Pro: Proline
His: Histidine
Tyr: Tyrosine

Fig. 13(b)

compounds having the general Formula I:

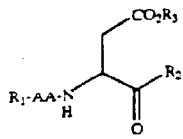

or pharmaceutically acceptable salts or prodrugs thereof, wherein:

R₁ is an N-terminal protecting group including t-butyloxycarbonyl, acetyl, and benzyloxycarbonyl; AA is a residue of any natural or non-natural α-amino acid, or β-amino acid, or a derivative of an α-amino acid or β-amino acid, e.g. Gly, Thr, Glu, Lys, Arg, Ser, Asn, Gln, Val, Ala, Leu, Ile, Met, and β-amino acids such as β-Ala, and which is not His, Tyr, Pro or Phe; R₂ is H or CH₂R₄, R₄ is an electronegative leaving group such as F, Cl, TsO-, MeO-, ArO-, ArCOO, ArN-, and ArS-; and R₃ is alkyl or H.

With respect to R₃, preferred alkyl groups are C₁₋₆ alkyl groups, e.g. methyl, ethyl, propyl, isopropyl, isobutyl, pentyl and hexyl groups.

Formula II:

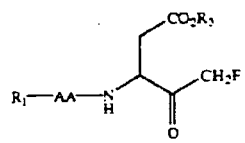

or pharmaceutically acceptable salts or prodrugs thereof wherein AA, R₁ and R₃ are as defined previously with respect to Formula I.

Preferred R₁ is t-butyloxycarbonyl, acetyl and benzyloxycarbonyl. Preferred R₃ is H, Me, Et or t-Bu. Preferred AA is Val, Ala, Leu, Ile, Met, and β-amino acids such as β-Ala.

Exemplary preferred inhibitors of apoptosis having Formula I include, without limitation:

Boc-Ala-Asp-CH₂F,
Boc-Val-Asp-CH₂F,
Boc-Leu-Asp-CH₂F,
Ac-Val-Asp-CH₂F,
Ac-Ile-Asp-CH₂F,
Ac-Met-Asp-CH₂F,
Cbz-Val-Asp-CH₂F,
Cbz-β-Ala-Asp-CH₂F
Cbz-Leu-Asp-CH₂F,
Cbz-Ile-Asp-CH₂F,
Boc-Ala-Asp(OMe)-CH₂F,
Boc-Val-Asp(OMe)-CH₂F,
Boc-Leu-Asp(OMe)-CH₂F,
Ac-Val-Asp(OMe)-CH₂F,
Ac-Ile-Asp(OMe)-CH₂F,
Ac-Met-Asp(OMe)-CH₂F,
Cbz-Val-Asp(OMe)-CH₂F,
Cbz-β-Ala-Asp(OMe)-CH₂F
Cbz-Leu-Asp(OMe)-CH₂F, and
Cbz-Ile-Asp(OMe)-CH₂F.

Fig. 13(c)

1. A compound of the following formula:

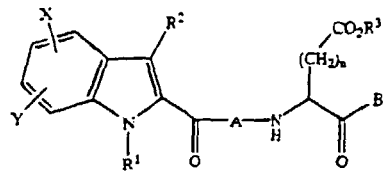

wherein:

n is 1 or 2;

$R^1$ is alkyl, cycloalkyl, (cycloalkyl)alkyl, phenyl, substitutedphenyl, phenylalkyl, substitutedphenylalkyl, heteroaryl, (heteroaryl)alkyl of $(CH_2)_mCO_2R^4$, wherein m=1–4, and $R^4$ is as defined below;

$R^2$ is a hydrogen atom, chloro, alkyl, cycloalkyl, (cycloalkyl)alkyl, phenyl, substitutedphenyl, phenylalkyl, substitutedphenylalkyl, heteroaryl, (heteroaryl)alkyl or $(C_2)_pCO_2R^5$, wherein p=0–4, and $R^5$ is as defined below;

$R^3$ is a hydrogen atom, alkyl, cycloalkyl, (cycloalkyl)alkyl, phenylalkyl, or substitutedphenylalkyl;

$R^4$ is a hydrogen atom, alkyl, cycloalkyl, (cycloalkyl)alkyl, phenylalkyl, or substitutedphenylalkyl;

$R^5$ is a hydrogen atom, alkyl, cycloalkyl, (cycloalkyl)alkyl, phenylalkyl, or substitutedphenylalkyl;

A is a natural or unnatural amino acid;

B is a hydrogen atom, a deuterium atom, alkyl, cycloalkyl, (cycloalkyl)alkyl, phenyl, substitutedphenyl, phenylalkyl, substitutedphenylalkyl, heteroaryl, (heteroaryl)alkyl, halomethyl, $CH_2ZR^6$, $CH_2OCO(aryl)$, or $CH_2OCO$ (heteroaryl), or $CH_2OPO(R^7)R^8$, where Z is an oxygen, OC(=O) or a sulfur atom;

$R^6$ is phenyl, substituted phenyl, phenylalkyl, (substituted phenyl)alkyl, heteroaryl or (heteroaryl)alkyl;

$R^7$ and $R^8$ are independently selected from a group consisting of alkyl, cycloalkyl, phenyl, substituted phenyl, phenylalkyl, (substituted phenyl)alkyl and (cycloalkyl)alkyl; and X and Y are independently selected from the group consisting of a hydrogen atom, halo, trihalomethyl, amino, protected amino, an amino salt, mono-substituted amino, di-substituted amino, carboxy, protected carboxy, a carboxylate salt, hydroxy, protected hydroxy, a salt of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl;

or a pharmaceutically acceptable salt or stereoisomer thereof.

2. The compound of claim 1 Wherein B is $CH_2ZR^6$.

3. The compound of claim 2 wherein B is $CH_2OC(=O)R^6$.

4. The compound of claim 3 wherein $R^6$ is substituted phenyl.

5. The compound of claim 3 where $R^6$ is heteroaryl.

6. The compound of claim 2 wherein B is $CH_2OR^6$

7. The compound of claim 6 wherein $R^6$ is substituted phenyl.

8. The compound of claim 7 wherein $R^6$ is tetra(halo)phenyl.

9. The compound of claim 8 wherein $R^6$ is optionally substituted naphthyl.

10. The compound of claim 9 wherein $R^6$ is naphthyl substituted with one or more heteroaryl groups.

Fig. 14(a)

| 1 | (3S)-3-[(1-Methylindole-2-Carbonyl)Alaninyl] Amino-4-Oxobutanoic Acid, t-Butyl Ester Semicarbazone |
|---|---|
| 2 | (3S)-3-[(1-Methylindole-2-Carbonyl)Alaninyl] Amino-4-Oxobutanoic Acid, Semicarbazone |
| 3 | (3S)-3-[(1-Methylindole-2-Carbonyl)Alaninyl] Amino-4-Oxobutanoic Acid |
| 4 | (3S)-3-(1-Methylindole-2-Carbonyl)Prolinyl]Amino-4-Oxo-Butanoic Acid, t-Butyl Ester Semicarbazone |
| 5 | (3S)-3-[(1-Methylindole-2-Carbonyl)Prolinyl] Amino-4-Oxo-Butanoic Acid, Semicarbazone |
| 6 | (3S)-3-[(1-Methylindole-2-Carbonyl)Prolinyl] Amino-4-Oxo-Butanoic Acid |
| 7 | (3S)-3-[1(1-Methylindole-2-Carbonyl)Valinyl] Amino-4-Oxo-Butanoic acid, t-Butyl Ester Semicarbazone |
| 8 | (3S)-3-[1(1-Methylindole-2-Carbonyl)Valinyl] Amino-4-Oxo-Butanoic Acid Semicarbazone |
| 9 | (3S)-3[1-Methylindole-2-Carbonyl)Valinyl] Amino-4-Oxo-Butanoic Acid |
| 10 | (3S)-3-[(1-Methylindole-2-Carbonyl)Leucinyl] Amino-4-Oxo-Butanoic Acid, t-Butyl Enter Semicarbazone |
| 11 | (3S)-3-[1-Methylindole-2-Carbonyl)Leucinyl] Amino-4-Oxo-Butanoic Acid Semicarbazone |
| 12 | (3S)-3-[(1-Methylindole-2- Carbonyl)Leucinyl] Amino-4-Oxo-Butanoic Acid |
| 13 | (3S)-3-[(1-Methylindole-2-Carbonyl)Phenylalaninyl] Amino-4-Oxabutanoic acid, t-Butyl Ester Semicarbazone |
| 14 | (3S)-3-[(1-Methylindole-2-Carbonyl)Phenylalaninyl] amino-4-Oxobutanoic Acid Semicarbazone |
| 15 | (3S)-3-[(1-Methylindole-2-Carbonyl)(Phenylalaninyl) Amino-4-Oxobutanoic Acid |
| 16 | (1-Methylindole-2-Carbonyl)Glycine, Methyl Ester |
| 17 | (1-Methylindole-2-Carbonyl)Glycine |

Fig. 14(b)

| 18 | (3S)-3-[(1-Methylindole-2-Carbonyl)Glycine] Amino-4-Oxo-Butanoic Acid, t-Butyl Ester Semicarbazone |
|---|---|
| 19 | (3S)-3-[(1-Methylindole-2-Carbonyl)Glycinyl] Amino-4-Oxo-Butanoic Acid, Semicarbazone |
| 20 | (3S)-3-[(1-Methylindole-2-Carbonyl)Glycinyl]-Amino-4-Oxo-Butanoic Acid |
| 21 | (3S)-3-[(1-Benzylindole-2-Carbonyl)Alaninyl] Amino-4-Oxo-Butanoic Acid, t-Butyl Ester Semicarbazone |
| 22 | (3S)-3-[(1-Benzylindole-2-Carbonyl)Alaninyl] Amino-4-Oxo-Butanoic Acid, Semicarbazone |
| 23 | (3S)-3-[(1-Benzylindole-2-Carbonyl)Alaninyl] Amino-4-Oxo-Butanoic Acid |
| 24 | (3S)-3-(1-(4'-Butenyl)Indole-2-Carbonyl)Valinyl] Amino-4-Oxobutanoic Acid, t-Butyl Ester Semicarbazone |
| 25 | (3S)-3-[(1-4'-Butenyl)Indole-2-Carbonyl)Valinyl] Amino-4-Oxobutanoic Acid, Semicarbazone |
| 26 | (3S)-3-[(1-(4'-Butenyl)indole-2-Carbonyl)Valinyl] Amino-4-Oxobutanoic Acid |
| 27 | (3S)-3-[(1-(2'-(1'-t-Butoxy-[1']-Oxo)Ethyl)Indole-2-Carbonyl)Alaninyl] Amino-4-Oxobutanoic Acid, t-Butyl Ester Semicarbazone |
| 28 | (3S)-3-[(1-(Carboxymethyl)-Indole-2-Carbonyl)Alaninyl] Amino-4-Oxabutanoic Acid, Semicarbazone |
| 29 | (3S)-3-[(1-(Carboxymethyl)Indole-2-Carbonyl)Alaninyl] Amino-4-Oxobutanoic Acid |
| 30 | (3S)-3-[(1-(3'-(1'-t-Butoxy-1'-Oxo)Proply)Indole-2-Carbonyl)Alaninyl] Amino-4-Oxobutanoic Acid, t-Butyl Ester Semicarbazone |
| 31 | (3S)-3-[1-(2'-Carboxyethyl)Indole-2-Carbonyl)Alaninyl] Amino-4-Oxobutanoic Acid, Semicarbazone |
| 33 | (3S)-3-(1-(2'-Carboxyethyl)Indole-2-Carbonyl)Alaninyl] Amino-4-Oxobutanoic Acid |
| 34 | 2,6-Dichlorobenzyloxyethanol |

Fig. 14(c)

| | |
|---|---|
| 35 | 5-(2'-6'-Dichlorobenzyloxy)-4-Hydroxy-3-Nitro-Pentanoic Acid, t-Butyl Ester |
| 36 | 3-Amino-5-(2',6'-Dichlorobezyloxy)-4-Hydroxy-Pentanoic Acid, t-Butyl Ester |
| 37 | N-(1,3-Dimethylindole-2-Carbonyl)Valine |
| 38 | N-[(1,3-Dimethylindole-2-Carbonyl)Valinyl]-3-Amino-4-Hydroxy-5(2',6'-Dichlorobenzyloxy) Pentanoic Acid, t-Butyl Ester |
| 39 | N-[(1,3-Dimethylindole-2-Carbonyl)Valinyl]-3- Amino-4-Oxo-5-(2'6'-Dichlorobenzyloxy)Pentanoic Acid, t-Butyl Ester |
| 40 | N-[1,3-Dimethylindole-2-Carbonyl)Valinyl]-3-Amino-4-Oxo-5-(2',6'-Dichlorobenzyloxy)Pentanoic Acid |
| 41 | N-[1,3-Dimethylindole-2-Carbonyl)Valinyl]-3-Amino-4-Hydroxy-5-Fluoropentanoic Acid, t-Butyl Ester |
| 42 | N-[(1,3-Dimethylindole-2-Carbonyl)Valinyl]-3-Amino-4-Oxo-5-Fluoropentanoic Acid, t-Butyl Ester |
| 43 | N-[(1,3-Dimethylindole-2-Carbonyl)Valinyl]-3- Amino-4-Oxo-5-Fluoropentanoic Acid |
| 44 | N-[(1-Methylindole-2-Carbonyl)Valinyl]-3-Amino-4-Hydroxy-5-Fluoropentanoic Acid, t-Butyl Ester |
| 45 | N-[(3-Chloro-1-Methylindole-2-Carbonyl)Valinyl]-3-Amino-4-Oxo-5-Fluoropentanoic Acid, t-Butyl Ester |
| 46 | N-[(3-Chloro-1,Methylindole-2-Carbonyl)Valinyl]-3-Amino-4-Oxo-5-Fluoropentanoic Acid |
| 47 | N-[(5-Fluoro-[1-Methylindole-2-Carbonyl)Valinyl]-3-Amino-4-Hydroxy-5-Fluoropentanoic Acid, t-Butyl Ester |
| 48 | N-[(3-Chloro-5-Fluoro-1Methylindole-2-Carbonyl)Valinyl]-3-Amino-4-Oxo-5-Fluoropentanoic Acid, t-Butyl Ester |
| 49 | N-[(3-Chloro-5-Fluoro-1-Methylindole-2-Carbonyl)Valinyl]-3-Amino-4-Oxo-5-Fluoropentanoic Acid |
| 50 | N-[(1-(3'-Phenylpropyl)Indole-2-Carbonyl)Valinyl]-3-Amino-4-Hydroxy-5-Fluoropentanoic Acid, t-Butyl Ester |
| 51 | N-(1-(3'-Phenylpropyl)Indole-2-Carbonyl)Valinyl]-3-Amino-4-Oxo-5-Fluoropentanoic Acid, t- Butyl Ester |

Fig. 14(d)

| 51 | N-(1-(3'-Phenylpropyl)Indole-2-Carbonyl)Valinyl]-3-Amino-4-Oxo-5-Fluoropentanoic Acid, t- Butyl Ester |
|---|---|
| 52 | N-[(1-(3'-Phenylpropyl)Indole-2-Carbonyl)Valinyl]-3-Amino-4-Oxo-5-Fluoropentanoic Acid |
| 53 | N-[(1-Phenylindole-2-Carbonyl)Valinyl]-3-Amino-4-Hydroxy-5-Fluoropentanoic Acid, t-Butyl Ester |
| 54 | N-[(1-Phenylindole-2-Carbonyl)Valinyl]-3-Amino-4-Oxo-5-Fluoropentanoic Acid, t-Butyl Ester |
| 55 | N-[(1-Phenylindole-2-Carbonyl)Valinyl]-3-Amino-4-Oxo-5-Fluoropentanoic Acid |
| 56 | N-[1-(2'-((1'-t-Butoxy-1'-Oxo)Ethyl)Indole-2-Carbonyl)Valinyl]-3-Amino-4-Hydroxy-5-Fluoropentanoic Acid, t-Butyl Ester |
| 57 | N-[(1-(2'((1'-t-Butoxy-1'-Oxo)Ethyl)Indole-2-Carbonyl(Valinyl]-3-Amino-4-Oxo-5-Fluoropentanoic Acid, t-Butyl Ester |
| 58 | N-[(1-(Carboxymethyl)Indole-2-Carbonyl)Valinyl]-3-Amino-4-Oxo-5-Fluoropentanoic Acid |
| 59 | N-[(1-Methylindole-2-carbonyl)valinyl]-3-amino-4-hydroxy-5-fluoropentanoic acid, t-butyl ester |
| 60 | N-(1-Methylindole-2-carbonyl)valinyl]-3-amino-4-oxo-5-fluoropentanoic acid, t-butyl ester |
| 61 | N-[(1-Methylindole-2-carbonyl)valinyl]-3-amino-4-oxo-5-fluoropentanoic acid |
| 62 | N-[1(1,3-Dimethyl-5-fluoroindole-2-carbonyl)valinyl]-3-amino-4-oxo-5-fluoropentanoic acid |
| 63 | N-[1-homoallylindole-2-carbonyl)valinyl)-3-amino-4-oxo-5-fluoropentanoic acid |
| 64 | N-[1-Methyl-5-fluoroindole-2-carbonyl)valinyl]-3-amino-4-oxo-5-fluoropentanoic acid |
| 65 | N-[(1-Methyl-3-isobutylindole2-carbonyl)valinyl]-3-amino-4-oxo-5-fluoropentanoic acid |
| 66 | N-[(1-Methyl-3-phenethylindolo-2-carbonyl)valinyl]-3-amino-4-oxo-5-fluoropentanoic acid |

Fig. 14(e)

| 67 | N-[(1-Methyl-5-O-benzylindole-2-carbonyl)valinyl]-3-amino-4-oxo-5-fluoropentanoic acid |
|---|---|
| 68 | N-(1,3-Dimenthyl-indole-2-carbonyl)-Valinyl-3-Amino-5-Bromo-4-Oxo-Pentanoic Acid, t-Butyl Ester |
| 69 | N-[(1,3-Dimethyl-indole-2-carbonyl)-Valinyl]-3-amino-5(2,6-dichlorobenzoyl)oxy-4-oxo-pentanoic acid, t-butyl ester |
| 70 | N-[N-(1,3-Dimethyl-indole-2-carbonyl)-Valinyl]-3-amino-5-(2,6-dichlorobenzoyl)oxy-4-oxo-pentanoic acid |
| 71 | N-(1,3-Dimethyl-indole-2-carbonyl)-Valinyl-3-amino-5-(diphenylphosphinyl)oxy-4-oxo-pentanoic acid |
| 72 | N-(1,3-Dimethyl-indole-2-carbonyl)-Valinyl-3-amino-5-(1-phenyl-3-(trifluoromethyl)pyrazol-5-yl)oxy-4-oxo-pentanoic acid |
| 73 | N-(1,3-Dimethyl-indole-2-carbonyl)-Valinyl-3-amino-5-(3-(N-phenyl)aminocarbonyl-2-naphthyl)oxy-4-oxo-pentanoic acid |
| 74 | N-(1,3-Dimethyl-indole-2-carbonyl)-Valinyl-3-amino-5-(2-aminocarbonyl-1-phenyl)oxy-4-oxo-pentanoic acid |
| 75 | N-(1,3-Dimethyl-indole-2-carbonyl)-Valinyl-3-amino-5-(dimethylphosphinyl)oxy-4-oxo-pentanoic acid |
| 76 | N-(valinyl)aspartic acid, α-methyl, [3-tert-butyl diester |
| 77 | N-[1,3-dimethyl-indole-2-carbonyl)valinyl]aspartic acid, β-tert-butyl ester |
| 78 | N-[(1,3-dimethyl-indole-2-carbonyl)valinyl]-3-amino-5-bromo-4-oxo-pentanoic acid, tert-butyl ester |
| 79 | N-[(1,3-dimethyl-indole-2-carbonyl)valinyl]-3-amino-5-[3-(imidazol-2-yl)-naphtyl-2-oxy]-4-oxo-pentanoic acid, tert-butyl ester |
| 80 | N-[(1,3-dimethyl-indole-2-carbonyl)valinyl]-3-amino-5[3-(imidazol-2-yl)-naphthyl-2-oxy]-4-oxo-pentanoic acid |
| 81 | N-[(1-methyl-3-isobutyl-indole-2-carbonyl)valinyl]-3-amino-5-bromo-4-oxo-N-pentanoic acid, tert-butyl ester |
| 82 | N-[(1-methyl-3-isobutyl-indole-2-carbonyl)valinyl]-3-amino-4-oxo-5-(2,3,5,6-tetrafluorophenyloxy)-pentanoic acid, tert-butyl ester |

Fig. 14(f)

| 83 | N-[(1-methyl-3-isobutyl-indole-2-carbonyl)valinyl]-3-amino-4-oxo-5-(2,3,5,6-(tetrafluorophenyloxy)-pentanoic acid |
|---|---|
| 84 | N-[(1-methyl-3-isobutyl-indole-2-carbonyl)valinyl]-3-amino-4-oxo-5-(4-fluorophenyloxy)-pentanoic acid, tert-butyl ester |
| 85 | N-[(1-methyl-3-isobutyl-indole-2-carbonyl)valinyl]-3-amino-4-oxo-5-(4-fluorophenyloxy)-pentanoic acid |
| 86 | N-[(1-methyl-3-isobutyl-indole-2-carbonyl)valinyl]-3-amino-4-oxo-5-(2-fluorophenyloxy)-pentanoic acid, tert-butyl ester |
| 87 | N-[(1-methyl-3-isobutyl-indole-2-carbonyl)valinyl]-3-amino-4-oxo-5-(2-fluorophenyloxy)-pentanoic acid |
| 88 | N-[(1-methyl-3-isobutyl-indole-2-carbonyl)leucinyl]-3-amino-5-bromo-4-oxo-pentanoic acid, tert-butyl ester |
| 89 | N-[1(1-methyl-3-isobutyl-indole-2-carbonyl)leucinyl]-3-amino-5-(2,6-dichlorobenzoyl)oxy-4-oxo pentanoic acid, tert-butyl ester |
| 90 | N-[(1-methyl-3-isobutyl-indole-2-carbonyl)leucinyl]-3-amino-5-(2,6-dichlorobenzoyl)oxy-4-oxo pentanoic acid |
| 91 | N-[(1-methyl-3-isobutyl-indole-2-carbonyl)leucinyl]-3-amino-4-oxo-5-(2,3,5,6-tetrafluorophenyloxy)-pentanoic acid, tert-butyl ester |
| 92 | N-[(1-methyl-3-isobutyl-indole-2-carbonyl)leucinyl]-3-amino-4-oxo-5-(2,3,5,6-tetrafluorophenyloxy)-pentanoic acid |
| 93 | N-[(1-methyl-3-isobutyl-indole-2-carbonyl)leucinyl]-3-amino-5-(diphenylphosphoroxy)-4-oxo-pentanoic acid, tert-butyl ester |
| 94 | N-[(1-methyl-3-isobutyl-indole-2-carbonyl)leucinyl]-3-amino-5-(diphenylphosphoroxy)-4-oxo-pentanoic acid |
| 95 | N-[(1-methyl-3-isobutyl-indole-2-carbonyl)cyclohexylaaninyl]-3-amino-5-bromo-4-oxo-pentanoic acid, tert-butyl ester |
| 96 | N-[(1-methyl-3-isobutyl-indole-2-carbonyl)cyclohexylaianinyl]-3-amino-4-oxo-5-(2,3,5,6-tetrafluorophenyloxy)-pentanoic acid, tert-butyl ester |
| 97 | N-[(1-methyl-3-isobutyl-indole-2-carbonyl)cyclohexylaianinyl]-3-amino-4-oxo-5-(2,3,5,6-tetrafluorophenyloxy)-pentanoic acid |
| 98 | N-[(1-methyl-3-isobutyl-indole-2-carbonyl)cyclohexylalaninyl]-3-amino- 5(2,6-dichlorobenzoyl)oxy-4-oxo-pentanoic acid, tert-butyl ester |

Fig. 14(g)

| 99 | N-[(1-methyl-3-isobutyl-indole-2-carbonyl)cyclohexylalaninyl]-3-amino-5-(2,6-dichlorobenzoyl)oxy-4-oxo-pentanoic acid |
|---|---|
| 100 | N-[(1-methyl-3-isobutyl-indole-2-carbonly)cyclohexylalaninyl]-3-amino-4-oxo-5-1-phenyl-3-(trifluoromethyl)pyrazol-5-yloxy]-pentanoic acid, tert-butyl ester |
| 101 | N-[(1-methyl-3-isobutyl-indole-2-carbonyl)cyclohexylalaninyl]-3-amino-4-oxo-5-[1-phenyl-3-(trifluoromethyl)pyrazol-5-yloxy]-pentanoic acid |
| 102 | N-[(carbobenzyloxycarbonyl)-valinyl]aspartic acid, β-tert-butyl ester |
| 103 | N-[(carbobenzyloxycarbonyl)valinyl]-3-amino-5-bromo-4-oxo-pentanoic acid, tert-butyl ester |
| 104 | N-[(carbobenzyloxycarbonyl)valinyl]-3-amino-4-oxo-5-(2,3,5,6-tetrafluorophenyloxy)-pentanoic acid, tert-butyl ester |
| 105 | N-[(carbobenzyloxycarbonyl)valinyl]-3-amino-4-hydroxy-5-(2,3,5,6-tetrafluorophenyloxy)-pentanoic acid, tert-butyl ester |
| 106 | N-(valinyl)-3-amino-4-hydroxy-5-(2,3,5,6-tetrafluorophenyloxy)-pentanoic acid, tert-butyl ester |
| 107 | N-[(1,3-dimethyl-indole-2-carbonyl)valinyl]-3-amino-4-hydroxy-5-(2,3,5,6-tetrafluorophenyloxy)-pentanoic acid, tert-butyl ester |
| 108 | N-[(1,3-dimethyl-indole-2-carbonyl)valinyl]-3-amino-4-oxo-5-(2,3,5,6-tetrafluorophenyloxy)-pentanoic acid, tert-butyl ester |
| 109 | N-[(1,3-dimethyl-indole-2-carbonyl)valinyl]-3-amino-4-oxo-5-(2,3,5,6-tetrafluorophenyloxy)-pentanoic acid |
| 110 | N-[(1-methyl-indole-2-carbonyl)valinyl]-3-amino-4-hydroxy-5-(2,3,5,6-tetrafluorophenyloxy)-pentanoic acid, tert-butyl ester |
| 111 | N-[(1-methyl-indole-2-carbonyl)valinyl]-3-amino-4-oxo-5-(2,3,5,6-tetrafluorophenyloxy)-pentanoic acid, tert-butyl ester |
| 112 | N-[(1-methyl-indole-2-carbonyl)valinyl]-3-amino-4-oxo-5-(2,3,5,6-tetrafluorophenyloxy)-pentanoic acid |
| 113 | N-[(5-fluoro-1-methyl-indole-2-carnonyl)valinyl]-3-amino-4-hydroxy-5-(2,3,5,6-tetrafluorophenyloxy)-pentanoic acid, tert-butyl ester |
| 114 | N-[(5-fluoro-methyl-indole-2-carbonyl)valinyl]-3-amino-4-oxo-5-(2,3,5,6-tetrafluorophenyloxy)-penanoic acid, tert-butyl ester |
| 115 | N-[(5-fluoro-1-methyl-indole-2-carbonyl)valinyl]-3-amino-4-oxo-5-(2,3,5,6-tetrafluorophenyloxy)-pentanoic acid |

Fig. 14(h)

| 115 | N-[(5-fluoro-1-methyl-indole-2-carbonyl)valinyl]-3-amino-4-oxo-5-(2,3,5,6-tetrafluorophenyloxy)-pentanoic acid |
|---|---|
| 116 | N-{[1-(tert-butyl)oxycarbonylmethyl-indole-2-carbonyl]valinyl}-3-amino-4-hydroxy-5-(2,3,5,6-tetrafluorophenyloxy)-pentanoic acid, tert-butyl ester |
| 117 | N-{[1-(tert-butyl)oxycarbonylmethyl-indole-2-carbonyl]valinyl}-3-amino-4-oxo-5-(2,3,5,6-tetrafluorophenyloxy)-pentanoic acid, tert-butyl ester |
| 118 | N-{[1-(carboxymethyl)-indole-2-carbonyl]valinyl}-3-amino-4-oxo-5-(2,3,5,6-tetrafluorophenyloxy)-pentanoic acid |

Fig. 14(i)

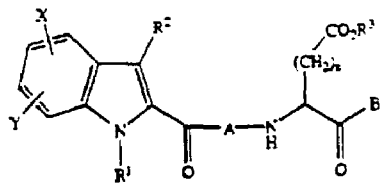

wherein:

n is 1 or 2;

R¹ is alkyl, cycloalkyl, (cycloalkyl)alkyl, phenyl, (substituted)phenyl, phenylalkyl, (substituted) phenylalkyl, heteroaryl, (heteroaryl)alkyl or (CH₂)ₘCO₂R⁴, wherein m=1–4, and R⁴ is as defined below;

R² is a hydrogen atom, chloro, alkyl, cycloalkyl, cycloalkyl)alkyl, phenyl, (substituted)phenyl, phenylalkyl, (substituted)phenylalkyl, heteroaryl, (heteroaryl)alkyl or (CH₂)ₚCO₂R⁵, wherein p=0–4, and R⁵ is as defined below;

R³ is a hydrogen atom, alkyl, cycloalkyl, (cycloalkyl) alkyl, phenylalkyl, or (substituted)phenylalkyl;

R⁴ is a hydrogen atom, alkyl, cycloalkyl, (cycloalkyl) alkyl, phenylalkyl, or (substituted)phenylalkyl;

R⁵ is a hydrogen atom, alkyl, cycloalkyl, (cycloalkyl) alkyl, phenylalkyl, or (substituted)phenylalkyl;

A is a natural or unnatural amino acid;

B is a hydrogen atom, a deuterium atom, alkyl, cycloalkyl, (cycloalkyl)alkyl, phenyl, (substituted) phenyl, phenylalkyl, (substituted)phenylalkyl, heteroaryl, (heteroaryl)alkyl, halomethyl, CH₂ZR⁶, CH₂OCO(aryl), or CH₂OCO(heteroaryl), or CH₂OPO (R⁷)R⁸, where Z is an oxygen, OC(=O) or a sulfur atom;

R⁶ is phenyl, substituted phenyl, phenylalkyl, (substituted phenyl)alkyl, heteroaryl or (heteroaryl)alkyl;

R⁷ and R⁸ are independently selected from a group consistent of alkyl, cycloalkyl, phenyl, substituted phenyl, phenylalkyl, (substituted phenyl)alkyl and (cycloalkyl)alkyl; and X and Y are independently selected from the group consisting of a hydrogen atom, halo, trihalomethyl, amino, protected amino, an amino salt, mono-substituted amino, di-substituted amino, carboxy, protected carboxy, a carboxylate salt, hydroxy, protected hydroxy, a salt of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl;

or a pharmaceutically acceptable salt or stereoisomer thereof.

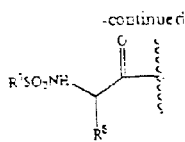

1. A compound of the following formula:

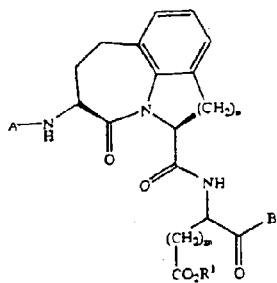

wherein:

n is 1 or 2;
m is 1 or 2;
A is $R^2CO-$, $R^3-O-CO-$, or $R^4SO_2-$,
or a group of the formula:

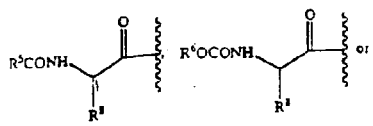

$R^1$ is a hydrogen atom, alkyl or phenylalkyl;
$R^2$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;
$R^3$ is alkyl, cycloalkyl, (cycloalkyl)alkyl, phenylalkyl, or (mono- or di-substituted phenyl)alkyl;
$R^4$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;
$R^5$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;
$R^6$ is alkyl, cycloalkyl, (cycloalkyl)alkyl, phenylalkyl, or (mono- or di-substituted phenyl)alkyl;
$R^7$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl; and
$R^8$ is an amino acid side chain of a naturally occurring α-amino acid or a non-protein α-amino acid; and B is a hydrogen atom, a deuterium atom, alkyl, cycloalkyl, (cycloalkyl)alkyl, phenyl, phenylalkyl, substituted phenyl, (mono- or di-substituted phenyl)alkyl, five- or six-membered heteroaryl, (five- or six-membered heteroaryl)alkyl, or halomethyl;

a group of the formula:

$-CH_2XR^9$;

a group of the formula:

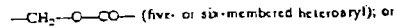

a group of the formula:

$-CH_2-O-PO-(R^{10})R^{11}$;

$R^9$ is phenyl, substituted phenyl, phenylalkyl, (mono- or di-substituted phenyl)alkyl five- or six-membered heteroaryl, or (five- or six-membered heteroaryl)alkyl; and X is an oxygen or a sulfur atom; and
$R^{10}$ and $R^{11}$ are independently alkyl, cycloalkyl, phenyl, substituted phenyl, phenylalkyl or (mono- or di-substituted phenyl)alkyl;

or a pharmaceutically-acceptable salt thereof.

Fig. 15(a)

1. A compound of the following formula:

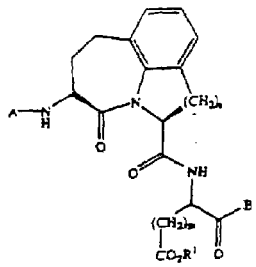

wherein:
n is 1 or 2;
m is 1 or 2;
A is $R^2CO-$, $R^3-O-CO-$, or $R^4SO_2-$, or a group of the formula:

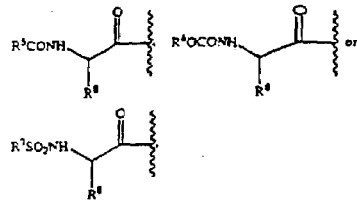

$R^1$ is a hydrogen atom, alkyl or phenylalkyl.

$R^2$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;

$R^3$ is alkyl, cycloalkyl (cycloalkyl)alkyl, phenylalkyl, or (mono- or di-substituted phenyl)alkyl;

$R^4$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;

$R^5$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;

$R^6$ is alkyl, cycloalkyl, (cycloalkyl)alkyl, phenylalkyl or (mono- or di-substituted phenyl)alkyl;

$R^7$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl; and $R^8$ is an amino acid side chain of a naturally occurring α-amino acid or a non-protein α-amino acid; and B is a hydrogen atom, a deuterium atom, alkyl, cycloalkyl, (cycloalkyl)alkyl, phenyl, phenylalkyl, substituted phenyl, (mono- or di-substituted phenyl)alkyl, five- or six-membered heteroaryl, (five- or six-membered heteroaryl)alkyl, or halomethyl;

a group of the formula:

a group of the formula:

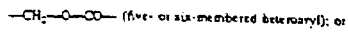

a group of the formula:

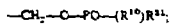

$R^9$ is phenyl, substituted phenyl, phenylalkyl, (mono- or di-substituted phenyl)alkyl, five- or six-membered heteroaryl, or (five- or six-membered heteroaryl)alkyl; and X is an oxygen or a sulfur atom; and $R^{10}$ and $R^{11}$ are independently alkyl, cycloalkyl phenyl, substituted phenyl, phenylalkyl, or (mono- or di-substituted phenyl)alkyl;

or a pharmaceutically-acceptable salt thereof.

Fig. 15(b)

| | |
|---|---|
| 1 | (2S-cis)-[5-Benzyloxycarbonylamino-1,2,4,5,6,7-hexahydro-4-oxoazepino[3,2,1-hi]indole-2-carbonyl)amino]-4-oxobutanoic acid tert-butyl ester semicarbazone |
| 2 | (2-cis)-[5-Benzyloxycarbonylamino-1,2,4,5,6,7-hexahydro-4-oxoazepino[3,2,1-hi]indole-2-carbonyl)-amino]-4-oxo-butanoic acid semicarbazone |
| 3 | (2S-cis)-5-[Benzyloxycarbonylamino-1,2,4,5,6,7-hexahydro-4-oxoazepino[3,2,1-hi]indole-2-carbonyl)amino]-4-oxo-butanoic acid |
| 4 | (2S-cis)-[5-Amino-1,2,3,4,5,6,7-hexahydro-4-Oxoazepino[3,2,1-hi]indole-2-carbonyl)-amino]-4-oxo-butanoic acid tert-butyl ester semicarbazone |
| 5 | (2S-cis)-[5-(N-Acetyl-(S)-aspartyl-β-tert-butyl ester)-amino-1,2,3,4,5,6,7-hexahydro-4-oxoazepino[3,2,1-hi]indole-2-carbonyl)-amino]-4-oxo-butanoic acid tert-butyl ester semicarbazone |
| 6 | (2S-cis)-[5-(N-Acetyl-(S)-aspartyl)amino-1,2,3,4,5,6,7-hexahydro-4-oxoazepino[3,2,1-hi]indole-2-carbonyl)-amino]-4-oxo-butanoic acid semicarbazone |
| 7 | (2S-cis)-[5-(N-Acetyl-(S)-aspartyl)amino-1,2,3,4,5,6,7-hexahydro-4-oxoazepino[3,2,1-hi]indole-2-carbonyl)-amino]-4-oxo-butanoic acid |
| 8 | (2S-cis)-[5-Succinylamino-1,2,3,4,5,6,7-hexahydro-4-oxoazepino[3,2,1-hi]indole-2-carbonyl)-amino]-4-oxo-butanoic acid tert-butyl ester Semicarbazone |
| 9 | (2S-cis)-[5-Succinylamino-1,2,3,4,5,6,7-hexahydro-4-oxoazepino[3,2,1-hi]indole-2-carbonyl)-amino]-4-oxo-butanoic acid semicarbazone |
| 10 | (2S-cis)-[5-Succinylamino-1,2,3,4,5,6,7-hexahydro-4-oxoazepino[3,2,1-hi]indole-2-carbonyl)-amino]-4-oxo-butanoic acid |
| 11 | (2S-cis)-[5-(N-Benzyloxycarbonyl-(S)-aspartyl)-Θ-tert-butyl ester)amino-1,2,3,4,5,6,7-hexahydro-4-oxoazepino[3,2,1-hi]indole-2-carbonyl)-amino]-4-oxo-butanoic acid tert-butyl ester semicarbazone |
| 12 | (2S-cis)-[5-(N-Benzyloxycarbonyl-(S)-aspartyl)amino-1,2,3,4,5,6,7-hexahydro-4-oxoazepino[3,2,1-hi]indole-2-carbonyl)-amino]-4-oxo-butanoic acid semicarbazone |
| 13 | (2S-cis)-[5-(N-Benzyloxycarbonyl-(S)-aspartyl)amino-1,2,3,4,5,6,7-hexahydro-4-oxoazepino[3,2,1-hi]indole-2-carbonyl)-amino]-4-oxo-butanoic acid |

Fig. 15(c)

| | |
|---|---|
| 14 | (2S-cis)-[5-Dihydrocinnamylamino-1,2,3,4,5,6,7-hexahydro-4-oxoazepino[3,2,1-hi]indole-2-carbonyl)-amino]-4-oxo-butanoic acid tert-butyl ester semicarbazone |
| 15 | (2S-cis)-[5-Dihydrocinnamylamino-1,2,3,4,5,6,7-hexahydro-4-oxoazepino[3,2,1-hi]indole-2-carbonyl)-amino]-4-oxo-butanoic acid semicarbazone |
| 16 | (2S-cis)-[5-Dihydrocinnamylamino-1,2,3,4,5,6,7-hexahydro-4-oxoazepino[3,2,1-hi]indole-2-carbonyl)-amino]-4-oxo-butanoic acid tert-butyl ester |
| 17 | (2S-cis)-[5-Acetylamino-1,2,3,4,5,6,7-hexahydro-4-oxoazepino[3,2,1-hi]indole-2-carbonyl)-amino]-4-oxo-butanoic acid tert-butyl ester semicarbazone |
| 18 | (2S-cis)-[5-Acetylamino-1,2,3,4,5,6,7-hexahydro-4-oxoazepino[3,2,1-hi]indole-2-carbonyl)-amino]-4-oxo-butanoic acid semicarbazone |
| 19 | (2S-cis)-[5-Acetylamino-1,2,3,4,5,6,7-hexahydro-4-oxoazepino[3,2,1-hi]indole-2-carbonyl)-amino]-4-oxo-butanoic acid |
| 20 | (2S-cis)-[5-(1-Naphthoyl)amino-1,2,3,4,5,6,7-hexahydro-4-oxoazepino[3,2,1-hi]indole-2-carbonyl)-amino]-4-oxo-butanoic acid tert-butyl ester semicarbazone |
| 21 | (2S-cis)-[5-(1-Naphthoyl)amino-1,2,3,4,5,6,7-hexahydro-4-oxoazepino[3,2,1-hi]indole-2-carbonyl)-amino]-4-oxo-butanoic acid semicarbazone |
| 22 | (2S-cis)-[5-(1-Naphthoyl)amino-1,2,3,4,5,6,7-hexahydro-4-oxoazepino[3,2,1-hi]indole-2-carbonyl)-amino]-4-oxo-butanoic acid |
| 23 | (2S-cis)-[5-Benzoylamino-1,2,3,4,5,6,7-hexahydro-4-oxoazepino[3,2,1-hi]indole-2-carbonyl)-amino]-4-oxo-butanoic acid tert-butyl ester semicarbazone |
| 24 | (2S-cis)-[5-Benzoylamino-1,2,3,4,5,6,7-hexahydro-4-oxoazepino[3,2,1-hi]indole-2-carbonyl)-amino]-4-oxo-butanoic acid semicarbazone |
| 25 | (2S-cis)-[5-Benzoylamino-1,2,3,4,5,6,7-hexahydro-4-oxoazepino[3,2,1-hi]indole-2-carbonyl)-amino]-4-oxo-butanoic acid |
| 26 | (3R,S-cis)-6-Benzyloxycarbonylamino-5-oxo-2,3,4,5,6,7,8-hexahydro-1H-azepino[3,2,1-hi]quinoline-3-carbonyl)-amino]-4-oxo-butanoic acid tert-butyl ester semicarbazone |
| 27 | (3R,S-cis)-6-Benzyloxycarbonylamino-5-oxo-2,3,4,5,6,7,8-hexahydro-1H-azepino[3,2,1-hi]quinoline-3-carbonyl)-amino]-4-oxo-butanoic acid semicarbazone |

Fig. 15(d)

| 28 | (3R,S-cis)-6-Benzyloxycarbonylamino-5-oxo-2,3,4,5,6,7,8-hexahydro-1H-azepino[3,2,1-hi]quinoline-3-carbonyl)-amino]-4-oxo-butanoic acid |
|---|---|
| 29 | 3{(2S-cis)-[5-Benzyloxycarbonylamino-1,2,3,4,5,6,7,-hexahydro-4-oxoazepino[3,2,1-hi]indole-2-carbonyl)-amino]}-5-fluoro-4-hydroxy-pentanoic acid tert-butyl ester |
| 30 | 3{(2S-cis)-[5-Benzyloxycarbonylamino-1,2,3,4,5,6,7,-hexahydro-4-oxoazepino[3,2,1-hi]indole-2-carbonyl)-amino]}-5-fluoro-4-oxo-pentanoic acid tert-butyl ester |
| 31 | 3{(2S-cis)-[5-Benzyloxycarbonylamino-1,2,3,4,5,6,7,-hexahydro-4-oxoazepino[3,2,1-hi]indole-2-carbonyl)-amino]}-5-fluoro-4-oxo-pentanoic acid |
| 32 | 3{(2S-cis)-[5-Benzyloxycarbonylamino-1,2,3,4,5,6,7,-hexahydro-4-oxoazepino[3,2,1-hi]indole-2-carbonyl)-amino]}-5-bromo-4-oxo-pentanoic acid, tert-butyl ester |
| 34 | 3{(2S-cis)-[5-Benzyloxycarbonylamino-1,2,3,4,5,6,7,-hexahydro-4-oxoazepino[3,2,1-hi]indole-2-carbonyl)-amino]}-5-(diphenylphosphinyl)oxy-4-oxo-pentanoic acid, tert-butyl ester |
| 35 | 3{(2S-cis)-[5-Benzyloxycarbonylamino-1,2,3,4,5,6,7,-hexahydro-4-oxoazepino[3,2,1-hi]indole-2-carbonyl]-amino]}-5-(diphenylphosphinyl)oxy-4-oxo-pentanoic acid |

Fig. 15(e)

compounds of the Formula 1:

FORMULA 1

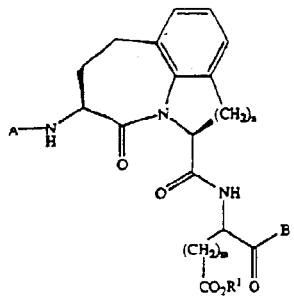

wherein:
n is 1 or 2;
m is 1 or 2;
A is $R^2CO-$, $R^3-O-CO-$, or $R^4SO_2-$;
a group of the formula:

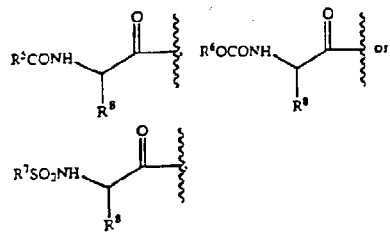

further wherein:
$R^1$ is a hydrogen atom, alkyl or phenylalkyl;
$R^2$ is alkyl, cycloalkyl, (cycloalkyl)alkyl, phenyl, phenylalkyl, substituted phenyl, (substituted phenyl)alkyl, heteroaryl, or (heteroaryl)alkyl;
$R^3$ is alkyl, cycloalkyl, (cycloalkyl)alkyl, phenylalkyl, or (substituted phenyl)alkyl;
$R^4$ is alkyl, cycloalkyl, (cycloalkyl)alkyl, phenyl, phenylalkyl, substituted phenyl, (substituted phenyl)alkyl, heteroaryl, or (heteroaryl)alkyl;
$R^5$ is alkyl, cycloalkyl, (cycloalkyl)alkyl, phenyl, phenylalkyl, substituted phenyl, (substituted phenyl)alkyl, heteroaryl, or (heteroaryl)alkyl;
$R^6$ is alkyl, cycloalkyl, (cycloalkyl)alkyl, phenylalkyl, or (substituted phenyl)alkyl;
$R^7$ is alkyl, cycloalkyl, (cycloalkyl)alkyl, phenyl, phenylalkyl, substituted phenyl, (substituted phenyl)alkyl, heteroaryl, or (heteroaryl)alkyl;
$R^8$ is an amino acid side chain chosen from the group consisting of natural and unnatural amino acids;
B is a hydrogen atom, a deuterium atom, alkyl, cycloalkyl, (cycloalkyl)alkyl, phenyl, phenylalkyl, (substituted)phenyl, (substituted)phenylalkyl, heteroaryl, (heteroaryl)alkyl, or halomethyl;

a group of the formula $-CH_2XR^9$;

wherein $R^9$ is phenyl, phenylalkyl, substituted phenyl, (substituted phenyl)alkyl, heteroaryl, or (heteroaryl)alkyl; and X is an oxygen or a sulfur atom;
a group of the formula:

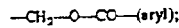

a group of the formula:

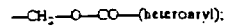

a group of the formula:

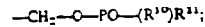

wherein $R^{10}$ and $R^{11}$ are independently selected from a group consisting of alkyl, cycloalkyl, phenyl, substituted phenyl, phenylalkyl, and (substituted phenyl)alkyl;
or a pharmaceutically-acceptable salt thereof.

Fig. 15(f)

1. A compound of the following formula:

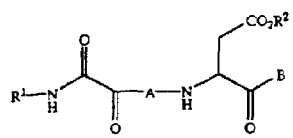

Formula I wherein:

A is a natural or unnatural amino acid of Formula IIa–i:

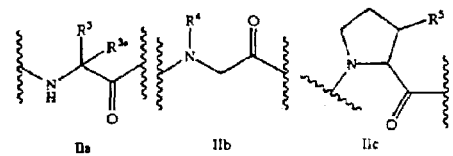

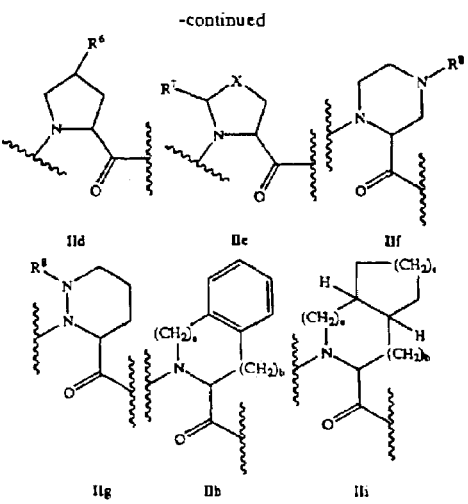

B is a hydrogen atom, a deuterium atom, $C_{1-10}$ straight chain or branched alkyl, cycloalkyl, phenyl, substituted phenyl, naphthyl, substituted naphthyl, 2-benzoxazolyl, substituted 2-oxazolyl, $(CH_2)_n$ cycloalkyl, $(CH_2)_n$phenyl, $(CH_2)_n$(substituted phenyl), $(CH_2)_n$(1 or 2-naphthyl), $(CH_2)_n$(heteroaryl), halomethyl, $CO_2R^{12}$, $CONR^{13}R^{14}$, $CH_2ZR^{15}$,

Fig. 16(a)

CH₂OCO(aryl), CH₂OCO(heteroaryl), or CH₂OPO(R³⁶)R³⁷, where Z is an oxygen or a sulfur atom, or B is a group of the Formula IIIa–c:

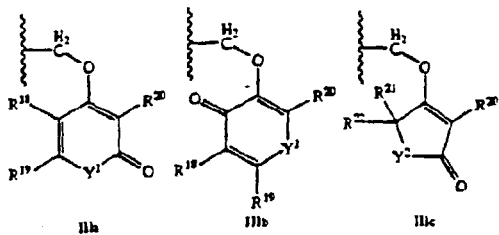

IIb  IIIb  IIIc

R¹ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, (heteroaryl)alkyl, R¹ᵃ(R¹ᵇ)N, R¹ᶜO, 2-phenoxyphenyl or 2- or 3- benzylphenyl; and R² is hydrogen, lower alkyl, cycloalkyl, (cycloalkyl)alkyl, phenylalkyl, or substituted phenylalkyl; and wherein:

R¹ᵃ and R¹ᵇ are independently hydrogen, alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, or (heteroaryl)alkyl, with the proviso that R¹ᵃ and R¹ᵇ cannot both be hydrogen;

R¹ᶜ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, or (heteroaryl)alkyl;

R³ is C₁₋₆ lower alkyl, cycloalkyl, phenyl, substituted phenyl, (CH₂)ₙNH₂, (CH₂)ₙNHCOR⁹, (CH₂)ₙN(C=NH)NH₂, (CH₂)ₙCO₂R⁸, (CH₂)ₙOR¹⁰, (CH₂)ₙSR¹¹,(CH₂)ₙcycloalkyl,(CH₂)ₙphenyl, (CH₂)ₙ(substituted phenyl), (CH₂)ₙ(1 or 2-naphthyl) or (CH₂)ₙ(heteroaryl), wherein heteroaryl includes pyridyl, thienyl, furyl, thiazolyl, imidazolyl, pyrazolyl, isoxazolyl, pyrazinyl, pyrimidyl, triazinyl, tetrazolyl, and indolyl;

R³ᵃ is hydrogen or methyl, or R³ and R³ᵃ taken together are —(CH₂)d— where d is an integer from 2 to 6;

R⁴ is phenyl, substituted phenyl, (CH₂)ₘphenyl, (CH₂)ₘ(substituted phenyl), cycloalkyl, or benzofused cycloalkyl;

R⁵ is hydrogen, lower alkyl, cycloalkyl, phenyl, substituted phenyl, (CH₂)ₙcycloalkyl, (CH₂)ₙphenyl, (CH₂)ₙ(substituted phenyl), or (CH₂)ₙ(1 or 2-naphthyl);

R⁶ is hydrogen, fluorine, oxo, lower alkyl, cycloalkyl, phenyl, substituted phenyl, naphthyl, (CH₂)ₙcycloalkyl, (CH₂)ₙphenyl, (CH₂)ₙ(substituted phenyl), (CH₂)ₙ(1 or 2-naphthyl), OR¹⁰, SR¹¹ or NHCOR⁹;

R⁷ is hydrogen, oxo, lower alkyl, cycloalkyl, phenyl, substituted phenyl, naphthyl, (CH₂)ₙcycloalkyl, (CH₂)ₙphenyl, (CH₂)ₙ(substituted phenyl), or (CH₂)ₙ(1 or 2-naphthyl);

R⁸ is lower alkyl, cycloalkyl, (CH₂)ₙcycloalkyl, (CH₂)ₙphenyl, (CH₂)ₙ(substituted phenyl), (CH₂)ₙ(1 or 2-naphthyl), or COR⁹;

R⁹ is hydrogen, lower alkyl, cycloalkyl, phenyl, substituted phenyl, naphthyl, (CH₂)ₙcycloalkyl, (CH₂)ₙphenyl, (CH₂)ₙ(substituted phenyl), (CH₂)ₙ(1 or 2-naphthyl), OR²², or NR¹³R¹⁴;

R¹⁰ is hydrogen, lower alkyl, cycloalkyl, phenyl, substituted phenyl, naphthyl, (CH₂)ₙcycloalkyl, (CH₂)ₙphenyl, (CH₂)ₙ(substituted phenyl), or (CH₂)ₙ(1 or 2-naphthyl);

R¹¹ is lower alkyl, cycloalkyl, phenyl, substituted phenyl, naphthyl, (CH₂)ₙcycloalkyl, (CH₂)ₙphenyl, (CH₂)ₙ(substituted phenyl), or (CH₂)ₙ(1 or 2-naphthyl);

R¹² is lower alkyl, cycloalkyl, (CH₂)ₙcycloalkyl, (CH₂)ₙphenyl, (CH₂)ₙ(substituted phenyl), or (CH₂)ₙ(1 or 2-naphthyl);

R¹³ is hydrogen, lower alkyl, cycloalkyl, phenyl, substituted phenyl, naphthyl, substituted naphthyl, (CH₂)ₙcycloalkyl, (CH₂)ₙphenyl, (CH₂)ₙ(substituted phenyl), or (CH₂)ₙ(1 or 2-naphthyl);

R¹⁴ is hydrogen or lower alkyl;

or R¹³ and R¹⁴ taken together form a five to seven membered carbocyclic or heterocyclic ring, such as morpholine, or N-substituted piperazine;

R¹⁵ is phenyl, substituted phenyl, naphthyl, substituted naphthyl, heteroaryl, (CH₂)ₙphenyl, (CH₂)ₙ(substituted phenyl), (CH₂)ₙ(1 or 2-naphthyl), or (CH₂)ₙ(heteroaryl);

R¹⁶ and R¹⁷ are independently lower alkyl, cycloalkyl, phenyl, substituted phenyl, naphthyl, phenylalkyl, substituted phenylalkyl, or (cycloalkyl)alkyl;

R¹⁸ and R¹⁹ are independently hydrogen, alkyl, phenyl, substituted phenyl, (CH₂)ₙphenyl, (CH₂)ₙ(substituted phenyl), or R¹⁸ and R¹⁹ taken together are —(CH=CH)₂—;

R²⁰ is hydrogen, alkyl, phenyl, substituted phenyl, (CH₂)ₙphenyl, (CH₂)ₙ(substituted phenyl);

R²¹, R²² and R²³ are independently hydrogen, or alkyl;

X is CH₂, (CH₂)₂, (CH₂)₃, or S;

Y¹ is O or NR²³;

Y² is CH₂, O, or NR²³;

a is 0 or 1 and b is 1 or 2, provided that when a is 1 then b is 1;

c is 1 or 2, provided that when c is 1 then a is 0 and b is 1;

m is 1 or 2; and n is 1, 2, 3 or 4;

or a pharmaceutically acceptable salt thereof.

2. The compound of claim 1 wherein A is

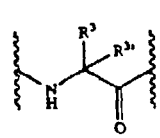

IIa

3. The compound of claim 2 wherein

R³ is lower alkyl, cycloalkyl, phenyl, substituted phenyl, (CH₂)ₙNH₂, (CH₂)ₙOR¹⁰, (CH₂)ₙSR¹¹, (CH₂)ₙcycloalkyl, (CH₂)ₙphenyl, (CH₂)ₙ(substituted phenyl), or (CH₂)ₙ(1 or 2-naphthyl); and R³ᵃ is hydrogen.

Fig. 16(b)

4. The compound of claim 1 wherein A is

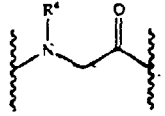

IIIb

5. The compound of claim 4 wherein R⁴ is phenyl, substituted phenyl, (CH₂)$_m$phenyl, (CH₂)$_m$(substituted phenyl), cycloalkyl, or 2-indanyl.

6. The compound of claim 1 wherein A is

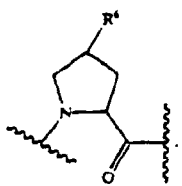

IId

7. The compound of claim 6 wherein R⁶ is hydrogen, fluorine, cycloalkyl, phenyl, substituted phenyl, naphthyl, (CH₂)$_n$cycloalkyl, (CH₂)$_n$phenyl, (CH₂)$_n$(substituted phenyl), (CH₂)$_n$(1 or 2-naphthyl), OR$^{20}$, or SR$^{22}$.

8. The compound of claim 1 wherein A is

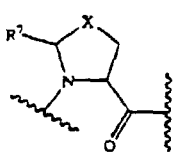

IIe

9. The compound of claim 8 wherein

R⁷ is hydrogen, oxo, cycloalkyl, phenyl, substituted phenyl, or naphthyl; and

X=CH₂, (CH₂)₂, (CH₂)₃, or S.

10. The compound of claim 1 wherein A is

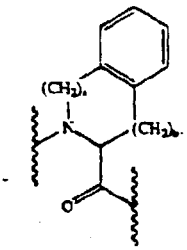

IIf

11. The compound of claim 10 wherein a is 0.

12. The compound of claim 1 wherein B is hydrogen, 2-benzoxazolyl, substituted 2-oxazolyl, CH₂ZR$^{15}$, CH₂OCO(aryl), or CH₂OPO(R$^{16}$)R$^{17}$, and wherein Z is an oxygen or a sulfur atom.

13. The compound of claim 1 wherein B is

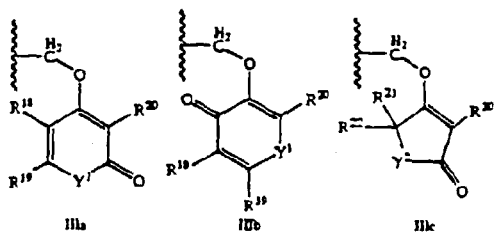

IIIa  IIIb  IIIc

14. The compound of claim 13 wherein R$^{18}$ and R$^{19}$ are independently hydrogen, alkyl, or phenyl, or wherein R$^{18}$ and R$^{19}$ taken together are —(CH=CH)₂—.

15. The compound of claim 1 wherein R¹ is phenyl, substituted phenyl, phenylalkyl, substituted phenylalkyl, naphthyl, substituted naphthyl, (1 or 2 naphthyl)alkyl, heteroaryl, or (heteroaryl)alkyl.

16. The compound of claim 3 wherein R³ is methyl, isopropyl, isobutyl, cyclohexylmethyl, t-butyl, cyclohexyl or phenyl.

17. The compound of claim 16 wherein B is CH₂O(2,3,5,6-tetrafluorophenyl).

18. The compound of claim 1 wherein R¹ is 1-naphthyl and A is valine.

19. The compound of claim 1 wherein R¹ is 1-naphthyl and B is CH₂O(2,3,5,6-tetrafluorophenyl).

20. A composition comprising a compound of claim 1 in combination with a pharmaceutically acceptable carrier.

Fig. 16(c)

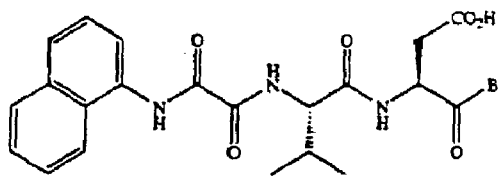

| Ex. | B | Formula | MW | MS(ES) pos. | neg. |
|---|---|---|---|---|---|
| 5 | CH₂O(2,6-diF—Ph) | C₂₈H₂₇F₂N₃O₇ | 555.53 | 578(M + Na) | 554(M − H) |
| 6 | CH₂O(2,4,6-triF—Ph) | C₂₈H₂₆F₃N₃O₇ | 573.52 | 596(M + Na) | 572(M − H) |
| 7 | CH₂O(2,3,5,6-tetraF—Ph) | C₂₈H₂₅F₄N₃O₇ | 591.51 | 614(M + Na) | 590(M − H) |
| 8 | CH₂O(6-Me-2-pyron-4-yl) | C₂₈H₂₉N₃O₉ | 551.55 | 574(M + Na) | 550(M − H) |
| 9 | CH₂O(2-Ph-5,6-benzopyran-4-on-3-yl) | C₃₇H₃₃N₃O₉ | 663.68 | 686(M + Na) | 662(M − H) |
| 10 | CH₂OPO(Me)Ph | C₂₉H₃₂N₃O₉P | 581.56 | 582(M + H) 604(M + Na) | 580(M − H) 694(M + TFA) |
| 11 | CH₂OPOPh₂ | C₃₄H₃₄N₃O₉P | 643.63 | 666(M + Na) | 642(M − H) |
| 12 | CH₂O(2-CF₃-pyrimidin-4-yl) | C₂₇H₂₈F₃N₅O₇ | 589.53 | 612(M + Na) | 588(M − H) |
| 13 | CH₂O(5-CO₂Me-isoxazol-3-yl) | C₂₇H₂₈N₄O₁₀ | 568.54 | 591(M + Na) | 567(M − H) |
| 14 | CH₂OPO(Me)(1-naphthyl) | C₃₃H₃₄N₃O₉P | 631.62 | 654(M + Na) | 630(M − H) 744(M + TFA) |

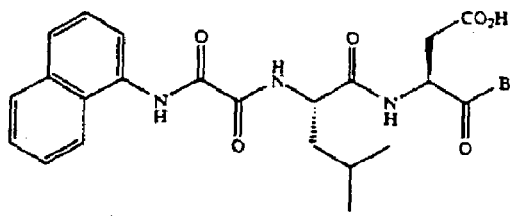

| Ex. | B | Formula | MW | MS(ES) pos. | neg. |
|---|---|---|---|---|---|
| 16 | CH₂OCO(2,6-diCl—Ph) | C₃₀H₂₉Cl₂N₃O₈ | 630.48 | 652/654(M + Na) | 628/630(M − H) |
| 17 | CH₂O(2,4,6-triF—Ph) | C₂₉H₂₈F₃N₃O₇ | 587.55 | 610(M + Na) | 586(M − H) |
| 18 | CH₂O(2,3,5,6-tetraF—Ph) | C₂₉H₂₇F₄N₃O₇ | 605.54 | 628(M + Na) | 604(M − H) |
| 19 | CH₂OPO(Me)Ph | C₃₀H₃₄N₃O₉P | 595.59 | 596(M + H) 618(M + Na) | 594(M − H) 708(M + TFA) |

Fig. 16(d)

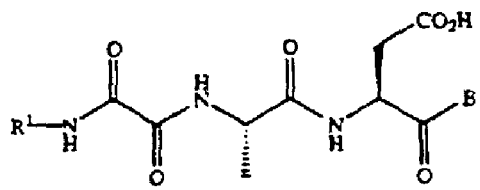

| Ex | R¹ | B | Formula | MW | MS(ES) pos. | neg. |
|---|---|---|---|---|---|---|
| 20 | (2-Ph)Ph | CH₂O(2-F—Ph) | C₂₈H₂₆FN₃O₇ | 535.53 | 558(M + Na) | |
| 21 | (2-Ph)Ph | CH₂OCO(2,6-di-Cl—Ph) | C₂₉H₂₅Cl₂N₃O₈ | 614.44 | 652/654(M + K) | 534(M − H) 612/614(M − H) |
| 22 | (2-Ph)Ph | CH₂OPOPh₂ | C₃₄H₃₂N₃O₈P | 641.61 | 664(M + Na) | 640(M − H) |
| 23 | (2-t-Bu)Ph | CH₂O(2-F—Ph) | C₂₆H₃₀FN₃O₇ | 515.54 | 680(M + K) 516(M + H) 538(M + Na) | 514(M − H) |
| 24 | (2-t-Bu)Ph | CH₂OPOPh₂ | C₃₂H₃₆N₃O₈P | 621.63 | 554(M + K) 644(M + Na) | 620(M − H) |
| 25 | 1-naphthyl-CH₂ | CH₂O(2,3,5,6-tetra-F—Ph) | C₂₇H₂₃F₄N₃O₇ | 577.48 | 666(M + K) 600(M + Na) | 576(M − H) |
| 26 | 1-naphthyl-CH₂ | CH₂OCO(2,6-di-Cl—Ph) | C₂₈H₂₅Cl₂N₃O₈ | 602.42 | 616(M + K) 624/626(M + Na) 640/642(M + K) | 600/602(M − H) |
| 27 | 1-naphthyl-CH₂ | CH₂OPOPh₂ | C₃₃H₃₂N₃O₈P | 629.60 | 652(M + Na) 668(M + K) | 714/716(M + TFA) 628(M − H) |

Fig. 16(e)

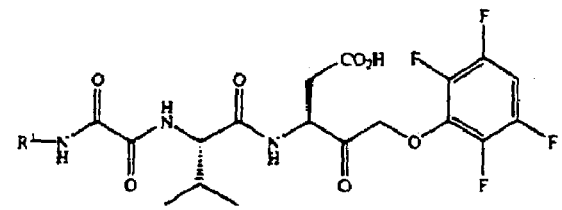

| Ex. | R¹ | Formula | MW | MS(ESI) pos. | MS(ESI) neg. |
|---|---|---|---|---|---|
| 29 | PhCH₂ | C₂₅H₂₅F₄N₃O₇ | 555.48 | 556(M + H)<br>578(M + Na) | 554(M − H) |
| 30 | Ph(CH₂)₂ | C₂₆H₂₇F₄N₃O₇ | 569.51 | 592(M + Na) | 568(M − H) |
| 31 | Ph₂CH | C₃₁H₂₉F₄N₃O₇ | 631.58 | 654(M + Na) | 630(M − H) |
| 32 | Ph | C₂₄H₂₃F₄N₃O₇ | 541.46 | 564(M + Na) | 540(M − H) |
| 33 | (2-Ph)Ph | C₃₀H₂₇F₄N₃O₇ | 617.55 | 640(M + Na) | 616(M − H)<br>730(M + TFA) |
| 34 | (2-PhCH₂)Ph | C₃₁H₂₉F₄N₃O₇ | 631.58 | 654(M + Na) | 630(M − H) |
| 35 | (2-PhO)Ph | C₃₀H₂₇F₄N₃O₈ | 633.55 | 634(M + H)<br>656(M + Na) | 632(M − H) |
| 36 | 4-Cl-1-naphthyl | C₂₈H₂₄ClF₄N₃O₇ | 625.96 | 648/650(M + Na) | 624/626(M − H) |
| 37 | 2-anthryl | C₃₂H₂₇F₄N₃O₇ | 641.57 | 642(M + H) | 640(M − H) |
| 38 | 2-benzimidazolyl | C₂₅H₂₃F₄N₅O₇ | 581.48 | 582(M + H)<br>604(M + Na) | 580(M − H) |
| 39 | 1-adamantanyl | C₂₈H₃₃F₄N₃O₇ | 599.58 | 600(M + H) | 598(M − H) |
| 40 | (2-F)Ph | C₂₄H₂₂F₅N₃O₇ | 559.45 | 582(M + Na) | 558(M − H)<br>672(M + TFA) |
| 41 | (4-F)Ph | C₂₄H₂₂F₅N₃O₇ | 559.45 | 582(M + Na) | 558(M − H)<br>672(M + TFA) |
| 42 | (2-CF₃)Ph | C₂₅H₂₂F₇N₃O₇ | 609.45 | 632(M + Na) | 608(M − H)<br>722(M + TFA) |
| 43 | (2-t-Bu)Ph | C₂₈H₃₁F₄N₃O₇ | 597.56 | 620(M + Na) | 596(M − H)<br>710(M + TFA) |
| 44 | (4-n-heptyl)Ph | C₃₁H₃₇F₄N₃O₇ | 639.64 | 662(M + Na) | 638(M − H) |
| 45 | (2-CH₃O)Ph | C₂₅H₂₅F₄N₃O₈ | 571.48 | 594(M + Na) | 570(M − H) |
| 46 | (2-PhO)Ph | C₃₀H₂₇F₄N₃O₈ | 633.55 | 656(M + Na) | 632(M − H)<br>746(M + TFA) |
| 47 | 2-naphthyl | C₂₈H₂₅F₄N₃O₇ | 591.51 | 614(M + Na) | 590(M − H) |
| 48 | 5,6,7,8-tetrahydro-1-naphthyl | C₂₈H₂₉F₄N₃O₇ | 595.55 | 618(M + Na) | 594(M − H) |
| 49 | 1-anthryl | C₃₂H₂₇F₄N₃O₇ | 641.57 | 664(M + Na) | 640(M − H) |
| 50 | 2-pyridinyl | C₂₃H₂₂F₄N₄O₇ | 542.44 | 543(M + H) | 541(M − H) |
| 51 | 4-pyridinyl | C₂₃H₂₂F₄N₄O₇ | 542.44 | 543(M + H) | 541(M − H) |
| 52 | 2,3,5,6-tetrafluoro-4-pyridinyl | C₂₃H₁₈F₈N₄O₇ | 614.40 | 615(M + H) | 613(M − H) |
| 53 | 2-pyrazinyl | C₂₂H₂₁F₄N₅O₇ | 543.43 | 544(M + H) | 542(M − H) |
| 54 | 1,2,3,4-tetrahydro-1-naphthyl | C₂₈H₂₉F₄N₃O₇ | 595.55 | 596(M + H)<br>618(M + Na)<br>634(M + K) | 594(M − H)<br>708(M + TFA) |
| 55 | (2-Cl)Ph | C₂₄H₂₂ClF₄N₃O₇ | 575.90 | 598/600(M + Na) | 574/576(M − H) |
| 56 | (2-Br)Ph | C₂₄H₂₂BrF₄N₃O₇ | 620.35 | 644/642(M + Na) | 620/618(M − H)<br>734/732(M + TFA) |
| 57 | (2-I)Ph | C₂₄H₂₂F₄IN₃O₇ | 667.35 | 690(M + Na)<br>706(M + K) | 666(M − H)<br>780(M + TFA) |
| 58 | (2,6-di-F)Ph | C₂₄H₂₂F₆N₃O₇ | 577.44 | 600(M + Na) | 576(M − H)<br>690(M + TFA) |
| 59 | (2,5-di-t-Bu)Ph | C₃₂H₃₉F₄N₃O₇ | 653.67 | 654(M + H)<br>676(M + Na)<br>692(M + K) | 652(M − H)<br>688(M + Cl)<br>766(M + TFA) |

Fig. 16(f)

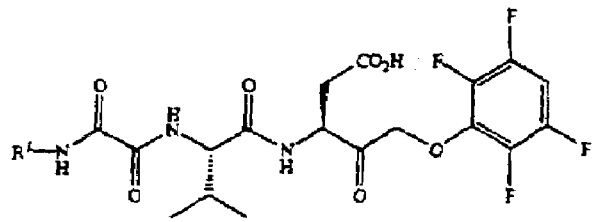

| Ex. | R¹ | Formula | MW | MS(ES) pos. | neg. |
|---|---|---|---|---|---|
| 60 | 5-indanyl | $C_{27}H_{27}F_4N_3O_7$ | 581.52 | 604(M + Na) 620(M + K) | 580(M − H) 694(M + TFA) |
| 61 | (3,4,5-tri-MeO)PhCH₂ | $C_{28}H_{31}F_4N_3O_{10}$ | 645.56 | 646(M + H) 668(M + Na) 684(M + K) | 644(M − H) |
| 62 | methyl | $C_{19}H_{23}F_4N_3O_7$ | 479.36 | 502(M + Na) | 478(M − H) 592(M + TFA) |
| 63 | n-heptyl | $C_{25}H_{35}F_4N_3O_7$ | 565.55 | 566(M + Na) 602(M + K) | 562(M − H) 676(M + TFA) |
| 64 | t-octyl | $C_{26}H_{37}F_4N_3O_7$ | 577.57 | 600(M + Na) | 576(M − H) |
| 65 | cyclo-hexyl | $C_{24}H_{29}F_4N_3O_7$ | 547.50 | 548(M + H) 570(M + Na) 586(M + K) | 546(M − H) 660(M + TFA) |
| 66 | 5-Ph-3-pyrazolyl | $C_{27}H_{28}F_4N_5O_7$ | 607.52 | 630(M + Na) 646(M + K) | 606(M − H) |
| 67 | (2-F-4-I)Ph | $C_{24}H_{23}F_5IN_3O_7$ | 685.34 | 686(M + H) 708(M + Na) 724(M + K) | 684(M − H) 720(M + Cl) |
| 68 | (2,3,4,5-tetra-F)Ph | $C_{24}H_{19}F_8N_3O_7$ | 613.41 | 614(M + H) 636(M + Na) 652(M + K) | 612(M − H) 726(M + TFA) |
| 69 | (2,3,4,6-tetra-F)Ph | $C_{24}H_{19}F_8N_3O_7$ | 613.41 | 614(M + H) 636(M + Na) 652(M + K) | 612(M − H) 726(M + TFA) |
| 70 | (2,3,5,6-tetra-Cl)Ph | $C_{24}H_{19}Cl_4F_4N_3O_7$ | 679.23 | 700/702/704(M + Na) 716/718/720(M + K) | 676/678/680(M − H) 790/792/794(M + TFA) |
| 71 | (2,3,4,5,6-penta-F)Ph | $C_{24}H_{18}F_9N_3O_7$ | 631.40 | 654(M + Na) 670(M + K) | 630(M − H) 666(M + Cl) |
| 72 | Ph₂N | $C_{30}H_{28}F_4N_4O_7$ | 632.57 | 633(M + H) 655(M + Na) | 631(M − H) 745(M + TFA) |
| 73 | PHCH₂(Ph)N | $C_{31}H_{30}F_4N_4O_7$ | 646.55 | 647(M + H) 669(M + Na) 685(M + K) | 645(M − H) 681(M + Cl) |
| 74 | PhCH₂O | $C_{25}H_{25}F_4N_3O_7$ | 571.48 | 594(M + Na) | 570(M − H) 684(M + TFA) |

Fig. 16(g)

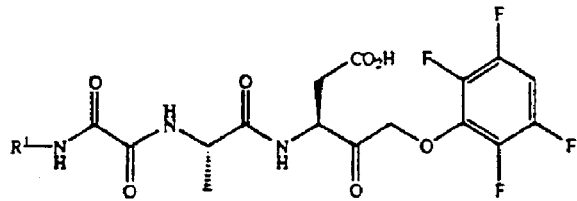

| Ex. | R¹ | Formula | MW | MS(ES) pos. | MS(ES) neg. |
|---|---|---|---|---|---|
| 76 | (2-CF₃)Ph | $C_{23}H_{19}F_7N_3O_7$ | 581.40 | 604(M + Na) | 580(M − H) |
| 77 | (2-Ph)Ph | $C_{28}H_{23}F_4N_3O_7$ | 589.50 | 612(M + Na) | 588(M − H) |
| 78 | (2-PhCH₂)Ph | $C_{29}H_{25}F_4N_3O_7$ | 603.53 | 604(M + H) | 602(M − H) |
| 79 | (2-PhO)Ph | $C_{28}H_{23}F_4N_3O_8$ | 605.50 | 628(M + Na) | 604(M − H) |
| 80 | (3-PhO)Ph | $C_{28}H_{23}F_4N_3O_8$ | 605.50 | 628(M + Na) | 604(M − H) |
| 81 | 5,6,7,8-tetrahydro-1-naphthyl | $C_{26}H_{25}F_4N_3O_7$ | 567.49 | 590(M + Na) | 566(M − H) |
| 82 | 1-naphthyl | $C_{26}H_{21}F_4N_3O_7$ | 563.46 | 586(M + Na) 608(M + K) | 562(M − H) |
| 83 | Ph | $C_{22}H_{19}F_4N_3O_7$ | 513.40 | 552(M + K) | 512(M − H) |
| 84 | (2,6-di-F)Ph | $C_{22}H_{17}F_6N_3O_7$ | 549.38 | 572(M + Na) | 548(M − H) 662(M + TFA) |
| 85 | (4-Ph)Ph | $C_{28}H_{23}F_4N_3O_7$ | 589.50 | — | 588(M − H) |
| 86 | (4-MeO)Ph | $C_{23}H_{21}F_4N_3O_8$ | 543.43 | 582(M + K) | 542(M − H) |
| 87 | Ph₂CH | $C_{29}H_{25}F_4N_3O_7$ | 603.53 | 642(M + K) | 602(M − H) |

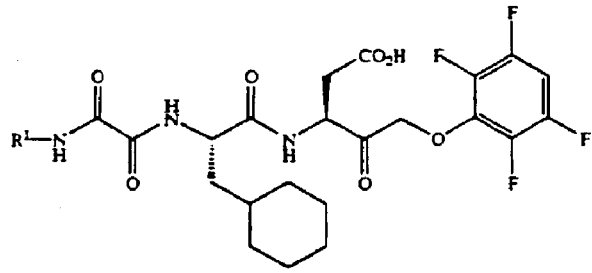

| Ex. | R¹ | Formula | MW | MS(ES) pos. | MS(ES) neg. |
|---|---|---|---|---|---|
| 89 | (2-Ph)Ph | $C_{34}H_{33}F_4N_3O_7$ | 671.64 | 672(M + H) 694(M + Na) | 670(M − H) 784(M + TFA) |
| 90 | (2-PhCH₂)Ph | $C_{35}H_{35}F_4N_3O_7$ | 685.67 | 708(M + Na) | 684(M − H) 798(M + TFA) |
| 91 | 1-naphthyl | $C_{32}H_{31}F_4N_3O_7$ | 645.61 | 668(M + Na) | 644(M − H) 758(M + TFA) |

Fig. 16(h)

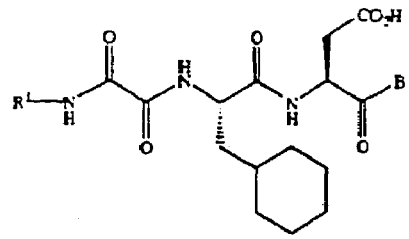

| Ex. | R¹ | B | Formula | MW | MS(ES) pos. | neg. |
|---|---|---|---|---|---|---|
| 93 | 5,6,7,8-tetrahydro-1-naphthyl | CH₂O(2,3,5,6-tetra-F-Ph) | C₃₂H₃₅F₄N₃O₇ | 649.64 | 672(M + Na) | 648(M − H) |
| 94 | 5,6,7,8-tetrahydro-1-naphthyl | CH₂OPO(Me)Ph | C₃₂H₄₂N₃O₈P | 639.68 | 662(M + Na) | 638(M − H), 752(M + TFA) |
| 95 | 5,6,7,8-tetrahydro-1-naphthyl | CH₂OPOPh₂ | C₃₈H₄₄N₃O₈P | 701.75 | 724(M + Na), 740(M + K) | 700(M − H) |
| 96 | (2-PhCH₂)Ph | CH₂OPO(Me)Ph | C₃₆H₄₂N₃O₈P | 675.72 | 698(M + Na), 714(M + K) | 674(M − H), 788(M + TFA) |
| 97 | (2-PhCH₂)Ph | CH₂OPOPh₂ | C₄₁H₄₄N₃O₈P | 737.79 | 760(M + Na), 776(M + K) | 736(M − H), 850(M + TFA) |
| 98 | (2-Ph)Ph | CH₂OPO(Me)Ph | C₃₅H₄₂N₃O₈P | 661.68 | 684(M + Na), 700(M + K) | 660(M − H), 774(M + TFA) |
| 99 | (2-Ph)Ph | CH₂OPOPh₂ | C₄₀H₄₀N₃O₈P | 723.75 | 746(M + Na), 762(M + K) | 722(M − H), 836(M + TFA) |

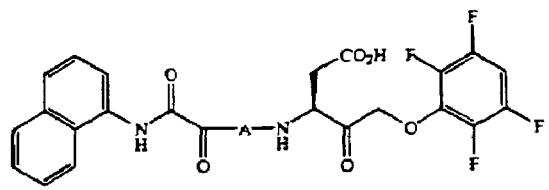

| Ex. | A | Formula | MW | MS(ES) pos. | neg. |
|---|---|---|---|---|---|
| 103 | norleucine | C₂₉H₂₇F₄N₃O₇ | 605.54 | 628(M + Na), 644(M + K) | 604(M − H), 640(M + Cl), 718(M + TFA) |
| 104 | (t-butyl)glycine | C₂₉H₂₇F₄N₃O₇ | 605.54 | 606(M + H), 628(M + Na), 644(M + K) | 604(M − H), 640(M + Cl), 718(M + TFA) |
| 105 | (t-butyl)alanine | C₃₀H₂₉F₄N₃O₇ | 619.57 | 620(M + H), 642(M + Na), 658(M + K) | 618(M − H), 732(M + TFA) |
| 106 | phenylglycine | C₃₁H₂₅F₄N₃O₇ | 625.53 | 626(M + H), 648(M + Na), 664(M + K) | 624(M − H), 660(M + Cl), 738(M + TFA) |
| 107 | phenylalanine | C₃₂H₂₇F₄N₃O₇ | 639.56 | 640(M + H), 662(M + Na), 678(M + K) | 638(M − H), 674(M + Cl), 712(M + TFA) |
| 108 | homophenylalanine | C₃₃H₂₉F₄N₃O₇ | 653.59 | 654(M + H), 676(M + Na), 692(M + K) | 652(M − H), 688(M + Cl), 766(M + TFA) |
| 109 | 1-aminocyclopentane carboxylic acid | C₂₉H₂₇F₄N₃O₇ | 603.53 | 626(M + Na), 642(M + K) | 602(M − H) |

Fig. 16(i)

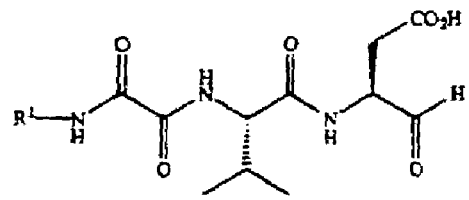

| Ex. | R¹ | Formula | MW | MS(ES) pos. | neg. |
|---|---|---|---|---|---|
| 114 | Ph | $C_{17}H_{21}N_3O_6$ | 363.37 | 386(M + Na) 402(M + K) | 362(M − H) |
| 115 | PhCH₂ | $C_{18}H_{23}N_3O_6$ | 377.40 | 400(M + Na) | 376(M − H) |
| 116 | Ph(CH₂)₂ | $C_{19}H_{25}N_3O_6$ | 391.42 | 414(M + Na) 430(M + K) | 390(M − H) 504(M + TFA) |
| 117 | (2-CF₃)Ph | $C_{18}H_{20}F_3N_3O_6$ | 431.37 | 454(M + Na) | 430(M − H) |
| 118 | (2-t-Bu)Ph | $C_{21}H_{30}N_3O_6$ | 419.48 | 442(M + Na) 458(M + K) | 418(M − H) 532(M + TFA) |
| 119 | (2-Ph)Ph | $C_{23}H_{25}N_3O_6$ | 439.47 | 462(M + Na) 478(M + K) | 438(M − H) 552(M + TFA) |
| 120 | (2-PhCH₂)Ph | $C_{24}H_{27}N_3O_6$ | 453.49 | 476(M + Na) 492(M + K) | 452(M − H) 566(M + TFA) |
| 121 | (2-PhO)Ph | $C_{23}H_{25}N_3O_7$ | 455.47 | 478(M + Na) 494(M + K) | 454(M − H) 568(M + TFA) |
| 122 | 2-naphthyl | $C_{23}H_{23}N_3O_6$ | 413.43 | 436(M + Na) 452(M + K) | 412(M − H) 526(M + TFA) |
| 123 | 1-naphthyl | $C_{21}H_{23}N_3O_6$ | 413.43 | 436(M + Na) 452(M + K) | 412(M − H) 526(M + TFA) |
| 124 | 4-Cl-1-naphthyl | $C_{21}H_{22}ClN_3O_6$ | 447.87 | 470/472 (M + Na) 486/488 (M + K) | 446/448(M − H) |
| 125 | 5,6,7,8-tetrahydro-1-naphthyl | $C_{21}H_{27}N_3O_6$ | 417.46 | 440(M + Na) 456(M + K) | 416(M − H) 530(M + TFA) |
| 126 | 1,2,3,4-tetrahydro-1-naphthyl | $C_{21}H_{27}N_3O_6$ | 417.46 | 440(M + Na) 456(M + K) | 416(M − H) 530(M + TFA) |
| 127 | (1-naphthyl)CH₂ | $C_{22}H_{25}N_3O_6$ | 427.46 | 450(M + Na) 466(M + K) | 426(M − H) 540(M + TFA) |

Fig. 16(j)

| | |
|---|---|
| 1 | (3S)-3-[N-(N'-(1-Naphthyl)Oxamyl)Leucinyl] Amino-4-Oxobutanoic Acid |
| 2 | (3RS)-3-[N-(N'-(1-Naphthyl)Oxamyl)Leucinyl] Amino-5-Fluoro-4-Oxopentanoic Acid |
| 3 | (3RS)-3-[N-(N'-(1-Naphthyl)Oxamyl)Valinyl] Amino-5-Fluoro-4-Oxopentanoic Acid |
| 4 | (3S)-3-[N-(N'-(1-Naphthyl)Oxamyl)Valinyl] Amino-5-(2',6'-Dichlorobenzoyloxy)-4-Oxopentanoic Acid |
| 15 | (3S)-3-[N-(N'-(1-Naphthyl)Oxamyl)Leucinyl] Amino-5(Diphenylphosphinyloxy)-4-Oxopentanoic Acid |
| 28 | (3S)-3[N-(N'-(1-Naphthylmethyl)Oxamyl)Valinyl) Amino-5-(2',3',5',6'-Tetrafluorophenoxy)-4-Oxopentanoic Acid |
| 75 | (3S)-3-[N-(N'-(2-tert-Butylphenyl)Oxamyl)Alaninyl]Amino-5-(2',3',5',6'-Tetraflluorophenoxy)-4-Oxopentanoic Acid |
| 88 | (3S)-3-[N-(N'-(2-Phenoxyphenyl)Oxamyl)Cyclohexylalaninyl]Amino-5-(2',3',5',6'-Tetraflluorophenoxy)-4-Oxopentanoic Acid |
| 92 | (3S)-3-[N-(N'-(5,6,7,8-Tetrahydro-1-Naphthyl)Oxamyl)-Cyclohexylalaninyl] Amino-5-(2',6'-Dichlorobenzoyloxy)-4-Oxopentanoic Acid |
| 100 | (3S)-3-[N-(N'-Naphthyl)Oxamyl)Homoprolinyl] Amino-5-(2',3',5',6'-Tetrafluorophenoxy)-4-Oxopentanoic Acid |
| 101 | (3S)-3-[N-(N'-(1-Naphthyl)Oxamyl)Indoline-2-Carbonyl]Amino-5-(2',3',5',6'-Tetrafluorophenoxy)-4-Oxopentanoic Acid |
| 102 | (3S)-3-[N-(N'-(1-Naphthyl)Oxamyl)Cyclohexylglycinyl]Amino-5-(2',3',5',6'-Tetrafluorophenoxy)-4-Oxopentanoic Acid |
| 110 | (3S)-3-[N-(N'-(1-Naphthyl)Oxamyl)Methioninyl](Sulfoxide)]Amino-5-(2',3',5',6'-Tetrafluorophenoxy)-4-Oxopentanoic Acid |
| 111 | (3S)-3-[N-(N'-(1-Naphthyl)Oxamyl)Homoprolinyl]Amino-4-Oxobutanoic Acid |
| 112 | (3S-3-[N-(N'-(2-(1H-Tetrazol-5-yl)Phenyl)Oxamyl)Valinyl]Amino-4-Oxobutanoic Acid |
| 113 | (3S)-3-[N-(N'-(1-Adamantanyl)Oxamyl)Valinyl] Amino-4-Oxybutanoic Acid |

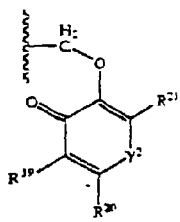

IIIc

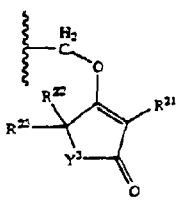

IIIc

R¹ is phenyl, substituted phenyl, naphthyl, substituted naphthyl, heteroaryl, or substituted heteroaryl;

R² is hydrogen, alkyl, cycloalkyl, phenyl, substituted phenyl, $(CH_2)_mNH_2$, $(CH_2)_mNHCOR^{10}$, $(CH_2)_mN(C=NH)NH_2$, $(CH_2)_pCO_2R^3$, $(CH_2)_pOR^{11}$, $(CH_2)_pSR^{12}$, $(CH_2)_m$cycloalkyl, $(CH_2)_m$phenyl, $(CH_2)_m$(substituted phenyl), $(CH_2)_m$(1 or 2-naphthyl), or $(CH_2)_m$heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

R³ is hydrogen, alkyl, cycloalkyl, (cycloalkyl)alkyl, phenylalkyl, or substituted phenylalkyl; and wherein R⁴ is alkyl, cycloalkyl, phenyl, substituted phenyl, $(CH_2)_mNH_2$, $(CH_2)_mNHCOR^{10}$, $(CH_2)_mN(C=NH)NH_2$, $(CH_2)_pCO_2R^3$, $(CH_2)_pOR^{11}$, $(CH_2)_pSR^{12}$, $(CH_2)_m$cycloalkyl, $(CH_2)_m$phenyl, $(CH_2)_m$(substituted phenyl), $(CH_2)_m$(1 or 2-naphthyl), or $(CH_2)_m$heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

R⁴ᵃ is hydrogen or methyl, or R⁴ and R⁴ᵃ taken together are $-(CH_2)_d-$ where d is an integer from 2 to 6;

R⁵ is phenyl, substituted phenyl, $(CH_2)_p$phenyl, $(CH_2)_p$(substituted phenyl), cycloalkyl, or benzofused cycloalkyl;

R⁶ is hydrogen, alkyl, cycloalkyl, phenyl, substituted phenyl, $(CH_2)_m$cycloalkyl, $(CH_2)_m$phenyl, $(CH_2)_m$(substituted phenyl), or $(CH_2)_m$(1 or 2-naphthyl);

R⁷ is hydrogen, fluorine, oxo (i.e., =O), alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), OR¹¹, SR¹², or NHCOR¹⁰;

R⁸ is hydrogen, oxo, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

R⁹ is alkyl, cycloalkyl, $(CH_2)_m$cycloalkyl, $(CH_2)_m$phenyl, $(CH_2)_m$(substituted phenyl), $(CH_2)_m$(1 or 2-naphthyl), or COR¹⁰;

R¹⁰ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), OR¹¹, or NR¹⁴R¹⁵;

R¹¹ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

R¹² is alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

R¹³ is alkyl, cycloalkyl, $(CH_2)_m$cycloalkyl, $(CH_2)_m$phenyl, $(CH_2)_m$(substituted phenyl), or $(CH_2)_m$(1 or 2-naphthyl);

R¹⁴ is hydrogen, alkyl, cycloalkyl, phenyl, substituted phenyl, naphthyl, substituted naphthyl, $(CH_2)_m$cycloalkyl, $(CH_2)_m$phenyl, $(CH_2)_m$(substituted phenyl), or $(CH_2)_m$(1 or 2-naphthyl);

R¹⁵ is hydrogen or alkyl; or

R¹⁴ and R¹⁵ taken together form a five, six or seven membered carbocyclic or heterocyclic ring, such as morpholine or N-substituted piperazine;

R¹⁶ is phenyl, substituted phenyl, naphthyl, substituted naphthyl, heteroaryl, $(CH_2)_m$phenyl, $(CH_2)_m$(substituted phenyl), $(CH_2)_m$(1 or 2-naphthyl), or $(CH_2)_m$heteroaryl;

R¹⁷ and R¹⁸ are independently alkyl, cycloalkyl, phenyl, substituted phenyl, naphthyl, or phenylalkyl, substituted phenylalkyl, or (cycloalkyl)alkyl;

R¹⁹ and R²⁰ are independently hydrogen, alkyl, phenyl, substituted phenyl, $(CH_2)_m$phenyl, or $(CH_2)_m$(substituted phenyl), or R¹⁹ and R²⁰ taken together are $-(CH=CH)_2-$;

R²¹ is hydrogen, alkyl, phenyl, substituted phenyl, $(CH_2)_m$phenyl, $(CH_2)_m$(substituted phenyl);

R²², R²³ and R²⁴ are independently hydrogen or alkyl;

Y¹ is $CH_2$, $(CH_2)_2$, $(CH_2)_3$, or S;

Y² is O or NR²⁴;

Y³ is $CH_2$, O, or NR²⁴;

a is 0 or 1 and b is 1 or 2, provided that when a is 1 then b is 1;

c is 1 or 2, provided that when c is 1 then a is 0 and b is 1;

m is 1, 2, 3 or 4; and p is 1 or 2;

or a pharmaceutically acceptable salt thereof.

Fig. 16(m)

1. An isolated compound of the following formula:
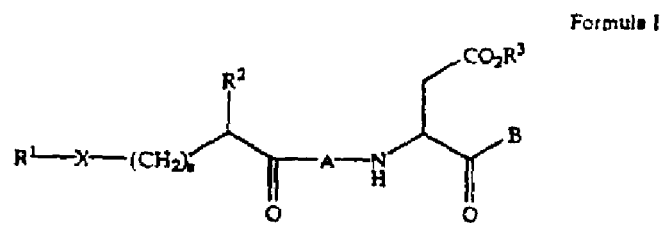
Formula I
wherein:
n is 0, 1 or 2;
X is $CH_2$, C=O, O, S or NH;

A is a moiety of Formula IIa-i:

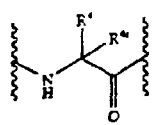  IIa

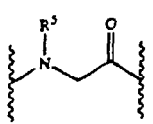  IIb

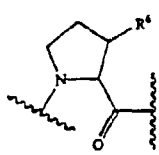  IIc

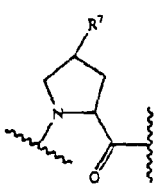  IId

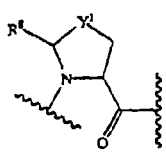  IIe

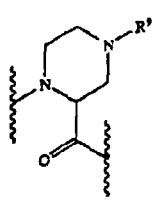  IIf

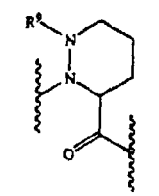  IIg

-continued

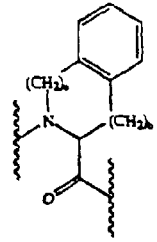  IIh

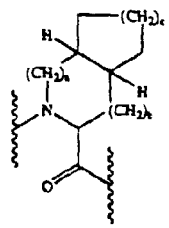  IIi

B is a hydrogen atom, a deuterium atom, $C_{1-10}$ straight chain branched alkyl, cycloalkyl, phenyl, substituted phenyl, naphthyl, substituted naphthyl, 2-benzoxazolyl, substituted 2-oxazolyl, $(CH_2)_m$ cycloalkyl, $(CH_2)_m$phenyl, $(CH_2)_m$(substituted phenyl), $(CH_2)_m$(1 or 2-naphthyl), $(CH_2)_m$heteroaryl, halomethyl, $CO_2R^{13}$, $CONR^{14}R^{15}$, $CH_2ZR^{16}$, $CH_2OCO$(aryl), $CH_2OCO$(heteroaryl), or $CH_2OPO(R^{17})R^{18}$, where Z is an oxygen or a sulfur atom, or B is a group of the Formula IIIa-c:

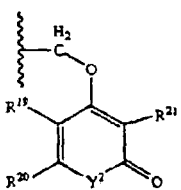  IIIa

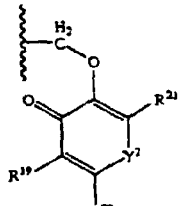  IIIb

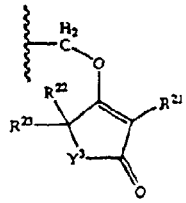  IIIc

Fig. 17(b)

$R^1$ is phenyl, substituted phenyl, naphthyl, substituted naphthyl, heteroaryl, or substituted heteroaryl;

$R^2$ is hydrogen, alkyl, cycloalkyl, phenyl, substituted phenyl, $(CH_2)_m NH_2$, $(CH_2)_m NHCOR^{10}$, $(CH_2)_m N(C=NH)NH_2$, $(CH_2)_e CO_2 R^3$, $(CH_2)_f OR^{11}$, $(CH_2)_p SR^{12}$, $(CH_2)_m$ cycloalkyl, $(CH_2)_m$ phenyl, $(CH_2)_m$ (substituted phenyl), $(CH_2)_m$(1 or 2-naphthyl), or $(CH_2)_m$ heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

$R^3$ is hydrogen, alkyl, cycloalkyl, (cycloalkyl)alkyl, phenylalkyl, or substituted phenylalkyl; and wherein $R^4$ is alkyl, cycloalkyl, phenyl, substituted phenyl, $(CH_2)_m NH_2$, $(CH_2)_m NHCOR^{10}$, $(CH_2)_m N(C=NH)NH_2$, $(CH_2)_e CO_2 R^3$, $(CH_2)_f OR^{11}$, $(CH_2)_p SR^{12}$, $(CH_2)_m$ cycloalkyl, $(CH_2)_m$ phenyl, $(CH_2)_m$(substituted phenyl), $(CH_2)_m$(1 or 2-naphthyl), or $(CH_2)_m$ heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

$R^{4a}$ is hydrogen, or methyl, or $R^4$ and $R^{4a}$ taken together are $-(CH_2)_d-$ where d is an interger from 2 to 6;

$R^5$ is phenyl, substituted phenyl, $(CH_2)_p$phenyl, $(CH_2)_p$(substituted phenyl), cycloalkyl, or benzofused cycloalkyl;

$R^6$ is hydrogen, alkyl, cycloalkyl, phenyl, substituted phenyl, $(CH_2)_m$cycloalkyl, $(CH_2)_m$phenyl, $(CH_2)_m$(substituted phenyl), or $(CH_2)_m$(1 or 2-naphthyl);

$R^7$ is hydrogen, fluorine, oxo, alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{13}$, $SR^{12}$, or $NHCOR^{10}$;

$R^8$ is hydrogen, oxo, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^9$ is alkyl, cycloalkyl, $(CH_2)_m$cycloalkyl, $(CH_2)_m$phenyl, $(CH_2)_m$(substituted phenyl), $(CH_2)_m$(1 or 2-naphthyl), or $COR^{10}$;

$R^{10}$ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{13}$, or $NR^{14}R^{15}$;

$R^{11}$ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^{12}$ is alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^{13}$ is alkyl, cycloalkyl, $(CH_2)_m$cycloalkyl, $(CH_2)_m$phenyl, $(CH_2)_m$(substituted phenyl), or $(CH_2)_m$(1 or 2-naphthyl);

$R^{14}$ is hydrogen, alkyl, cycloalkyl, phenyl, substituted phenyl, naphthyl, substituted naphthyl, $(CH_2)_m$cycloalkyl, $(CH_2)_m$phenyl, $(CH_2)_m$(substituted phenyl), or $(CH_2)_m$(1 or 2-naphthyl);

$R^{15}$ is hydrogen or alkyl; or $R^{14}$ and $R^{15}$ taken together form a five, six or seven membered carbocyclic or heterocyclic ring, such as morpholine or N-substituted piperazine;

$R^{16}$ is phenyl, substituted phenyl, naphthyl, substituted naphthyl, heteroaryl, $(CH_2)_p$phenyl, $(CH_2)_m$(substituted phenyl), $(CH_2)_m$(1 or 2-naphthyl), or $(CH_2)_m$heteroaryl;

$R^{17}$ and $R^{18}$ are independently alkyl, cycloalkyl, phenyl, substituted phenyl, naphthyl, or phenylalkyl, substituted phenylalkyl, or (cycloalkyl)alkyl;

$R^{19}$ and $R^{20}$ are independently hydrogen, alkyl, phenyl, substituted phenyl, $(CH_2)_m$phenyl, or $(CH_2)_m$(substituted phenyl), or $R^{19}$ and $R^{20}$ taken together are $-(CH=CH)_2-$;

$R^{21}$ is hydrogen, alkyl, phenyl, substituted phenyl, $(CH_2)_m$ phenyl, $(CH_2)_m$(substituted phenyl);

$R^{22}$, $R^{23}$ and $R^{24}$ are independently hydrogen or alkyl;

$Y^1$ is $CH_2$, $(CH_2)_2$, $(CH_2)_3$, or S;

$Y^2$ is O or $NR^{24}$;

$Y^3$ is $CH_2$, O, or $NR^{24}$;

a is 0 or 1 and b is 1 or 2, provided that when a is 1 then b is 1;

c is 1 or 2, provided that when c is 1 then a is 0 and b is 1;

m is 1,2,3 or 4; and p is 1 or 2;

or a salt thereof.

2. The compound of claim 1 where X is oxygen.

3. The compound of claim 1 where X is sulfur.

4. The compound of claim 1 where X is NH.

5. The compound of claim 1 where X is $CH_2$.

6. The compound of claim 1 where X is C=O.

7. The compound of claim 1 wherein A is

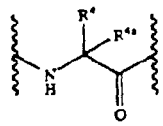

IIa

8. The compound of claim 1 wherein $R^4$ is lower alkyl, cycloalkyl, phenyl, substituted phenyl, $(CH_2)_n NH_2$, $(CH_2)_n OR^{10}$, $(CH_2)_n SR^{11}$, $(CH_2)_n$ cycloalkyl, $(CH_2)_n$phenyl, $(CH_2)_n$(substituted phenyl), or $(CH_2)_n$(1 or 2-naphthyl); and $R^{4a}$ is hydrogen.

9. The compound of claim 1 wherein A is

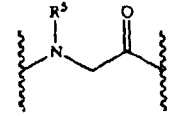

IIb

10. The compound of claim 9 wherein $R^5$ is phenyl, substituted phenyl, $(CH_2)_m$phenyl, $(CH_2)_m$(substituted phenyl), cycloalkyl, or 2-indanyl.

Fig. 17(c)

11. The compound of claim 1 wherein A is

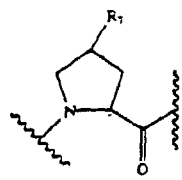
IIc

12. The compound of claim 11 wherein $R^7$ is hydrogen, fluorine, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, or $SR^{11}$.

13. The compound of claim 1 wherein A is

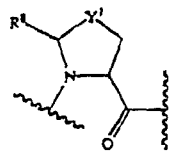
IId

14. The compound of claim 13 wherein
$R^8$ is hydrogen, oxo, cycloalkyl, phenyl, substituted phenyl, or naphthyl; and
$Y^1$ is $CH_2$, $(CH_2)_2$, $(C_2)_3$, or S.

15. The compound of claim 1 wherein A is

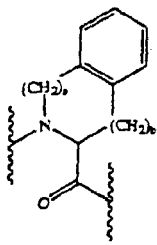
IIb

16. The compound of claim 15 wherein a is 0.
17. The compound of claim 1 wherein
B is hydrogen, 2-benzoxazolyl, substituted 2-oxazolyl, $CH_2ZR^{15}$, $CH_2OCO(aryl)$, or $CH_2OPO(R^{16})R^{17}$; and
Z is O or S.
18. The compound of claim 1 wherein B is

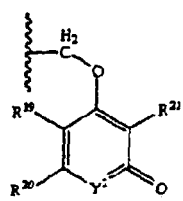
IIIa

-continued

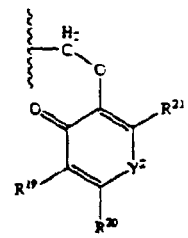
IIIb

IIIc

19. The compound of claim 18 wherein $R^{19}$ and $R^{20}$ are independently hydrogen, alkyl, or phenyl, or wherein $R^{19}$ and $R^{20}$ taken together are $-(CH=CH)_2-$.
20. The compound of claim 1 wherein
X is O or NH;
n is 0 or 1;
$R^1$ is substituted phenyl, naphthyl, or substituted naphthyl;
$R^2$ is hydrogen, lower alkyl, $(CH_2)_fCO_2R^3$, $(CH_2)_m$(substituted phenyl), $(CH_2)_m$(1- or 2-naphthyl), or $(CH_2)_m$tetrazolyl; and
$R^3$ is hydrogen or lower alkyl.
21. The compound of claim 20 wherein $R^1$ is 1-naphthyl.
22. The compound of claim 20 wherein $R^1$ is 2-naphthyl.
23. The compound of claim 20 wherein $R^1$ is substituted naphthyl.
24. The compound of claim 23 wherein substituted naphthyl is 2-carboxy-1-naphthyl.
25. The compound of claim 20 wherein $R^1$ is substituted phenyl.
26. The compound of claim 25 wherein substituted phenyl is 2-substituted phenyl.
27. The compound of claim 26 wherein 2-substituted phenyl is (2-phenyl)phenyl.
28. The compound of claim 20 wherein A is alanine, valine, leucine cyclohexylalanine, phenylglycine or t-butylglycine.
29. The compound of claim 28 wherein $R^1$ is 1-naphthyl.
30. The compound of claim 28 wherein $R^1$ is 2-naphthyl.
31. The compound of claim 28 wherein $R^1$ is substituted naphthyl.
32. The compound of claim 31 wherein substituted naphthyl is 2-carboxy-1-naphthyl.
33. The compound of claim 28 wherein $R^1$ is 2-substituted phenyl.
34. The compound of claim 33 wherein 2-substituted phenyl is (2-phenyl)phenyl.
35. The compound of claim 20 wherein $R^2$ is $(CH_2)_2CO_2R^3$ and n is 0.
36. A composition comprising a compound of claim 1 in combination with a carrier.

Fig. 17(d)

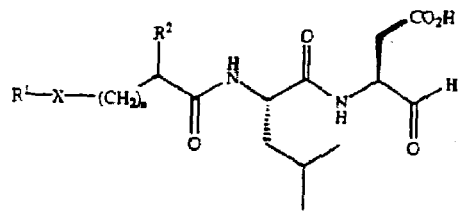

(Formula Ib)

| Ex. No. | R¹ | X | n | R² | mICE I₅₀(μM) | CPP32 I₅₀(μM) | MCH2 I₅₀(μM) | MCH3 I₅₀(μM) | MCH5 I₅₀(μM) |
|---|---|---|---|---|---|---|---|---|---|
| 11 | 1-naphthyl | $CH_2$ | 0 | H | 1.86 | 1.59 | 4.19 | 8.78 | 12.2 |
| 12 | 1-naphthyl | O | 0 | H | 0.597 | 0.139 | 0.846 | 1.95 | 0.821 |
| 13 | 2-naphthyl | O | 0 | H | 2.57 | 0.944 | 18.6 | 8.87 | >10 |
| 14 | 1-naphthyl | O | 0 | $CH_3$ | 3.99 | 0.376 | 1.28 | 1.32 | 2.43 |
| 15 | 6-Br-1-naphthyl | O | 0 | $CH_3$ | 6.84 | 4.81 | 13.8 | 32.4 | 29.1 |
| 16 | 1-naphthyl | S | 0 | H | 2.75 | 0.195 | 1.43 | 1.74 | 7.42 |
| 17 | 2-naphthyl | S | 0 | H | 0.792 | 0.269 | 3.16 | 2.52 | 11.0 |
| 18 | 2-naphthyl | $CH_2$ | 1 | H | 1.80 | 2.76 | 14.5 | 18.2 | >50 |
| 19 | 1-naphthyl | C=O | 1 | H | 0.408 | 0.967 | 11.8 | 11.3 | 11.2 |
| 20 | 1-naphthyl | C=O | 1 | $CH_3$ | 4.55 | 9.88 | 24.9 | 29.8 | 3.25 |
| 21 | 2-naphthyl | C=O | 1 | H | 0.543 | 1.42 | 10.3 | 7.43 | 5.23 |
| 22 | 1-naphthyl | O | 1 | H | 0.686 | 0.059 | 0.305 | 1.37 | 9.81 |
| 23 | 2-naphthyl | O | 1 | H | 1.32 | 0.910 | 5.90 | 9.65 | 15.2 |
| 24 | 1-naphthyl | S | 1 | H | 0.563 | 0.412 | 2.72 | 3.60 | 16.3 |
| 25 | 2-naphthyl | S | 1 | H | 0.611 | 0.837 | 1.62 | 5.89 | 15.0 |
| 26 | 2-Me-1-naphthyl | O | 0 | H | 0.843 | 0.375 | 32.4 | 4.16 | 4.14 |
| 27 | 4-MeO-1-naphthyl | O | 0 | H | 0.831 | 0.263 | 22.6 | 4.08 | 1.45 |
| 28 | 4-Cl-1-naphthyl | O | 0 | H | 0.429 | 0.231 | 12.0 | 3.38 | 1.69 |
| 29 | 2,4-diCl-1-naphthyl | O | 0 | H | 0.141 | 0.357 | 21.4 | 3.61 | 3.04 |
| 30 | 1-isoquinolinyl | O | 0 | H | 44.2 | 1.57 | >50 | 34.7 | >50 |
| 31 | 4-quinolinyl | O | 0 | H | 35.3 | 0.232 | >50 | 4.57 | >50 |
| 32 | 5-quinolinyl | O | 0 | H | 5.25 | 0.412 | >50 | 3.85 | 4.02 |
| 33 | 5-isoquinolinyl | O | 0 | H | 5.14 | 0.407 | 42.7 | 3.48 | 3.64 |
| 34 | 8-quinolinyl | O | 0 | H | 13.7 | 0.147 | 12.5 | 1.51 | 2.24 |
| 35 | phenyl | $CH_2$ | 0 | H | >10 | 9.74 | ND | >10 | >10 |
| 36 | phenyl | O | 0 | $CH_3$ | 20.4 | 1.77 | >10 | 8.27 | >10 |
| 37 | phenyl | O | 1 | H | 9.42 | 0.439 | >50 | 6.04 | >10 |
| 38 | phenyl | O | 0 | H | >10 | 3.40 | >50 | >10 | >10 |
| 39 | 2-biphenyl | O | 0 | H | 0.636 | 0.095 | 0.717 | 2.02 | 1.71 |
| 40 | 3-biphenyl | O | 0 | H | 1.10 | 0.311 | 14.5 | 3.75 | 3.86 |
| 41 | 4-biphenyl | O | 0 | H | 1.90 | 0.763 | 20.5 | 12.0 | 7.53 |
| 42 | (2-benzyl)phenyl | O | 0 | H | 0.521 | 0.490 | 10.1 | 3.36 | 6.05 |
| 43 | (4-benzyl)phenyl | O | 0 | H | 1.80 | 0.346 | 18.9 | 4.41 | 4.72 |
| 44 | (4-phenoxy)phenyl | O | 0 | H | 2.21 | 0.545 | 21.2 | 6.82 | 9.28 |
| 45 | (2-benzyloxy)phenyl | O | 0 | H | 2.40 | 0.222 | 9.75 | 2.20 | 4.34 |
| 46 | (4-benzyloxy)phenyl | O | 0 | H | 2.51 | 0.570 | 33.4 | 7.25 | 8.60 |
| 47 | (2-cyclo-pentyl)-phenyl | O | 0 | H | 0.538 | 0.197 | 3.37 | 1.49 | 1.86 |
| 48 | (4-cyclo-pentyl)-phenyl | O | 0 | H | 2.20 | 0.319 | 51.2 | 5.23 | 5.90 |

| Ex. No. | R¹ | X | n | R² | mICE I₅₀(μM) | CPP32 I₅₀(μM) | MCH2 I₅₀(μM) | MCH3 I₅₀(μM) | MCH5 I₅₀(μM) |
|---|---|---|---|---|---|---|---|---|---|
| 49 | [2-(1-adamantanyl)-4-Me]phenyl | O | 0 | H | 1.43 | 0.474 | 5.86 | 2.79 | 3.87 |
| 50 | 4-(1-adamantanyl)-phenyl | O | 0 | H | 1.83 | 0.528 | 32.5 | 8.24 | 4.35 |
| 51 | 5,6,7,8-tetrahydro-1-naphthyl | O | 0 | H | 1.81 | 0.324 | 11.8 | 2.74 | 1.75 |
| 52 | 5,6,7,8-tetrahydro-2-naphthyl | O | 0 | H | 2.57 | 0.162 | 28.6 | 2.31 | 4.95 |

Fig. 17(e)

| Ex. | R¹ | X | n | R² | Formula | MW | MS(ES) pos. | neg. |
|---|---|---|---|---|---|---|---|---|
| 54 | 2-naphthyl | O | 0 | H | $C_{22}H_{25}FN_2O_6$ | 432.45 | 433(M + H) 455(M + Na) 471(M + K) | 431(M − H) 545(M + TFA) |
| 55 | 1-naphthyl | O | 1 | H | $C_{23}H_{27}FN_2O_6$ | 446.47 | 447(M + H) 489(M + Na) | 445(M − H) 559(M + TFA) |
| 56 | (2-Ph)Ph | O | 0 | H | $C_{24}H_{27}FN_2O_6$ | 458.49 | 481(M + Na) 497(M + K) | 457(M − H) 571(M + TFA) |

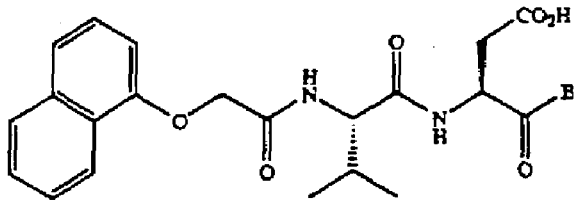

| Ex. | B | Formula | MW | MS(ES) pos. | neg. |
|---|---|---|---|---|---|
| 63 | CH$_2$OCO(2,6-diCl—Ph) | C$_{30}$H$_{28}$Cl$_2$N$_2$O$_8$ | 603.45 | 603/605 (M + H) | 601/603 (M − H) |
| 64 | CH$_2$OPh | C$_{28}$H$_{30}$N$_2$O$_7$ | 506.55 | 507(M + H) 529(M + Na) 545(M + K) | 505(M − H) |
| 65 | CH$_2$O(2-F—Ph) | C$_{28}$H$_{29}$FN$_2$O$_7$ | 524.54 | 525(M + H) | 523(M − H) |
| 66 | CH$_2$O(3-F—Ph) | C$_{28}$H$_{29}$FN$_2$O$_7$ | 524.54 | 525(M + H) | 523(M − H) |
| 67 | CH$_2$O(4-F—Ph) | C$_{28}$H$_{29}$FN$_2$O$_7$ | 524.54 | 547(M + Na) | 523(M − H) |
| 68 | CH$_2$O(2,3-diF—Ph) | C$_{28}$H$_{28}$F$_2$N$_2$O$_7$ | 542.54 | 543(M + H) 565(M + Na) | 541(M − H) 655(M + TFA) |
| 69 | CH$_2$O(2,4-diF—Ph) | C$_{28}$H$_{28}$F$_2$N$_2$O$_7$ | 542.54 | 543(M + H) 565(M + Na) 581(M + K) | 541(M − H) |
| 70 | CH$_2$O(2,5-diF—Ph) | C$_{28}$H$_{28}$F$_2$N$_2$O$_7$ | 542.54 | 543(M + H) 565(M + Na) 581(M + K) | 541(M − H) |
| 71 | CH$_2$O(2,6-diF—Ph) | C$_{28}$H$_{28}$F$_2$N$_2$O$_7$ | 542.54 | 543(M + H) 565(M + Na) | 541(M − H) |
| 72 | CH$_2$O(3,4-diF—Ph) | C$_{28}$H$_{28}$F$_2$N$_2$O$_7$ | 542.54 | 543(M + H) 581(M + K) | 541(M − H) |
| 73 | CH$_2$O(3,5-diF—Ph) | C$_{28}$H$_{28}$F$_2$N$_2$O$_7$ | 542.54 | 543(M + H) 565(M + Na) 581(M + K) | 541(M − H) |
| 74 | CH$_2$O(2,3,4-triF—Ph) | C$_{28}$H$_{27}$F$_3$N$_2$O$_7$ | 560.53 | 561(M + H) 583(M + Na) 599(M + K) | 559(M − H) |
| 75 | CH$_2$O(2,3,5-triF—Ph) | C$_{28}$H$_{27}$F$_3$N$_2$O$_7$ | 560.53 | 561(M + H) 583(M + Na) 599(M + K) | 559(M − H) 673(M + TFA) |
| 76 | CH$_2$O(2,3,6-triF—Ph) | C$_{28}$H$_{27}$F$_3$N$_2$O$_7$ | 560.53 | 561(M + H) 583(M + Na) 599(M + K) | 559(M − H) 673(M + TFA) |
| 77 | CH$_2$O(2,4,5-triF—Ph) | C$_{28}$H$_{27}$F$_3$N$_2$O$_7$ | 560.53 | 561(M + H) 583(M + Na) 599(M + K) | 559(M − H) |
| 78 | CH$_2$O(2,4,6-triF—Ph) | C$_{28}$H$_{27}$F$_3$N$_2$O$_7$ | 560.53 | 561(M + H) 583(M + Na) | 559(M − H) |
| 79 | CH$_2$O(2,3,5,6-tetra-Ph) | C$_{28}$H$_{26}$F$_4$N$_2$O$_7$ | 578.52 | 579(M + H) 601(M + Na) 617(M + K) | 577(M − H) |

Fig. 17(g)

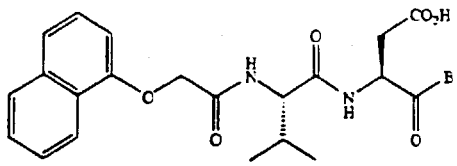

| Ex. | B | Formula | MW | MS(ES) pos. | neg. |
|---|---|---|---|---|---|
| 80 | CH₂O(2,3,4,5,6-pentaF—Ph) | C₂₈H₂₅F₅N₂O₇ | 596.51 | 619(M + Na) | 595(M − H) |
| 81 | CH₂O(2-CF₃—Ph) | C₂₉H₂₉F₃N₂O₇ | 574.55 | 597(M + Na) | 573(M − H) |
| 82 | CH₂O(3-CF₃—Ph) | C₂₉H₂₉F₃N₂O₇ | 574.55 | 597(M + Na) | 573(M − H) |
| 83 | CH₂O(4-CF₃—Ph) | C₂₉H₂₉F₃N₂O₇ | 574.55 | 597(M + Na) | 573(M − H) |
| 84 | CH₂O(3,5-diCF₃—Ph) | C₃₀H₂₈F₆N₂O₇ | 642.55 | 643(M + H) 665(M + Na) 681(M + K) | 641(M − H) |
| 85 | CH₂O(2-F,3-CF₃—Ph) | C₂₉H₂₈F₄N₂O₇ | 592.54 | 593(M + H) 615(M + Na) 631(M + K) | 591(M − H) |
| 86 | CH₂O(2,6-diCl—Ph) | C₂₈H₂₈Cl₂N₂O₇ | 575.44 | 575/577(M + H) | 573/575 (M − H) |
| 87 | CH₂O(2-NO₂—Ph) | C₂₈H₂₉N₃O₉ | 551.55 | 552(M + H) 574(M + Na) 590(M + K) | 550(M − H) |
| 88 | CH₂O(4-NO₂—Ph) | C₂₈H₂₉N₃O₉ | 551.55 | 552(M + H) 574(M + Na) | 550(M − H) |
| 89 | CH₂O(2-F,4-NO₂—Ph) | C₂₈H₂₈FN₃O₉ | 569.54 | 570(M + H) 592(M + Na) | 568(M − H) |
| 90 | CH₂O(4-CN—Ph) | C₂₉H₂₉N₃O₇ | 531.56 | 554(M + Na) | 530(M − H) |
| 91 | CH₂O(4-CF₃O—Ph) | C₂₉H₂₉F₃N₂O₈ | 590.55 | 591(M + H) | 589(M − H) 703(M + TFA) |
| 92 | CH₂O(4-H₂NCO—Ph) | C₂₉H₃₁N₃O₈ | 549.58 | 550(M + H) 572(M + Na) | 548(M − H) 662(M + TFA) |
| 93 | CH₂O(4-PhCO—Ph) | C₃₅H₃₄N₂O₈ | 610.66 | 611(M + H) 633(M + Na) | 609(M − H) |
| 94 | CH₂O(4-Ph—Ph) | C₃₄H₃₄N₂O₇ | 582.65 | 583(M + H) 605(M + Na) 621(M + K) | 581(M − H) 695(M + TFA) |
| 95 | CH₂O(4-C₆F₅-2,3,5,6-tetraF—Ph) | C₃₄H₂₅F₉N₂O₇ | 744.57 | 745(M + H) 767(M + Na) 783(M + K) | 743(M − H) |
| 96 | CH₂O(4-PhO—Ph) | C₃₄H₃₄N₂O₈ | 598.65 | 599(M + H) 621 (M + Na) | 597(M − H) |
| 97 | CH₂O[4-(4′-CF₃—PhO)Ph] | C₃₅H₃₃F₃N₂O₈ | 666.65 | 667(M + H) 689(M + Na) | 665(M − H) |
| 98 | CH₂O(3-AcNH—Ph) | C₃₀H₃₃N₃O₈ | 563.61 | 564(M + H) 586(M + Na) | 562(M − H) |
| 99 | CH₂O(3,4-OCOS—Ph) | C₂₉H₂₈N₂O₉S | 580.61 | 581(M + H) 603(M + Na) 619(M + K) | 693(M + TFA) |
| 100 | CH₂O(2-pyridinyl) | C₂₇H₂₉N₃O₇ | 507.54 | 508(M + H) | 506(M − H) |
| 101 | CH₂O(4,5-diCl-3-pyridazinyl) | C₂₆H₂₆Cl₂N₄O₇ | 577.42 | 577/579(M + H) | 575/577 (M − H) 689/691 (M + TFA) |
| 102 | CH₂O(2-naphthyl) | C₃₂H₃₂N₂O₇ | 556.61 | 557(M + H) | 555(M − H) |
| 103 | CH₂OPOPh₂ | C₃₄H₃₅N₂O₈P | 630.63 | 631(M + H) 653(M + Na) | 629(M − H) |
| 104 | CH₂OPO(Me)Ph | C₂₉H₃₃N₂O₈P | 568.56 | 569(M + H) | 567(M − H) |
| 105 | CH₂OPOMe₂ | C₂₄H₃₁N₂O₈P | 506.49 | 529(M + Na) | 505(M − H) |
| 106 | CH₂OPO(n-hexyl)Ph | C₃₄H₄₃N₂O₈P | 638.28 | 639(M + H) 661(M + Na) 677(M + K) | 637(M − H) 751(M + TFA) |
| 107 | CH₂OPO(PhCH₂)Ph | C₃₅H₃₇N₂O₈P | 644.66 | 645(M + H) 667(M + Na) 683(M + K) | 643(M − H) 757(M + TFA) |
| 108 | CH₂OPO(Me)(4-F—Ph) | C₂₉H₃₂FN₂O₈P | 586.55 | 587(M + H) 609(M + Na) | 585(M − H) 699(M + TFA) |
| 109 | CH₂OPO(n-hexyl)(4-F—Ph) | C₃₄H₄₂FN₂O₈P | 656.69 | 679(M + Na) | 655(M − H) |
| 110 | CH₂OPO(Me)(1-naphthyl) | C₃₃H₃₅N₂O₈P | 618.62 | 619(M + H) 641(M + Na) | 731(M + TFA) |
| 111 | CH₂O(6-Me-2-pyron-4-yl) | C₂₈H₃₀N₂O₉ | 538.55 | 539(M + H) | |
| 112 | CH₂O(4-coumarinyl) | C₃₁H₃₀N₂O₉ | 574.59 | 575(M + H) 597(M + Na) | 537(M − H) 687(M + TFA) |

Fig. 17(h)

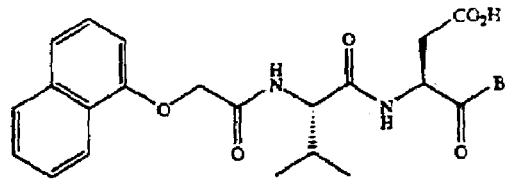

| Ex. | B | Formula | MW | MS(ES) pos. | neg. |
|---|---|---|---|---|---|
| 113 | $CH_2O$(2-Me-4-pyron-3-yl) | $C_{28}H_{30}N_2O_9$ | 538.55 | 539(M + H) 561(M + Na) | 537(M − H) 651(M + TFA) |
| 114 | $CH_2O$[1,2-diMe-4(1H)-pyridon-3-yl] | $C_{29}H_{33}N_3O_8$ | 551.59 | 552(M + H) | 550(M − H) |
| 115 | $CH_2O$(3-flavonyl) | $C_{37}H_{34}N_2O_9$ | 650.68 | 653(M + H) | 649(M − H) |
| 116 | $CH_2O$(4,6-diMe-2-pyrimidinyl) | $C_{28}H_{32}N_4O_7$ | 536.58 | 537(M + H) | 535(M − H) |
| 117 | $CH_2O$(4-$CF_3$-2-pyrimidinyl) | $C_{27}H_{27}F_3N_4O_7$ | 576.53 | 577(M + H) | 575(M − H) |
| 118 | $CH_2S$(4,6-diMe-2-pyrimidinyl) | $C_{28}H_{32}N_4O_6S$ | 552.64 | 553(M + H) 575(M + Na) | 551(M − H) 665(M + TFA) |
| 119 | $CH_2O$(2,6-diMe-4-pyrimidinyl) | $C_{28}H_{32}N_4O_7$ | 536.58 | 537(M + H) | 535(M − H) |
| 120 | $CH_2O$(6-$CF_3$-4-pyrimidinyl) | $C_{27}H_{27}F_3N_4O_7$ | 576.53 | 577(M + H) | 575(M − H) |
| 121 | $CH_2O$(2-$CF_3$-4-pyrimidinyl) | $C_{27}H_{27}F_3N_4O_7$ | 576.53 | 577(M + H) | 575(M − H) |
| 122 | $CH_2S$(2-imidazolyl) | $C_{25}H_{28}N_4O_6S$ | 512.58 | 513(M + H) | 511(M − H) 625(M + TFA) |
| 123 | $CH_2S$(1-Me-2-imidazolyl) | $C_{26}H_{30}N_4O_6S$ | 526.61 | 527(M + H) | 525(M − H) |
| 124 | $CH_2S$(1H-1,2,4-triazol-3-yl) | $C_{24}H_{27}N_5O_6S$ | 513.57 | 514(M + H) | 512(M − H) |
| 125 | $CH_2S$(4-Me-4H-1,2,4-triazol-3-yl) | $C_{25}H_{29}N_5O_6S$ | 527.59 | 528(M + H) | 526(M − H) 640(M + TFA) |
| 126 | $CH_2S$(1-Me-5-tetrazolyl) | $C_{24}H_{28}N_6O_6S$ | 528.58 | 529(M + H) | 527(M − H) |
| 127 | $CH_2S$(1-Ph-5-tetrazolyl) | $C_{29}H_{30}N_6O_6S$ | 590.65 | 591(M + H) | 589(M − H) |
| 128 | $CH_2S$(5-Me-1,3,4-thiadiazol-2-yl) | $C_{25}H_{28}N_4O_6S_2$ | 544.64 | 545(M + H) | 543(M − H) |
| 129 | $CH_2S$(5-Ph-1,3,4-oxadiazol-2-yl) | $C_{30}H_{30}N_4O_7S$ | 590.65 | 591(M + H) 613(M + Na) | 589(M − H) 703(M + TFA) |
| 130 | $CH_2S$(3-Ph-1,2,4-oxadiazol-5-yl) | $C_{30}H_{30}N_4O_7S$ | 590.65 | 591(M + H) | 589(M − H) |
| 131 | $CH_2S$(4-Ph-2-thiazolyl) | $C_{31}H_{31}N_3O_6S_2$ | 605.72 | 606(M + H) 628(M + Na) | 604(M − H) |
| 132 | $CH_2S$(4,5-diPh-2-imidazolyl) | $C_{37}H_{36}N_4O_6S$ | 664.77 | 665(M + H) | 663(M − H) |
| 133 | $CH_2O$(2-benzothiazolyl) | $C_{29}H_{29}N_3O_7S$ | 563.62 | 564(M + H) 586(M + Na) | 562(M − H) |
| 134 | $CH_2O$(2-benzimidazolyl) | $C_{29}H_{30}N_4O_7$ | 546.58 | 547(M + H) 569(M + Na) | 545(M − H) |
| 135 | $CH_2S$(2-benzothiazolyl) | $C_{29}H_{29}N_3O_6S_2$ | 579.68 | 580(M + H) | 578(M − H) |
| 136 | $CH_2S$(2-benzimidazolyl) | $C_{29}H_{30}N_4O_6S$ | 562.64 | 563(M + H) | 561(M − H) 675(M + TFA) |
| 137 | $CH_2O$(2-quinolinyl) | $C_{31}H_{31}N_3O_7$ | 557.60 | 558(M + H) 580(M + Na) | 556(M − H) 670(M + TFA) |
| 138 | $CH_2O$(3-isoquinolinyl) | $C_{31}H_{31}N_3O_7$ | 557.60 | 558(M + H) | 556(M − H) |
| 139 | $CH_2O$(1-isoquinolinyl) | $C_{31}H_{31}N_3O_7$ | 557.60 | 558(M + H) 580(M + Na) | 556(M − H) 670(M + TFA) |
| 140 | $CH_2O$(4-quinazolinyl) | $C_{31}H_{30}N_4O_7$ | 558.59 | 559(M + H) | 557(M − H) |
| 141 | $CH_2O$(8-quinolinyl) | $C_{31}H_{31}N_3O_7$ | 557.60 | 558(M + H) | 556(M − H) 670(M + TFA) |
| 142 | $CH_2O$(3-Me-4-$CO_2$Et-isoxazol-5-yl) | $C_{29}H_{33}N_3O_{10}$ | 583.59 | 584(M + H) | 582(M − H) |
| 143 | $CH_2O$(1-Ph-3-$CF_3$-pyrazol-5-yl) | $C_{32}H_{31}F_3N_4O_7$ | 640.61 | 641(M + H) | 639(M − H) |
| 144 | $CH_2O$(5-$CO_2$Me-isoxazol-3-yl) | $C_{27}H_{29}N_3O_{10}$ | 555.54 | 556(M + H) 578(M + Na) | 554(M − H) |
| 145 | $CH_2O$(5-iPr-isoxazol-3-yl) | $C_{28}H_{33}N_3O_8$ | 539.58 | 540(M + H) | 538(M − H) |
| 146 | $CH_2O$(3-benzoisoxazolyl) | $C_{29}H_{29}N_3O_8$ | 547.56 | 548(M + H) | 546(M − H) |
| 147 | $CH_2O$(1-Me-5-$CF_3$-pyrazol-3-yl) | $C_{27}H_{29}F_3N_4O_7$ | 578.54 | 579(M + H) 601(M + Na) | 577(M − H) |
| 148 | $CH_2O$(1-benzotriazolyl) | $C_{28}H_{29}N_5O_7$ | 547.57 | 548(M + H) | 660(M + TFA) |
| 149 | $CH_2O$(N-phthalimidyl) | $C_{30}H_{29}N_3O_9$ | 575.57 | 576(M + H) | 574(M + H) 688(M + TFA) |

Fig. 17(i)

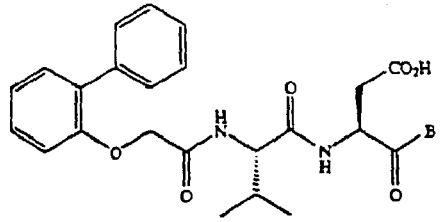

| Ex. | B | Formula | MW | MS(ES) pos. | neg. |
|---|---|---|---|---|---|
| 150 | CH₂OCO(2,6-di-Cl—Ph) | C₃₁H₃₀Cl₂N₂O₈ | 629.49 | 629/631(M + H) 651/653(M + Na) 667/669(M + K) | 627/629(M - H) 741/743(M + TFA) |
| 151 | CH₂O(2,4,6-triF—Ph) | C₃₀H₂₉F₃N₂O₇ | 586.57 | 587(M + H) 609(M + Na) 625(M + K) | 585(M - H) 699(M + TFA) |
| 152 | CH₂O(2,3,5,6-tetraF—Ph) | C₃₀H₂₈F₄N₂O₇ | 604.56 | 605(M + H) | 603(M - H) 717(M + TFA) |
| 153 | CH₂OPOPh₂ | C₃₆H₃₇N₂O₈P | 656.67 | 679(M + Na) 695(M + K) | 655(M - H) 769(M + TFA) |
| 154 | CH₂OPO(Me)Ph | C₃₁H₃₅N₂O₈P | 594.60 | 617(M + Na) 633(M + K) | 593(M - H) 707(M + TFA) |

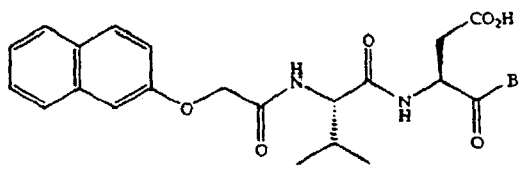

| Ex. | B | Formula | MW | MS(ES) pos. | neg. |
|---|---|---|---|---|---|
| 155 | CH₂OCO(2,6-di-Cl-Ph) | C₂₉H₂₈Cl₂N₂O₈ | 603.45 | 603/605(M + H) 625/627(M + Na) | 601/603(M - H) 715/717(M + TFA) |
| 156 | CH₂O(2,4,6-triF—Ph) | C₂₈H₂₇F₃N₂O₇ | 560.53 | 583(M + Na) | 559(M - H) 673(M + TFA) |
| 157 | CH₂O(2,3,5,6-tetraF—Ph) | C₂₈H₂₆F₄N₂O₇ | 578.52 | 601(M + Na) | 577(M - H) 891(M + TFA) |

Fig. 17(j)

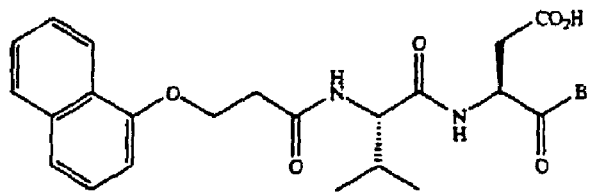
| Ex. | B | Formula | MW | MS(ES) pos. | neg. |
|---|---|---|---|---|---|
| 158 | CH₂OCO(2,6-di-Cl—Ph) | C₃₀H₃₀Cl₂N₂O₈ | 617.48 | 617/619(M + H) 639/641(M + Na) | 615/617(M − H) 729/731(M + TFA) |
| 159 | CH₂O(1-Ph-5-CF₃— pyrazol-3-yl) | C₃₃H₃₂F₃N₄O₇ | 654.64 | 677(M + Na) | 653(M − H) 767(M + TFA) |
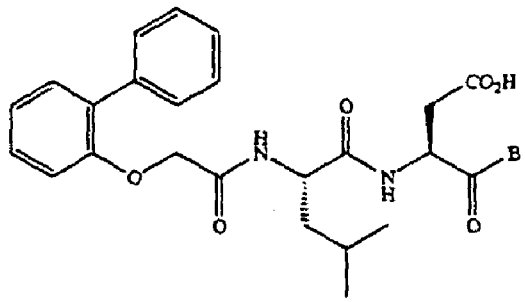
| Ex. | B | Formula | MW | MS(ES) pos. | neg. |
|---|---|---|---|---|---|
| 162 | CH₂OCO(2,6-di-Cl—Ph) | C₃₂H₃₂Cl₂N₂O₈ | 643.52 | 665/667(M + Na) | 641/643(M − H) 755/757(M + TFA) |
| 163 | CH₂O(2,4,6-triF—Ph) | C₃₁H₃₁F₃N₂O₇ | 600.60 | 623(M + Na) | 599(M − H) 713(M + TFA) |
| 164 | CH₂O(2,3,5,6-tetraF—Ph) | C₃₁H₃₀F₄N₂O₇ | 618.59 | 641(M + Na) | 731(M + TFA) |
Fig. 17(k)

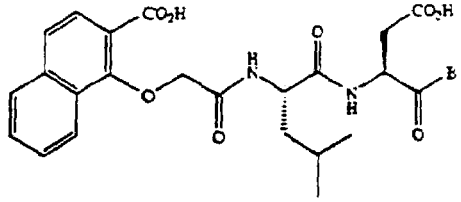

| Ex. | B | Formula | MW | MS(ES) pos. | neg. |
|---|---|---|---|---|---|
| 166 | CH₂OPOPh₂ | C₃₆H₃₇N₂O₁₀P | 688.67 | 689(M + H) | 687(M - H) |
| 167 | CH₂O(2,3,5,6-tetraF—Ph) | C₃₀H₂₈F₄N₂O₉ | 636.55 | 637(M + H) 659(M + Na) 675(M + K) | 635(M - H) |

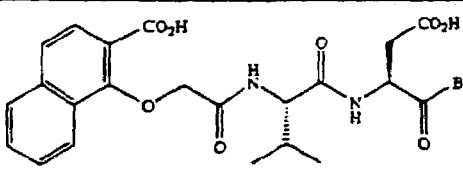

| Ex. | B | Formula | MW | MS(ES) pos. | neg. |
|---|---|---|---|---|---|
| 169 | CH₂O(2,3,5,6-tetraF—Ph) | C₂₉H₂₆F₄N₂O₉ | 622.53 | 645(M + Na) | 621(M - H) |
| 170 | CH₂OCO(2,6-diCl—Ph) | C₃₀H₂₉Cl₂N₂O₁₀ | 647.46 | 669/671 (M + Na) | 645/647 (M - H) |
| 171 | CH₂OPOPh₂ | C₃₅H₃₅N₂O₁₀P | 674.64 | 697(M + Na) | 673(M - H) |

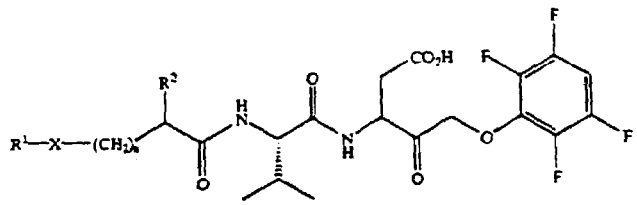

| Ex. | R¹ | X | n | R² | Formula | MW | MS(ES) pos. | neg. |
|---|---|---|---|---|---|---|---|---|
| 173 | 2-naphthyl | O | 0 | H | C₃₂H₃₂F₄N₂O₇ | 632.61 | 633(M + H) 655(M + Na) 671(M + K) | 631(M - H) 745(M + TFA) |
| 174 | 2-naphthyl | O | 1 | H | C₃₃H₃₄F₄N₂O₇ | 646.63 | 647(M + H) 669(M + Na) 685(M + K) | 645(M - H) 759(M + TFA) |
| 175 | (2-Ph)Ph | O | 0 | H | C₃₄H₃₄F₄N₂O₇ | 658.65 | 659(M + H) 681(M + Na) 697(M + K) | 657(M - H) 771(M + TFA) |

Fig. 17(l)

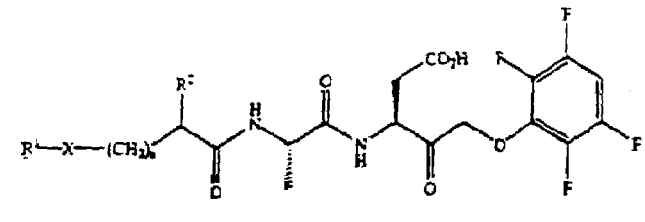
| Ex. | R¹ | X | n | R² | Formula | MW | MS(ES) pos. | neg. |
|---|---|---|---|---|---|---|---|---|
| 176 | 2-naphthyl | O | 0 | H | $C_{26}H_{22}F_4N_2O_7$ | 550.46 | 551(M + H) 573(M + Na) | 549(M − H) 663(M + TFA) |
| 177 | (2-Ph)Ph | O | 0 | H | $C_{27}H_{24}F_4N_2O_7$ | 576.50 | 577(M + H) 599(M + Na) | 575(M − H) 689(M + TFA) |
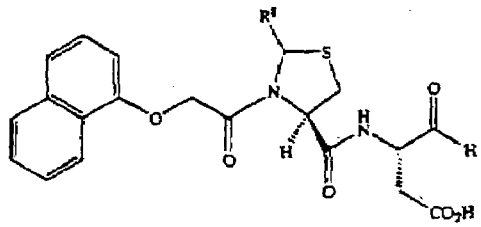
| Ex. | R¹ | Formula | MW | MS(ES) pos. | neg. |
|---|---|---|---|---|---|
| 180 | n-propyl | $C_{23}H_{26}N_2O_6S$ | 458.53 | — | 457(M − H) |
| 181 | n-hexyl | $C_{26}H_{32}N_2O_6S$ | 500.61 | 501(M + H) 539(M + Na) | 499(M − H) |
| 182 | iso-propyl | $C_{23}H_{26}N_2O_6S$ | 458.53 | 459(M + H) | 457(M − H) |
| 183 | cyclo-hexyl | $C_{26}H_{30}N_2O_6S$ | 498.59 | 499(M + H) | 497(M − H) |
| 184 | H | $C_{20}H_{22}N_2O_6S$ | 416.45 | — | 415(M − H) |
Fig. 17(m)

| Ex. | R¹ | X | n | R² | Formula | MW | MS(SE) pos. | neg. |
|---|---|---|---|---|---|---|---|---|
| 190 | (2-t-Bu)Ph | O | 0 | H | $C_{21}H_{30}N_2O_6$ | 406.48 | 429(M + Na) 445(M + K) | 405(M − H) |
| 191 | (2-Ph)Ph | O | 0 | H | $C_{23}H_{26}N_2O_6$ | 426.47 | 449(M + Na) 465(M + K) | 425(M − H) |
| 192 | (2-Ph)Ph | O | 0 | CH₃ | $C_{24}H_{28}N_2O_6$ | 440.50 | 463(M + Na) | 439(M − H) |
| 193 | (2-Ph)Ph | O | 1 | H | $C_{24}H_{28}N_2O_6$ | 440.50 | 441(M + H) 463(M + Na) 479(M + K) | 439(M − H) 553(M + TFA) |
| 194 | 1-naphthyl | O | 1 | H | $C_{22}H_{26}N_2O_6$ | 414.46 | 415(M + H) 437(M + Na) 453(M + K) | 413(M − H) |

| 1 | (3S)-3-[N-((1-Naphthyloxy)Acetyl)Leucinyl]Amino-4-Oxobutanoic Acid |
|---|---|
| 2 | (3S)-3-[N-((1-Naphthyloxy)Acetyl)Valinyl]Amino-4-Oxobutanoic Acid |
| 3 | (3S,2'S)-3-[N-((2'-(1-Naphthyloxy)-4'-Carboxy)Butyryl)Leucinyl]Amino-4-Oxobutanoic Acid |
| 5 | (3S)-3-[N-((1'-Carboxy)-2'-1-Naphthyloxy)Acetyl)Valinyl]Amino-4-Oxobutanoic Acid |
| 8 | (3S)-3-[N-((1-Naphthylamino)Acetyl)Leucinyl]Amino-4-Oxobutanoic Acid |
| 9 | (3S,2'RS)-3-[N-((2'-(1-Naphthylamino)Propionyl)Leucinyl]Amino-4-Oxobutanoic Acid |
| 10 | (3S)-3-[N-((2',3-Dihydro-2,2-Dimethyl-7-Benzofuranyloxy)Acetyl)Leucinyl]Amino-4-Oxobutanoic Acid |
| 53 | (3RS)-3-[N-((1-Naphthyloxy)Acetyl)Valinyl]Amino-5-Fluoro-4-Oxopentanoic Acid |
| 57 | (3RS)-3-[N-((2-Phenylphenoxy)Acetyl)Leucinyl]Amino-5-Fluoro-4-Oxopentanoic Acid |
| 61 | (2'S,3RS)-N-[((1-Naphthyloxy)Acetyl)Indoline-2'-Carbonyl]Amino-5-Fluoro-4-Oxopentanoic Acid |
| 62 | (3S)-3-[N-((1-Naphthyloxy)Acetyl)Valinyl]Amino-5-(1',2',3'-Benzotriazin-4'(3H)-on-3'-yloxy)-4-Oxopentanoic Acid |
| 161 | (3S)-3-[N-((2-Phenoxyphenyl)Acetyl)Leucinyl]Amino-5-(Diphenylphosphinyloxy)-4-Oxopentanoic Acid |
| 165 | (3S)-3-[N-((2'-Carboxy-1'-Naphthyloxy)Acetyl)Leucinyl]Amino-5-(2',6'-(Dichlorobenzoyloxy)-4-Oxopentanoic Acid |
| 168 | (3S)-3-[N-((2'-Carboxy-1'-Naphthyloxy)Acetyl)Valinyl]Amino-5-(2'-Fluorophenoxy)-4-Oxopentanoic Acid |
| 172 | (3RS)-3-[N-((1'-Naphthyloxy)Acetyl)Cyclohexylalaninyl]-Amino-5-(2',3',5',6'-Tetrafluorophenoxy)-4-Oxoxypentanoic Acid |
| 179 | (3S,2'RS,4'R)-3-[3'-((1-Naphthyloxy)Acetyl)-2'-Phenylthiazolidine-4'-Carbonyl]Amino-4-Oxobutanoic Acid |
| 185 | (3S)-3-[N-((1-Naphthyloxy)Acetyl)-4'(trans)-Hydroxyprolinyl]Amino-4-Oxobutanoic Acid |

Fig. 17(o)

| 187 | (3S)-3-[N-((3'-Trifluoromethylsulfonylamino-2'-Naphthyloxy)Acetyl)Valinyl]Amino-4-Oxobutanoic Acid |
|---|---|
| 188 | (3S)-3-[N-((5'-Trifluoromethylsulfonylamino-1'-Naphthyloxy)Acetyl)Valinyl]Amino--4-Oxobutanoic Acid |
| 189 | (3S)-3-[N-(4-(1'-Naphthyloxy)Butyryl)Valinyl]Amino-4-Oxobutanoic Acid |

Fig. 17(p)

compounds of the Formula I:

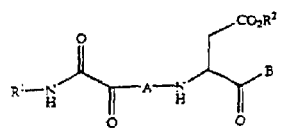

Formula I wherein:
A is a natural or unnatural amino acid of Formula IIa-i:

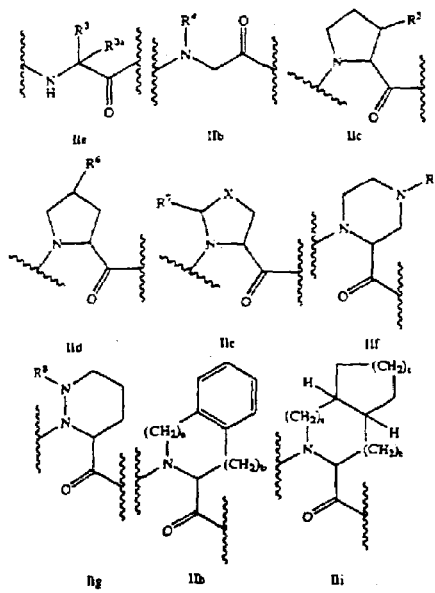

B is a hydrogen atom, a deuterium atom, alkyl, cycloalkyl, phenyl, substituted phenyl, naphthyl, substituted naphthyl, 2-benzoxazolyl, substituted 2-oxazolyl, $(CH_2)_n$cycloalkyl, $(CH_2)_n$phenyl, $(CH_2)_n$(substituted phenyl), $(CH_2)_n$(1 or 2-naphthyl), $(CH_2)_n$(heteroaryl), halomethyl, $CO_2R^{12}$, $CONR^{13}R^{14}$, $CH_2ZR^{15}$, $CH_2OCO(aryl)$, $CH_2OCO(heteroaryl)$, or $CH_2OPO(R^{16})R^{17}$, where Z is an oxygen or a sulfur atom; or B is a group of the Formula IIIa-c:

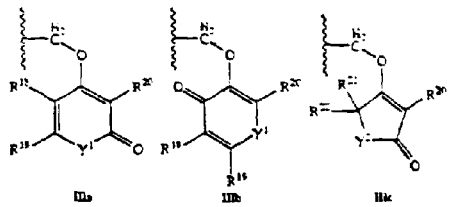

$R^1$ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, (heteroaryl)alkyl, $R^{1a}(R^{1b})N$, or $R^{1c}O$; and $R^2$ is hydrogen, lower alkyl, cycloalkyl, (cycloalkyl)alkyl, phenylalkyl, or substituted phenylalkyl;

and wherein:

$R^{1a}$ and $R^{1b}$ are independently hydrogen, alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, or (heteroaryl)alkyl, with the proviso that $R^{1a}$ and $R^{1b}$ cannot both be hydrogen;

$R^{1c}$ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, or (heteroaryl)alkyl;

$R^3$ is $C_{1-6}$ lower alkyl, cycloalkyl, phenyl, substituted phenyl, $(CH_2)_n NH_2$, $(CH_2)_n NHCOR^6$, $(CH_2)_n N(C=NH)NH_2$, $(CH_2)_n CO_2R^2$, $(CH_2)_n OR^{10}$, $(CH_2)_m SR^{11}$, $(CH_2)_n$cycloalkyl, $(CH_2)_n$phenyl, $(CH_2)_n$(substituted phenyl), $(CH_2)_n$(1 or 2-naphthyl) or $(CH_2)_n$(heteroaryl), wherein heteroaryl includes pyridyl, thienyl, furyl, thiazolyl, imidazolyl, pyrazolyl, isoxazolyl, pyrazinyl, pyrimidyl, triazinyl, tetrazolyl, and indolyl;

$R^{3a}$ is hydrogen or methyl, or $R^3$ and $R^{3a}$ taken together are $-(CH_2)_d-$ where d is an integer from 2 to 6;

$R^4$ is phenyl, substituted phenyl, $(CH_2)_n$phenyl, $(CH_2)_m$ (substituted phenyl), cycloalkyl, or benzofused cycloalkyl;

$R^5$ is hydrogen, lower alkyl, cycloalkyl, phenyl, substituted phenyl, $(CH_2)_n$cycloalkyl, $(CH_2)_n$phenyl, $(CH_2)_n$ (substituted phenyl), or $(CH_2)_n$(1 or 2-naphthyl);

$R^6$ is hydrogen, fluorine, oxo, lower alkyl, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, $SR^{11}$ or $NHCOR^9$;

$R^7$ is hydrogen, oxo (i.e., =O), lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

$R^8$ is lower alkyl, cycloalkyl, $(CH_2)_n$cycloalkyl, $(CH_2)_n$phenyl, $(CH_2)_n$(substituted phenyl), $(CH_2)_n$(1 or 2-naphthyl), or $COR^6$;

$R^9$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{12}$, or $NR^{13}R^{14}$;

$R^{10}$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

Fig. 17(q)

$R^{11}$ is lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

$R^{12}$ is lower alkyl, cycloalkyl, $(CH_2)_n$cycloalkyl, $(CH_2)_n$phenyl, $(CH_2)_n$(substituted phenyl), or $(CH_2)_n$(1 or 2-naphthyl);

$R^{13}$ is hydrogen, lower alkyl, cycloalkyl, phenyl, substituted phenyl, naphthyl, substituted naphthyl, $(CH_2)_n$cycloalkyl, $(CH_2)_n$phenyl, $(CH_2)_n$(substituted phenyl), or $(CH_2)_n$(1 or 2-naphthyl);

$R^{14}$ is hydrogen or lower alkyl;

or $R^{13}$ and $R^{14}$ taken together form a five to seven membered carbocyclic or heterocyclic ring, such as morpholine, or N-substituted piperazine;

$R^{15}$ is phenyl, substituted phenyl, naphthyl, substituted naphthyl, heteroaryl, $(CH_2)_n$phenyl, $(CH_2)_n$(substituted phenyl), $(CH_2)_n$(1 or 2-naphthyl), or $(CH_2)_n$(heteroaryl);

$R^{16}$ and $R^{17}$ are independently lower alkyl, cycloalkyl, phenyl, substituted phenyl, naphthyl, phenylalkyl, substituted phenylalkyl, or (cycloalkyl)alkyl;

$R^{18}$ and $R^{19}$ are independently hydrogen, alkyl, phenyl, substituted phenyl, $(CH_2)_n$phenyl, $(CH_2)_n$(substituted phenyl), or $R^{18}$ and $R^{19}$ taken together are —$(CH=CH)_2$—;

$R^{20}$ is hydrogen, alkyl, phenyl, substituted phenyl, $(CH_2)_n$phenyl, $(CH_2)_n$(substituted phenyl);

$R^{21}$, $R^{22}$ and $R^{23}$ are independently hydrogen, or alkyl;

X is $CH_2$, $(CH_2)_2$, $(CH_2)_3$, or S;

$Y^1$ is O or $NR^{23}$;

$Y^2$ is $CH_2$, O, or $NR^{23}$;

a is 0 or 1 and b is 1 or 2, provided that when a is 1 then b is 1;

c is 1 or 2, provided that when c is 1 then a is 0 and b is 1;

m is 1 or 2; and n is 1, 2, 3 or 4;

or a pharmaceutically acceptable salt thereof.

Fig. 17(r)

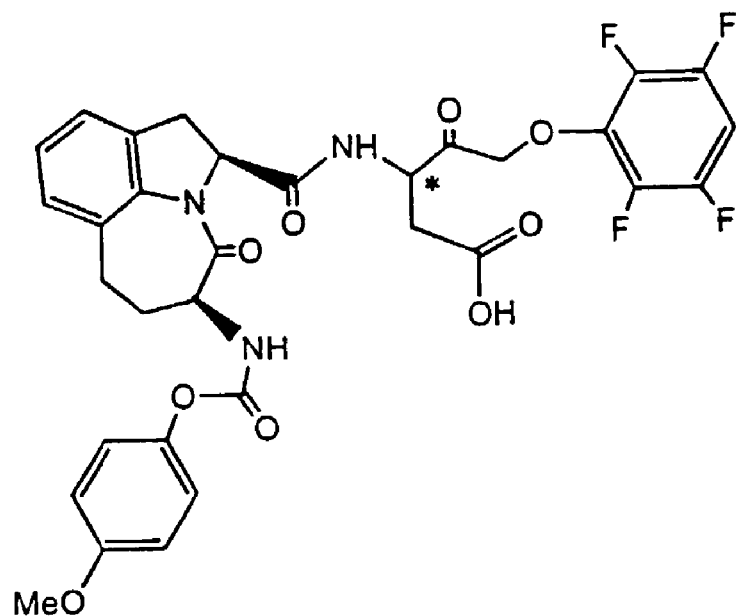
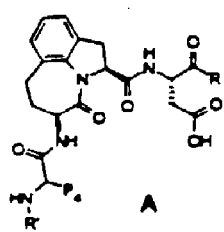
P = amino acid
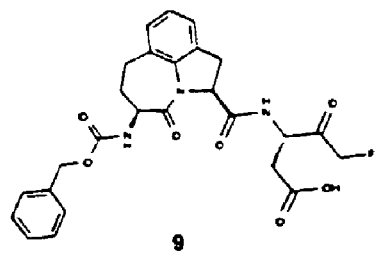
FIG.18(a)

fmk = fluoromethyl ketone

| Compound | Formula |
|---|---|
| 1 | 1-naphthylOAc-E-Asp-aldehyde |
| 2 | z-F-Asp-aldehyde |
| 3 | z-E-D-Asp-fmk |
| 4 | (1-Naphthyl)OAc-E-Asp-fmk |
| 5 | z-Glu(tetrazolyl)-Glu-D-CH2O(F2-Ph) |
| 6 | z-G-Asp-aldehyde |
| 7 | acetyl-G-Asp-aldehyde |
| 8 | z-Asp-G-aldehyde |
| 9 | z-G-Asp-fmk |
| 10 | z-G-Asp-CH2OPOPh2 |
| 11 | z-G-Asp-CH2O(2,3,5,6-F4Ph) |

G (n=1)

R-G-Asp-tfpmk analogues (tfpmk = tetra fluoro phenoxy methyl ketone)

| Compound | "R" group |
|---|---|
| 12 | (1-Naphthyl)CH2CO |
| 13 | PhCH2CO |
| 14 | PropargylOCO |
| 15 | 3,4,5-(MeO)3PhOCO |
| 16 | 3,4-MethylenedioxyPhOCO |
| 17 | 4-CH3OPHOCO |
| 18 | 4-CH3OBenzylNCO |
| 19 | PhSCO |
| 20 | F3COPhSO2 |
| 21 | Me2NSO2 |
| 22 | Ph2PO |

1. A compound of formula I:

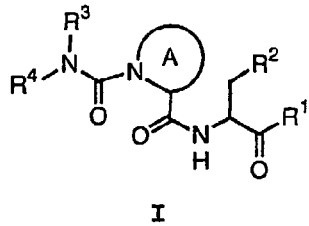

I wherein:

Ring A is an optionally substituted piperidine, tetrahydroquinoline or tetrahydroisoquinoline ring;

$R^1$ is hydrogen, CN, $CHN_2$, R, or $CH_2Y$;

R is an optionally substituted group selected from an aliphatic group, an aryl group, or an aralkyl group;

Y is an electronegative leaving group;

$R^2$ is $CO_2H$, $CH_2CO_2H$, or esters, amides or isosteres thereof; and $R^3$ is hydrogen, an optionally substituted aryl group, an optionally substituted aralkyl group or an optionally substituted $C_{1-6}$ aliphatic group, $R^4$ is an optionally substituted group selected from an aryl group or a heterocyclyl group, or $R^3$ and $R^4$ taken together with the nitrogen to which they are attached optionally form a substituted or unsubstituted monocyclic, bicyclic or tricyclic ring.

2. The compound according to claim 1 having one or more features selected from the group consisting of:

(a) $R^1$ is $CH_2Y$ where Y is an electronegative leaving group;

(b) $R^2$ is $CO_2H$, esters, amides or isosteres thereof; and

Fig. 19 (a)

(c) $R^3$ is a hydrogen atom, an optionally substituted aryl group, an optionally substituted aralkyl group or an optionally substituted $C_{1-6}$ aliphatic group, $R^4$ is an optionally substituted group selected from an aryl group or a heterocyclyl group, or $R^3$ and $R^4$, taken together with the nitrogen to which they are attached, optionally form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine. purine, quinolizine, quinoline, isoquinoline, cinnoline, phthalazine, quinazoline, quinoxaline, 1,8-naphthyridine, pteridine, quinuclidine, and phenazine.

3. The compound of claim 2, wherein:

(a) $R^1$ is $CH_2Y$ where Y is an electronegative leaving group;

(b) $R^2$ is $CO_2H$, esters, amides or isosteres thereof; and (c) $R^3$ is a hydrogen atom, an optionally substituted aryl group, an optionally substituted aralkyl group or an optionally substituted $C_{1-6}$ aliphatic group, $R^4$ is an optionally substituted group selected from an aryl group, or a heterocyclyl group; or $R^3$ and $R^4$, taken together with the nitrogen to which they are attached, optionally form aring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline,

Fig. 19 (b)

pyrazolidine, triazole, piperidine, morpholine, thiomorpholine, piperazine, carbazole, phenothiazine, phenoxazine, phenanthridine, acridine. purine, quinolizine, quinoline, isoquinoline, cinnoline, phthalazine, quinazoline, quinoxaline, 1,8-naphthyridine, pteridine, quinuclidine, and phenazine.

4. The compound according to claim 3 wherein $-CH_2Y$ is $-CH_2F$.

5. The compound according to claim 4 wherein $R^3$ and $R^4$, taken together with the nitrogen to which they are attached, form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine. purine, quinolizine, quinoline, isoquinoline, cinnoline, phthalazine, quinazoline, quinoxaline, 1,8-naphthyridine, pteridine, quinuclidine, and phenazine.

Fig. 19 (c)

1. A compound of the formula I:

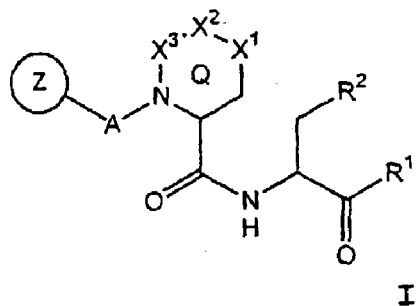

I wherein:

$R^1$ is hydrogen, CN, CHN$_2$, R, or -CH$_2$Y;

R is an aliphatic group, a substituted aliphatic group, an aryl group, a substituted aryl group, an aralkyl group, a substituted aralkyl group, a non-aromatic heterocyclic group, or a substituted non-aromatic heterocyclic group;

Y is an electronegative leaving group, -OR, -SR, -OC=O(R), or -OPO($R^3$)($R^4$);

$R^3$ and $R^4$ are independently R or OR;

$R^2$ is CO$_2$H, CH$_2$CO$_2$H, or optionally substituted esters, amides or isosteres thereof;

A is C=O or SO$_2$;

$X^1$ is oxygen, sulfur, -NH, or -CH$_2$, wherein -NH is optionally substituted by an alkyl group, a cycloalkyl group, a (cycloalkyl)alkyl group, an amino acid N-terminal protecting group, or COR and -CH$_2$ is optionally substituted by fluorine, an alkyl group, a cycloalkyl group, a (cycloalkyl)alkyl group, an aralkyl group, an aryl group, an alkyloxy group, an

Fig. 20(a)

alkylthioxy group, an aryloxy group, an arylthioxy
group, an oxo group (i.e., =O), or a NHCOR group;

$X^2$ is oxygen, sulfur, -NH, or -CH$_2$, wherein -NH is
optionally substituted by an alkyl group, or an amino
acid N-terminal protecting group and -CH$_2$ is
optionally substituted by an alkyl group, an aryl
group, an alkyloxy group, an alkylthioxy group, an
aryloxy group, an arylthioxy group, or an oxo (i.e.
=O) group, a NHCOR group; $X^1$ and $X^2$ optionally form
part of a phenyl ring that is fused to the adjoining
ring Q;

$X^3$ is CH$_2$ or $X^2$ and $X^3$ optionally form part of a phenyl
ring that is fused to the adjoining ring Q, provided
that when $X^2$ forms a ring with $X^3$, then $X^2$ does not
form a ring with $X^1$;

any two hydrogens attached to adjacent positions in
ring Q are optionally replaced by a double bond; and Z is an optionally substituted ring selected from
the group consisting of a carbocyclic, an aryl, a
saturated heterocycle, a partially saturated
heterocycle, and a heteroaryl wherein the ring is
connected to A at a ring carbon;

or a pharmaceutically acceptable derivative thereof.

2. The compound of claim 1 wherein $R^1$ is
CH$_2$Y and Y is F, OR, SR, or -OC(=O)(R).

3. The compound of claim 2 wherein Y is
F.

4. The compound of claim 2 wherein $R^2$ is
CO$_2$H, an ester, amide, or carboxylic acid isostere.

Fig. 20(b)

5. The compound of claim 4 wherein $R^2$ is $CO_2H$.

6. The compound of claim 4 wherein $X^1$ and $X^2$ are each $CH_2$, or $X^1$ and $X^2$ combine to form part of an optionally substituted phenyl ring fused to ring Q.

7. The compound of claim 6 wherein $X^1$ and $X^2$ are each $CH_2$.

8. The compound of claim 7 wherein A is CO.

9. The compound of claim 8 wherein Z is an optionally substituted aryl which is connected to A at a ring carbon.

10. The compound of claim 1 selected from Table 1 below:

Table 1. Representative Compounds

| No. | Z |
|---|---|
| 1 | 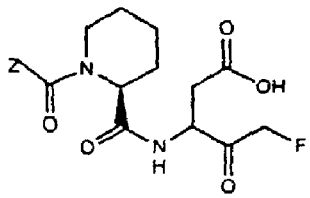 |

Fig. 20(c)

CASPASE INHIBITOR PRODRUGS

CROSS REFERENCE TO RELATED APPLICATIONS

This application claims priority to United States Provisional Patent Application No. 60/355,889, filed Feb. 11, 2002, the content of which is incorporated herein by reference.

TECHNICAL FIELD OF THE INVENTION

This invention relates to prodrugs of caspase inhibitors comprising a phospholipid moiety covalently linked, via a bridging group, to a caspase inhibitor, such that the active species is released at the required site of action.

This invention also relates to processes for preparing these prodrugs of caspase inhibitors.

This invention further relates to pharmaceutical compositions comprising said prodrugs and to the use thereof for the treatment of diseases and disorders related to inflammatory or degenerative conditions.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders [see generally *Science*, 281, pp. 1283-1312 (1998); and Ellis et al., *Ann. Rev. Cell. Biol.*, 7, p. 663 (1991)].

Caspases are a family of cysteine protease enzymes that are key mediators in the signaling pathways for apoptosis and cell disassembly [N. A. Thornberry, *Chem. Biol.*, 5, pp. R97-R103 (1998)]. These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock [H. Yaoita et al., *Circulation*, 97, pp. 276-281 (1998); M. Endres et al., *J. Cerebral Blood Flow and Metabolism*, 18, pp. 238-247, (1998); Y. Cheng et al., *J. Clin. Invest.*, 101, pp. 1992-1999 (1998); A. G. Yakovlev et al., *J. Neurosci.*, 17, pp. 7415-7424 (1997); I. Rodriquez et al., *J. Exp. Med.*, 184, pp. 2067-2072 (1996); and Grobmyer et al., *Mol. Med.*, 5, p. 585 (1999)]. However, due to their peptidic nature, such inhibitors are typically characterized by undesirable pharmacological properties, such as poor cellular penetration and cellular activity, poor oral absorption, poor stability and rapid metabolism [J. J. Plattner and D. W. Norbeck, in *Drug Discovery Technologies*, C. R. Clark and W. H. Moos, Eds. (Ellis Horwood, Chichester, England, 1990), pp. 92-126]. This has hampered their development into effective drugs. These and other studies with peptidic caspase inhibitors have demonstrated that an aspartic acid residue is involved in a key interaction with the caspase enzyme [K. P. Wilson et al., *Nature*, 370, pp. 270-275 (1994); and Lazebnik et al., *Nature*, 371, p. 346 (1994)].

Accordingly, peptidyl and non-peptidyl aspartic acid compounds are useful as caspase inhibitors. For examples, WO96/03982 reports azaaspartic acid analogs effective as interleukin-1β converting enzyme ("ICE") inhibitors.

However, due to their acidic nature such peptidic and non-peptidyl aspartic acid derivatives are charged at physiological pH. This has inhibited their ability to cross the blood brain barrier and to penetrate cells at therapeutically useful levels.

Accordingly, it would be advantageous to have drug derivatives that are targeted at the diseased organs, especially the brain and central nervous system. In addition, it would be advantageous to have drug derivatives that are targeted at the diseased cells rather than at healthy cells, thus reducing undesirable side-effects.

The use of prodrugs imparts desired characteristics such as increased bioavailability or increased site-specificity for known drugs. Various lipids and phospholipids can be used in the preparation of particular types of prodrugs.

WO94/22483 reports cell permeable prodrugs, comprising a pharmacologically active carboxylic acid such as branched-chain aliphatic carboxylic acids (e.g., valproic acid), salicylic acids (e.g., acetylsalicylic acid), steroidal carboxylic acids (e.g., lysergic and isolysergic acids, monoheterocyclic carboxylic acids (e.g., nicotinic acid) and polyheterocyclic carboxylic acids (e.g., penicillins and cephalosporins), covalently linked to an intracellular transporting adjuvant. One such embodiment of the intracellular transporting adjuvant is a lysophospholipid.

WO99/02485 reports compounds of the formula:

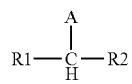

wherein R1 is a saturated or unsaturated chain of 1-5 carbons in length; R2 is a saturated or unsaturated chain of 3-10 carbons in length; and A is COOL or CONR'R", wherein L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophophatidylethanolamine, and N-mono and N,N-di-($C_{1-4}$)alkyl derivatives of the amines thereof; and R' and R" are each independently selected from the group consisiting of hydrogen and a lower alkyl group comprising 1-5 carbon atoms.

WO00/31083 reports compounds of the formula:

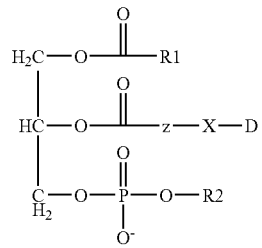

wherein R1 is a saturated or unsaturated, substituted or unsubstituted hydrocarbon chain having from 2 to 30 carbon atoms; R2 is H or a phospholipid head group; D is a residue of a non-steroidal anti-inflammatory drug having a functional group selected from the group consisting of carboxyl, hydroxyl, amine and thiol, wherein D is attached through said functional group to a bridging group, —C(O)-Z-X—, wherein Z is a saturated or unsaturated carbon chain having from 2 to 15 atoms, and X is selected from amino, hydroxy, thio and carbonyl groups, such that when the functional group of D is carboxyl, X is selected from amino, hydroxy and thio, and when the functional group of D is amino, hydroxy or thio, X is a carbonyl group.

WO01/19320 reports compounds of the formula:

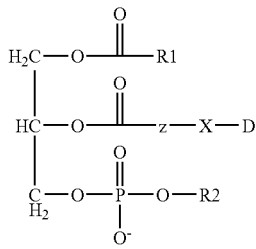

wherein R1 is a saturated or unsaturated, straight-chain or branched, substituted or unsubstituted hydrocarbon chain having from 2 to 30 carbon atoms; R2 is H or a phospholipid head group; Z is a saturated or unsaturated, straight-chain or branched, substituted or unsubstituted hydrocarbon chain having from 2 to 15 carbon atoms, which may include cyclic elements, and optionally is interrupted by one or more atoms selected from oxygen and sulfur atoms; X is a direct covalent bond or selected from the group consisting of O, S, NH and C(O) groups; and D is a residue of an anti-proliferative drug, wherein the bound anti-proliferative drug residue is an inactive form of the drug which is selectively activated in cells and tissues with elevated phospholipase activity.

WO02/11666 reports compounds of the formula:

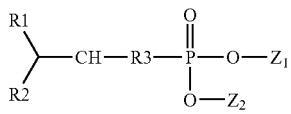

or a pharmaceutically acceptable salt thereof, wherein R1 and R2 are the same or different, saturated or unsaturated aliphatic chain comprising from 2 to 30 carbon atoms; R3 is A-[CH$_2$]$_m$—B—[CH$_2$]$_n$—C—[CH$_2$]$_p$-D, wherein m, n and p are each independently zero or an integer from 1 to 12, and A, B, C and D are each independently selected from a covalent bond, amino, amido, oxygen, thio, carbonyl, carboxyl, oxycarbonyl, thiocarbonyl, phosphate, amino phosphate, mono-, di- and tri-amino phosphate group with the proviso that no two oxygen atoms are directly connected to each other; $Z_1$ and $Z_2$ are the same or different, each may be absent or independently selected from a) hydrogen, sodium, lithium, potassium, ammonium, mono-, di-, tri- and tetraalkylammonium, or b) together with the phospho group form a phospho ester of glycerol, choline, ethanolamine, inositol, serine, mono- or oligosaccharide.

WO03/000173 reports compounds of formula (I):

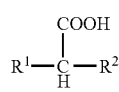

and pharmaceutically acceptable salts thereof, wherein R$^1$ is a saturated or unsaturated chain of 1-18 carbons in length; and R$^2$ is a saturated or unsaturated chain of 1-18 carbons in length, with the proviso that R$^1$ and R$^2$ are not both propyl; and compounds of formula (II):

and pharmaceutically acceptable salts thereof, wherein R$^1$ is a saturated or unsaturated chain of 1-18 carbons in length; R$^2$ is a saturated or unsaturated chain of 1-18 carbons in length; and A is selected from the group consisting of PO$_4$—X, COOL and COHR'—R", wherein X is a hydrogen or choline, L is a lipid moiety selected from the group consisting of glycerol, C$_{3-20}$ fatty acid monoglycerides, C$_{3-20}$ fatty acid diglycerides, hydroxy-C$_{2-6}$-alkyl esters of C$_{3-20}$ fatty acids, hydroxy-C$_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono-(C$_{1-4}$)alkyl and N,N-di-(C$_{1-4}$)alkyl and quaternary derivatives of the amines thereof; and R' and R" are each independently selected from the group consisting of hydrogen and a lower alkyl group comprising 1-5 carbon atoms.

SUMMARY OF THE INVENTION

The present invention relates to prodrugs of caspase inhibitors. These compounds have the general formula I:

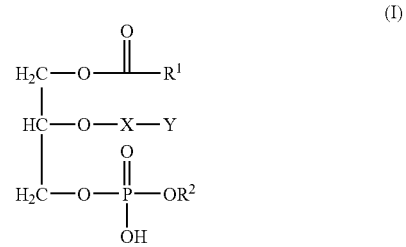

or a pharmaceutically acceptable salt thereof, wherein:

R$^1$ is a saturated or unsaturated, straight-chain or branched, substituted or unsubstituted hydrocarbon chain;

R$^2$ is H or a phospholipid head group;

X is a direct covalent bond or a group C(O)LR$^3$ wherein L is a saturated or unsaturated, straight-chain or branched, substituted or unsubstituted hydrocarbon chain having from 2 to 15 carbon atoms, which optionally includes cyclic elements, and is optionally interrupted by one or more atoms selected from the group consisting of oxygen, sulfur and N(R$^4$); R$^3$ is selected from the group consisting of O, S and N(R$^4$), wherein R$^4$ is H or a saturated or unsaturated hydrocarbon chain having 1 to 6 carbon atoms; and Y is a residue of a caspase inhibitor.

This invention further provides pharmaceutical compositions comprising these prodrugs. This invention also relates to the release of the caspase inhibitor from the prodrug by selective bond cleavage. This invention also relates to methods of using said pharmaceutical compositions for treatment of caspase-mediated diseases including inflammatory and degenerative diseases. This invention further relates to methods for preparing compounds of this invention.

BRIEF DESCRIPTION OF THE FIGURES

FIG. 1 depicts compounds and pharmaceutical compositions of this invention. Said compounds and compositions are also described in PCT Publication WO 00/55114.

FIG. 3 depicts compounds and pharmaceutical compositions of this invention. Said compounds and compositions are also described in PCT Publication WO 00/61542.

FIG. 5 depicts compounds and pharmaceutical compositions of this invention. Said compounds and compositions are also described in PCT Publication WO 01/10383.

FIG. 6 depicts compounds and pharmaceutical compositions of this invention. Said compounds and compositions are also described in PCT Publication WO 01/16093.

FIG. 7 depicts compounds and pharmaceutical compositions of this invention. Said compounds and compositions are also described in PCT Publication WO 01/42216.

FIG. 9 depicts compounds and pharmaceutical compositions of this invention. Said compounds and compositions are also described in PCT Publication WO 01/90070.

Figure 11L:
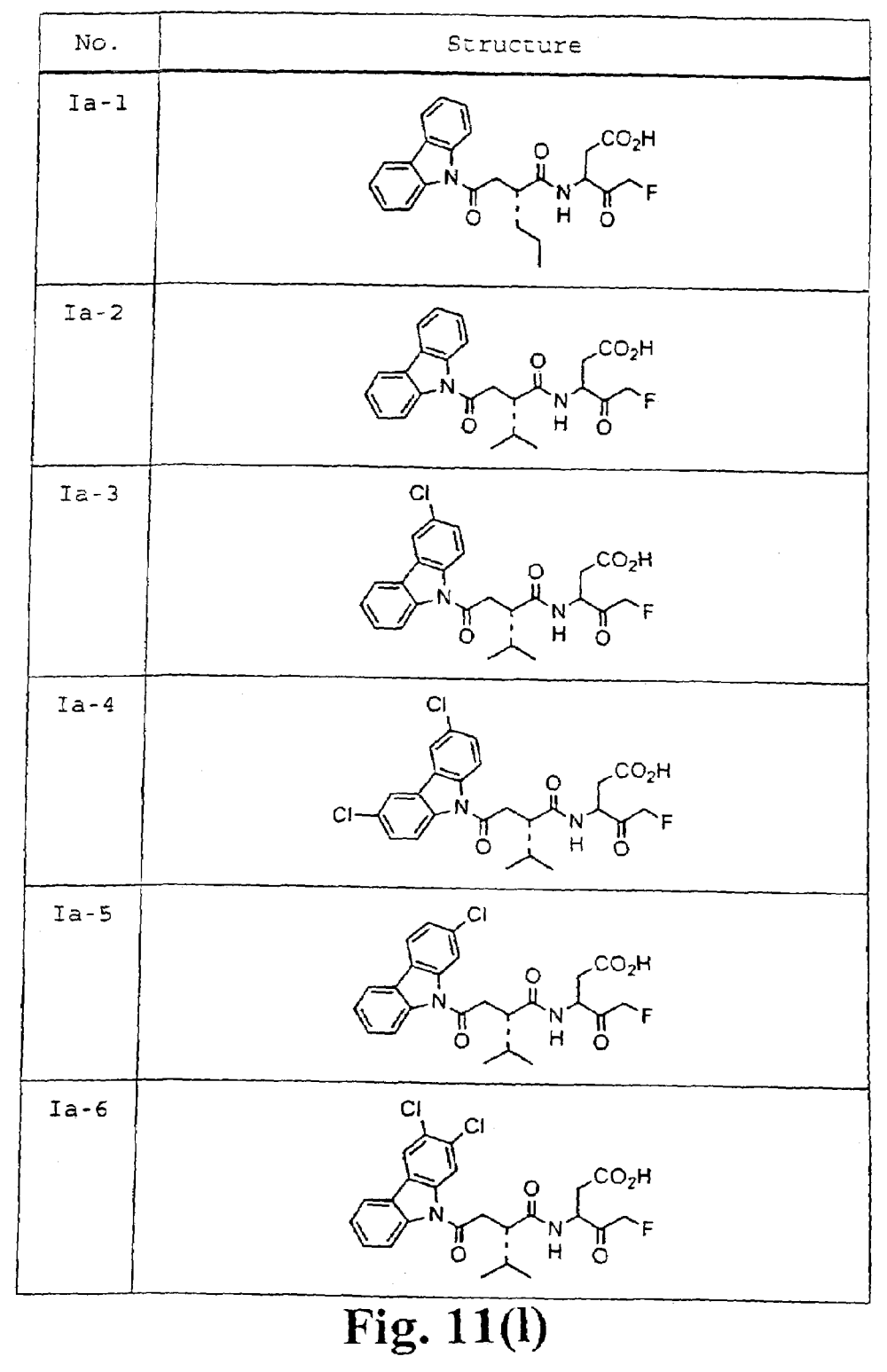
Figure 11N:
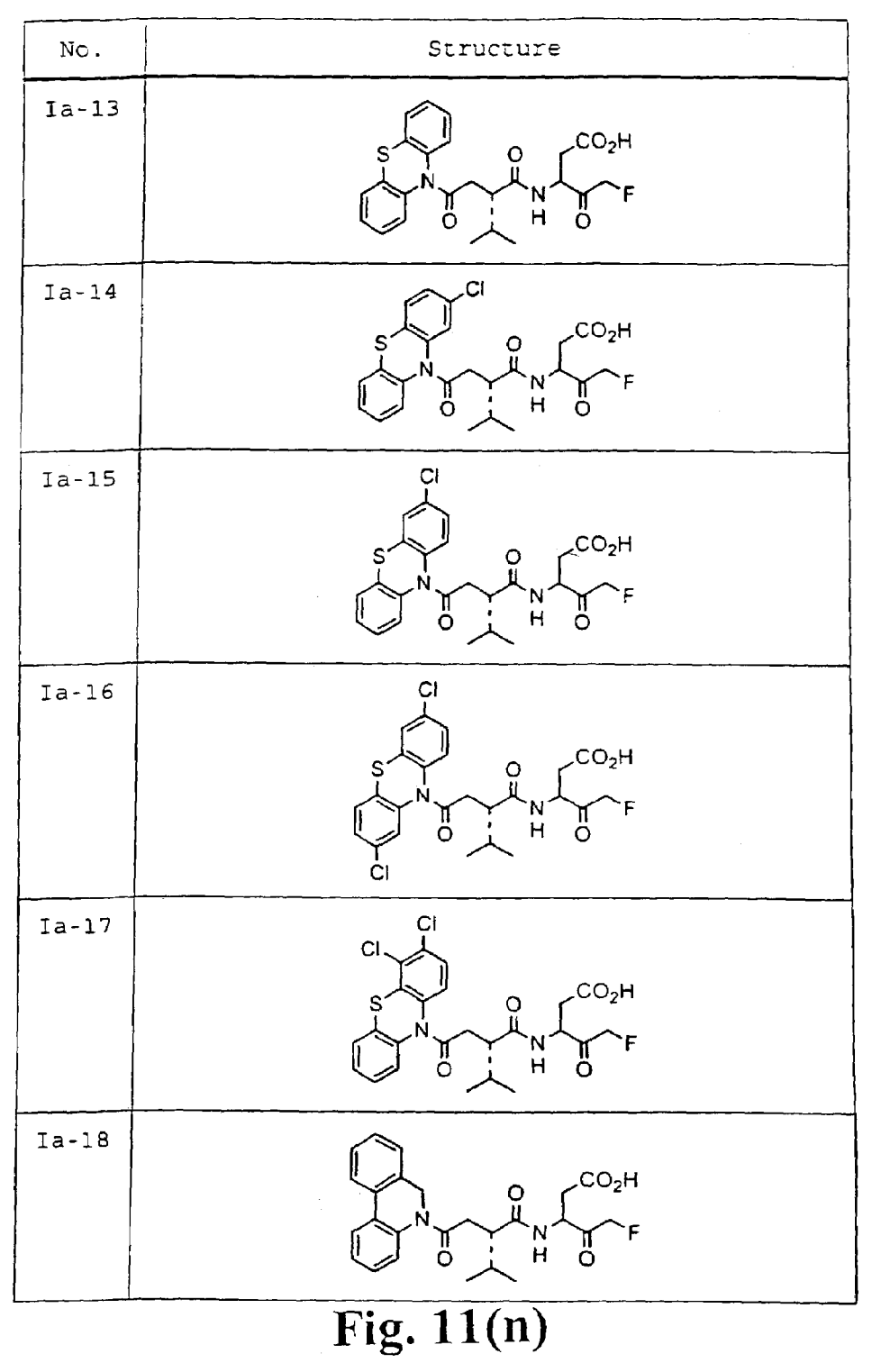
Figure 11Q:
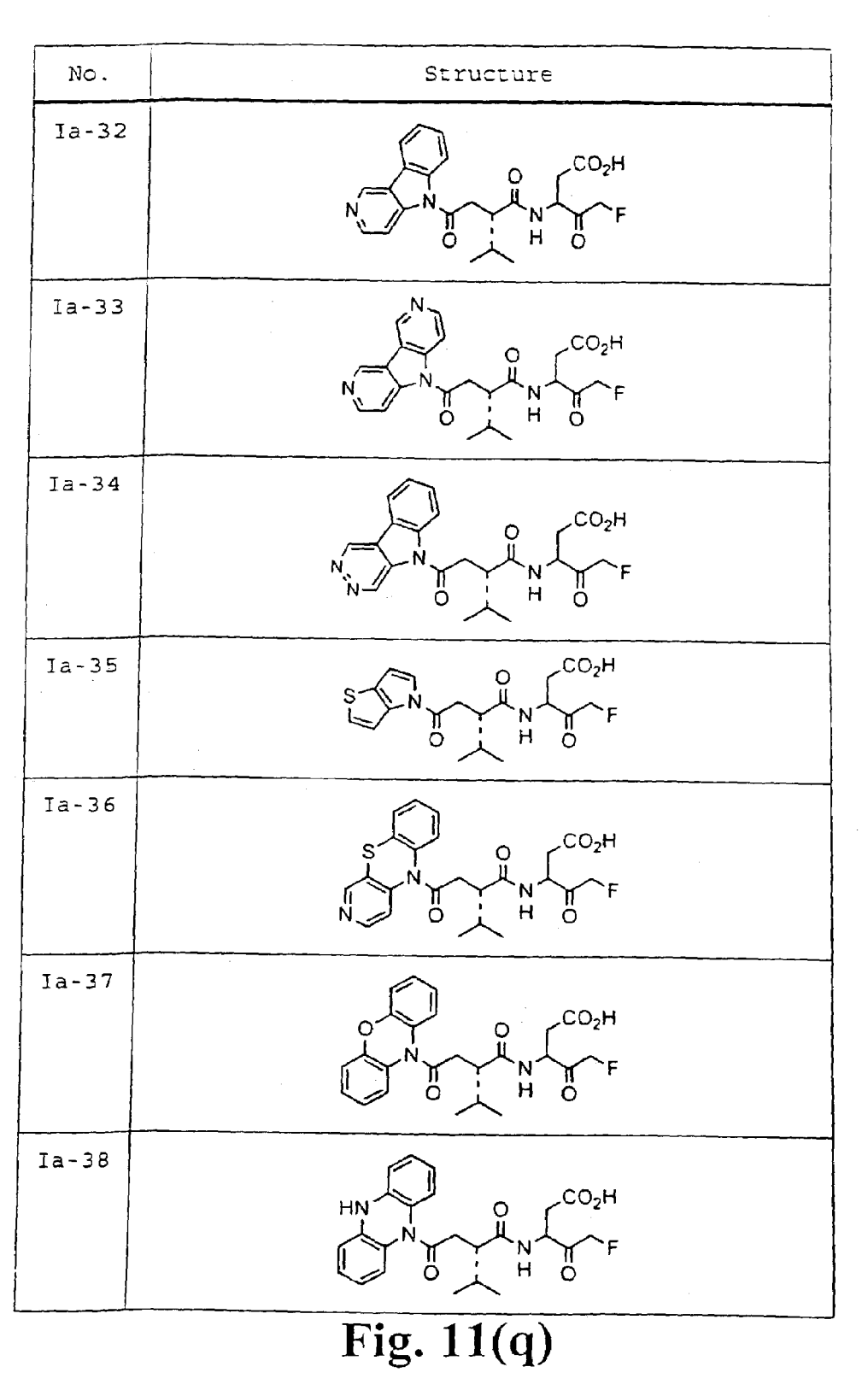

FIG. 11 depicts compounds and pharmaceutical compositions of this invention. Said compounds and compositions are also described in PCT Publication WO 02/094263.

FIG. 12 depicts compounds and pharmaceutical compositions of this invention. Said compounds and compositions are also described in PCT Publication WO 02/42278.

FIG. 13 depicts compounds and pharmaceutical compositions of this invention. Said compounds and compositions are also described in U.S. Pat. No. 6,184,210.

FIG. 14 depicts compounds and pharmaceutical compositions of this invention. Said compounds and compositions are also described in U.S. Pat. No. 6,184,244.

FIG. 15 depicts compounds and pharmaceutical compositions of this invention. Said compounds and compositions are also described in U.S. Pat. No. 6,187,771.

FIG. 19 depicts compounds and pharmaceutical compositions of this invention. Said compounds and compositions are also described in PCT Publication WO 02/22611.

DETAILED DESCRIPTION OF THE INVENTION

The present invention provides prodrug agents with improved ability, relative to the corresponding drug, to inhibit caspases in diseases where caspase activation is implicated. The present invention also provides prodrugs of caspase inhibitors that undergo activation within the disease-affected cells and tissues.

The prodrugs comprise a phospholipid moiety covalently linked, via an optional bridging group, to a caspase inhibitor such that the active species is preferentially released at the required site of action. Preferably, the active species is released by enzymatic cleavage.

Thus, the present invention provides a prodrug of general formula I:

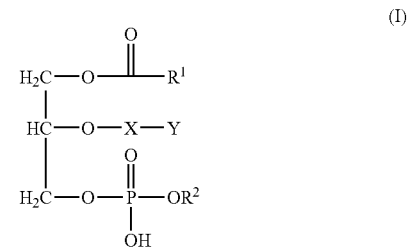

(I)

or a pharmaceutically acceptable salt thereof, wherein:

$R^1$ is a saturated or unsaturated, straight-chain or branched, substituted or unsubstituted hydrocarbon chain;

$R^2$ is H or a phospholipid head group;

X is a direct covalent bond or a group $C(O)LR^3$ wherein L is a saturated or unsaturated, straight-chain or branched, substituted or unsubstituted hydrocarbon chain having from 2 to 15 carbon atoms, which optionally includes cyclic elements, and is optionally interrupted by one or more atoms selected from the group consisting of oxygen, sulfur and $N(R^4)$; $R^3$ is selected from the group consisting of O, S and $N(R^4)$, wherein $R^4$ is a saturated or unsaturated hydrocarbon chain having 1 to 6 carbon atoms;

and Y is a residue of a caspase inhibitor.

In one embodiment, Y is a bound caspase inhibitor residue which is an inactive form of the drug that is selectively released in cells and tissues with elevated phospholipase activity. In another embodiment, Y corresponds to a reversible caspase inhibitor residue. In yet another embodiment, Y corresponds to an irreversible caspase inhibitor residue.

In one embodiment of the invention, the $R^1$ hydrocarbon chain has from 2 to 30 carbon atoms.

In another embodiment, the $R^1$ hydrocarbon chain has from 2 to 24 carbon atoms.

In another embodiment, $R^2$ is a phospholipid head group. Preferably, the phospholipid head group is choline.

In another embodiment, X is a direct covalent bond.

Figures 1G, 2:
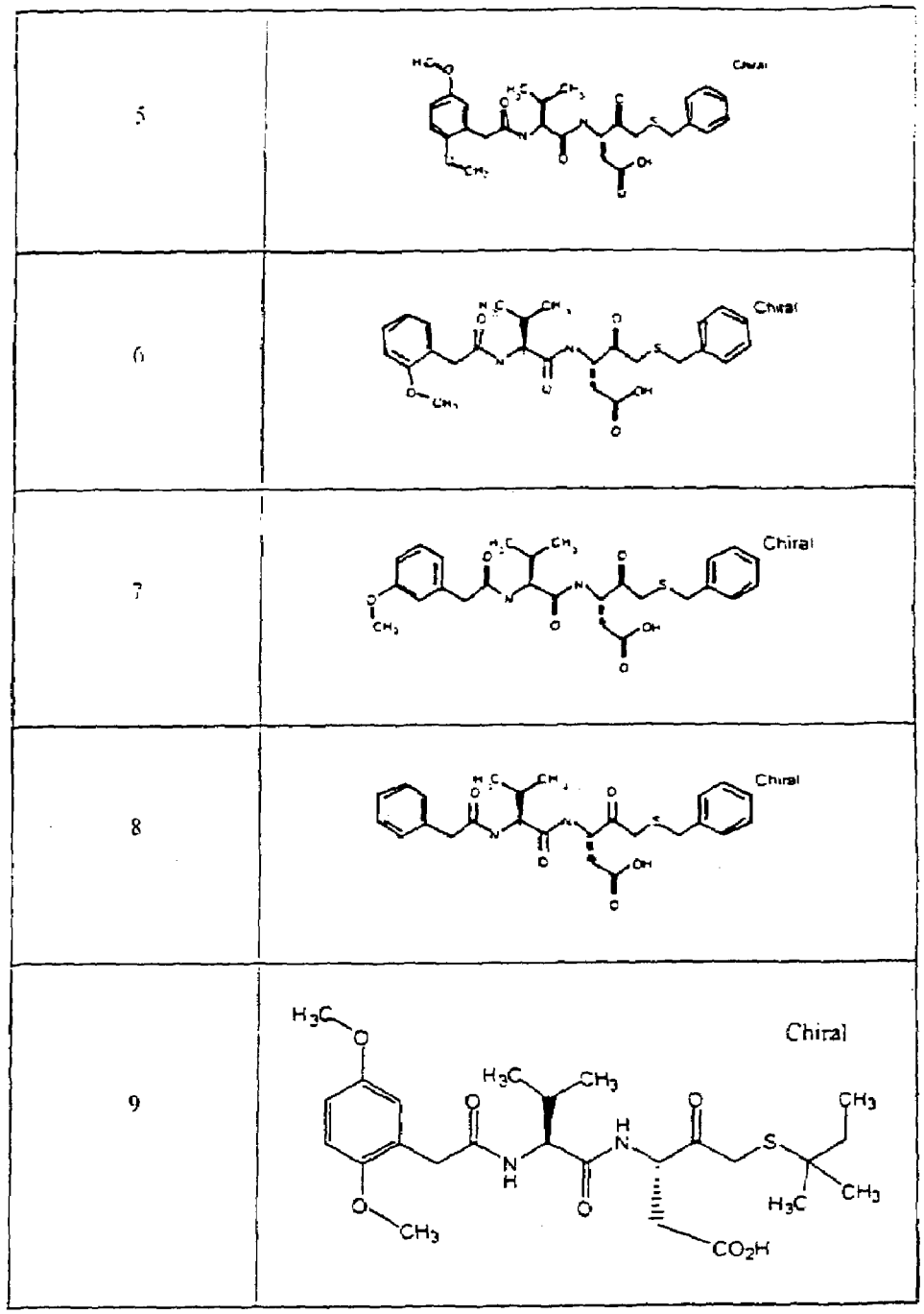
FIG. 2 depicts compounds and pharmaceutical compositions of this invention. Said compounds and compositions are also described in PCT Publication WO 00/55127.
Figures 1H, 2:
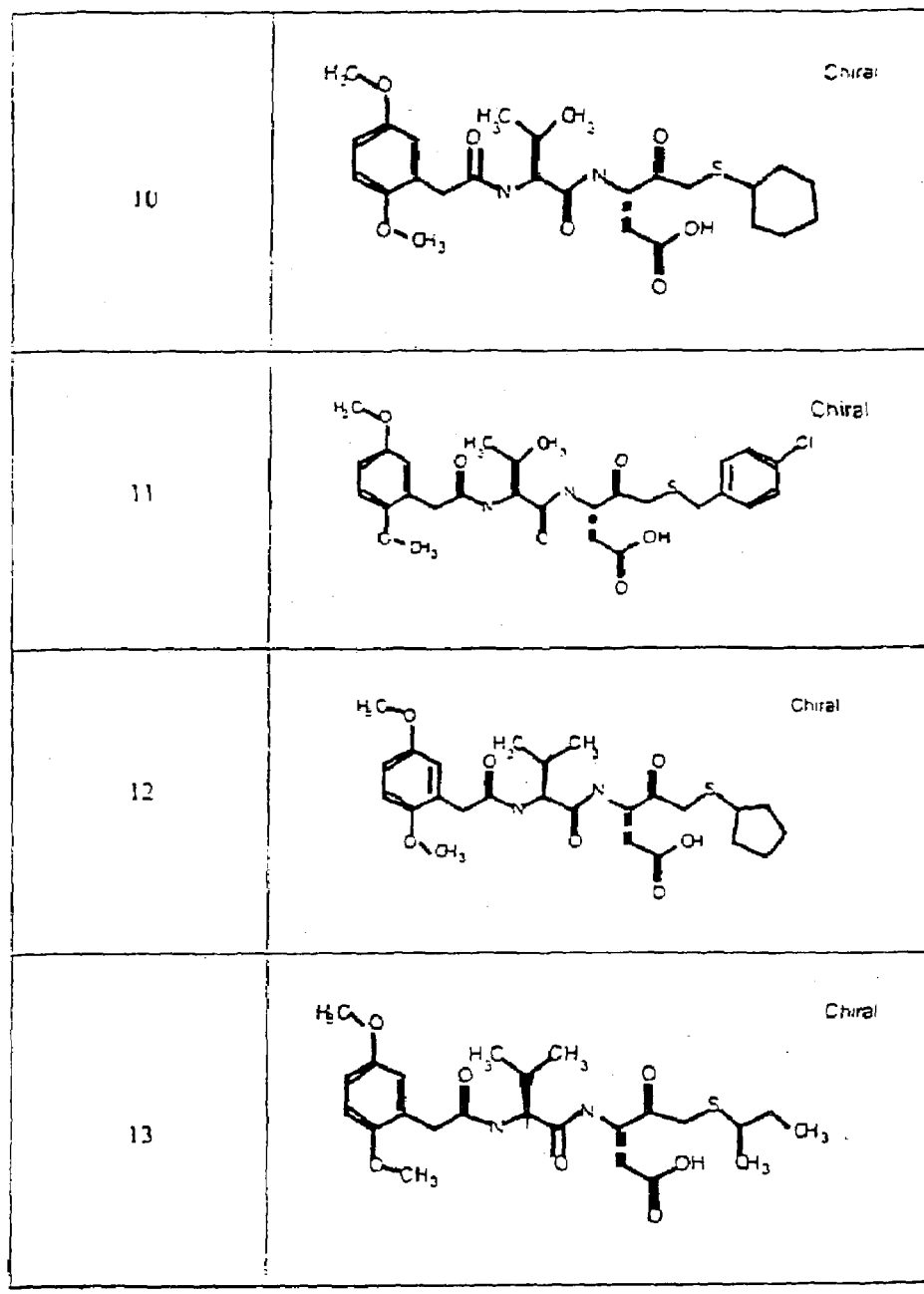
Figures 1I, 2:
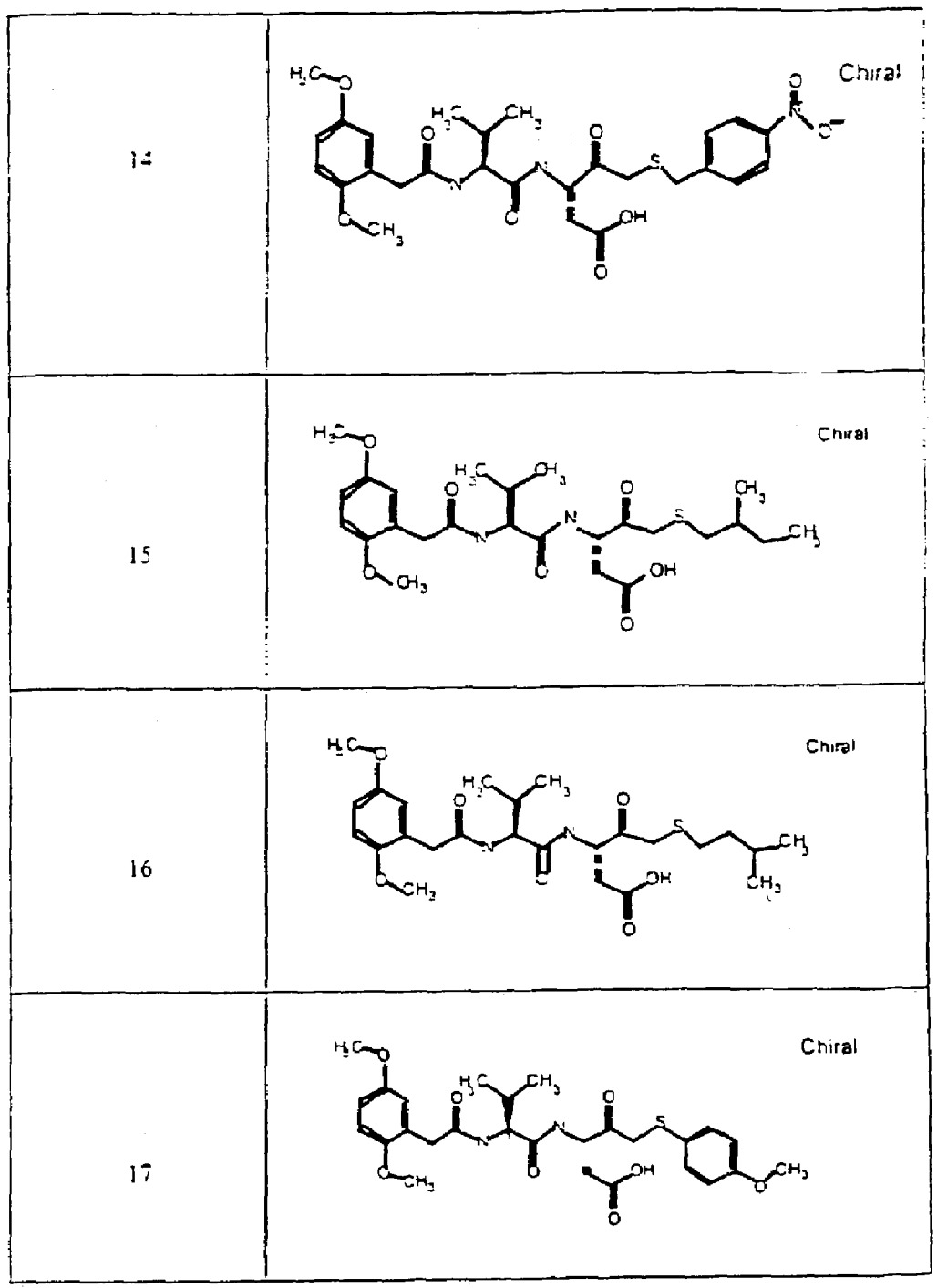
Figures 1J, 2:
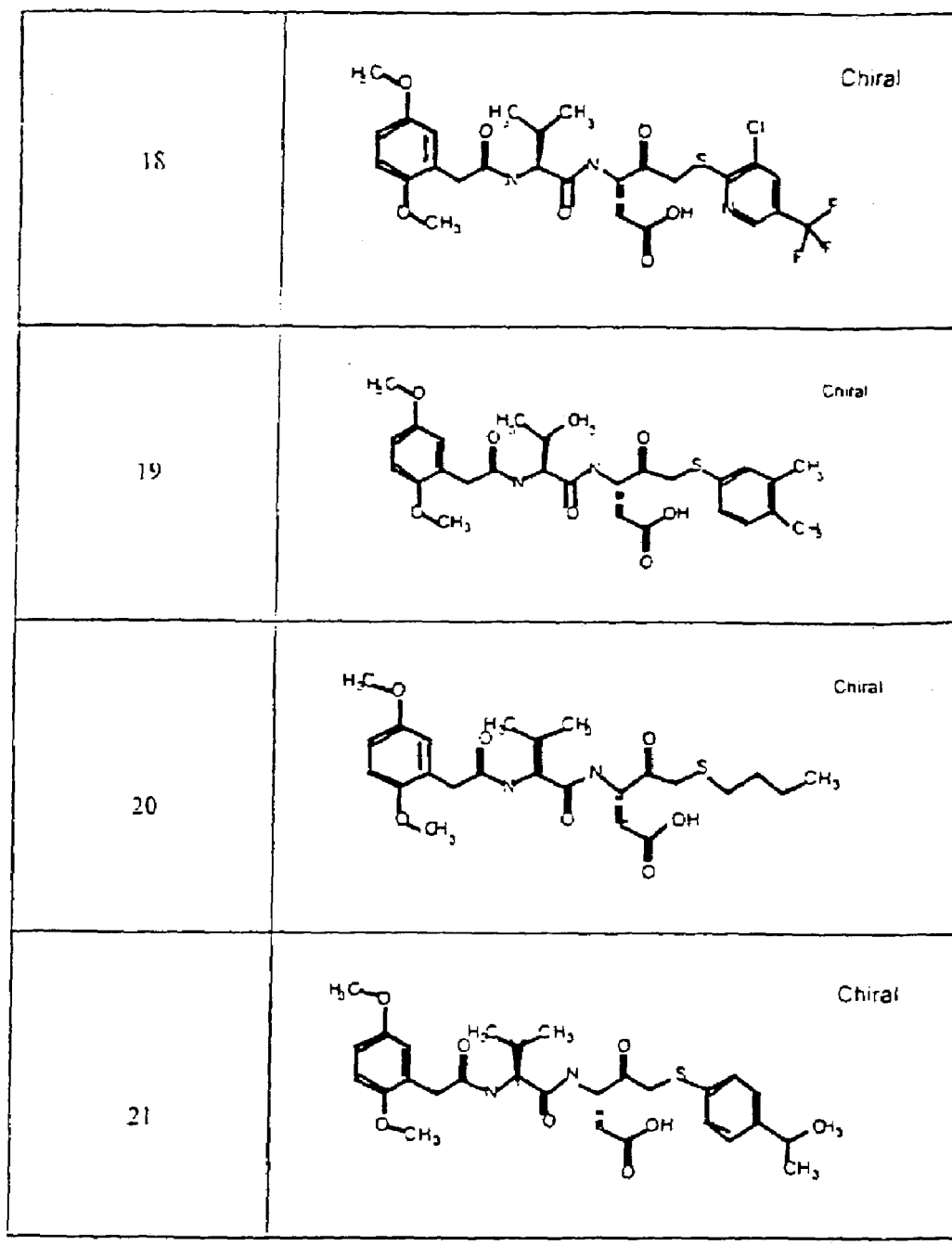
Figures 1K, 2:
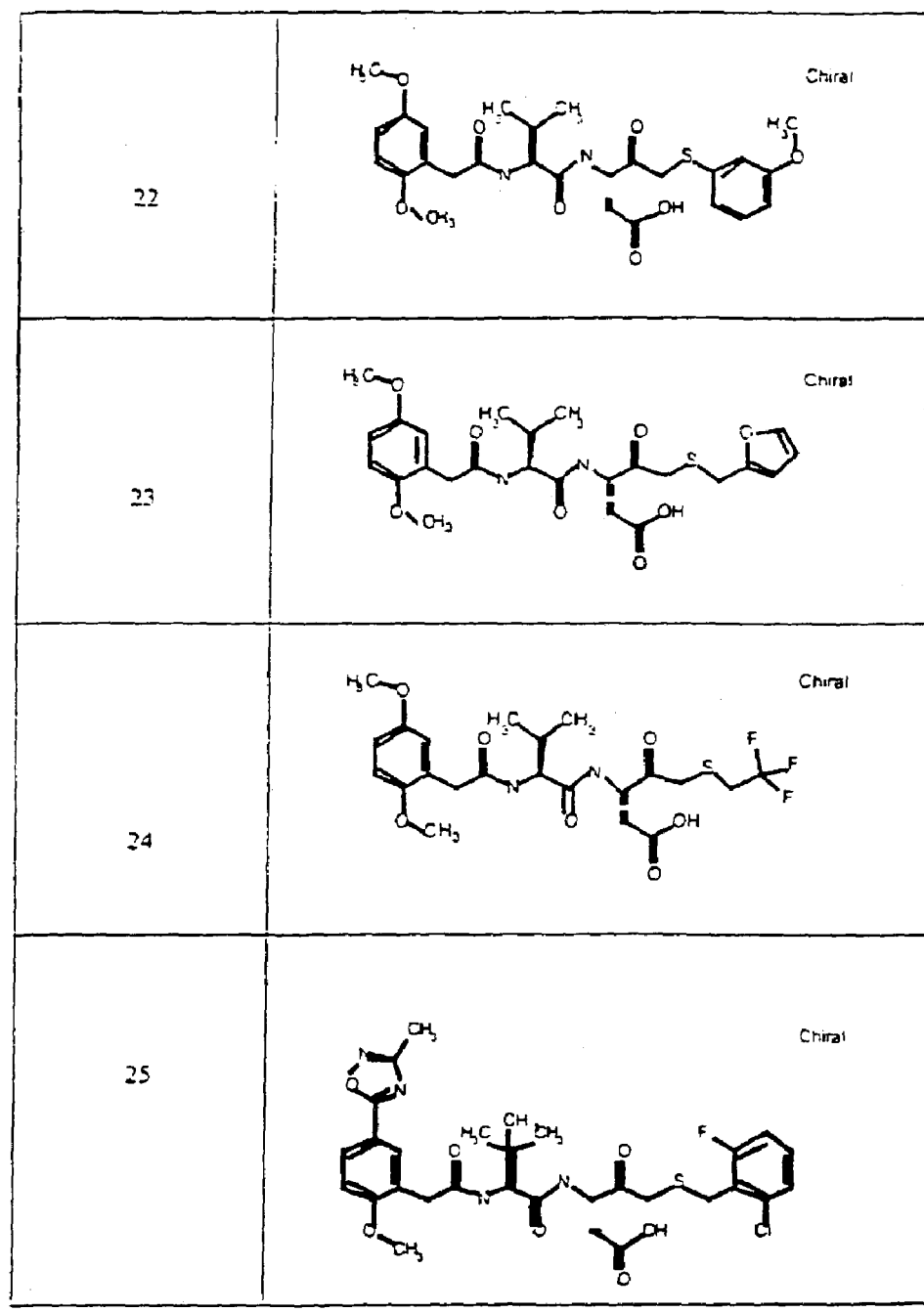
Figures 1L, 2:
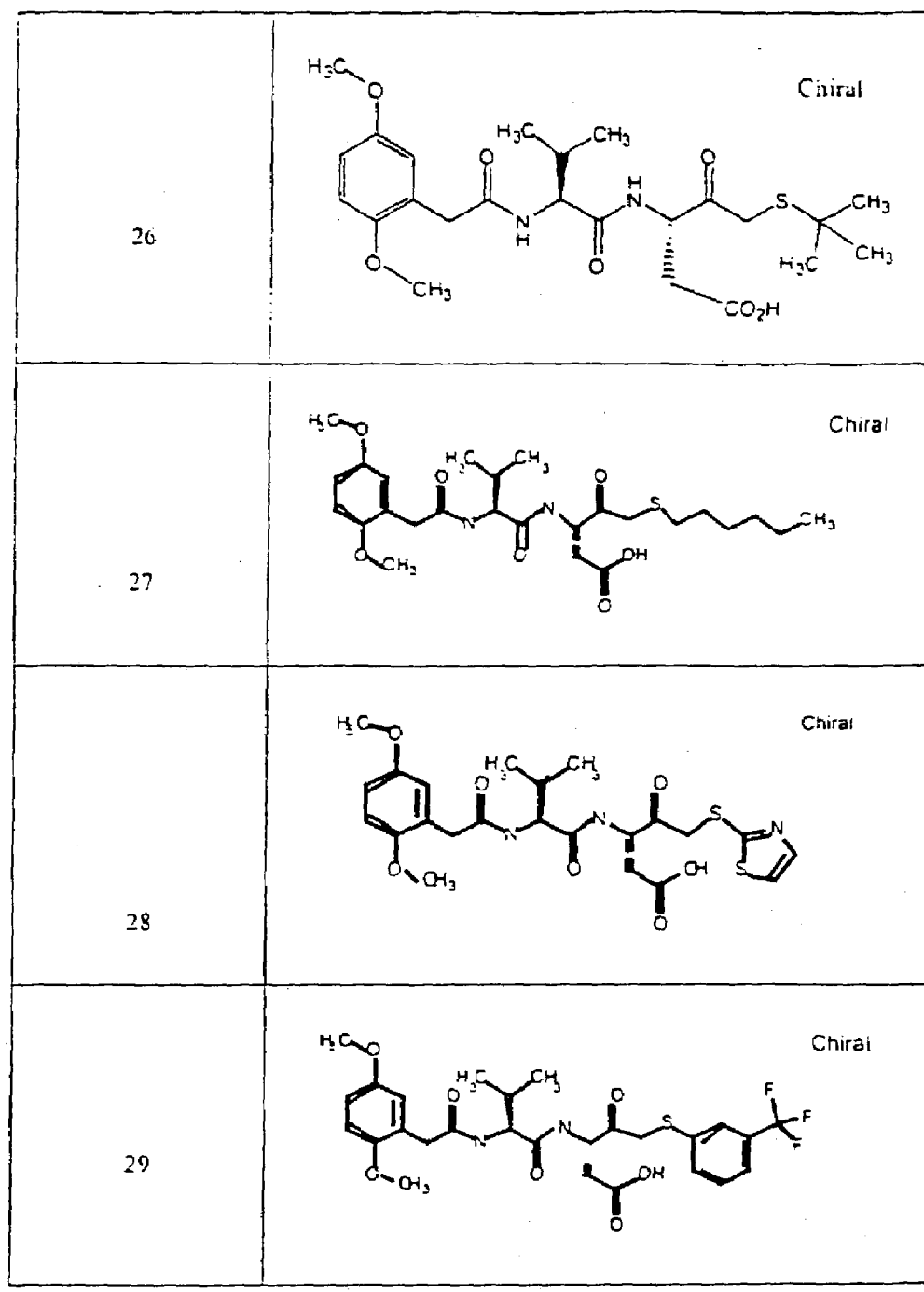
Figures 1M, 2:
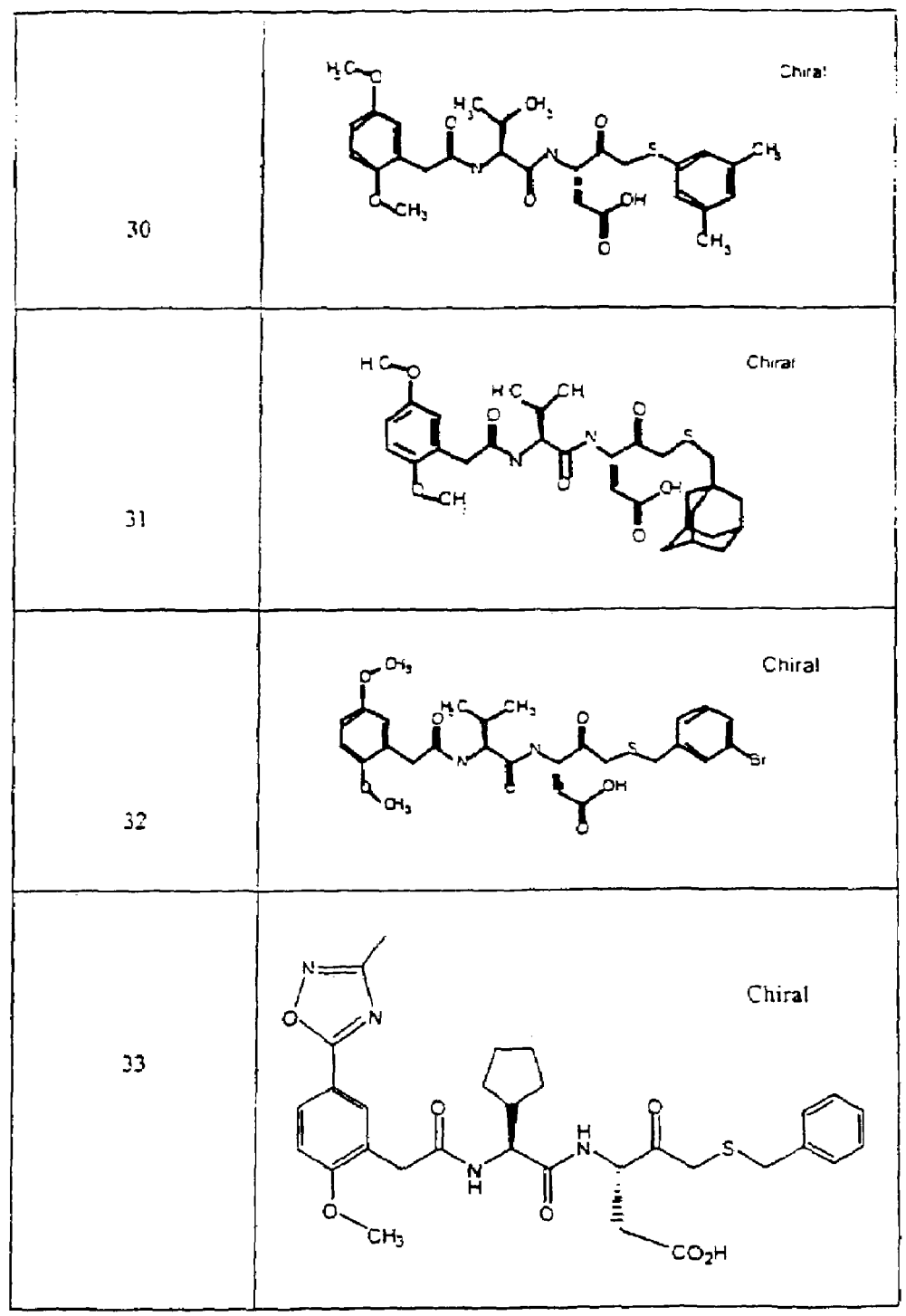
Figures 1N, 2:
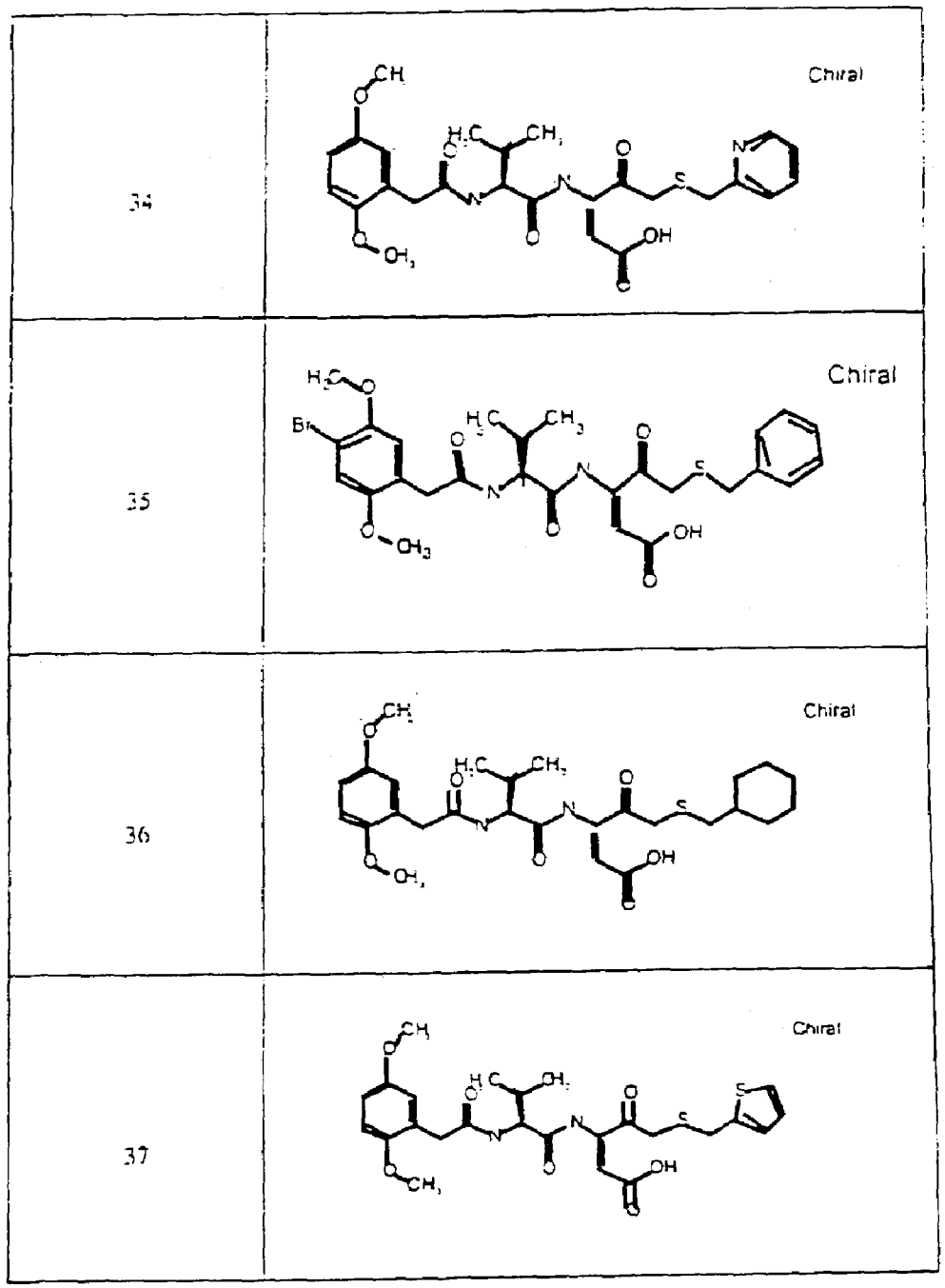
Figures 1O, 2:
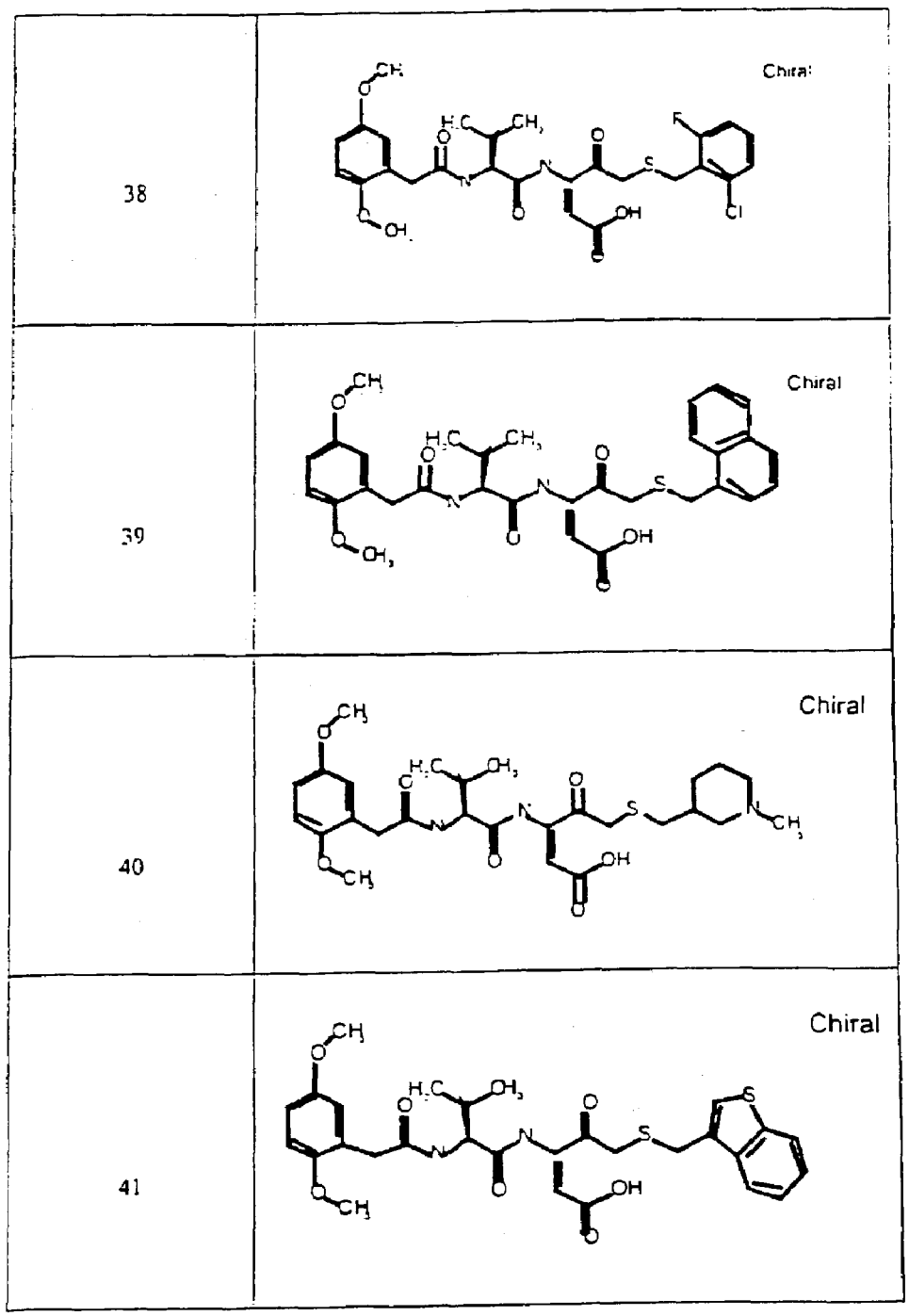
Figures 1P, 2:
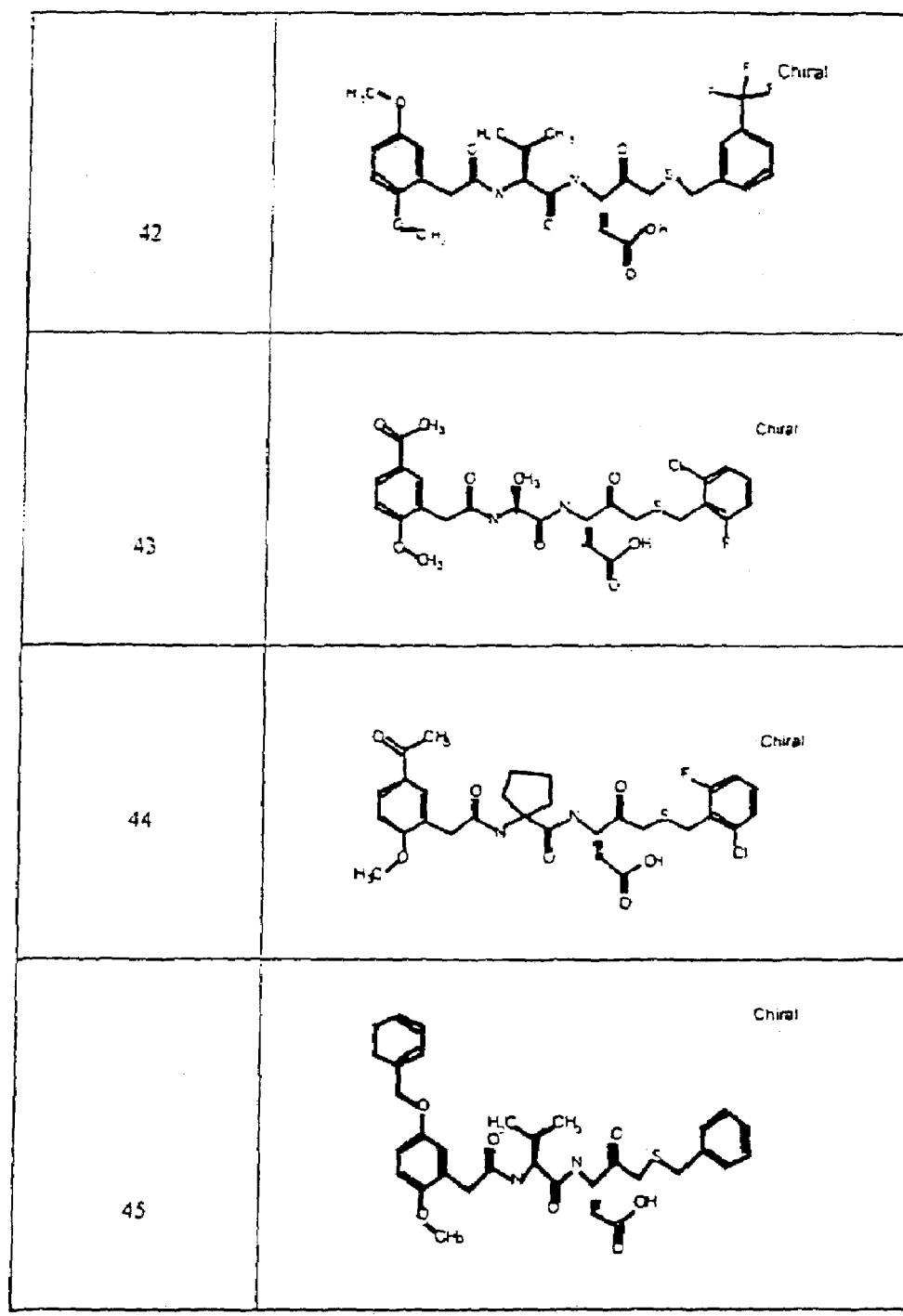
Figures 1Q, 2:
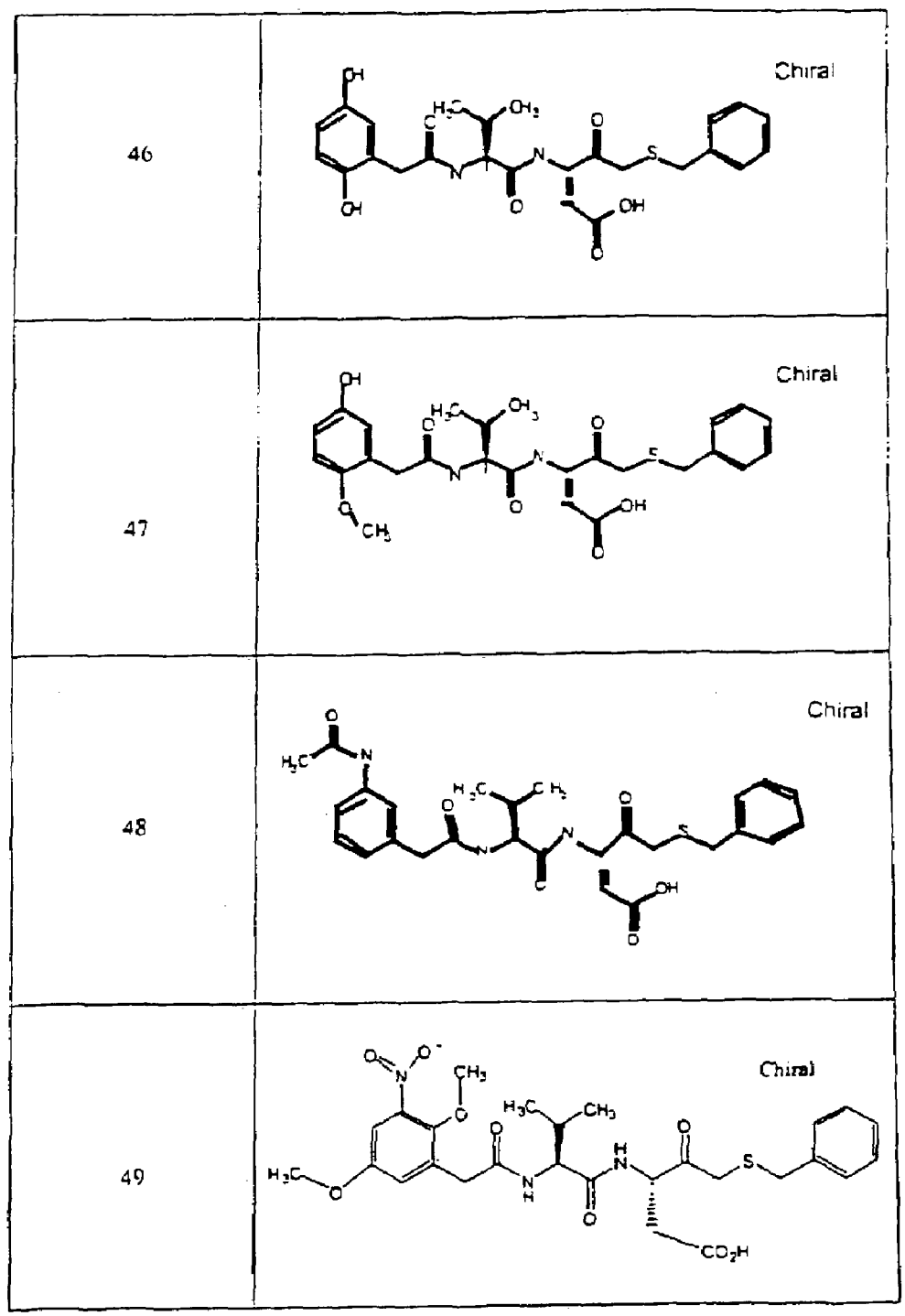
Figures 1R, 2:
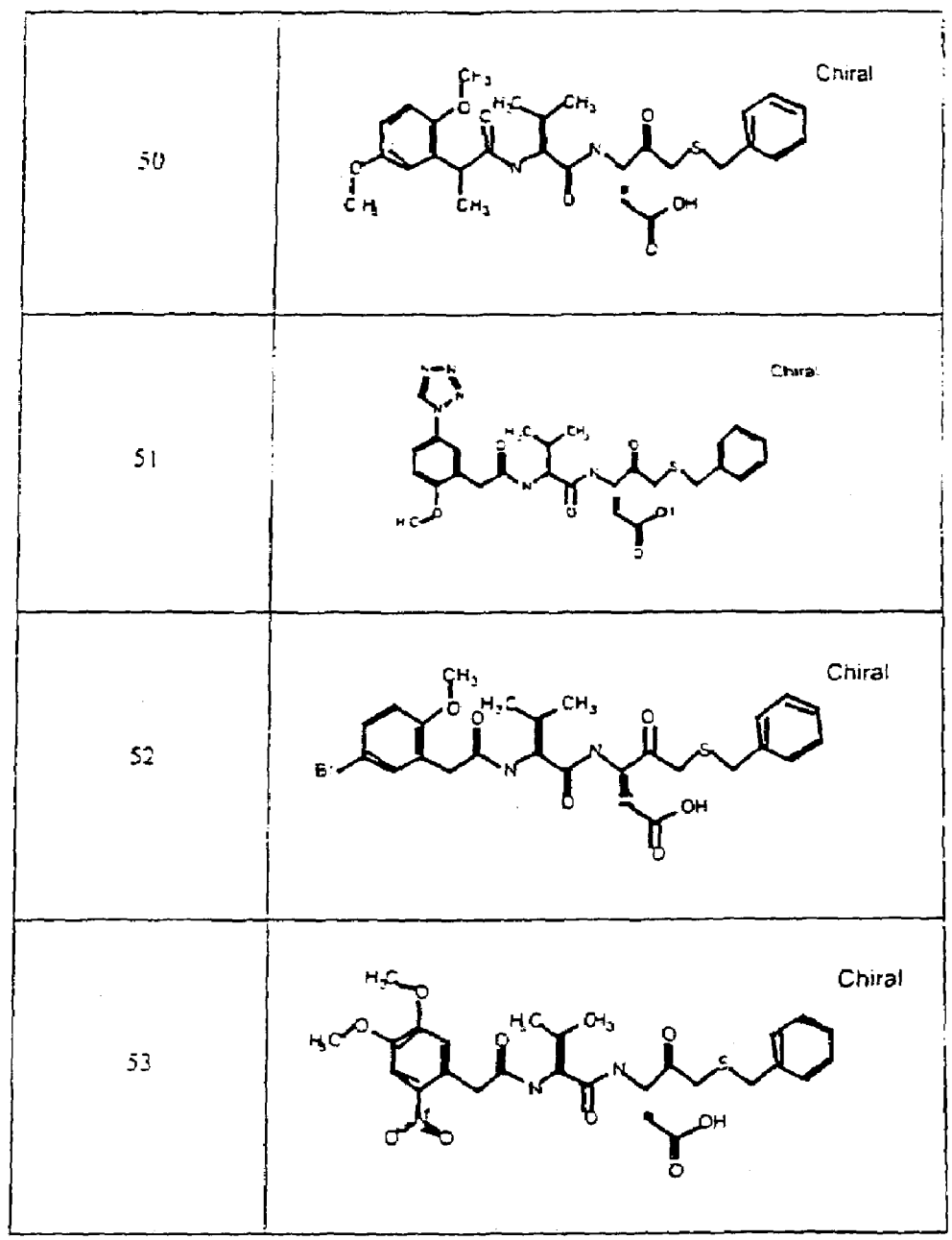
Figures 1S, 2:
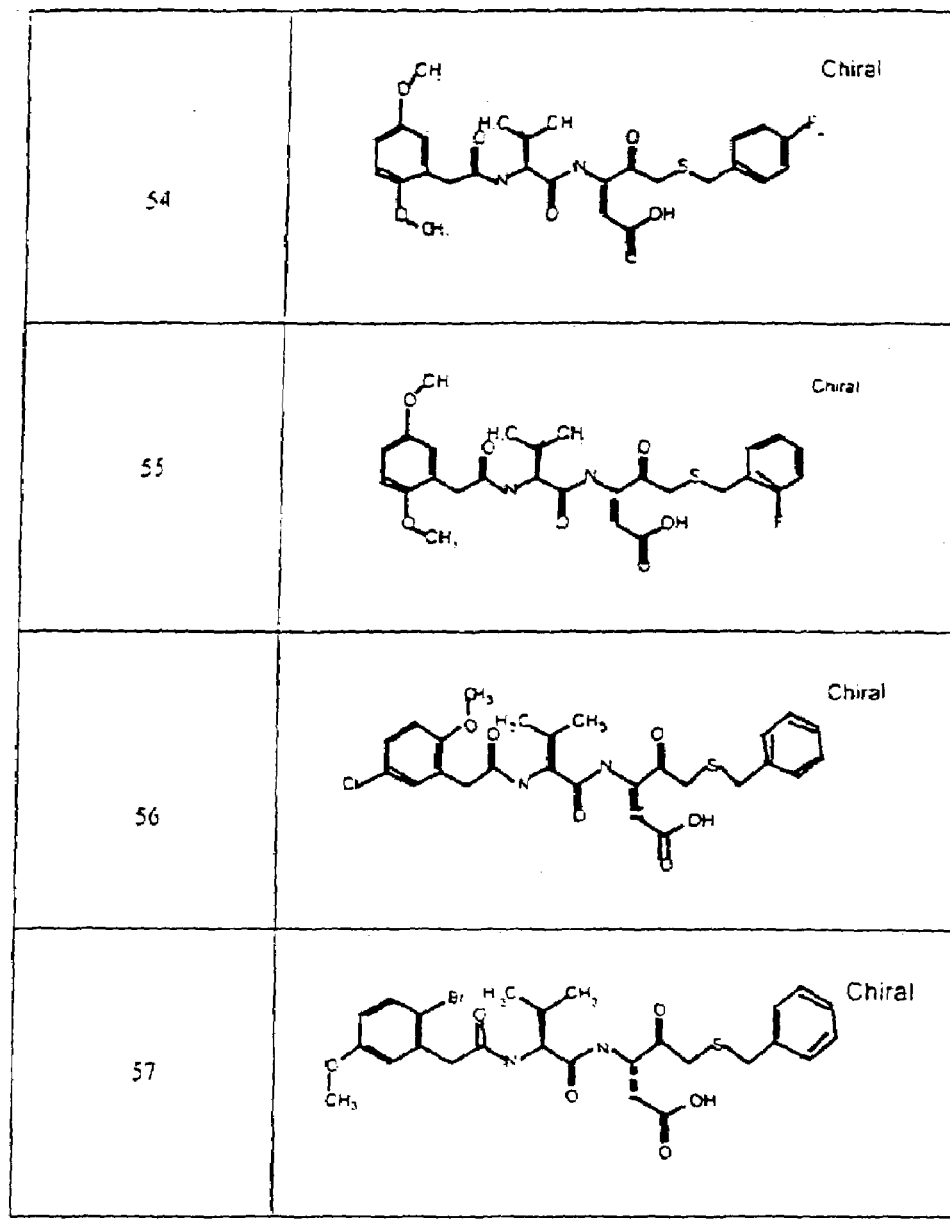
Figures 1T, 2:
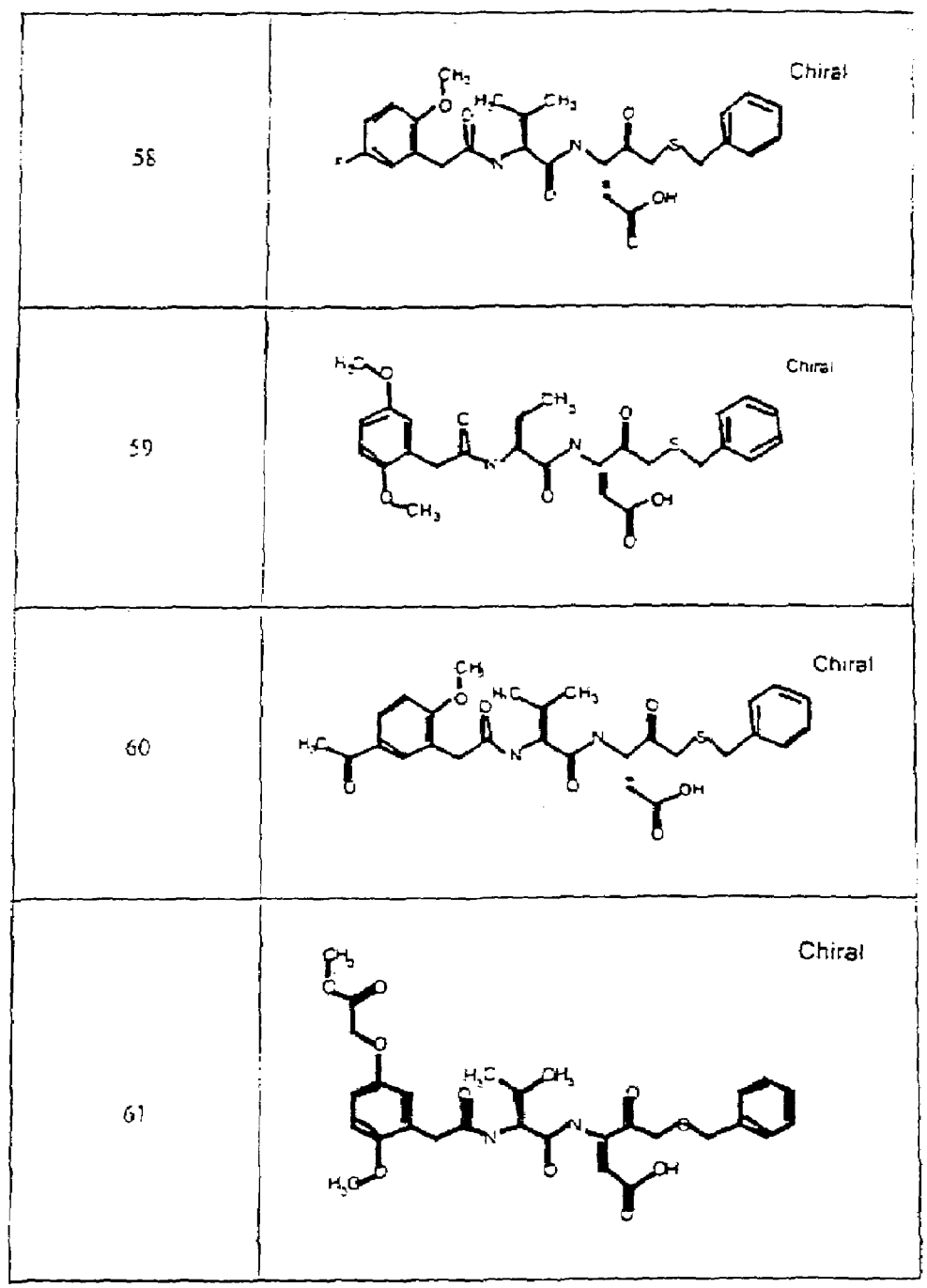
Figures 1U, 2:
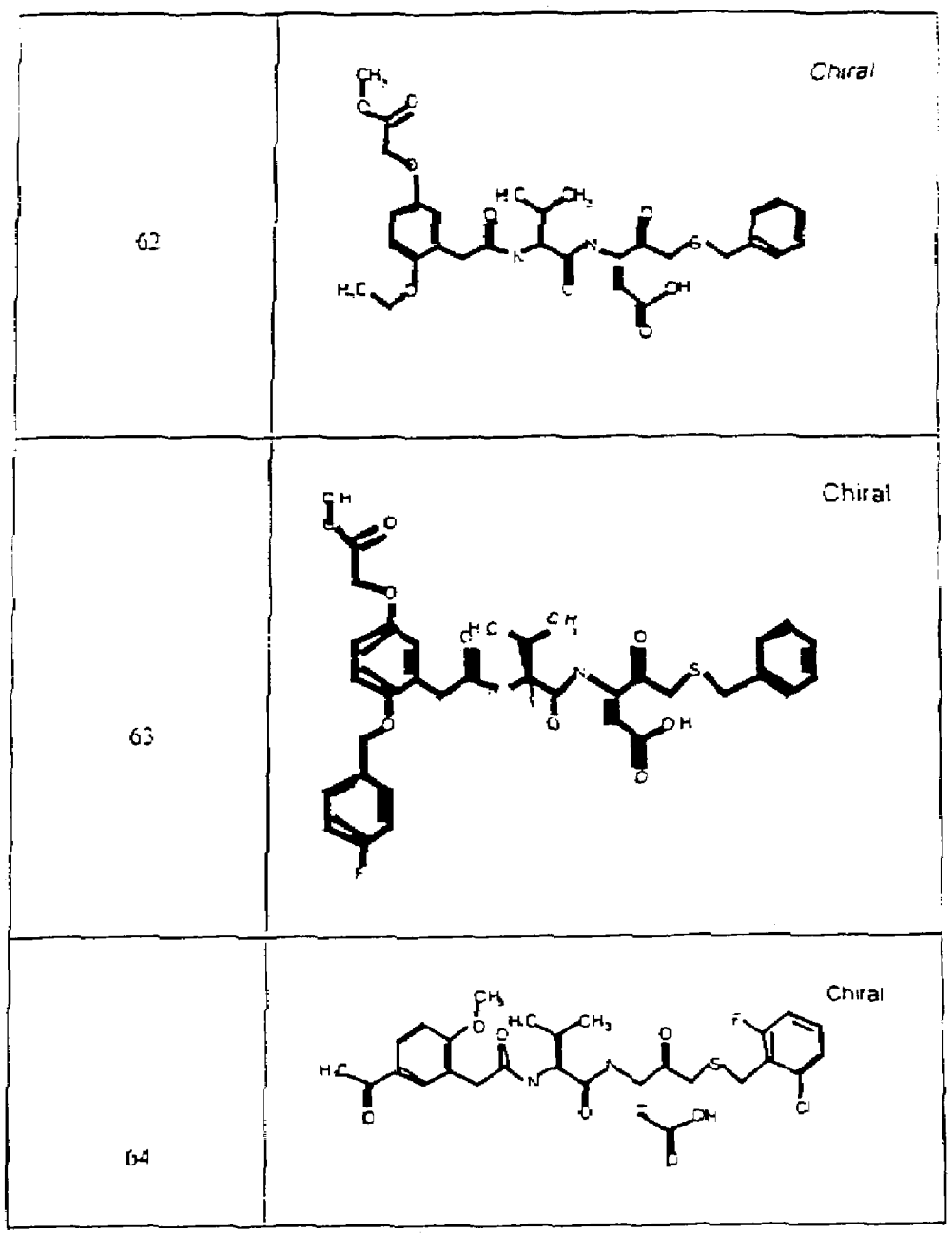
Figures 1V, 2:
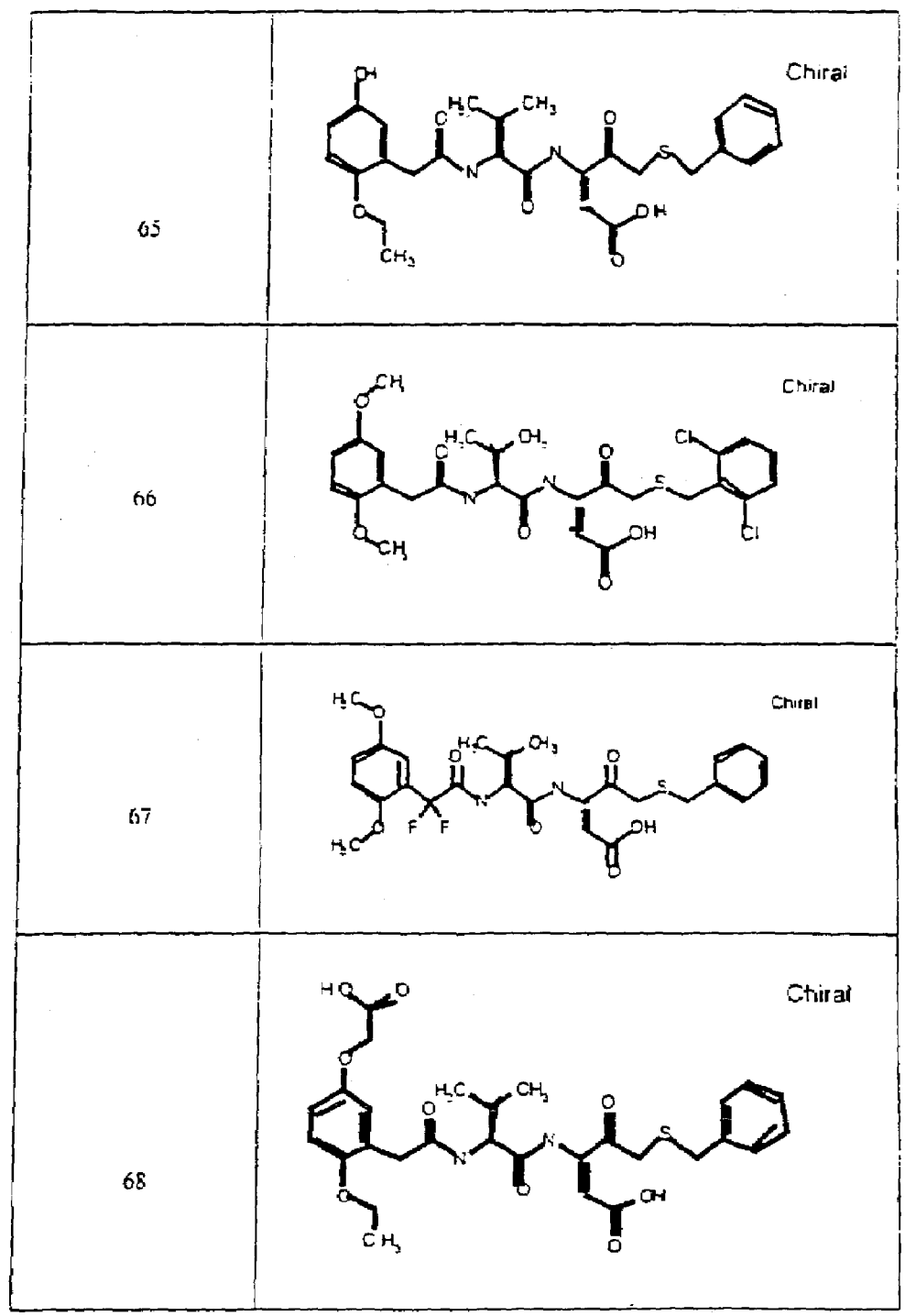
Figures 1W, 2:
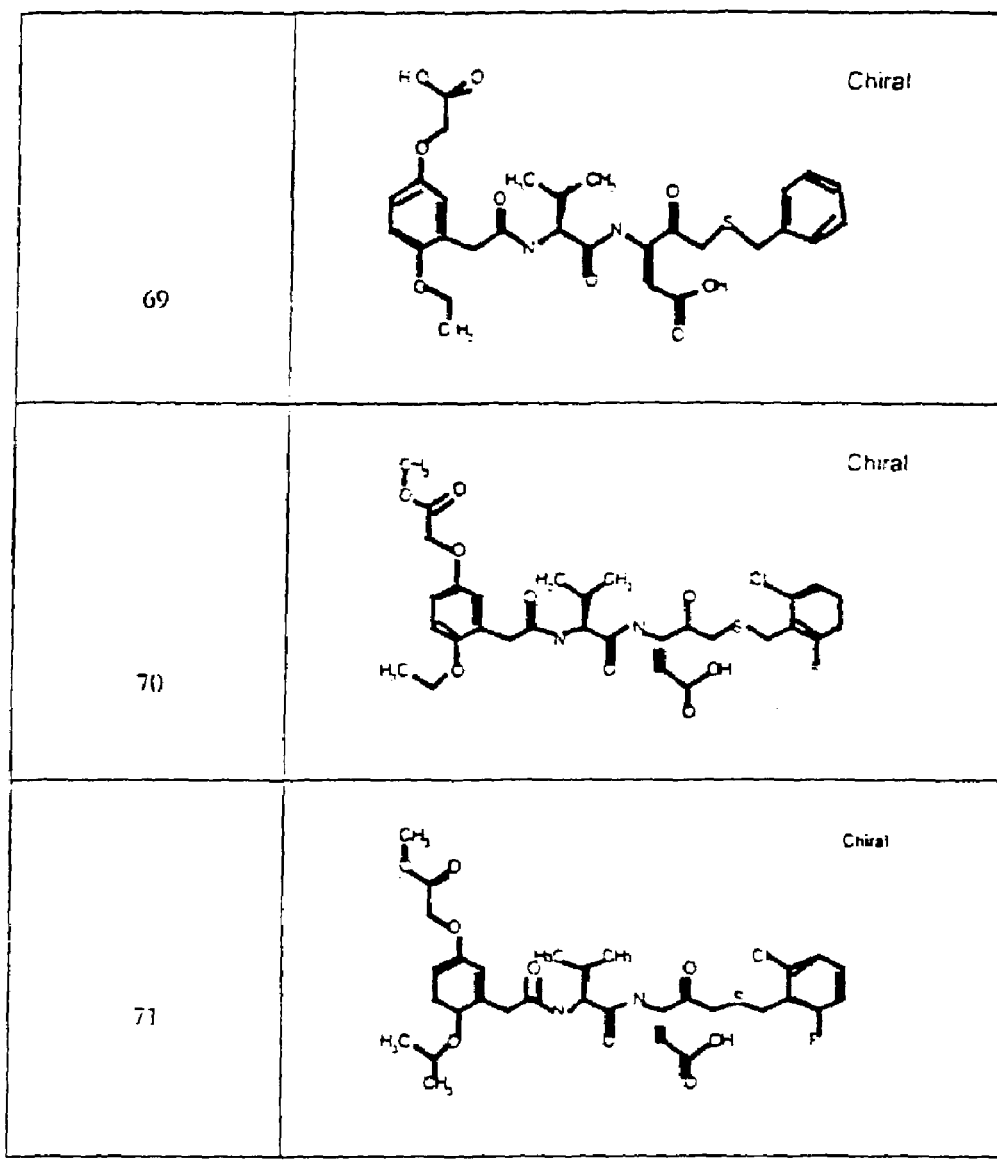
Figures 1X, 2:
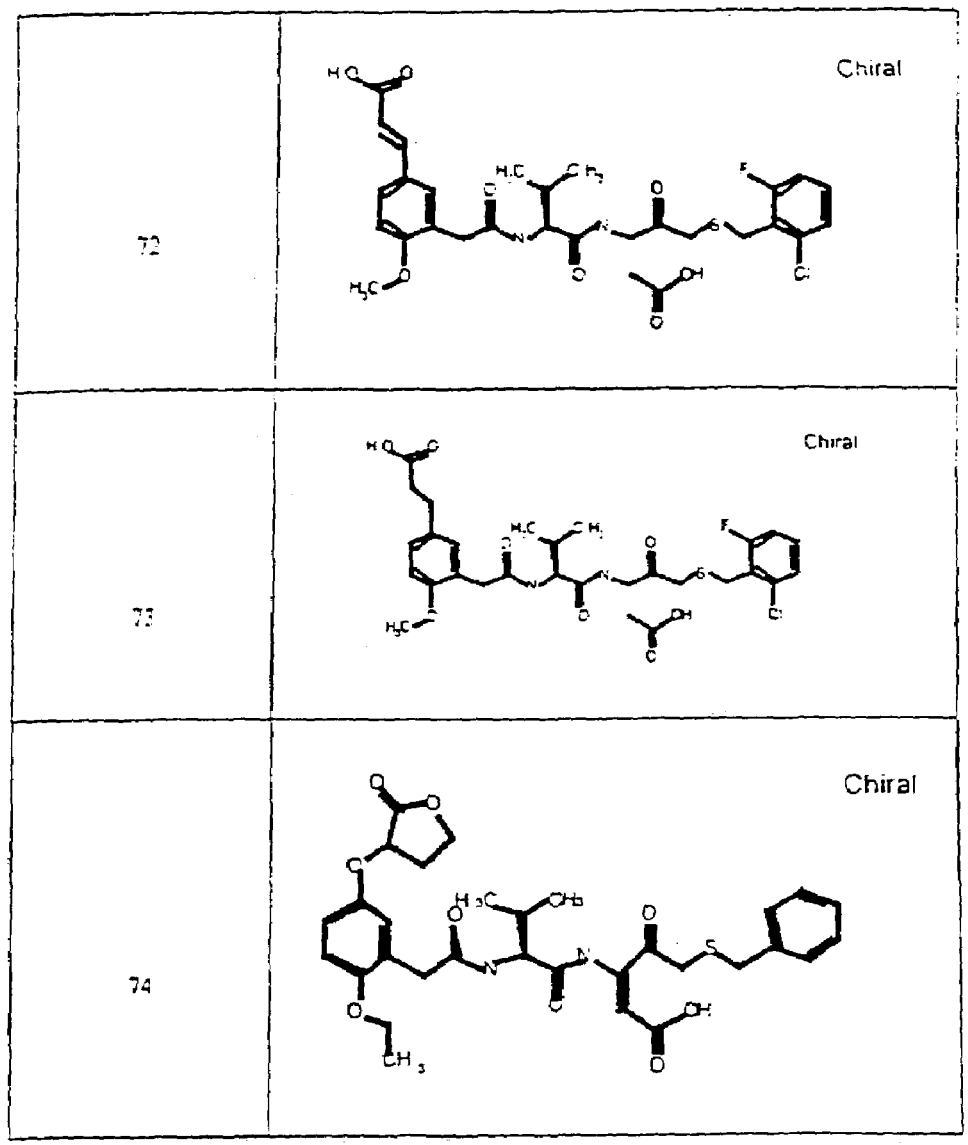
Figures 1Y, 2:
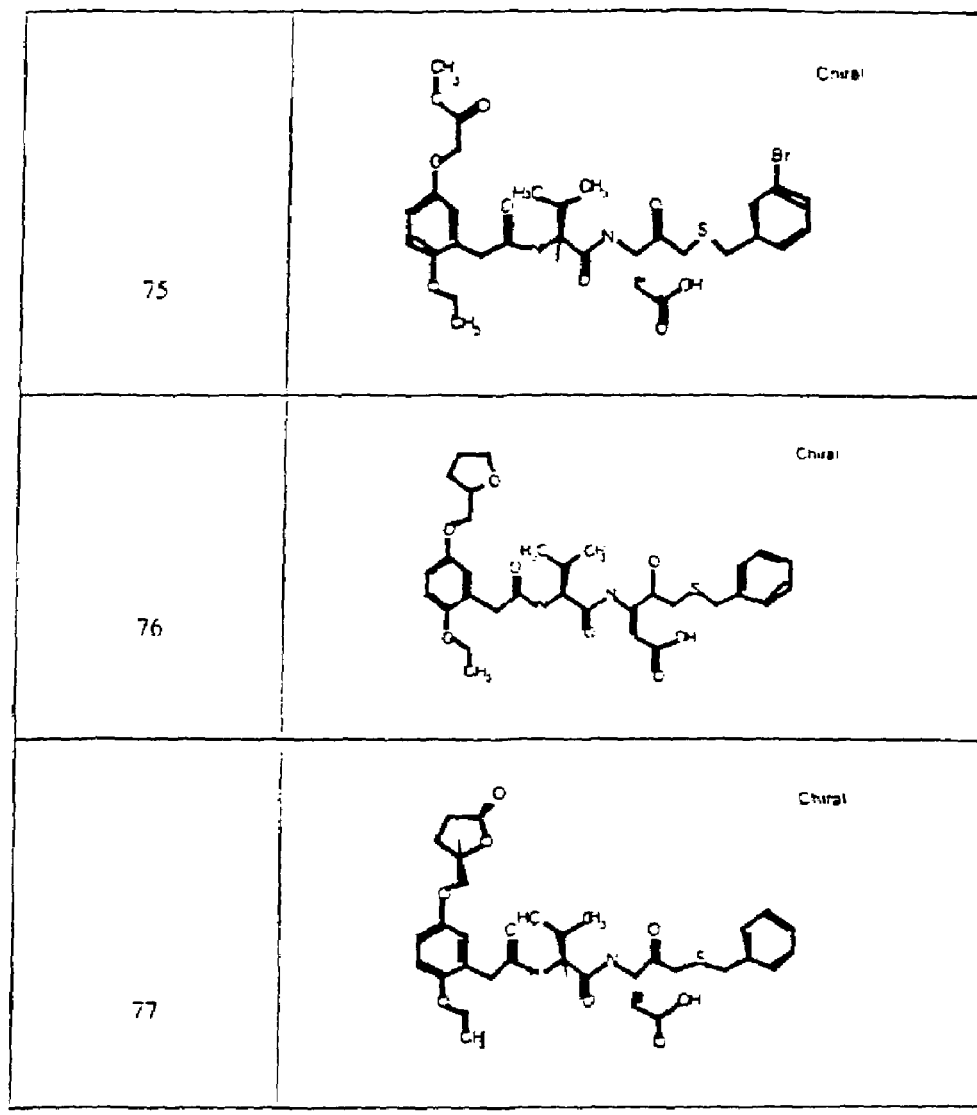
Figures 1Z, 2:
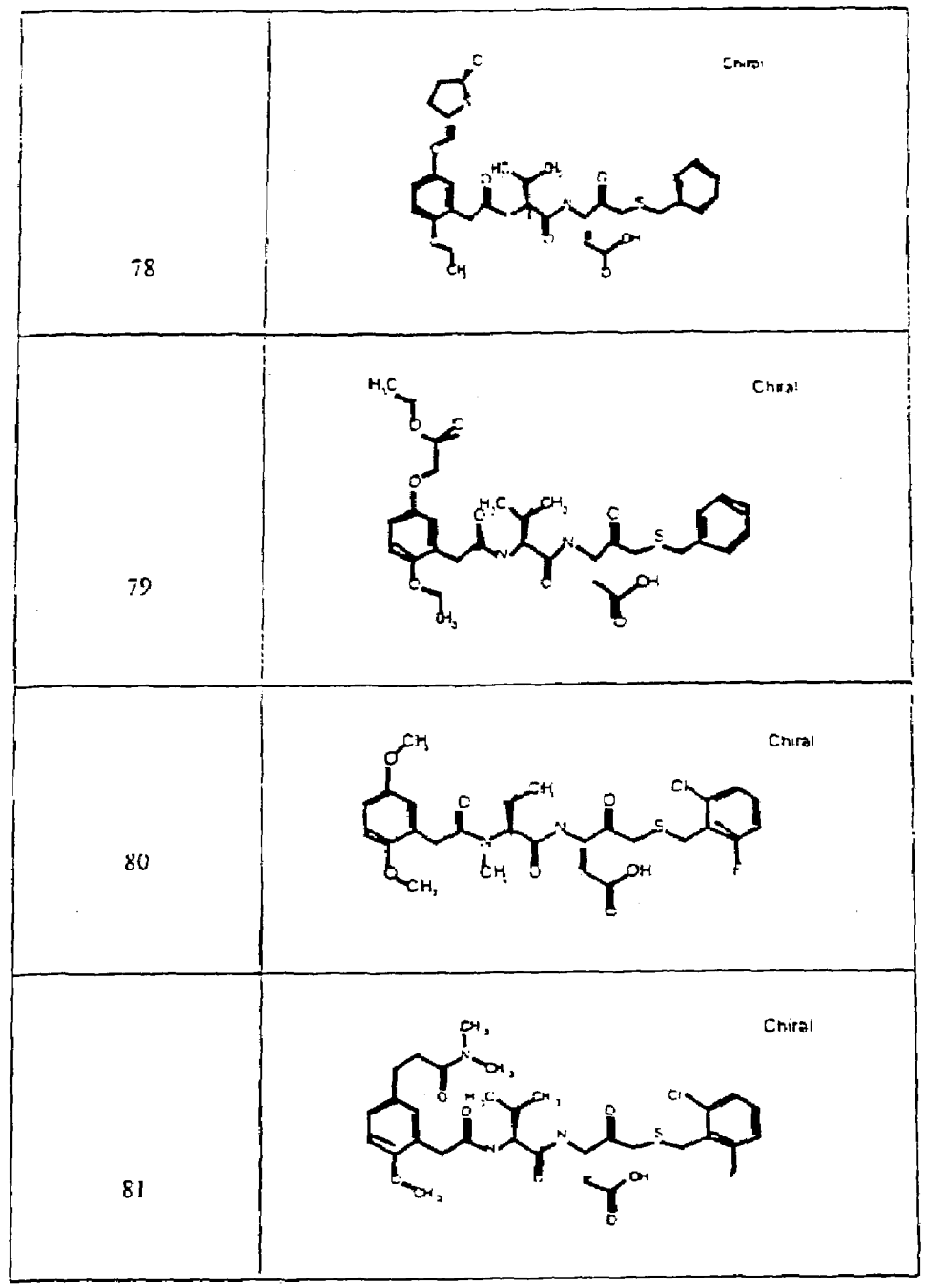
Figures 2, 2A:
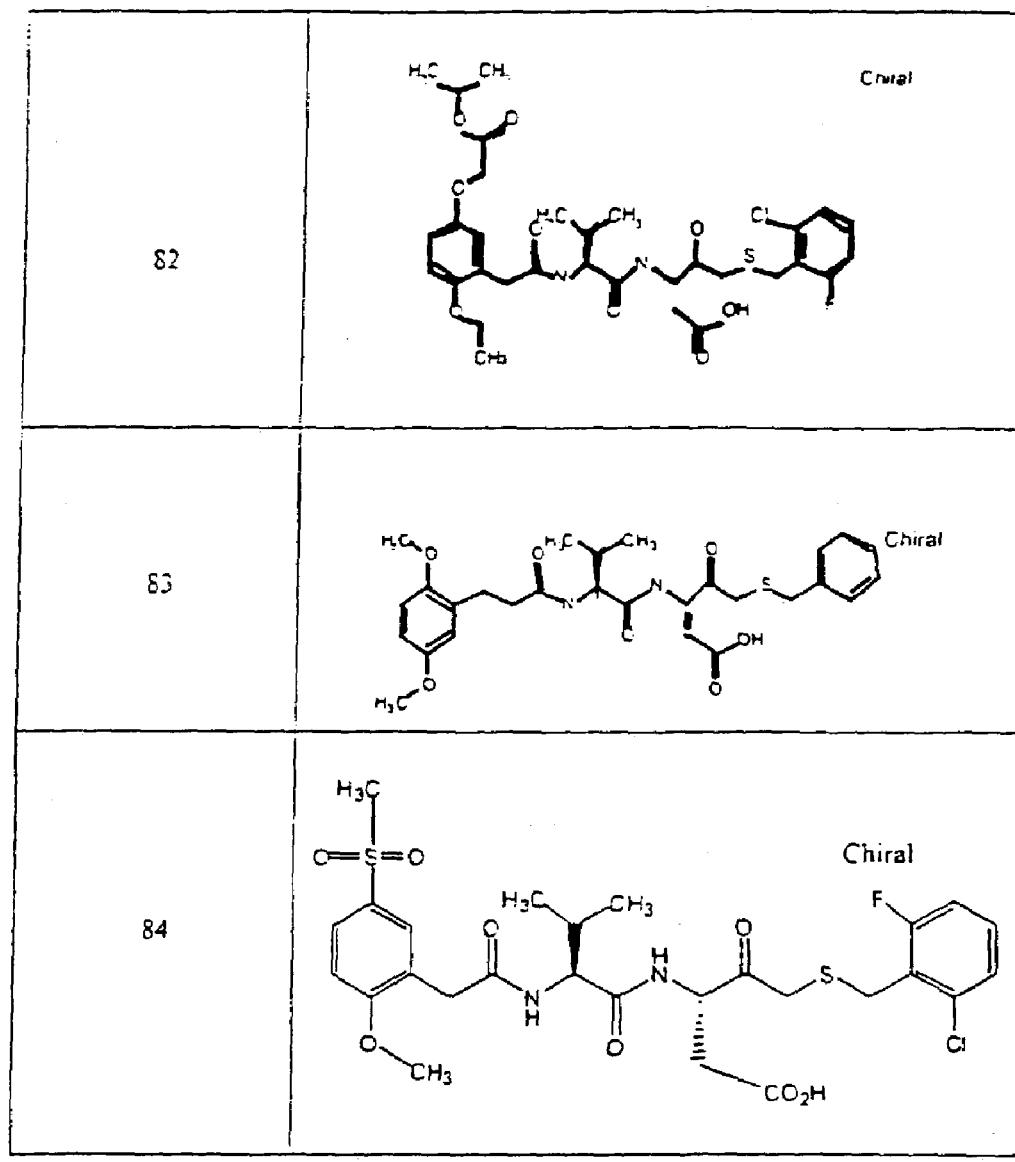
Figures 2, 2B:
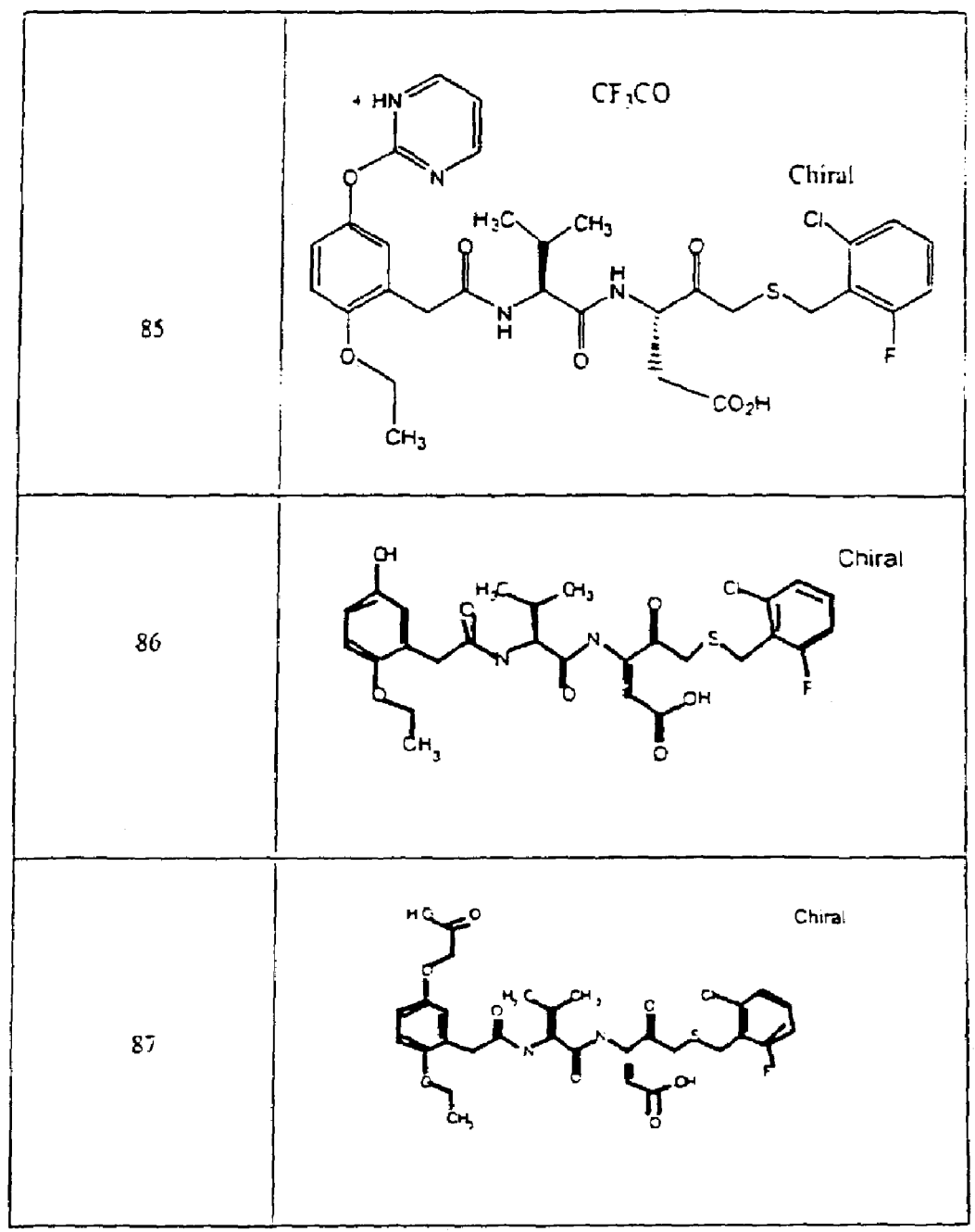
Figures 2, 2C:
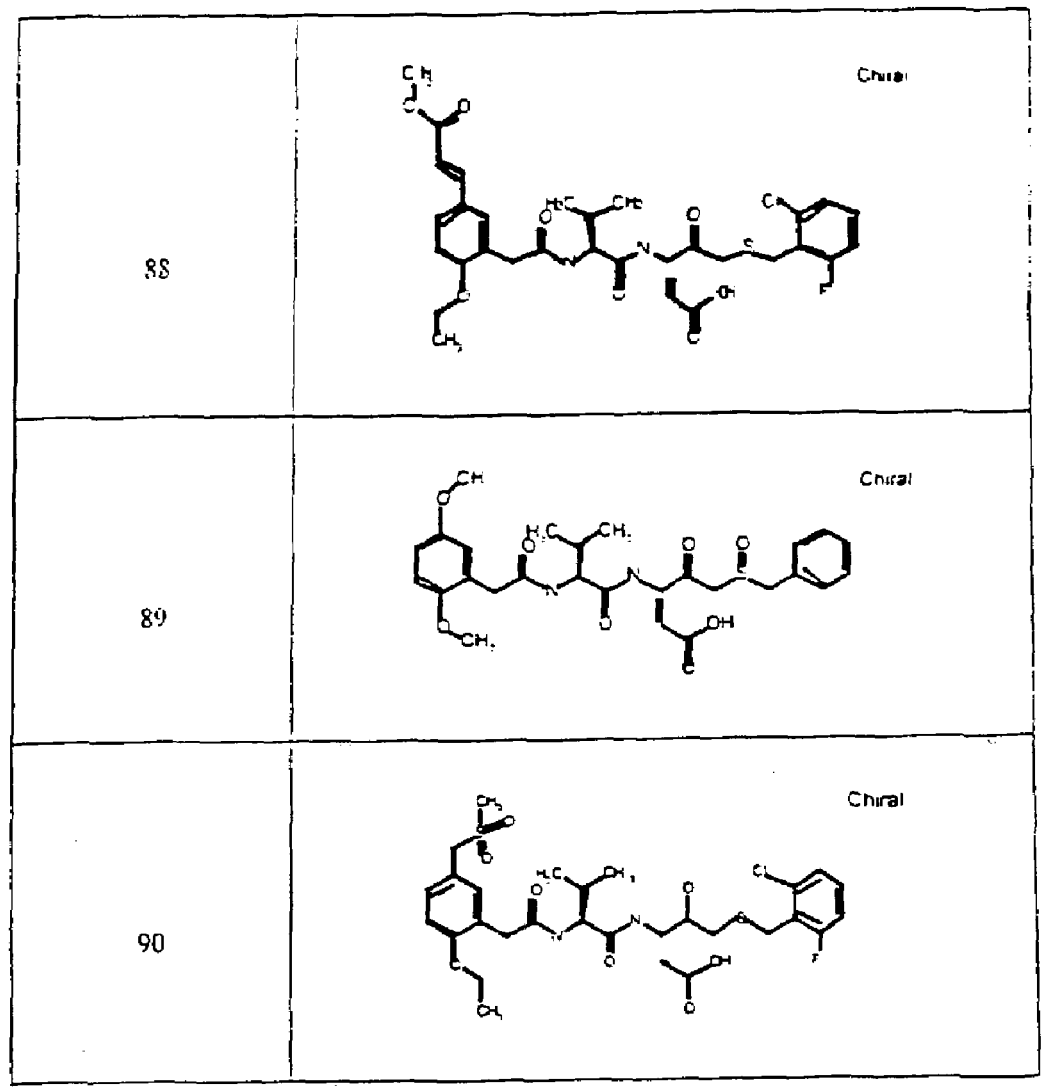
Figures 2, 2D:
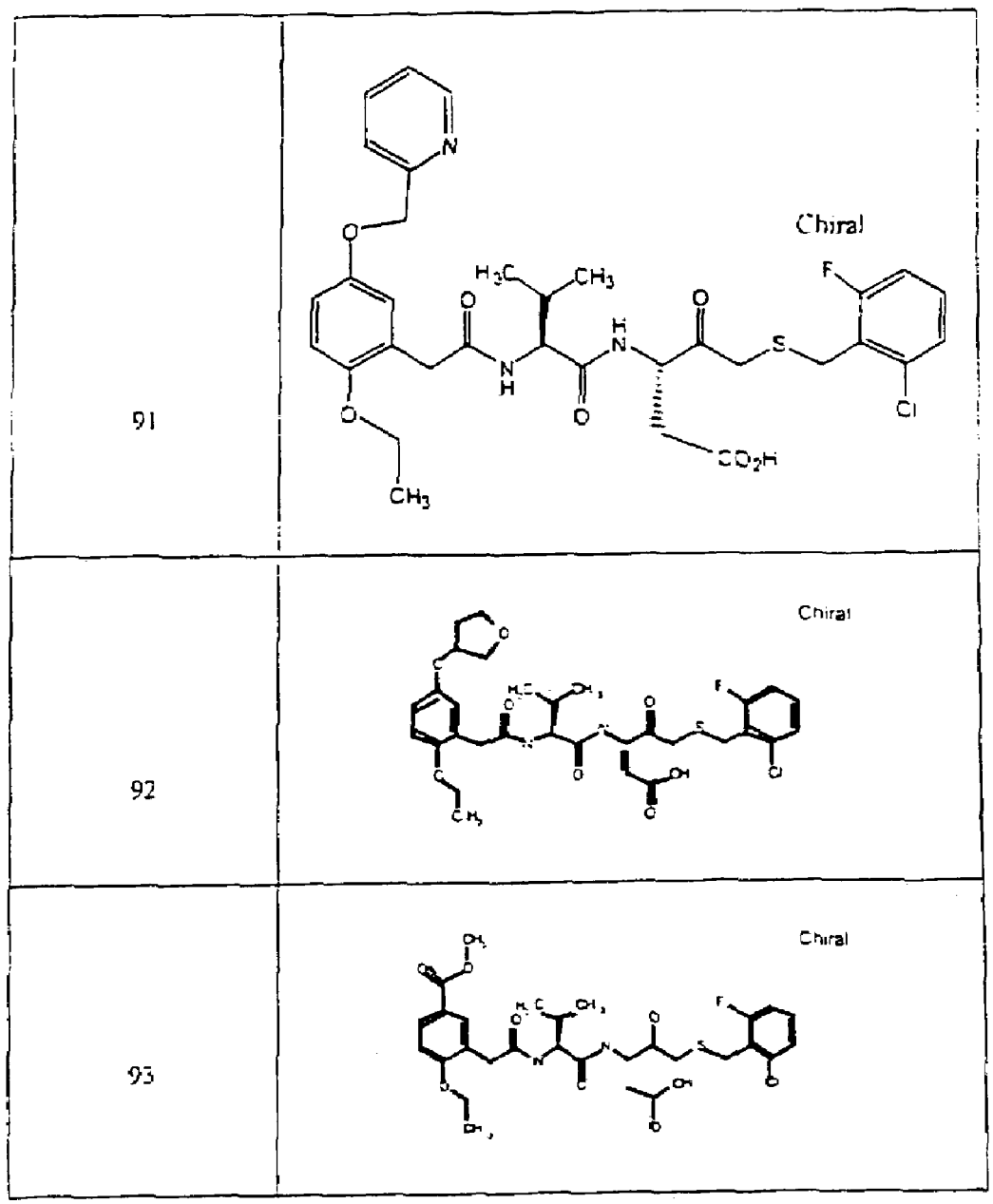
Figures 2, 2E:
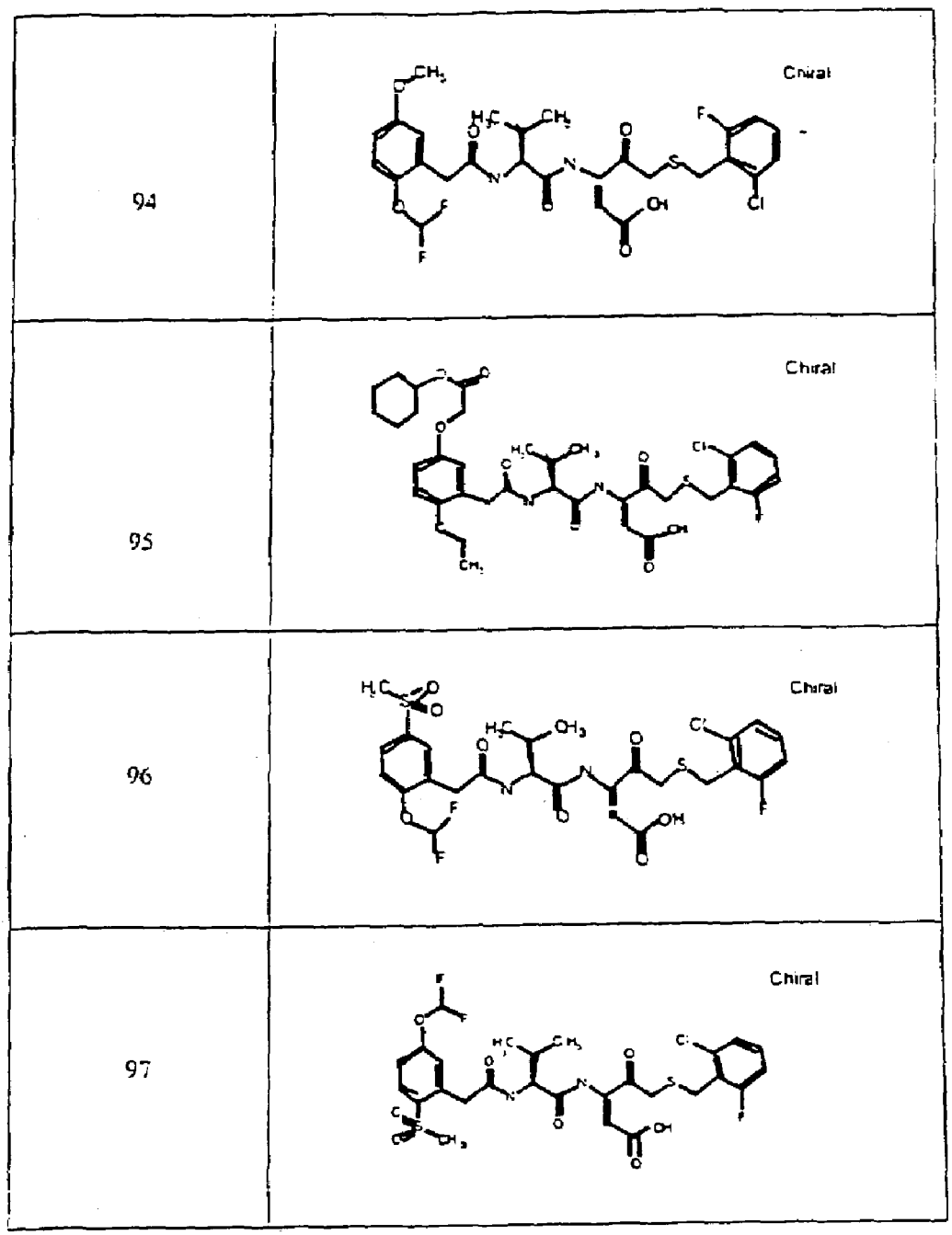
Figures 2, 2F:
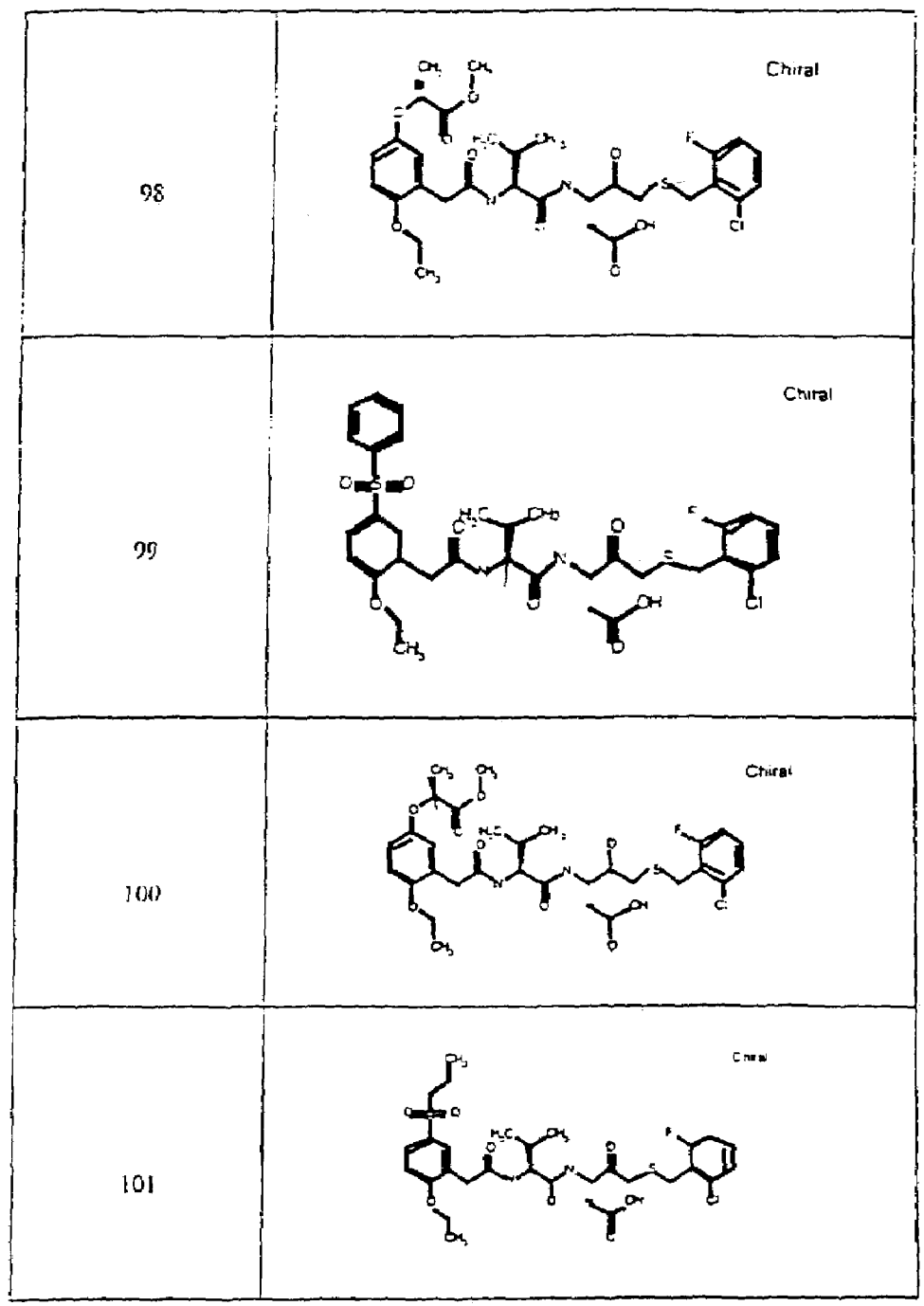
Figures 2, 2G:
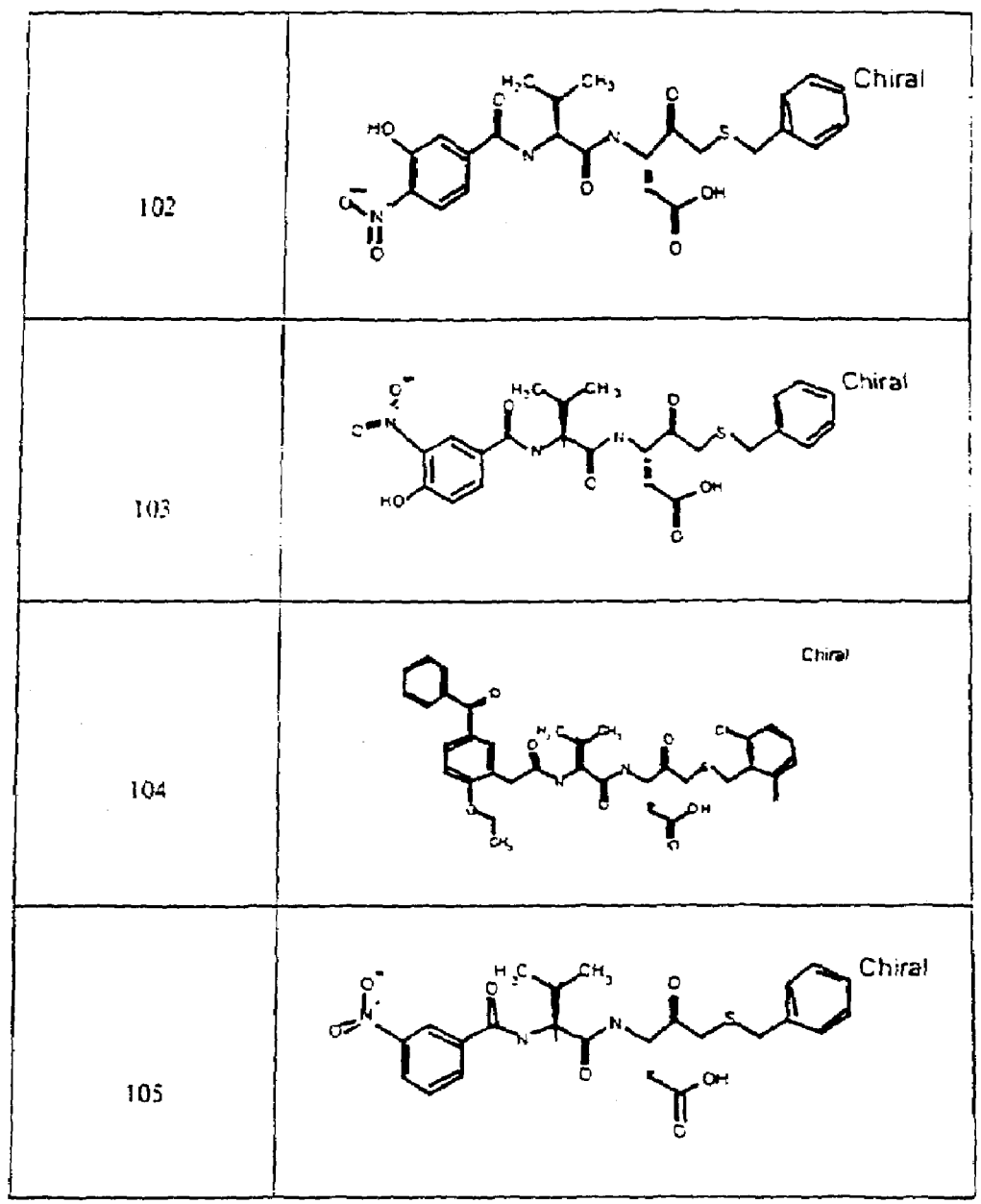
Figures 2, 2H:
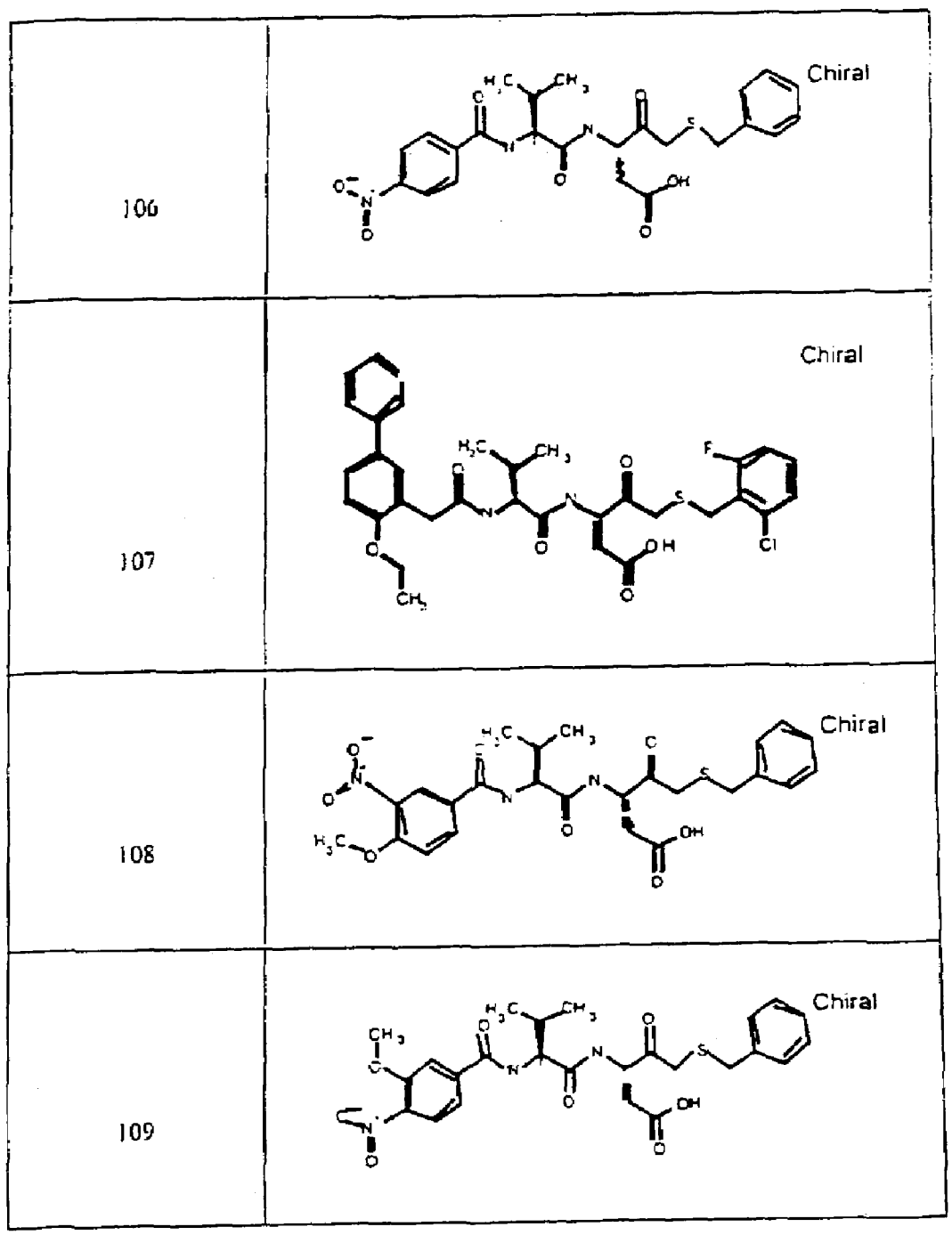
Figures 2, 2I:
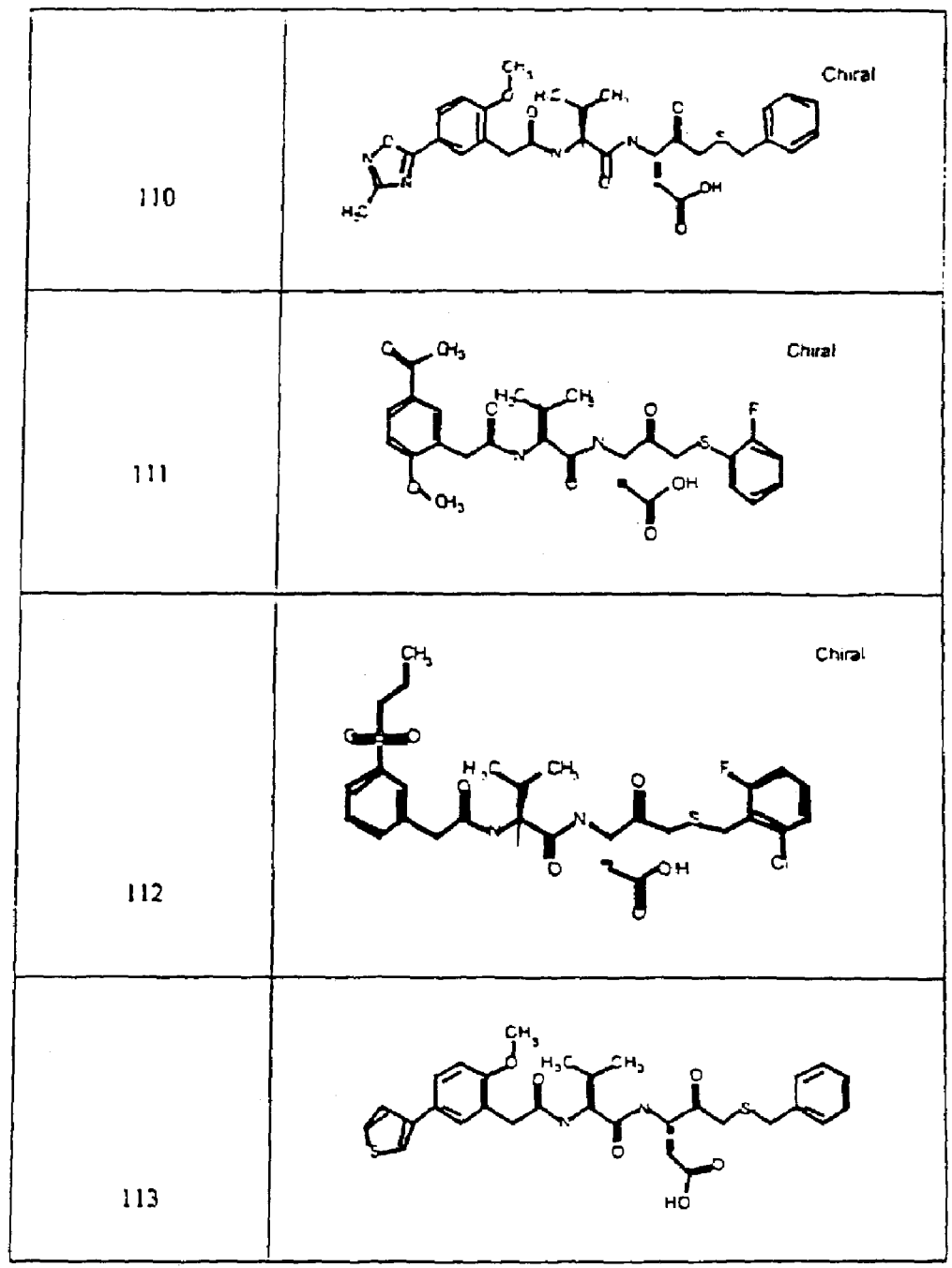
Figures 2, 2J:
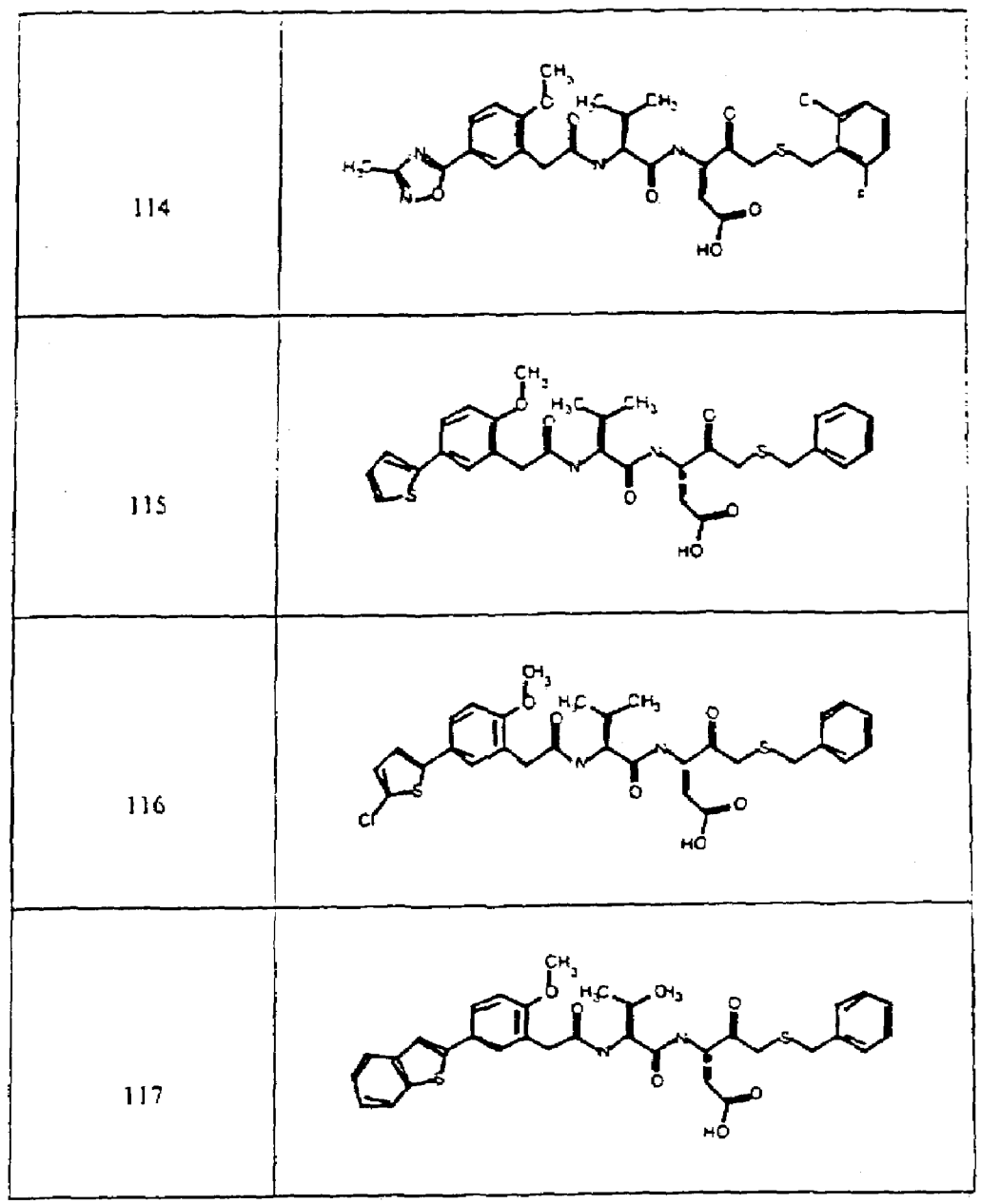
Figures 2, 2K:
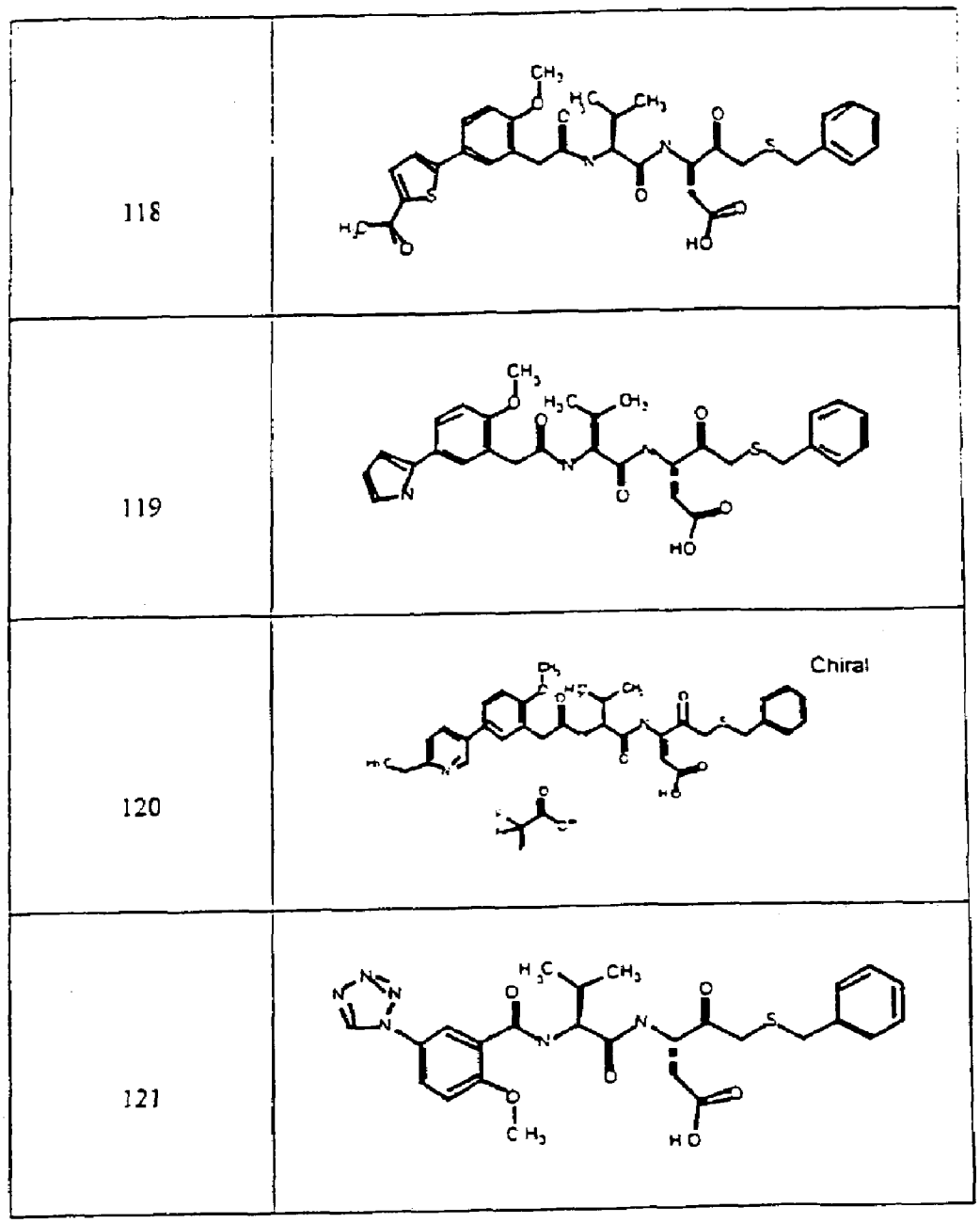
Figures 2, 2L:
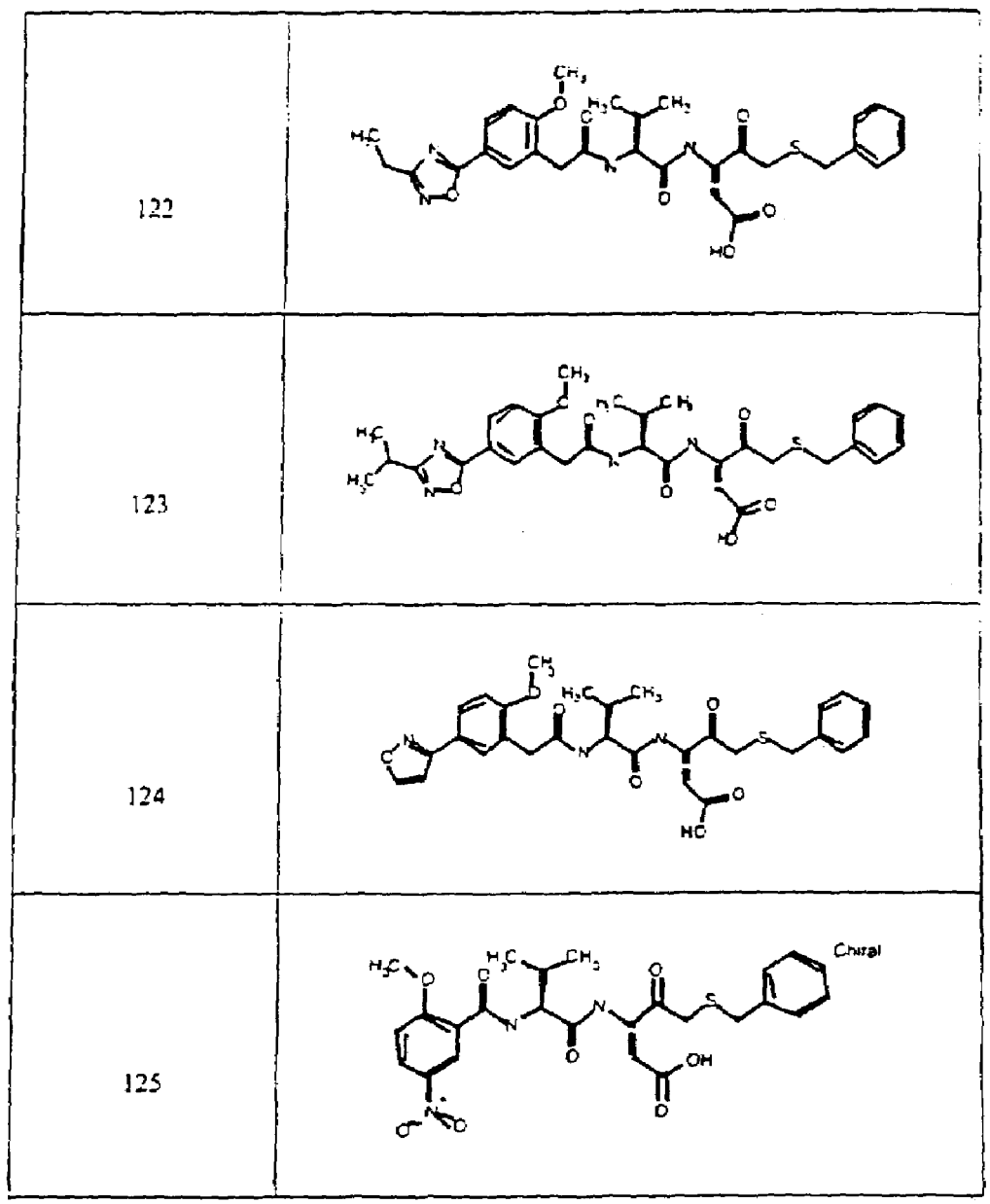
Figures 2, 2M:
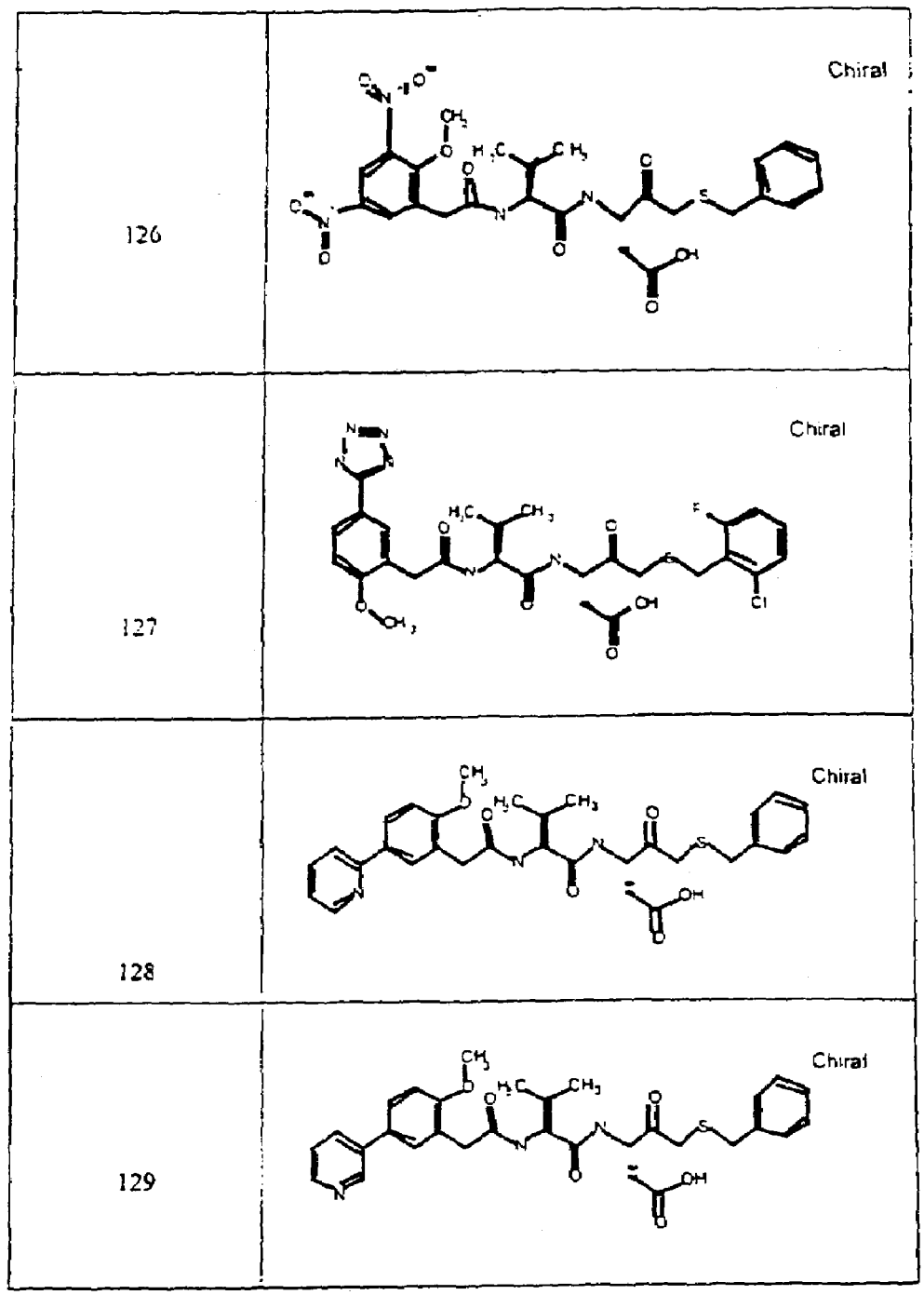
Figures 2, 2N:
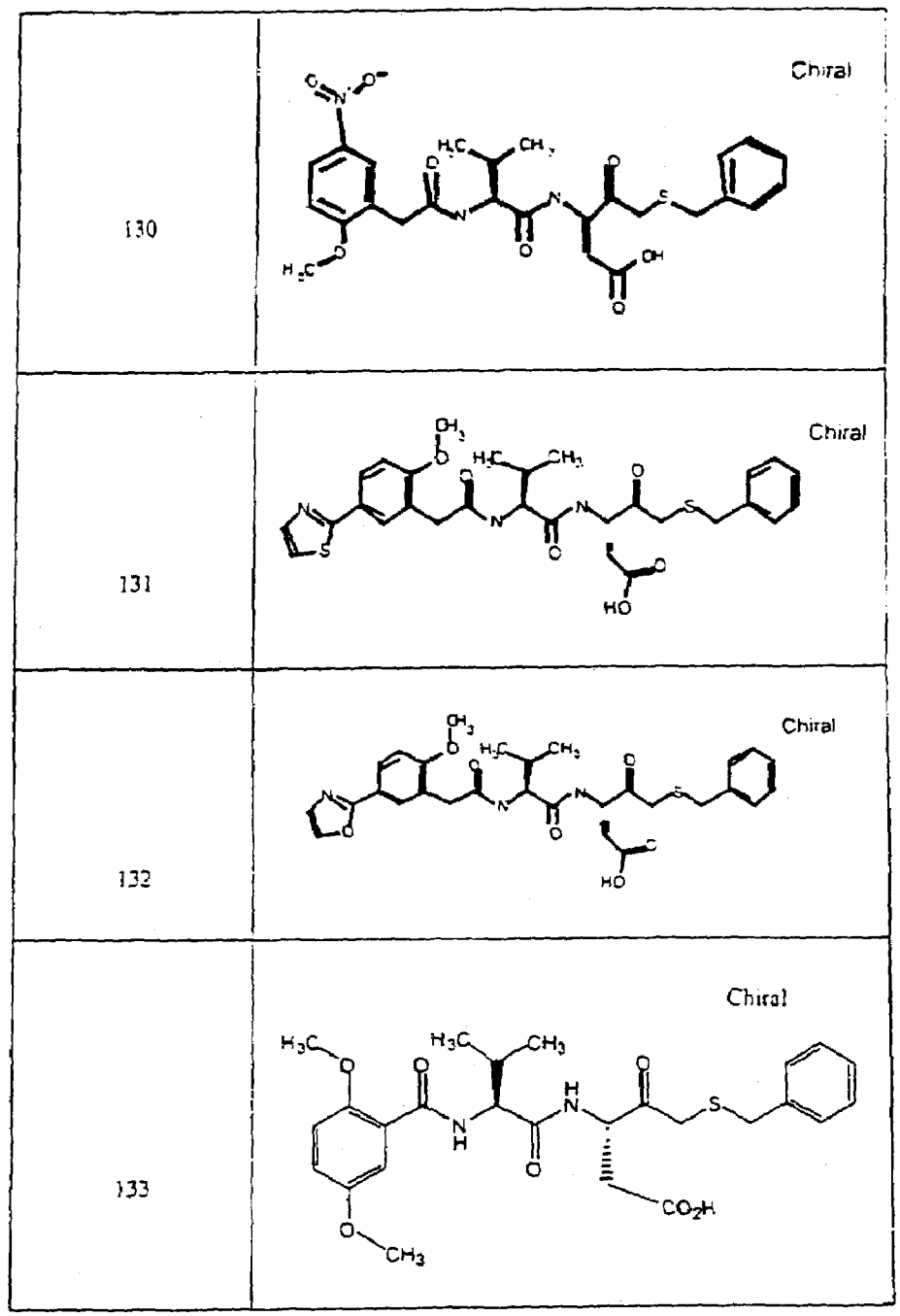
Figures 2, 2O:
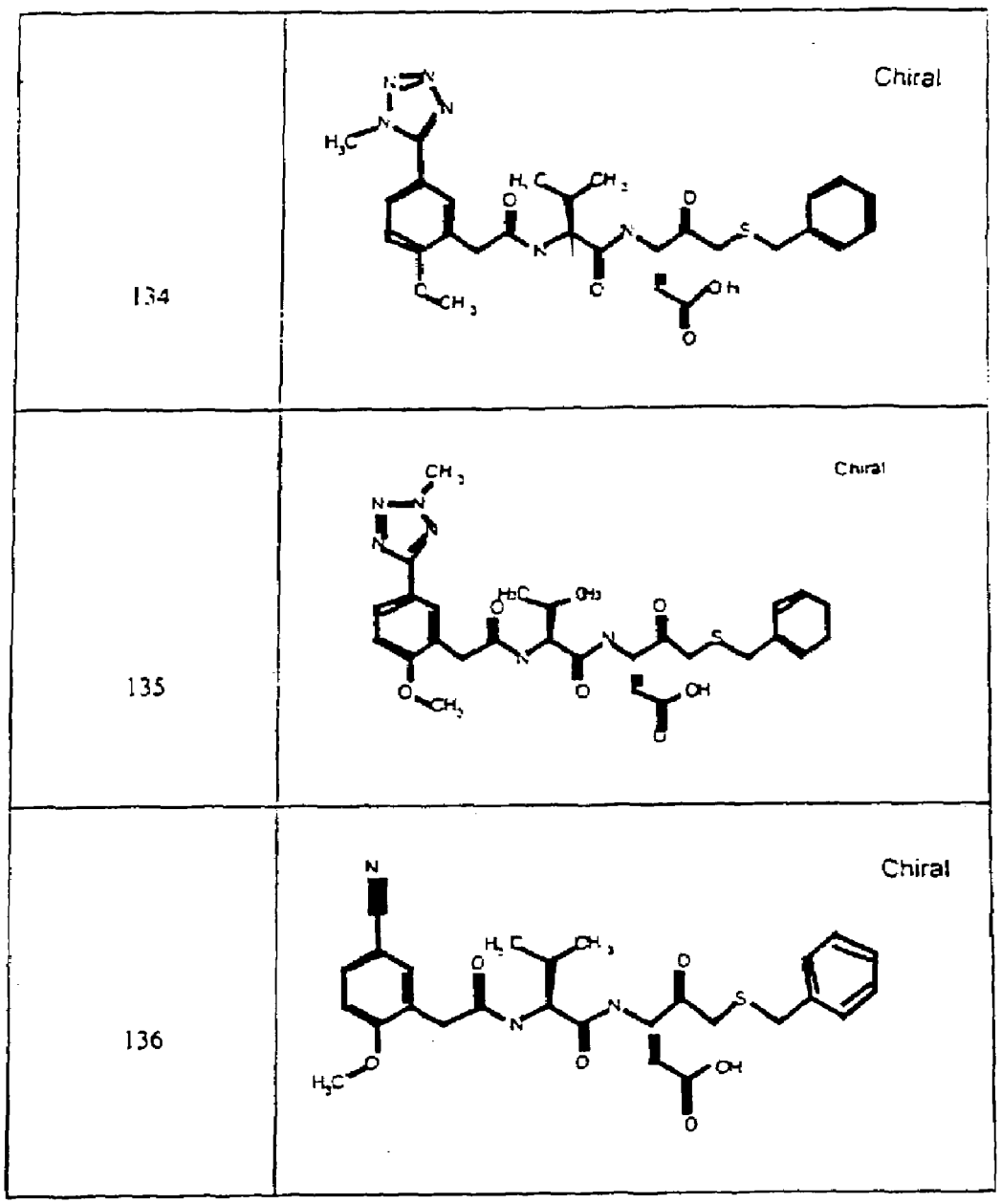
Figures 2, 2P:
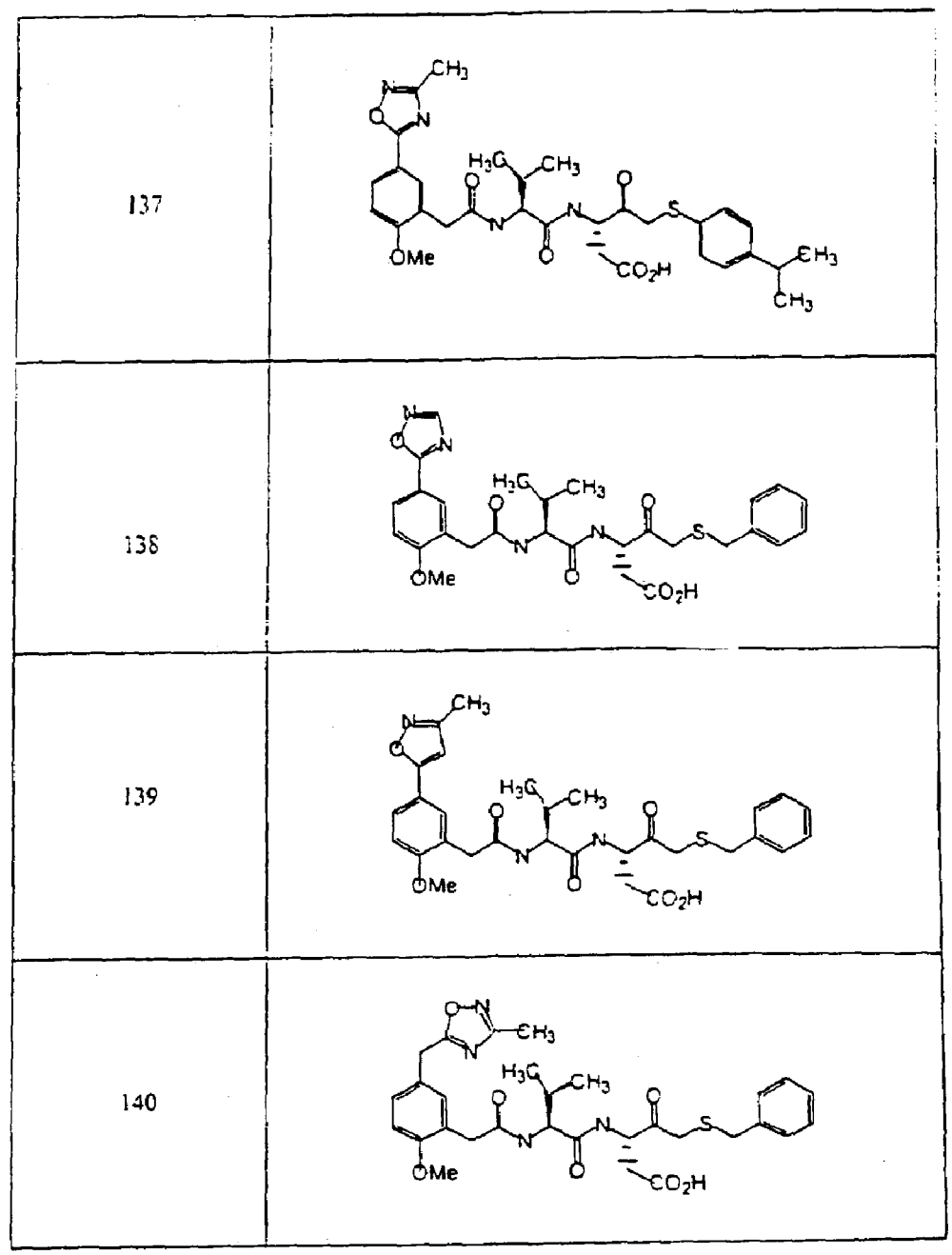
Figures 2, 2Q:
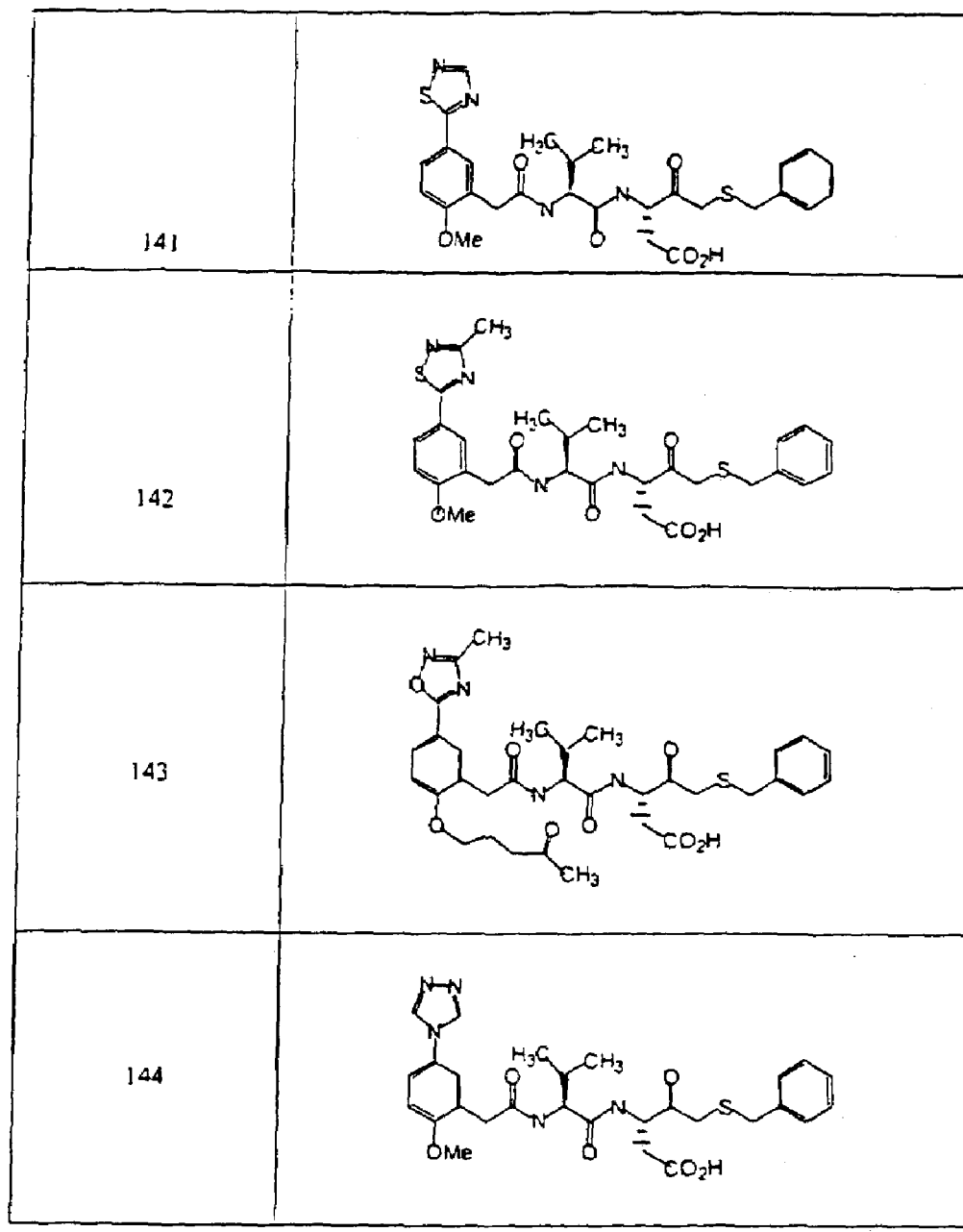
Figures 2, 2S:
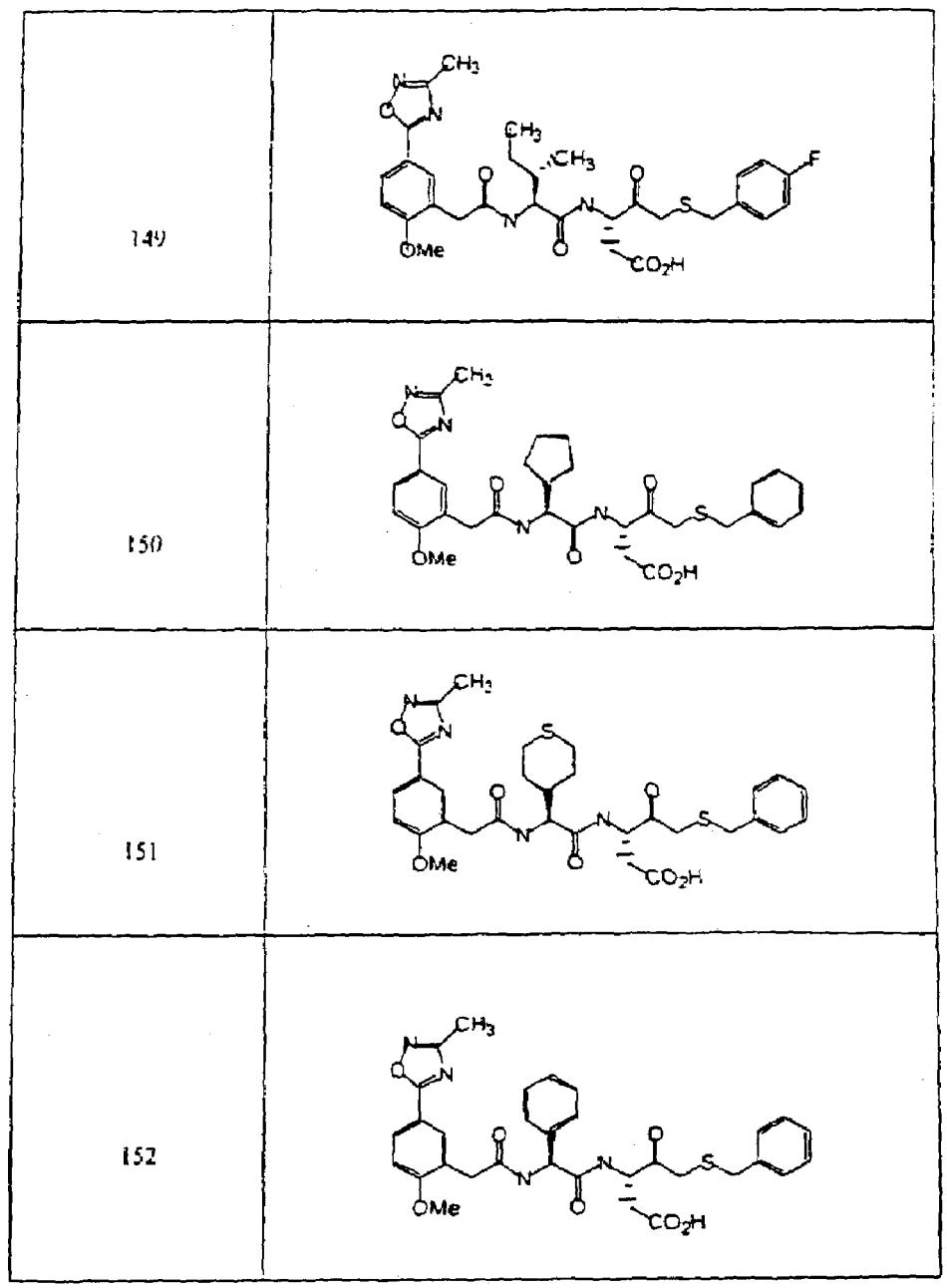
Figure 4B:
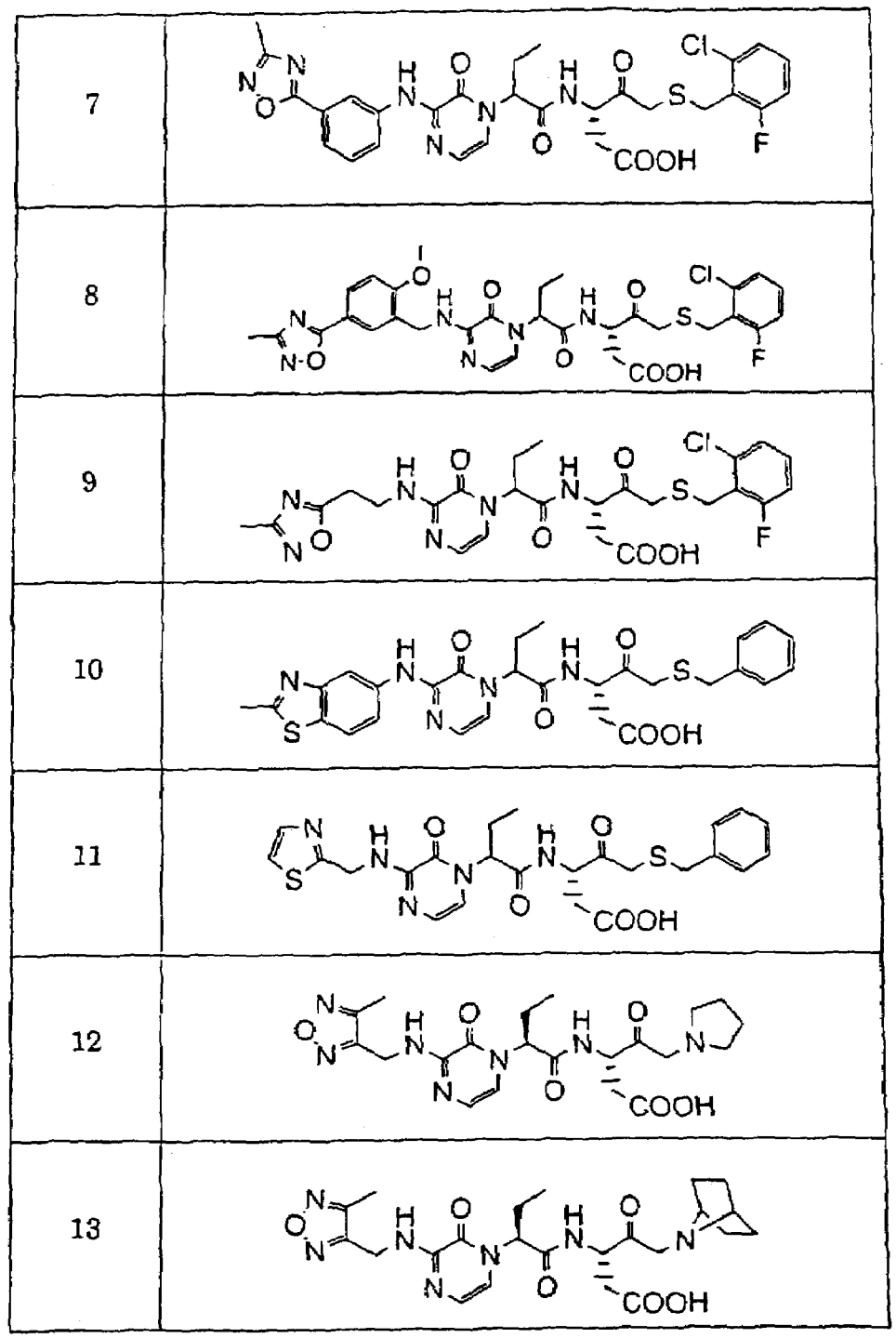
FIG. 4 depicts compounds and pharmaceutical compositions of this invention. Said compounds and compositions are also described in PCT Publication WO 01/05772.
Figure 4C:
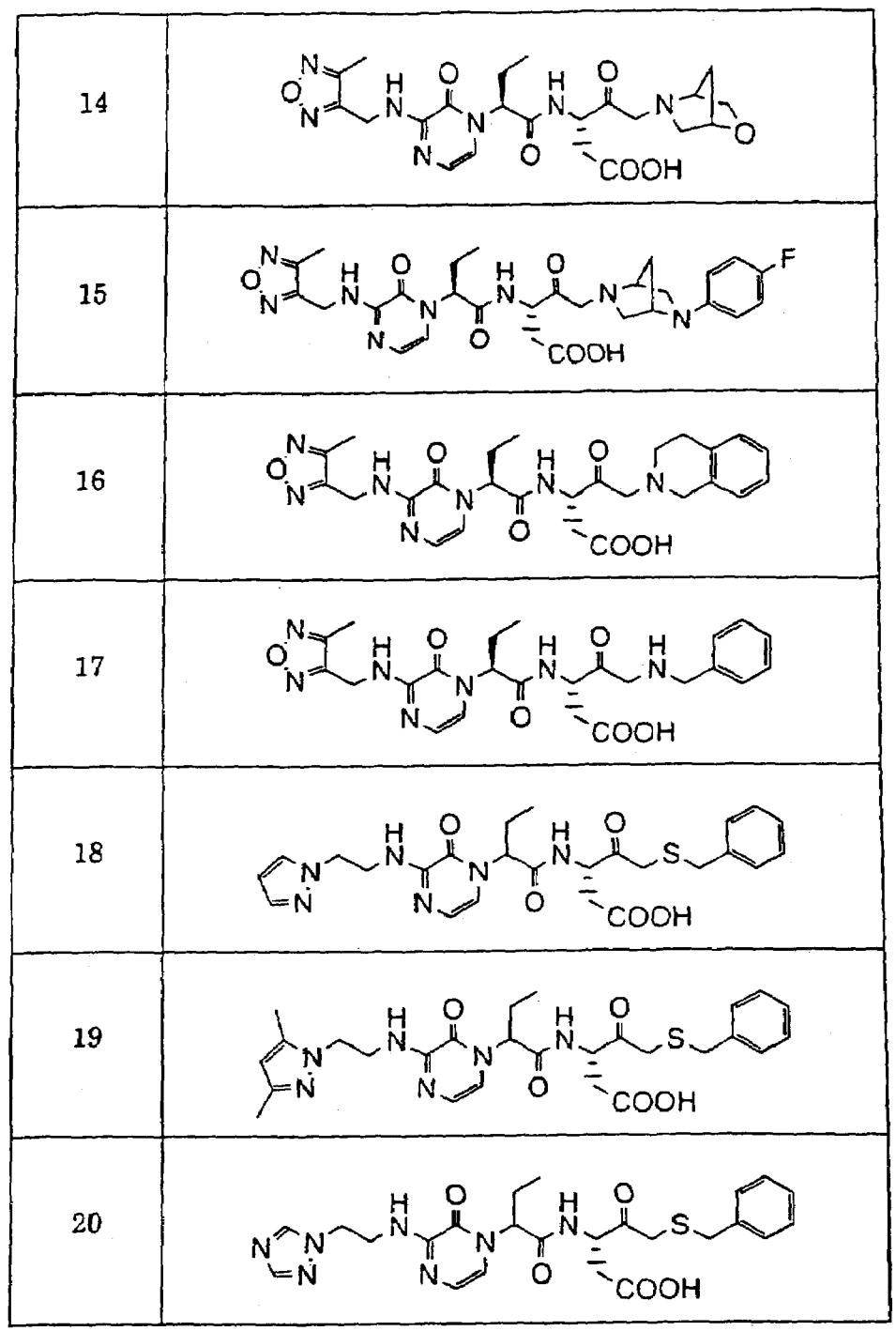
Figure 4E:
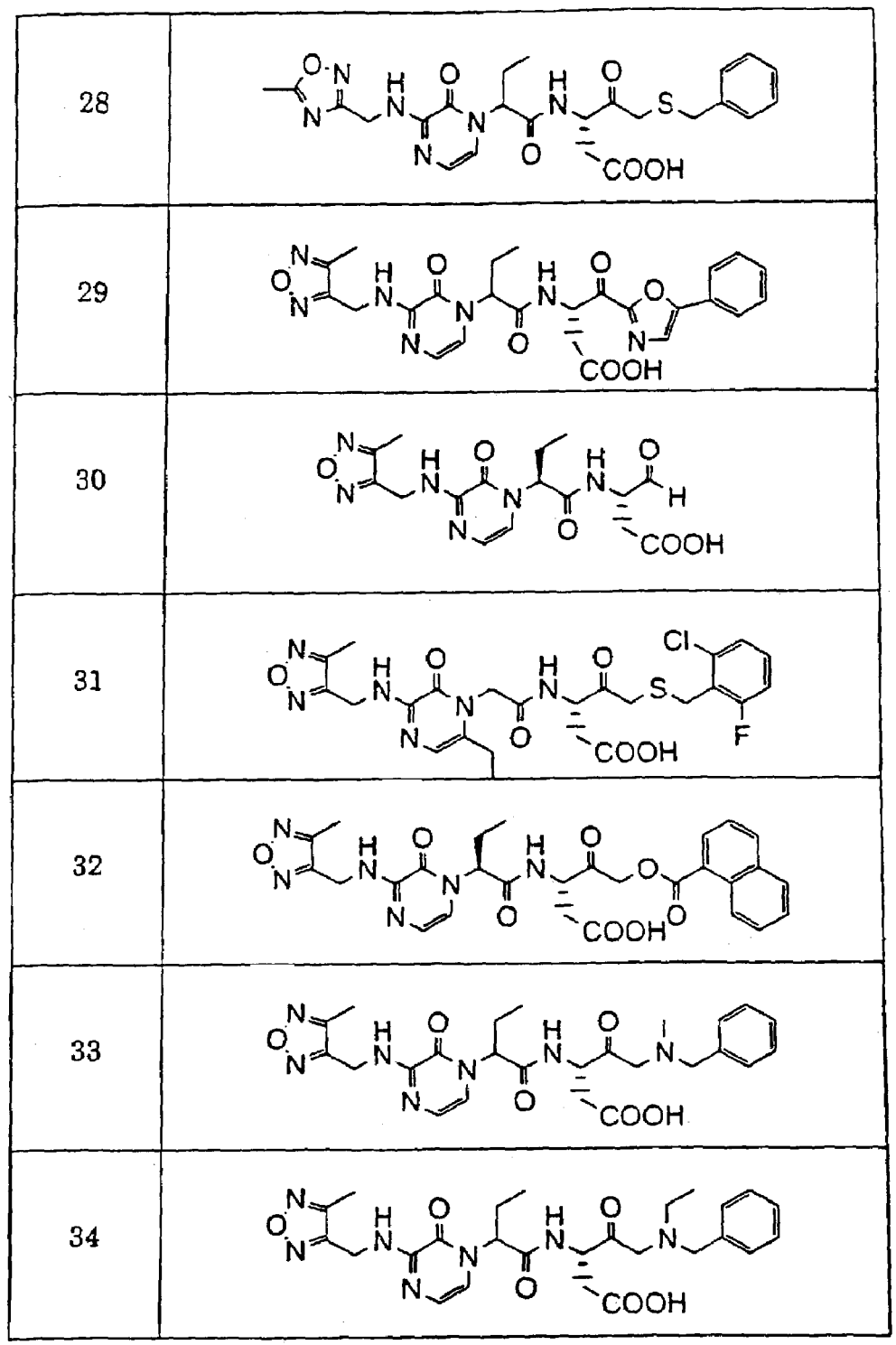
Figure 4G:
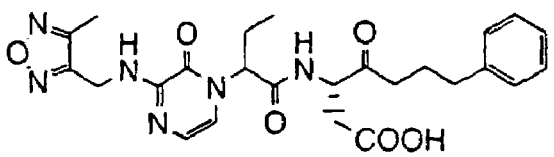
Figure 4H:
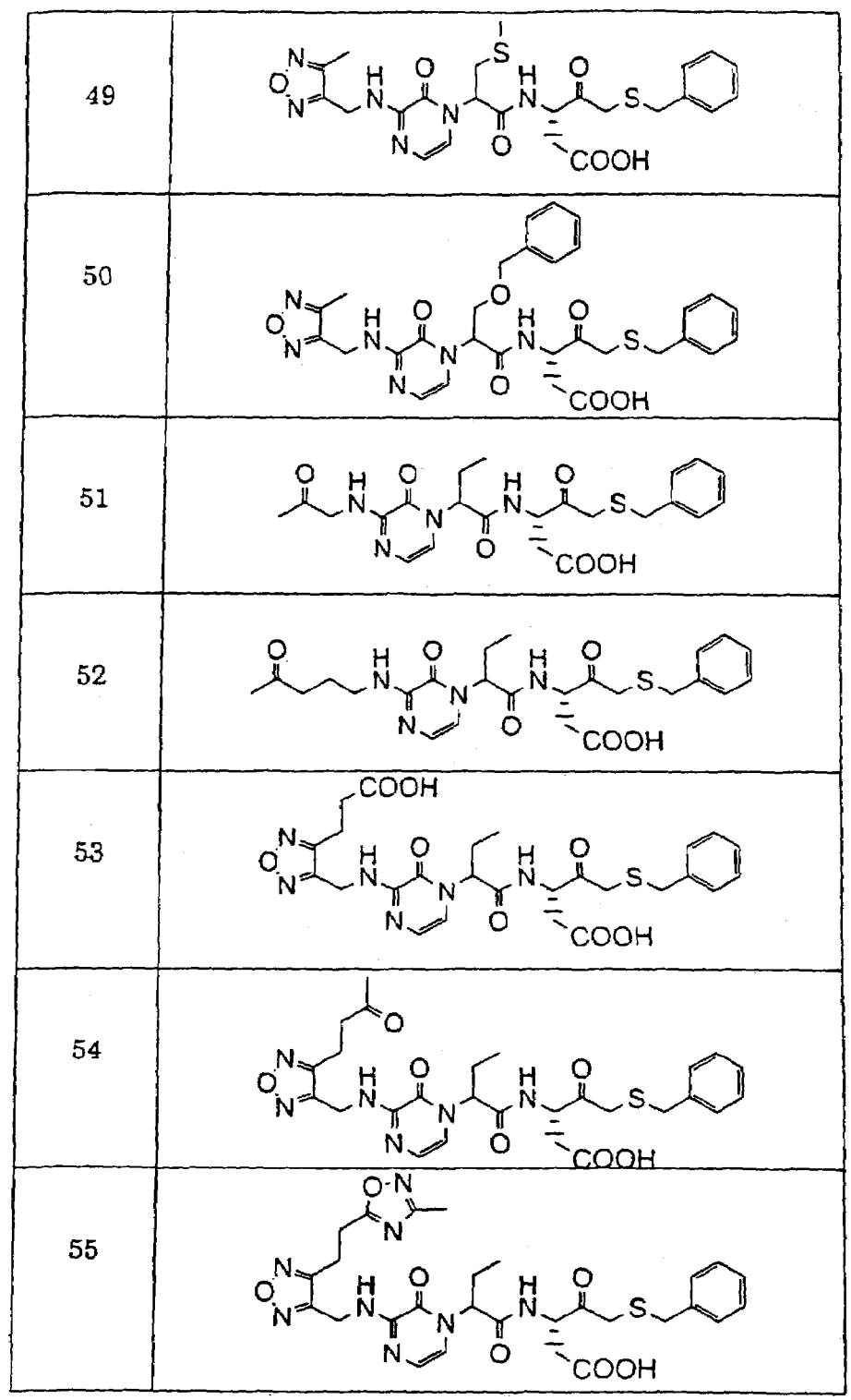
Figure 4I:
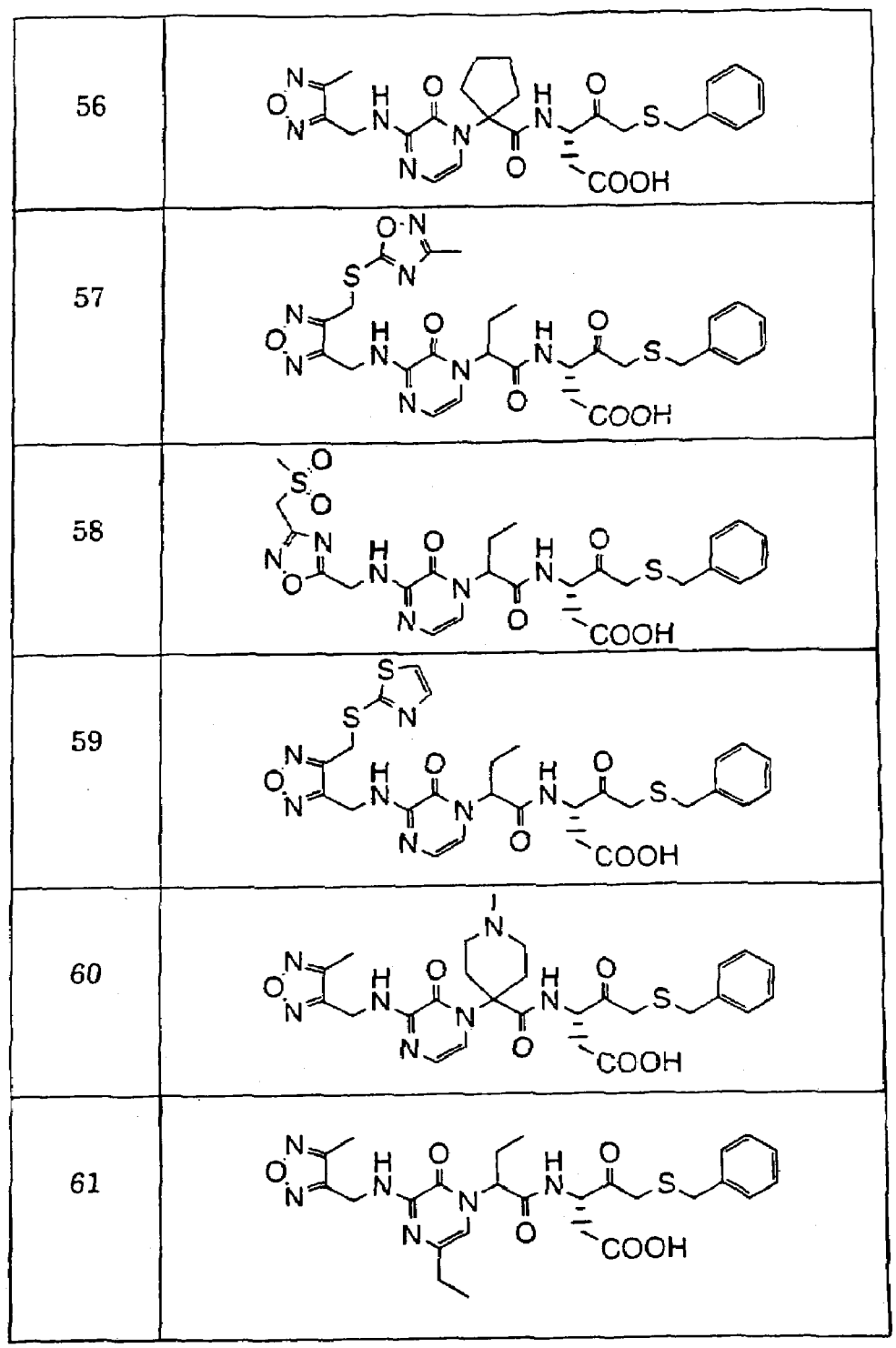
Figure 4N:
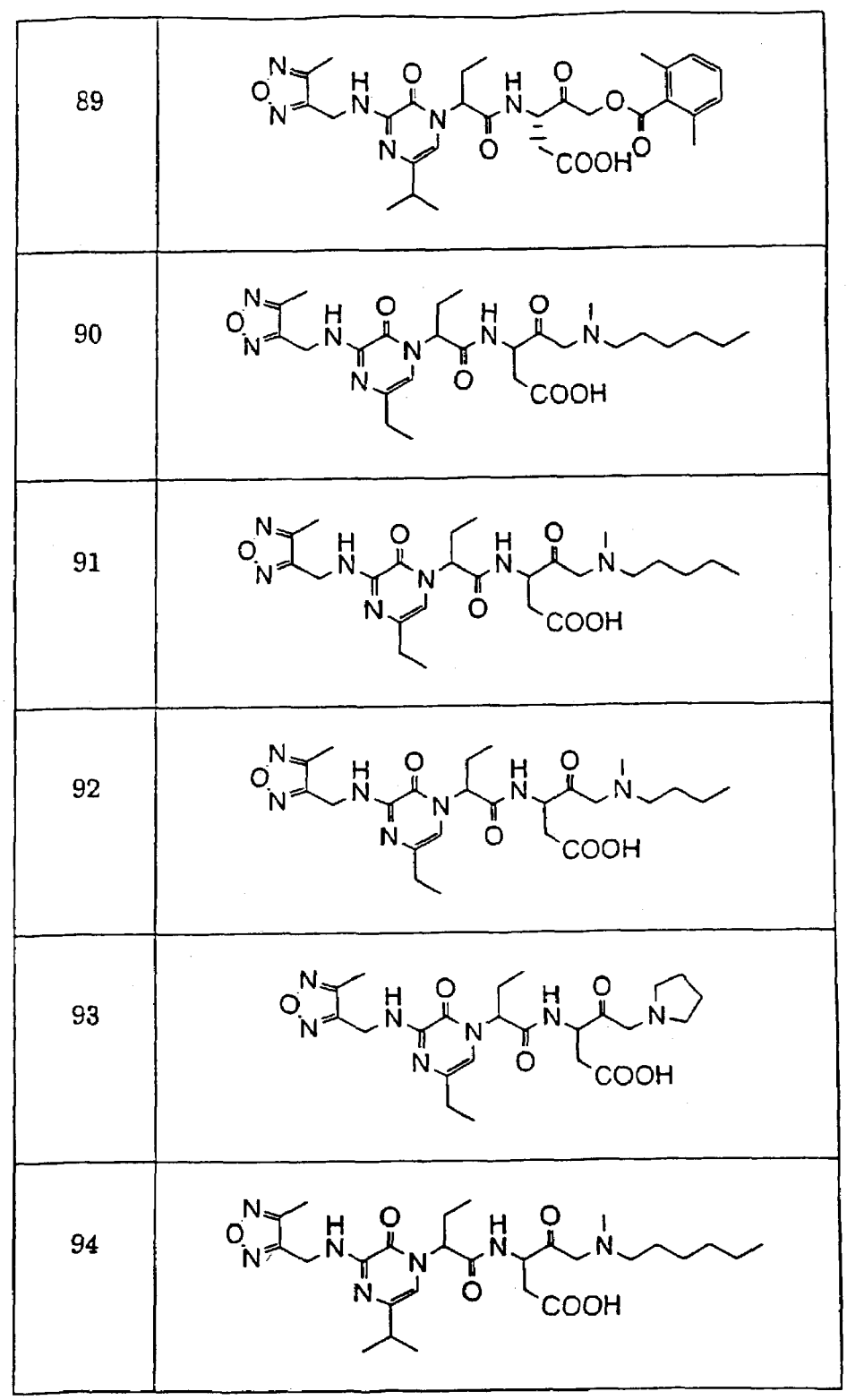
Figure 8F:
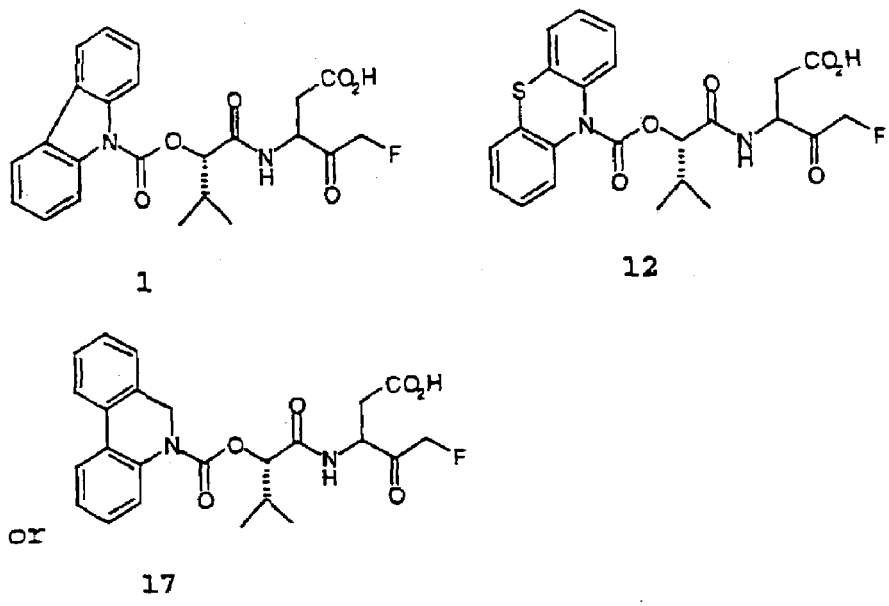
FIG. 8 depicts compounds and pharmaceutical compositions of this invention. Said compounds and compositions are also described in PCT Publication WO 01/72707.
Figure 10D:
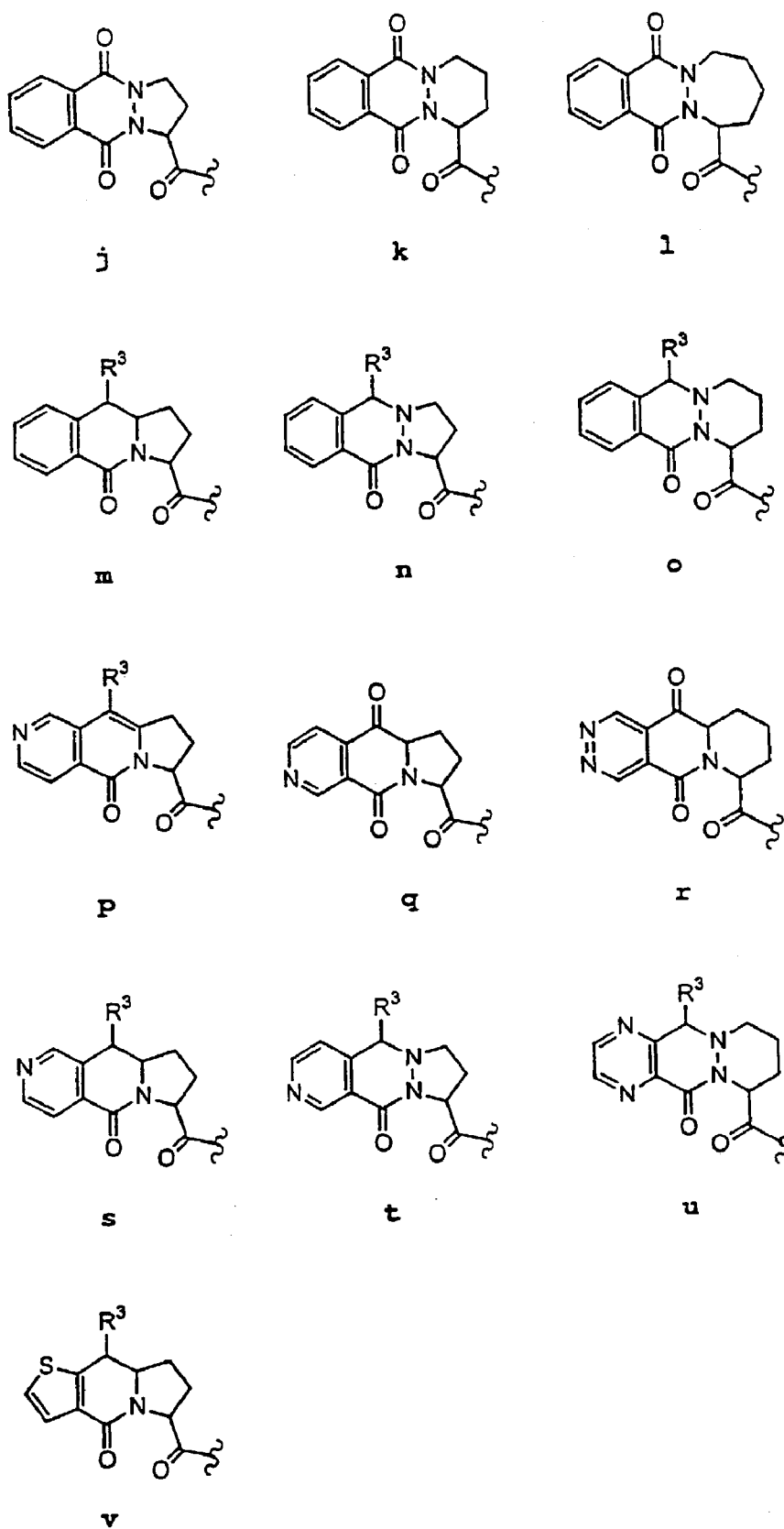
FIG. 10 depicts compounds and pharmaceutical compositions of this invention. Said compounds and compositions are also described in PCT Publication WO 01/94351.
Figure 10E:
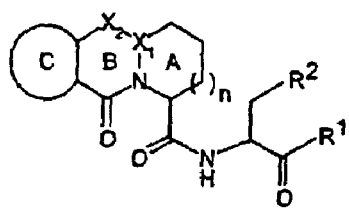
Figure 16L:
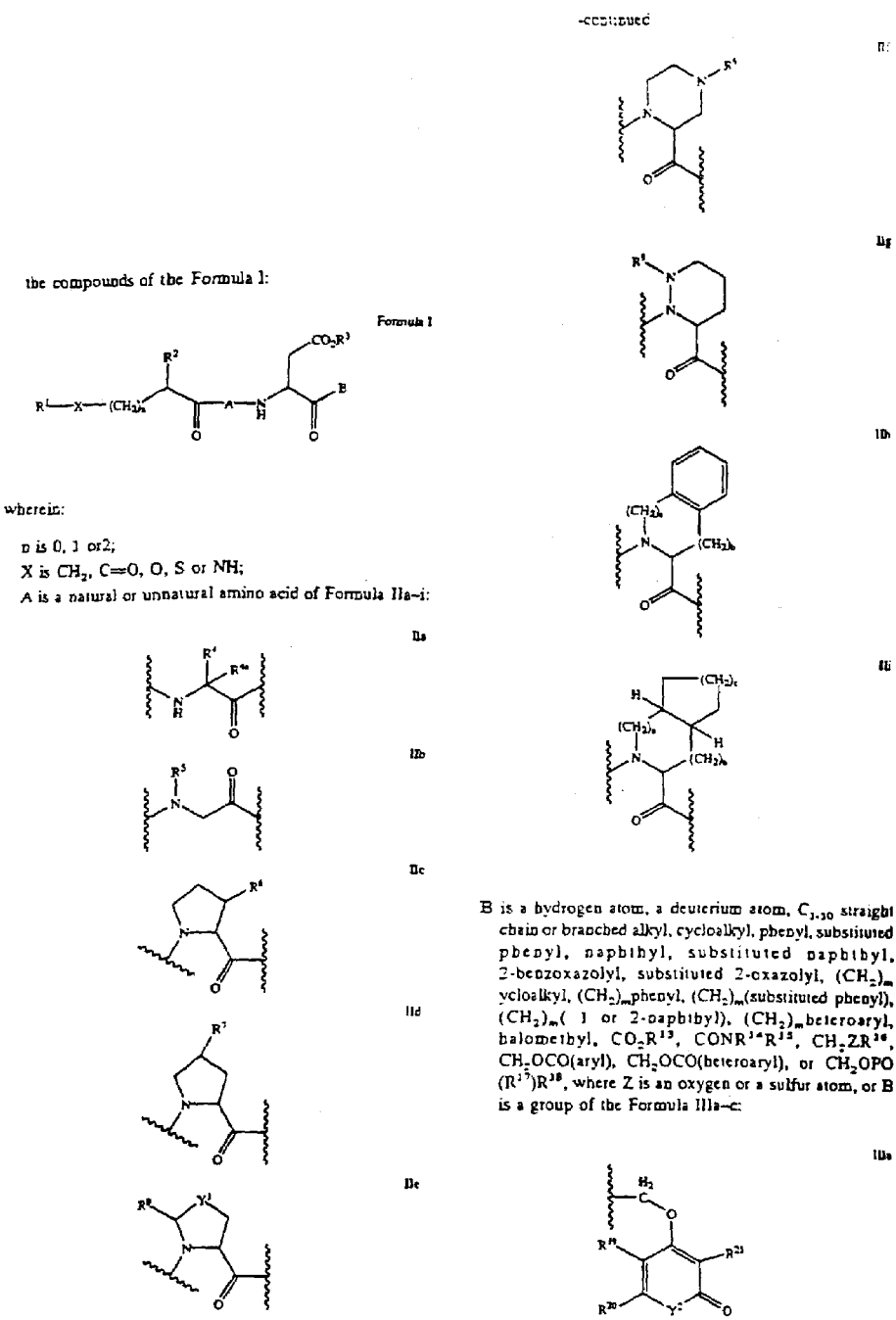
FIG. 16 depicts compounds and pharmaceutical compositions of this invention. Said compounds and compositions are also described in U.S. Pat. No. 6,197,750.
Figure 17F:
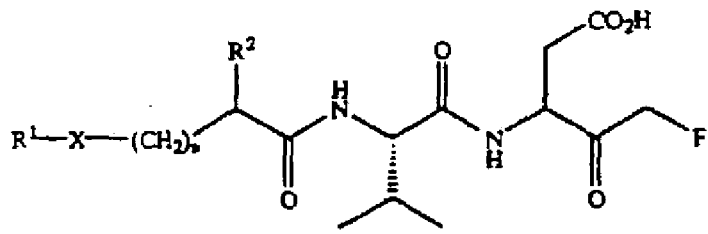
FIG. 17 depicts compounds and pharmaceutical compositions of this invention. Said compounds and compositions are also described in U.S. Pat. No. 6,242,422.
Figure 17N:
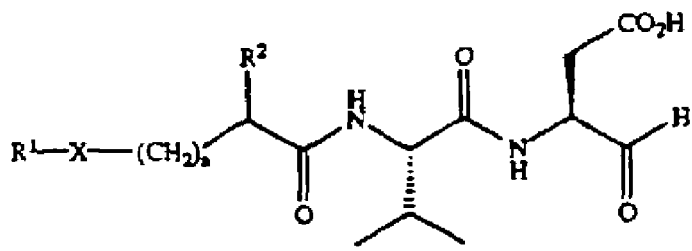
Figure 18B:
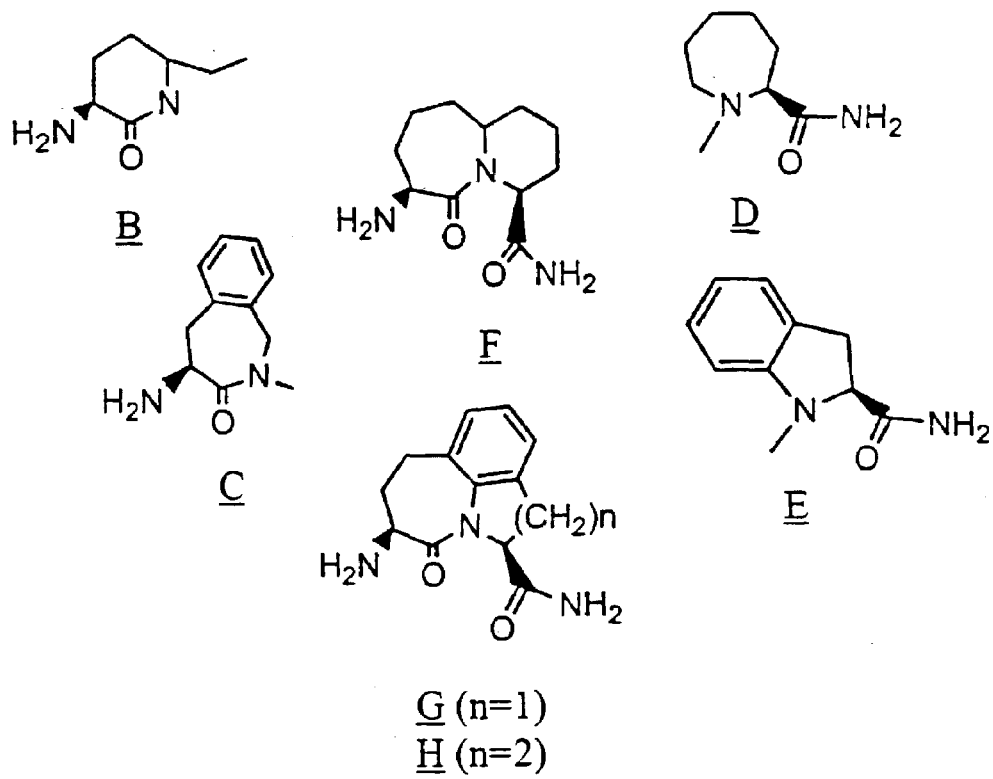
FIG. 18 depicts compounds and pharmaceutical compositions of this invention. Said compounds and compositions were also described at the April 2001 American Chemical Society (ACS) meeting in San Diego, Calif., USA.
Figure 18C:
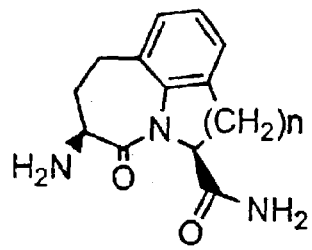
Figure 20D:
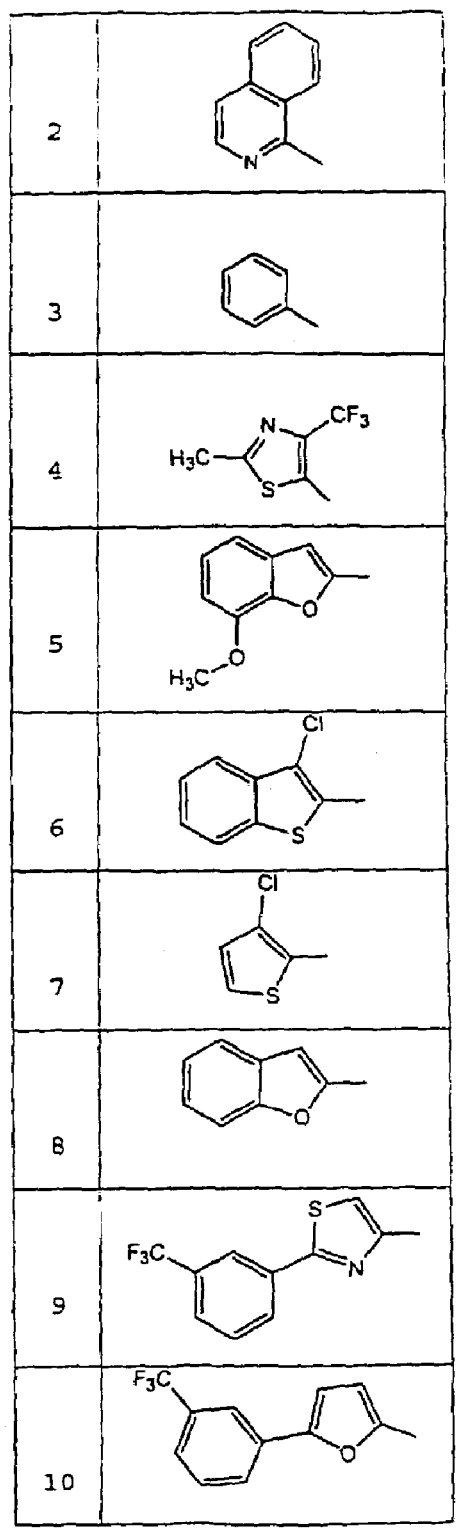
FIG. 20 depicts compounds and pharmaceutical compositions of this invention. Said compounds and compositions are also described in PCT Publication WO 02/085899.
Figure 20E:
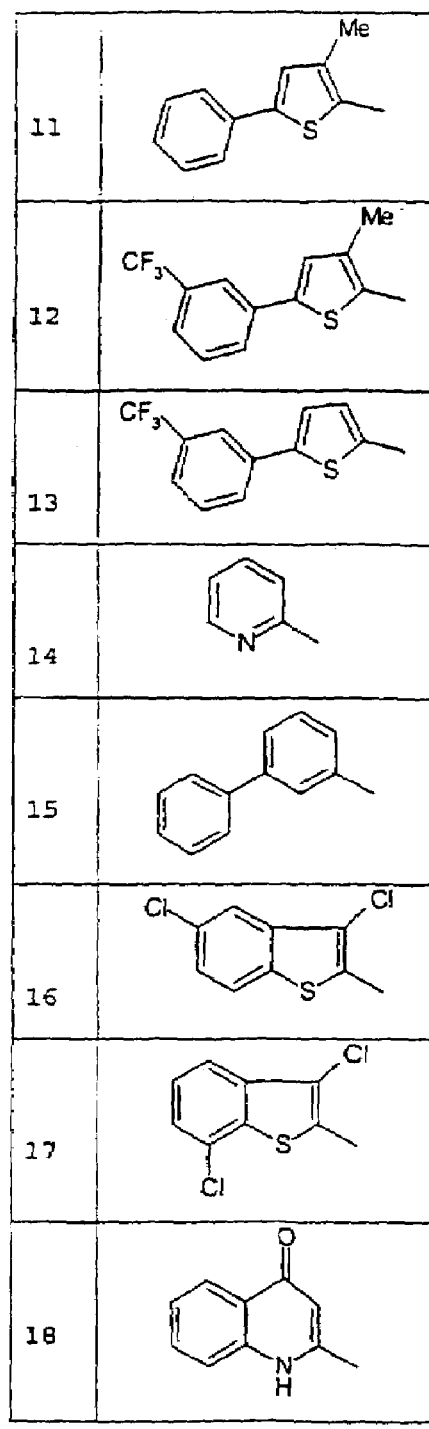
Figure 20F:
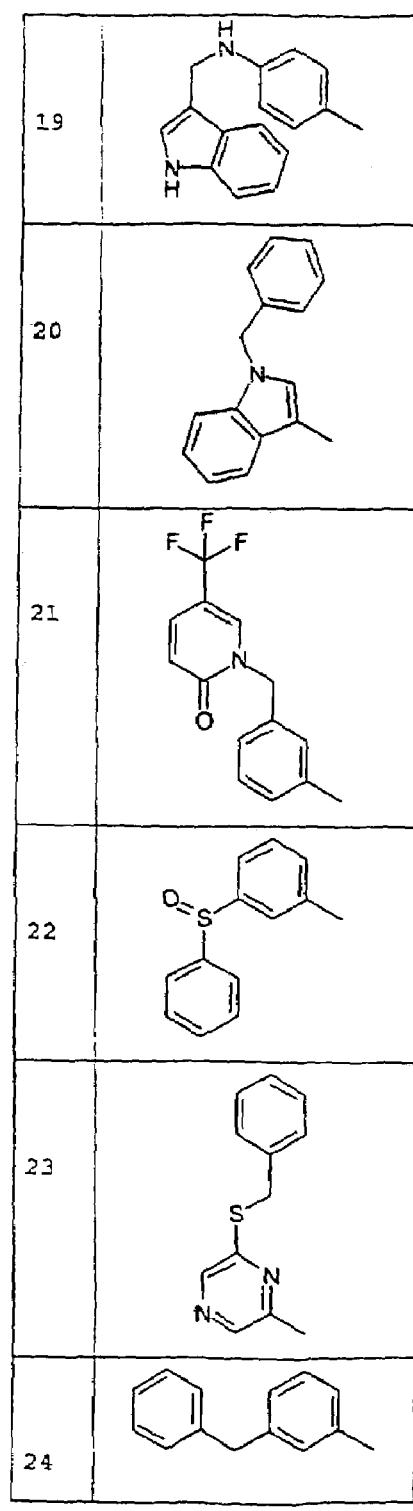
Figure 20G:
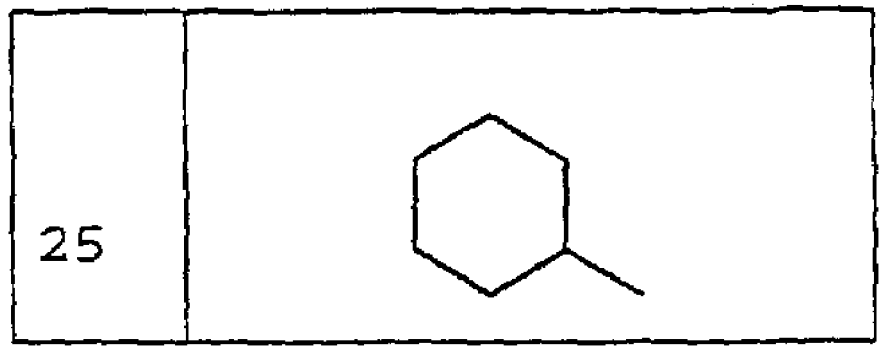

In another embodiment of the present invention, the compound is a caspase inhibitor as described in any of the following documents, each of which is incorporated herein by reference: United States Patent Number ("USP") U.S. Pat. No. 6,187,771 (FIG. 15); American Chemical Society ("ACS") Meeting, San Diego, April 2001 (FIG. 18); U.S. Pat. No. 6,184,244 (FIG. 14); U.S. Pat. No. 6,242,422 (FIG. 17); U.S. Pat. No. 6,197,750 (FIG. 16); WO 01/72707 (FIG. 8); WO 01/42216 (FIG. 7); WO 01/10383 (FIG. 5); WO 01/90070 (FIG. 9); WO 01/94351 (FIG. 10); WO 02/22611 (FIG. 19); WO 02/42278 (FIG. 12); WO 02/085899 (FIG. 20); WO 02/094263 (FIG. 11); WO 00/55127 (FIG. 2); WO 01/05772

(FIG. 4); U.S. Pat. No. 6,184,210 (FIG. 13); WO 00/61542 (FIG. 3); WO 01/16093 (FIG. 6); and WO 00/55114 (FIG. 1).

The structures of representative caspase inhibitors in each of these documents are depicted in Table 1.

TABLE 1

Structures of Selected Caspase Inhibitors

| Comp. No. | Structure | Citation |
|---|---|---|
| 1 | 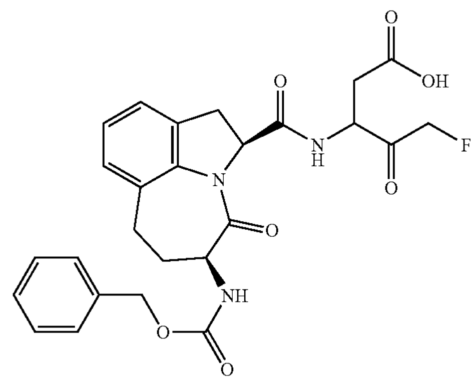 | U.S. Pat. No. 6,187,771 |
| 2 | 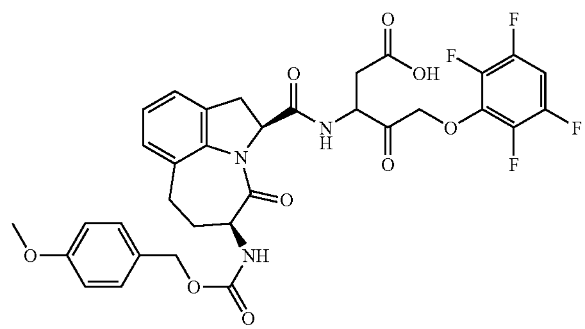 | ACS Meeting, San Diego, April 2001 |
| 3 | 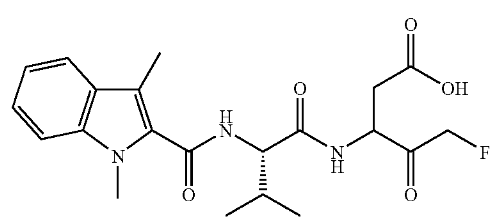 | U.S. Pat. No. 6,184,244 |
| 4 | 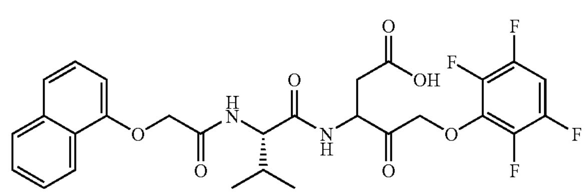 | U.S. Pat. No. 6,242,422 |
| 5 | 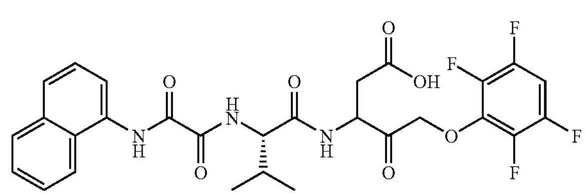 | U.S. Pat. No. 6,197,750 |

TABLE 1-continued
Structures of Selected Caspase Inhibitors
| Comp. No. | Structure | Citation |
|---|---|---|
| 6 | 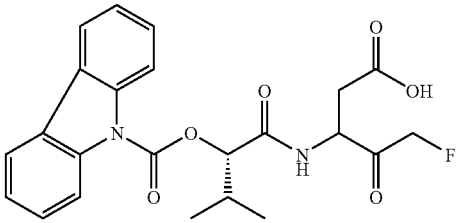 | WO 01/72707 |
| 7 | 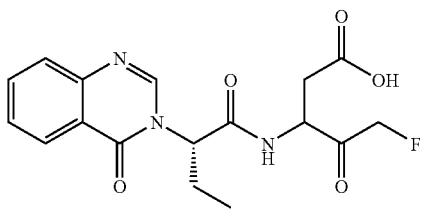 | WO 01/42216 |
| 8 | 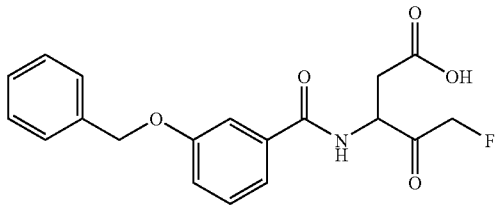 | WO 01/10383 |
| 9 | 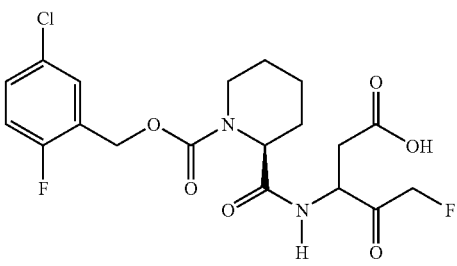 | WO 01/90070 |
| 10 | 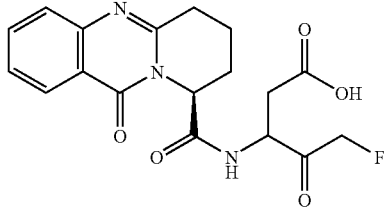 | WO 01/94351 |
| 11 | 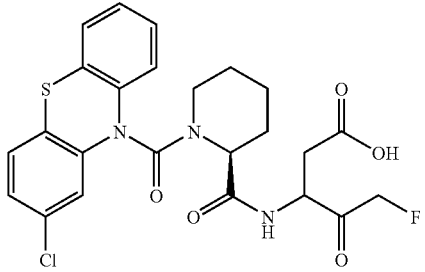 | WO 02/22611 |

TABLE 1-continued
Structures of Selected Caspase Inhibitors
| Comp. No. | Structure | Citation |
|---|---|---|
| 12 | 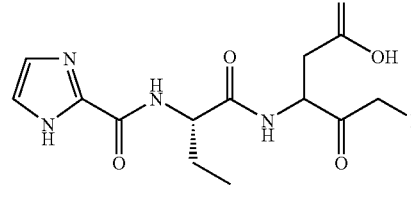 | WO 02/42278 |
| 13 | 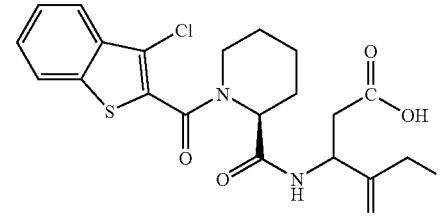 | WO 02/085899 |
| 14 | 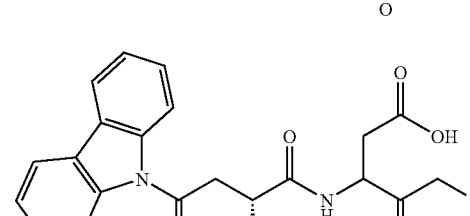 | WO 02/094263 |
| 15 | 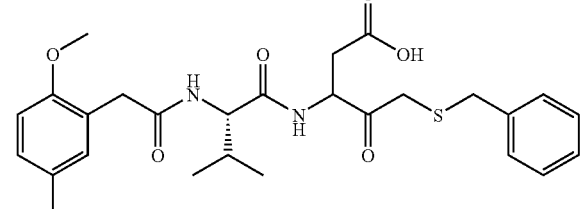 | WO 00/55127 |
| 16 | 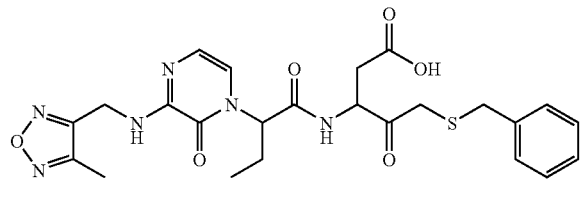 | WO 01/05772 |
| 17 | 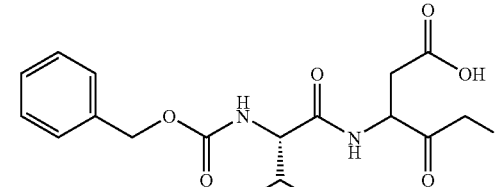 | U.S. Pat. No. 6,184,210 |

TABLE 1-continued

Structures of Selected Caspase Inhibitors

| Comp. No. | Structure | Citation |
|---|---|---|
| 18 | 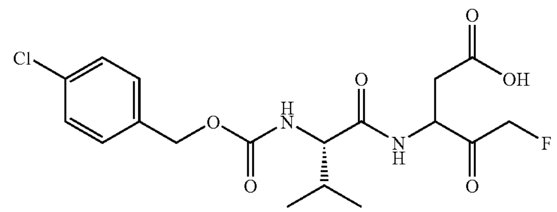 | WO 00/61542 |
| 19 | 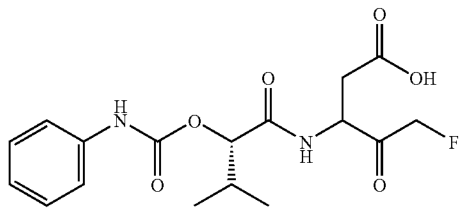 | WO 01/16093 |
| 20 | 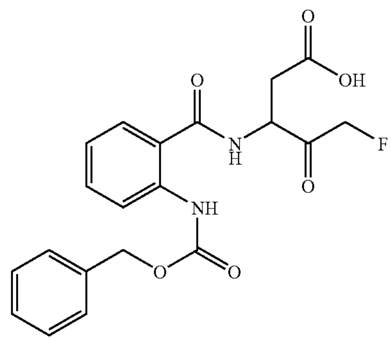 | WO 00/55114 |

It will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

As used herein, the term "prodrug" refers to a derivative of a biologically active compound, wherein the derivative has little or no activity of the biologically active compound.

Examples of the substituents of the hydrocarbon chains include, but are not limited to, halogen and small alkyl (e.g., $C_{1-6}$ alkyl). Examples of phospholipid head groups include, but are not limited to, choline, ethanolamine, inositol, monosaccharide, oligosaccharide, glycerol, phosphatidic acid and serine.

Accordingly, the compound represented by formula I has little or no caspase inhibitor activity. However, an active caspase inhibitor is obtained by cleavage of the bond that links the residue to the lipid portion of the compound of formula I. This cleavage is preferably carried out enzymatically by, for example, a phospholipase. When the cleavage is carried out by a phospholipase, the residue is selectively cleaved in cells and tissues with elevated phospholipase activity. Caspase inhibitor activity is; therefore obtained selectively in cells and tissues with elevated phospholipase activity. This preferential release of the caspase inhibitor is one embodiment of this invention.

Other mechanisms of cleavage, such as hydrolytic mechanisms or cleavage by other enzymes are also within the scope of this invention. These other mechanisms of cleavage may result in non-preferential release of the caspase inhibitor.

The compounds of this invention may be prepared in general by methods known to those skilled in the art for analogous compounds, as illustrated by the general schemes and examples below.

Therefore, one embodiment of this invention provides a process for preparing a compound of formula I, comprising the step of coupling compound 1:

Compound 1

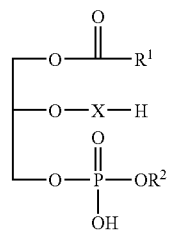

with a compound 2, YH, wherein compound 2 comprises a carboxylic acid group with H being the hydrogen of the carboxylic acid group ($R^1$, $R^2$, and Y are as defined in any of the embodiments of this invention). The coupling may be carried out under standard carboxylic acid coupling conditions. As would be appreciated by a skilled practitioner, appropriate functional groups in compound 1 and compound 2 may be protected [see, e.g., T. W. Greene & P. G. M. Wutz, *Protective Groups in Organic Synthesis*, John Wiley & Sons, New York, 1999].

The compounds of this invention may be assayed for their ability to inhibit apoptosis, the release of IL-1β or caspase activity. Assays for each of the activities are known in the art (see generally, WO 01/42216, the content of which is incorporated herein by reference). However, as would be recognized by a skilled practitioner, the prodrug compounds of this invention should be active only in assays where the phospholipid prodrug moiety would be cleaved, typically in in vivo assays.

One embodiment of this invention relates to a composition comprising a compound of formula I or a pharmaceutically acceptable salt thereof, and a pharmaceutically acceptable carrier.

Another embodiment of this invention provides a method for inhibiting caspase activity in a mammal comprising administering to said mammal a compound of formula I or a pharmaceutically acceptable salt thereof, and a pharmaceutically acceptable carrier.

This invention also provides methods of using the compounds and compositions of this invention.

When pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with agents such as lower alkyl halides, e.g., methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and/or alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compounds and compositions are particularly useful in therapeutic applications relating to an IL-1 mediated disease, an apoptosis mediated disease, an inflammatory disease, an autoimmune disease, a destructive bone disorder, a proliferative disorder, an infectious disease, a degenerative disease, a disease associated with cell death, an excess dietary alcohol intake disease, a viral mediated disease, retinal disorders, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyrbiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, organ apoptosis after burn injury, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, hemorrhagic shock, sepsis, septic shock, burns, Shigellosis, Alzheimer's disease, Parkinson's disease, Huntington's disease, Kennedy's disease, prion disease, cerebral ischemia, epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, Japanese encephalitis, various forms of liver disease, renal disease, polycystic kidney disease, H. pylori-associated gastric and duodenal ulcer disease, HIV infection, tuberculosis, and meningitis. The compounds and compositions are also useful in treating complications associated with coronary artery bypass grafts. The compounds and compositions are also useful for decreasing IGIF or IFN-γ production. The compounds and compositions are also useful in immunotherapy for treatment of cancer.

The present compounds and compositions may also be used in methods for preserving cells. These methods would be useful for preserving organs, particularly those intended for transplant, or blood products. Similar uses for caspase inhibitors have been reported [Schierle et al., *Nature Medicine*, 1999, 5, 97]. The method involves treating the cells or tissue to be preserved with a solution comprising a compound of this invention. The amount of a compound of this invention needed will depend on the effectiveness of the free caspase inhibitor for the given cell type and the length of time required to preserve the cells from apoptotic cell death.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention.

The amount of compound present in the compositions of this invention should be sufficient to cause a detectable decrease in the release of IL-1$\beta$, cellular apoptosis or caspase activity, or in the severity of caspase-mediated diseases, as measured by any of the assays known in the art.

Dosage levels of between about 0.01 and about 100 mg/kg body weight per day, preferably between about 0.5 and about 75 mg/kg body weight per day and more preferably between about 1 and about 50 mg/kg body weight per day of the active ingredient compound are useful in a monotherapy.

Typically, a compound or composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of this invention and one or more additional therapeutic or prophylactic agents, both the compound and the additional agent should be present at dosage levels of between about 10% to about 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

As the skilled practitioner will appreciate, lower or higher doses than those recited above may be required. It should be understood that a specific dosage and treatment regimens for any particular patient will depend upon a variety of factors, including the activity of the specific compound employed, the age, body weight, general health, sex, diet, time of administration, rate of excretion, drug combination, the severity and course of the particular disease, the patient's disposition to the disease being treated, and the judgment of the treating physician. The amount of active ingredients will also depend upon the particular compound and other therapeutic agent, if present, in the composition.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

The compounds of this invention are particularly suitable for methods involving inhibition of caspase activity. Without being bound by theory, upon in vivo administration of a prodrug of this invention, the phospholipid group is cleaved to provide a corresponding acid-containing compound (e.g., a compound of Table 1). As would be recognized by a skilled practitioner, a prodrug of this invention or the corresponding parent compound may be further metabolized in vivo. Any such metabolites are included within the scope of this invention.

In order that this invention be more fully understood, the following examples are set forth. These examples are for the purpose of illustration only and are not to be construed as limiting the scope of the invention in any way.

EXAMPLE 1

Scheme 1
Preparation of Compounds of Formula I

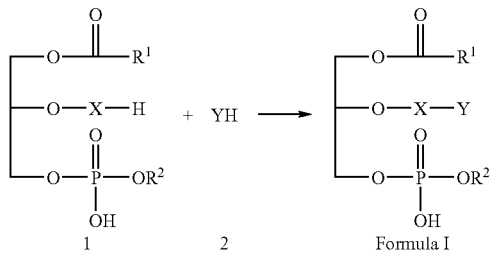

Scheme 1 depicts a synthetic route for obtaining compounds of formula I, where compound 2 is a caspase inhibitor comprising a carboxylic acid moiety. Reaction of a lipid compound 1 with a compound 2, under standard carboxylic acid coupling conditions (for example, the conditions as described below in Example 2) provides compounds of formula I. Compounds of formula 1 may be isolated using standard procedures.

In the lipid compound 1, the X—H moiety and/or the OH moiety may be protected with a suitable protecting group. A lipid compound 1 wherein both moieties are protected would have the structure depicted by compound 3 below, wherein P is a suitable protecting group (and wherein each P may be the same or different). As would be recognized by a skilled practitioner, if the X—H moiety of compound 1 is protected, the protecting group must be removed prior to reacting compound 1 with compound 2. However, if the O—H moiety is protected, the protecting group does not need to be removed prior to reacting compound 1 with compound 2. Furthermore, the deprotection of the X—H moiety may be done in situ. Depending on the nature of the substituents on Y, suitable protecting groups may be used in association with Y.

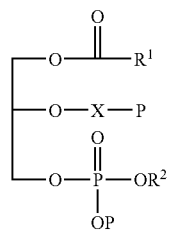

EXAMPLE 2

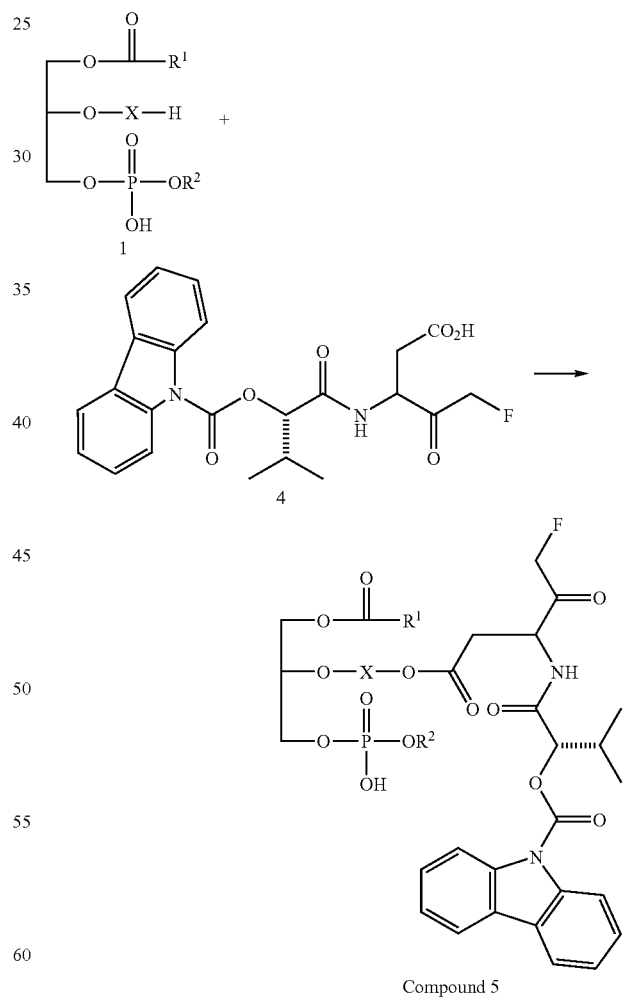

Scheme 2 depicts a synthetic route for obtaining compounds of this invention where Y is the residue of a caspase inhibitor of WO 01/72707 (wherein $R^1$, $R^2$, and X are as defined herein). Reaction of a lipid compound 1 with compound 4 in the presence of EDC [1-(3-dimethylaminopropyl)-3-ethylcarbodiimide hydrochloride] or CDI (1,1'-carbonyldiimidazole) under standard carboxylic acid coupling conditions provides compound 5. Compound 5 may be isolated using standard procedures.

As described above in Example 1, the lipid compound 1, may be protected with a suitable protecting group.

While we have described a number of embodiments of this invention, it is apparent that our basic examples may be altered to provide other embodiments, which utilize the compounds, compositions, and methods of this invention.

We claim:

1. A compound of the formula I:

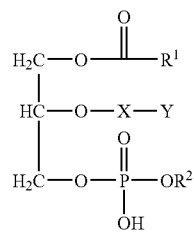

or a pharmaceutically acceptable salt thereof, wherein:
  $R^1$ is a saturated or unsaturated, straight-chain or branched, unsubstituted hydrocarbon chain;
  $R^2$ is choline;
  X is a direct covalent bond; and
  Y is a residue of a caspase inhibitor selected from a structure in Table 1 below:

TABLE 1

Structures of Selected Caspase Inhibitors

| Comp. No. | Structure |
|---|---|
| 1 | 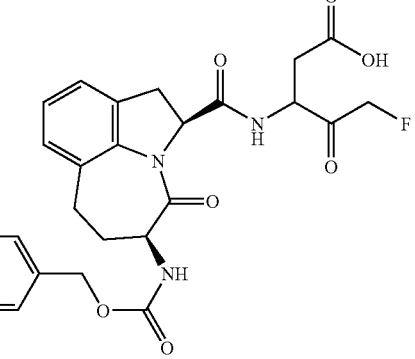 |
| 2 | 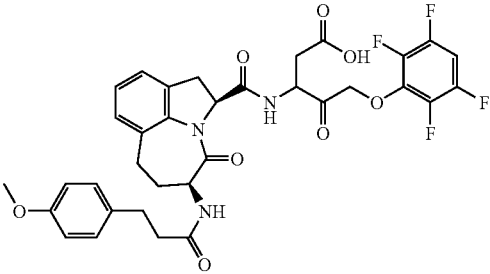 |
| 3 | 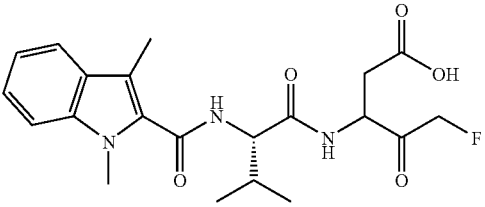 |
| 4 | 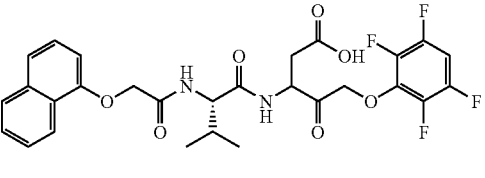 |
| 5 | 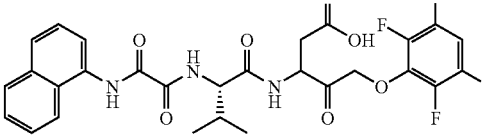 |
| 6 | 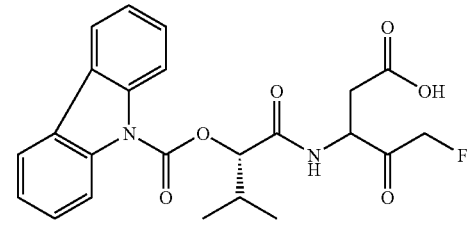 |
| 7 | 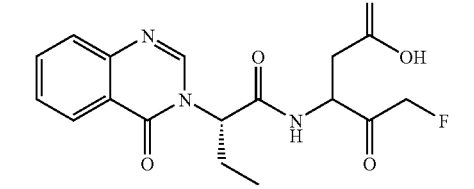 |
| 8 | 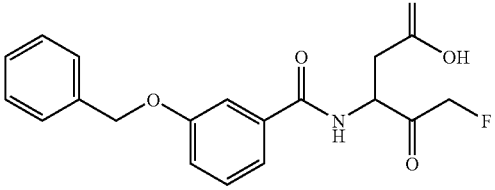 |
| 9 | 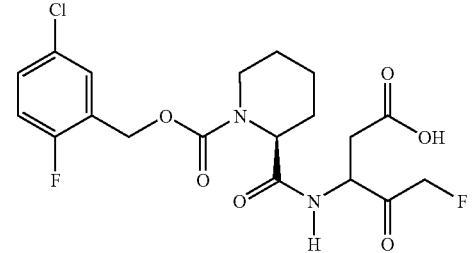 |

TABLE 1-continued

Structures of Selected Caspase Inhibitors

| Comp. No. | Structure |
|---|---|
| 10 | 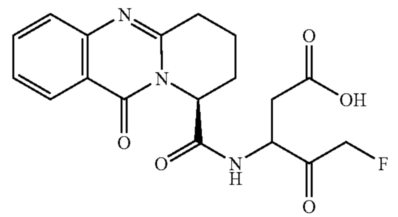 |
| 11 | 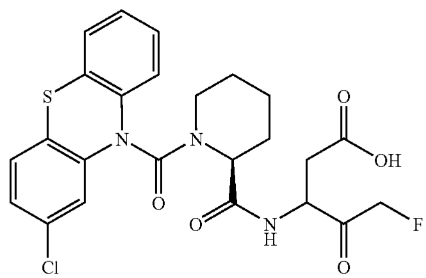 |
| 12 | 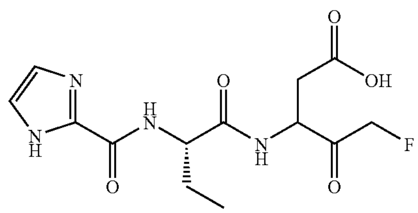 |
| 13 | 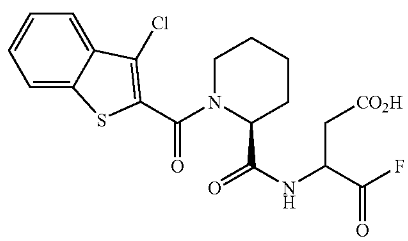 |
| 14 | 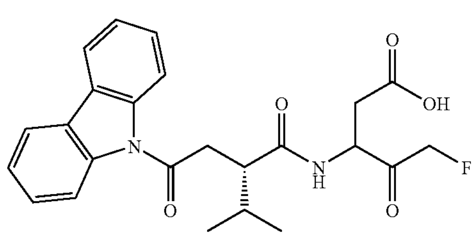 |
| 15 | 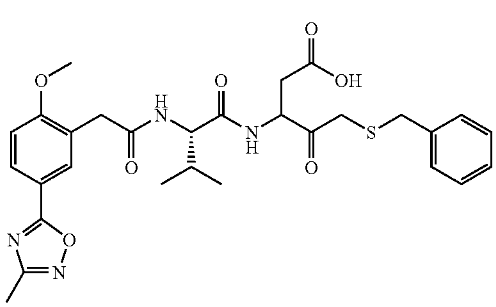 |
| 16 | |
| 17 | |
| 18 | |
| 19 | |
| 20 | |

2. The compound of claim 1, wherein the $R^1$ hydrocarbon chain has from 2 to 30 carbon atoms.

3. The compound of claim 2, wherein the $R^1$ hydrocarbon chain has from 2 to 24 carbon atoms.

4. The compound of claim 1, wherein Y is a reversible caspase inhibitor.

5. The compound of claim 1, wherein Y is an irreversible caspase inhibitor.

6. A pharmaceutical composition comprising: a) a compound according to any one of claims 1-3 or 4-5; and b) a pharmaceutically acceptable carrier.

7. A method for treating a disease selected from the group consisting of osteoarthritis, pancreatitis, rheumatoid arthritis, chronic active hepatitis, inflammatory bowel disease, Crohn's disease, psoriasis, organ transplant rejection, sepsis, septic shock, cerebral ischemia, myocardial ischemia, myocardial infarction, amyotrophic lateral sclerosis, multiple sclerosis, neurological damage due to stroke, hepatitis-B, hepatitis-C, hepatitis-G and liver disease, in a mammal comprising administering to said mammal a compound according to any one of claims 1-3 or 4-5 or a composition according to claim 6.

8. A method for treating complications associated with coronary artery bypass grafts in a mammal comprising administering to said mammal a compound according to any one of claims 1-3 or 4-5 or a composition according to claim 6.

9. The method according to any one of claims 7 or 8, wherein said mammal is a human.

10. A method for preserving cells in vitro comprising treating the cells with a solution comprising an effective amount of a compound according to any one of claims 1-5 or a composition according to claim 6.

11. The method according to claim 10, wherein said compound or composition is used for an organ transplant or for preserving blood products.

12. The method according to any one of claims 7 or 8, wherein said compound or composition is administered with an additional therapeutic agent.

13. The method according to claim 12, wherein said additional therapeutic agent is a thrombolytic agent.

14. The method according to claim 13, wherein said thrombolytic agent is selected from the group consisting of tissue plasminogen activator and streptokinase.

15. A method for decreasing IGIF or IFN-γ production in a mammal in need thereof comprising administering to said mammal a compound according to any one of claims 1-5 or a composition according to claim 6, wherein the method is used to treat a disease selected from the group consisting of osteoarthritis, pancreatitis, rheumatoid arthritis, chronic active hepatitis, inflammatory bowel disease, Crohn's disease, psoriasis, organ transplant rejection, sepsis, septic shock, cerebral ischemia, myocardial ischemia, myocardial infarction, amyotrophic lateral sclerosis, multiple sclerosis, neurological damage due to stroke, hepatitis-B, hepatitis-C, hepatitis-G, and liver disease.

* * * * *

UNITED STATES PATENT AND TRADEMARK OFFICE
CERTIFICATE OF CORRECTION

PATENT NO.      : 7,410,956 B2
APPLICATION NO. : 10/366192
DATED           : August 12, 2008
INVENTOR(S)     : Michael Mortimore et al.

It is certified that error appears in the above-identified patent and that said Letters Patent is hereby corrected as shown below:

Col. 21, line 55-65, Compound 2 should appear as follows:

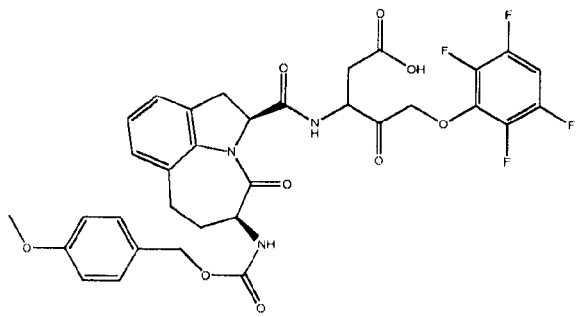

Signed and Sealed this

Thirtieth Day of December, 2008

JON W. DUDAS
*Director of the United States Patent and Trademark Office*